United States Patent
Callahan et al.

(10) Patent No.: US 11,117,905 B2
(45) Date of Patent: Sep. 14, 2021

(54) BISARYL HETEROCYCLES AS NRF2 ACTIVATORS

(71) Applicant: GLAXOSMITHKLINE INTELLECTUAL PROPERTY DEVELOPMENT LIMITED, Middlesex (GB)

(72) Inventors: James Francis Callahan, King of Prussia, PA (US); Roderick S. Davis, King of Prussia, PA (US); Nicole Cathleen Goodwin, King of Prussia, PA (US); Jeffrey K. Kerns, King of Prussia, PA (US)

(73) Assignee: GLAXOSMITHKLINE INTELLECTUAL PROPERTY DEVELOPMENT LIMITED, Middlesex (GB)

( * ) Notice: Subject to any disclaimer, the term of this patent is extended or adjusted under 35 U.S.C. 154(b) by 0 days.

(21) Appl. No.: 16/467,193

(22) PCT Filed: Dec. 11, 2017

(86) PCT No.: PCT/IB2017/057801
§ 371 (c)(1),
(2) Date: Jun. 6, 2019

(87) PCT Pub. No.: WO2018/109643
PCT Pub. Date: Jun. 21, 2018

(65) Prior Publication Data
US 2020/0062781 A1 Feb. 27, 2020

Related U.S. Application Data

(60) Provisional application No. 62/434,013, filed on Dec. 14, 2016.

(51) Int. Cl.
| | | |
|---|---|---|
| *A61K 8/00* | (2006.01) | |
| *A61K 9/00* | (2006.01) | |
| *C07D 243/08* | (2006.01) | |
| *C07D 281/02* | (2006.01) | |
| *C07D 291/08* | (2006.01) | |
| *C07D 513/04* | (2006.01) | |
| *C07D 515/04* | (2006.01) | |
| *C07D 285/36* | (2006.01) | |
| *C07D 409/14* | (2006.01) | |

(52) U.S. Cl.
CPC .......... *C07D 515/04* (2013.01); *A61K 9/0019* (2013.01); *A61K 9/0053* (2013.01); *A61K 9/0073* (2013.01); *C07D 243/08* (2013.01); *C07D 285/36* (2013.01); *C07D 291/08* (2013.01); *C07D 409/14* (2013.01); *C07D 513/04* (2013.01)

(58) Field of Classification Search
CPC .. C07D 515/04; C07D 513/04; C07D 243/08; C07D 281/36; C07D 291/08; A61K 9/0053; A61K 8/0019; A61K 9/0073
USPC .............................. 540/490, 491; 514/211.1
See application file for complete search history.

(56) References Cited

U.S. PATENT DOCUMENTS 10,144,731 B2 * 12/2018 Davies ...................... A61P 9/12

FOREIGN PATENT DOCUMENTS

| WO | WO 2015/092713 A1 | 6/2015 |
|---|---|---|
| WO | WO 2016/027253 A1 | 2/2016 |
| WO | WO 2016/202253 A1 | 12/2016 |

OTHER PUBLICATIONS

Huang et al. Journal of Nutritional Biochemistry 26 (2015) 1401-1413.*
Carmen Almansa, et al. "Diphenylpropionic Acids as New AT 1 Selective Angiotensin II Antagonists". J. Med. Chem., 39(11): 2197-2206 (Jan. 1, 1996).
Boutten, A., et al. "NRF2 Targeting: A Promising Therapeutic Strategy in Chronic Obstructive Pulmonary Disease". Trends in Molec. Med., 17(7): 363-371 (Jul. 1, 2011).
Davies, et al. "Mono-acidic Inhibitors of the Kelch-like ECH-Associated Protein 1: Nuclear Factor Erythroid 2-related Factor 2 (KEAP1 :NRF2) Protein-Protein Interaction with High Cell Potency Identified by Fragment-based Discovery". J. Med. Chern., 59: 3991-4006 (2016).
Heightman, et al. "Structure-Activity and Structure-Conformation Relationships of Aryl Propionic Acid Inhibitors of the Kelch-like ECH-associated protein 1: Nuclear factor erythroid 2-related factor 2 (KEAP1:NRF2) protein-protein interaction". J. Med. Chern., 62: 4683-4702 (2019).

* cited by examiner

*Primary Examiner* — Brenda L Coleman
(74) *Attorney, Agent, or Firm* — Nora Stein; Scott Young; Duke M. Fitch

(57) ABSTRACT

The present invention relates to bisaryl heterocycle compounds, methods of making them, pharmaceutical compositions containing them and their use as NRF2 activators. In particular, the invention relates to bisaryl heterocycles of Formula (I),

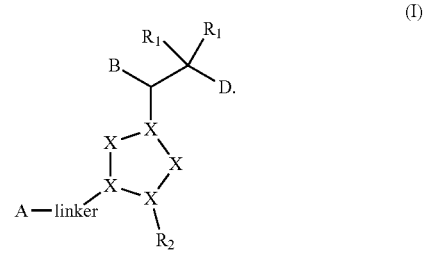

10 Claims, No Drawings

BISARYL HETEROCYCLES AS NRF2 ACTIVATORS

This application is a § 371 national phase entry of International Application No. PCT/IB2017/057801, filed 11 Dec. 2017, which claims the benefit of U.S. Provisional Application No. 62/434,013, filed 14 Dec. 2016.

FIELD OF THE INVENTION

The present invention relates to bisaryl heterocycle compounds, methods of making them, pharmaceutical compositions containing them and their use as NRF2 activators.

BACKGROUND OF THE INVENTION

NRF2 (NF-E2 related factor 2) is a member of the cap-n-collar family of transcription factors containing a characteristic basic-leucine zipper motif. Under basal conditions, NRF2 levels are tightly controlled by the cytosolic actin-bound repressor, KEAP1 (Kelch-like ECH associating protein 1), which binds to NRF2 and targets it for ubiquitylation and proteasomal degradation via the Cul3-based E3-ubiquitin ligase complex. Under conditions of oxidative stress, DJ1 (PARK7) is activated and stabilizes NRF2 protein by preventing NRF2 from interacting with KEAP1. Also, modification of reactive cysteines on KEAP1 can cause a conformational change in KEAP1 that alters NRF2 binding and promotes NRF2 stabilization. Thus, the levels of NRF2 in the cell are usually kept low in normal conditions but the system is designed to respond quickly to environmental stress by increasing NRF2 levels and thus downstream NRF2 activity.

Inappropriately low NRF2 activity in the face of on-going oxidative stress appears to be a pathological mechanism underlying chronic obstructive pulmonary disease (COPD). Yamada, K., et al. *BMC Pulmonary Medicine*, 2016, 16: 27. This may be a result of an altered equilibrium between NRF2 activators with both inappropriate lack of positive activators such as DJ1, and overabundance of negative activators such as Keap1 and Bach1. Therefore, restoration of NRF2 activity in the lungs of COPD patients should result in repair of the imbalance and mitigation of deleterious processes such as apoptosis of structural cells (including alveolar epithelial and endothelial cells) and inflammation. The results of these effects would be enhanced cytoprotection, preservation of lung structure, and structural repair in the COPD lung, thus slowing disease progression. Therefore, NRF2 activators may treat COPD (Boutten, A., et al. 2011. *Trends Mol. Med.* 17:363-371) and other respiratory diseases, including asthma, Acute Lung Injury (ALI) (Cho, H. Y., and Kleeberger, S. R., 2015, *Arch Toxicol.* 89:1931-1957; Zhao, H. et al., 2017, *Am J Physiol Lung Clee Mol Physiol* 312:L155-L162, first published Nov. 18, 2016); doi:10.1152/ajplung.00449.2016), Acute Respiratory Distress Syndrome (ARDS) and pulmonary fibrosis (Cho, H. Y., and Kleeberger, S. R. 2010. *Toxicol. Appl. Pharmacol.* 244:43-56).

The therapeutic potential of an NRF2 activator is exemplified in pulmonary macrophages from COPD patients where NRF2 pathway appears maladaptive. These cells have impaired bacterial phagocytosis compared with similar cells from control patients, and this effect is reversed by the addition of NRF2 activators in vitro. Therefore, in addition to the effects mentioned above, restoration of appropriate NRF2 activity could also rescue COPD exacerbations by reducing lung infection.

This is demonstrated by the NRF2 activator, Sulforaphane, which increases the expression of Macrophage Receptor with Collagenous structure (MARCO) by COPD macrophages and alveolar macrophages from cigarette smoke-exposed mice, thereby improving in these cells bacterial phagocytosis (*Pseudomonas aeruginosa*, non-typable *Haemophilus influenzae*) and bacterial clearance both ex vivo and in vivo. (Harvey, C. J., et al. 2011. *Sci. Transl. Med.* 3:78ra32).

The therapeutic potential of targeting NRF2 in the lung is not limited to COPD. Rather, targeting the NRF2 pathway could provide treatments for other human lung and respiratory diseases that exhibit oxidative stress components such as chronic asthma and acute asthma, lung disease secondary to environmental exposures including but not limited to ozone, diesel exhaust and occupational exposures, fibrosis, acute lung infection (e.g., viral (Noah, T. L. et al. 2014. PLoS ONE 9(6): e98671), bacterial or fungal), chronic lung infection, α1 antitrypsin disease, ALI, ARDS and cystic fibrosis (CF, Chen, J. et al. 2008. *PLoS One.* 2008; 3(10): e3367).

A therapy that targets the NRF2 pathway also has many potential uses outside the lung and respiratory system. Many of the diseases for which an NRF2 activator may be useful are autoimmune diseases (psoriasis, IBD, MS), suggesting that an NRF2 activator may be useful in autoimmune diseases in general.

In the clinic, a drug targeting the NRF2 pathway (bardoxolone methyl) has shown efficacy in diabetic patients with diabetic nephropathy/chronic kidney disease (CKD) (Aleksunes, L. M., et al. 2010. *J. Pharmacol. Exp. Ther.* 335:2-12), though phase III trials with this drug in patients with the most severe stage of CKD were terminated. Furthermore, there is evidence to suspect that such a therapy would be effective in sepsis-induced acute kidney injury, other acute kidney injury (AKI) (Shelton, L. M., et al. 2013. *Kidney International.* June 19. doi: 10.1038/ki.2013.248.), and kidney disease or malfunction seen during kidney transplantation.

In the cardiac area, bardoxolone methyl is currently under investigation in patients 30 with Pulmonary Arterial Hypertension and so a drug targeting NRF2 by other mechanisms may also be useful in this disease area. Oxidative stress is increased in the diseased myocardium, resulting in accumulation of reactive oxygen species (ROS) which impairs cardiac function [*Circ* (1987) 76(2); 458-468] and increases susceptibility to arrhythmia [*J of Mol & Cell Cardio* (1991) 23(8); 899-918] by a direct toxic effect of increased necrosis and apoptosis [*Circ Res* (2000) 87(12); 1172-1179]. In a mouse model of pressure overload (TAC), NRF2 gene and protein expression is increased during the early stage of cardiac adaptive hypertrophy, but decreased in the later stage of maladaptive cardiac remodeling associated with systolic dysfunction [*Arterioscler Thromb Vasc Biol* (2009) 29(11); 1843-5 1850; *PLOS ONE* (2012) 7(9); e44899]. In addition, NRF2 activation has been shown to suppress myocardial oxidative stress as well as cardiac apoptosis, fibrosis, hypertrophy, and dysfunction in mouse models of pressure overload [*Arterioscler Thromb Vasc Biol* (2009) 29(11); *J of Mol & Cell Cardio* (2014) 72; 305-315; and 1843-1850; *PLOS ONE* (2012) 7(9); e44899]. NRF2 activation has also been shown to protect against cardiac I/R injury in mice 10 [*Circ Res* (2009) 105(4); 365-374; *J of Mol & Cell Cardio* (2010) 49(4); 576-586] and reduce myocardial oxidative damage following cardiac I/R injury in rat. Therefore, a drug targeting NRF2 by other mechanisms may be useful in a variety of cardiovascular diseases including but not limited to atherosclerosis, hypertension, and heart failure (Oxidative Medicine and Cellular Longevity Volume 2013 (2013), Article ID 104308, 10 pages), acute coronary 15 syndrome, myocardial infarction, myocardial repair, cardiac remodeling, cardiac arrhythmias, heart failure with preserved ejection fraction, heart failure with reduced ejection fraction and diabetic cardiomyopathy.

A drug activating the NRF2 pathway could also be useful for treatment of several neurodegenerative diseases including Parkinson's disease (PD), Alzheimer's disease (AD), amyotrophic lateral sclerosis (ALS) (Brain Res. 2012 Mar. 29; 1446:109-18. 2011.12.064. Epub 2012 Jan. 12.) and multiple sclerosis (MS). Multiple in vivo models have shown that NRF2 KO mice are more sensitive to neurotoxic insults than their wild-type counterparts. Treatment of rats with the NRF2 activator tert-butylhydroquinone (tBHQ) reduced cortical damage in rats in a cerebral ischemia-reperfusion model, and cortical glutathione levels were increased in NRF2 wild-type but not KO mice after administration of tBHQ (Shih, A. Y., et al. 2005. *J. Neurosci.* 25: 10321-10335). Tecfidera™ (dimethyl fumarate), which activates NRF2 among other targets, is approved in the U.S. to treat relapsing-remitting multiple sclerosis (MS). Activation of NRF2 may also help treat cases of Friedreich's Ataxia, where increased sensitivity to oxidative stress and impaired NRF2 activation has been reported (Paupe V., et al, 2009. PLoS One; 4(1):e4253. Omaveloxolone (RTA-408) is also in clinical trials for Friedreich's Ataxia.

There is preclinical evidence of the specific protective role of the NRF2 pathway in models of inflammatory bowel disease (IBD, Crohn's Disease and Ulcerative Colitis) and/or colon cancer (Khor, T. O., et al 2008. *Cancer Prev. Res. (Phila)* 1:187-191).

Age-related macular degeneration (AMD) is a common cause of vision loss in people over the age of 50. Cigarette smoking is a major risk factor for the development of non-neovascular (dry) AMD and perhaps also neovascular (wet) AMD. Findings in vitro and in preclinical species support the notion that the NRF2 pathway is involved in the antioxidant response of retinal epithelial cells and modulation of inflammation in pre-clinical models of eye injury (Schimel, et al. 2011. *Am. J. Pathol.* 178:2032-2043). Fuchs Endothelial Corneal Dystrophy (FECD) is a progressive, blinding disease characterized by corneal endothelial cells apoptosis. It is a disease of aging and increased oxidative stress related to low levels of NRF2 expression and/or function (Bitar, M. S., et al. 2012. *Invest Ophthalmol. Vis. Sci.* Aug. 24, 2012 vol. 53 no. 9 5806-5813). In addition, an NRF2 activator may be useful in uveitis or other inflammatory eye conditions.

Non-alcoholic steatohepatitis (NASH) is a disease of fat deposition, inflammation, and damage in the liver that occurs in patients who drink little or no alcohol. In pre-clinical models, development of NASH is greatly accelerated in KO mice lacking NRF2 when challenged with a methionine- and choline-deficient diet (Chowdhry S., et al. 2010. *Free Rad. Biol. & Med.* 48:357-371). Administration of the NRF2 activators oltipraz and NK-252 in rats on a choline-deficient L-amino acid-defined diet significantly attenuated progression of histologic abnormalities, especially hepatic fibrosis (Shimozono R. et al. 2012. *Molecular Pharmacology.* 84:62-70). Other liver diseases that may be amenable to NRF2 modulation are toxin-induced liver disease (e.g., acetaminophen-induced hepatic disease), viral hepatitis, and cirrhosis (Oxidative Medicine and Cellular Longevity Volume 2013 (2013), Article ID 763257, 9 page).

Recent studies have also begun to elucidate the role of ROS in skin diseases such as psoriasis. A study in psoriasis patients showed an increase in serum malondialdehyde and nitric oxide end products and a decrease in erythrocyte-superoxide dismutase activity, catalase activity, and total antioxidant status that correlated in each case with disease severity index (Dipali P. K., et al. Indian J Clin Biochem. 2010 October; 25(4): 388-392). Also, an NRF2 activator may be useful in treating the dermatitis/topical effects of radiation (Schafer, M. et al. 2010. *Genes & Devl.* 24:1045-1058), and the immunosuppression due to radiation exposure (Kim, J. H. et al., J. Clin. Invest. 2014 Feb. 3; 124(2): 730-41).

There are also data suggesting that an NRF2 activator may be beneficial in preeclampsia, a disease that occurs in 2-5% of pregnancies and involves hypertension and proteinuria (*Annals of Anatomy—Anatomischer Anzeiger* Volume 196, Issue 5, September 2014, Pages 268-277).

Preclinical data has shown that compounds with NRF2 activating activity are better at reversing high altitude-induced damage than compounds without NRF2 activity, using animal and cellular models of Acute Mountain Sickness (Lisk C. et al, 2013, Free Radic Biol Med. October 2013; 63: 264-273.)

SUMMARY OF THE INVENTION

In one aspect, this invention provides for bisaryl heterocycle analogs, or a salt, particularly a pharmaceutically acceptable salt thereof, and pharmaceutical compositions containing them. In particular, the compounds of this invention include a compound of Formula (I):

The present invention provides for compounds of Formula (I):

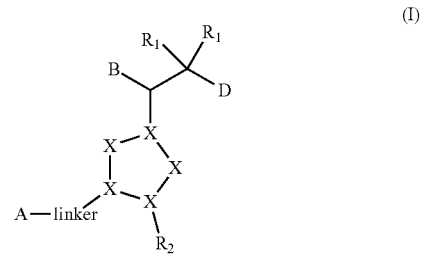

wherein:
B is benzotriazolyl, phenyl, triazolopyridinyl, —O—(CH$_2$)-triazolyl, or —(CH$_2$)$_2$-triazolyl wherein each of benzotriazolyl, phenyl, triazolopyridinyl, —O—(CH$_2$)-triazolyl, or —(CH$_2$)$_2$-triazolyl is unsubstituted or substituted by 1, 2, or 3 substituents independently selected from —C$_{1-3}$alkyl, —O—C$_{1-3}$alkyl, —CN, —(CH$_2$)$_2$—O—(CH$_2$)$_2$—OR$_3$ and halo;
D is —C(O)OH, —C(O)NR$_3$R$_4$, —C(O)NHSO$_2$CH$_3$, —SO$_2$NHC(O)CH$_3$, -5-(trifluoromethyl)-4H-1,2,4-triazol-2-yl, —NR$_3$—C(O)—R$_4$, —NR$_3$—C(O)—NR$_3$R$_4$, —NR$_3$—C(O)—O—R$_4$ or tetrazolyl;
R$_1$ is independently hydrogen, —C$_{1-3}$alkyl, F, —C$_{3-6}$spirocycloalkyl, oxetane, or the two R$_1$ groups together with the carbon to which they are attached form a cyclopropyl group;
R$_2$ is hydrogen, methyl, —CF$_3$, or halo;
R$_3$ is hydrogen or —C$_{1-3}$alkyl;
R$_4$ is hydrogen, —C$_{1-5}$alkyl, —C$_{3-7}$cycloalkyl, —C$_{4-8}$heterocycloalkyl, —C$_{1-5}$alkoxy, —C$_{1-3}$alkyl-O—C$_{1-3}$alkyl, —C$_{1-3}$alkyl-NH—C$_{1-3}$alkyl, —C$_{1-3}$alkyl-SO$_2$C$_{1-3}$alkyl, —C$_{1-3}$alkyl-C$_{4-8}$heterocycloalkyl, —C$_{1-3}$alkyl-C(O)NR$_4$R$_5$, aryl or heteroaryl, wherein each of —C$_1$ alkyl, —C$_{3-7}$ cycloalkyl, —C$_{4-7}$ heterocycloalkyl, —C$_{1-5}$alkoxy, —C$_{1-3}$alkyl-O—C$_{1-3}$alkyl, —C$_{1-3}$alkyl-NH—C$_{1-3}$alkyl, —C$_{1-3}$alkyl-C(O)NR$_4$R$_5$, aryl or heteroaryl is unsubstituted or substituted by one or two substituents selected from —OH, —CO$_2$H, —C(O)NR$_4$R$_5$, —C(O)OR$_3$, —N—C(O)—C$_{1-3}$alkyl, F, —CN, —CH—F$_2$, —CF$_3$, —(CH$_2$)$_n$—O—(CH$_2$)$_m$—CH$_3$, —C$_{3-7}$cycloalkyl and a 5-6-membered heteroaryl ring containing 1, 2 or 3 heteroatoms selected from O, N and S;

or R$_3$ and R$_4$ together with the nitrogen atom to which they are attached form a 5-8-membered heterocyclic ring, an 8-11-membered bicyclic heterocyclic ring or a 9-10-membered bridged bicyclic heterocyclic ring, wherein each 5-8-membered ring, 8-11-membered bicyclic ring, or 9-10-membered bridged bicyclic ring optionally includes one —C(O) or one —S(O)$_2$, and wherein each 5-8-membered ring, 8-11-membered bicyclic ring, or 9-10-membered bridged bicyclic ring optionally contains one, two or three oxygen ring atoms, one, two or three sulfur ring atoms or one, two or three nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$alkyl, —C$_{3-7}$cycloalkyl, —C$_{4-7}$heterocycloalkyl, —(CH$_2$)phenyl, halogen, —NR$_3$R$_5$, —CHF$_2$, —CF$_3$, and —(CH$_2$)$_n$—O—(CH$_2$)$_m$—CH$_3$;

Linker is —CH$_2$—, —CH$_2$—N(-cyclopropyl)-CH$_2$—, —CH$_2$—N(CH$_3$)—CH$_2$— or —N—(CH$_3$)—CH$_2$—;

A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;

wherein each of tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl is unsubstituted or substituted by 1, 2, or 3 substituents independently selected from —C$_{1-3}$alkyl, —C$_{3-6}$spirocycloalkyl, halo, —CN, —O—C$_{1-3}$alkyl, —CH$_2$—O—CH$_3$, and —OH;

and wherein the piperidinyl is further unsubstituted or substituted by a substituent independently selected from pyrazolyl, —CH$_2$pyrazolyl, and oxadiazolyl, each of which is unsubstituted or substituted by —C$_{1-3}$alkyl, or, when A is piperidinyl, it is unsubstituted or substituted by —SO$_2$R, wherein R is —C$_{1-3}$alkyl, phenyl or —C$_{3-7}$cycloalkyl; and wherein the oxazepane is further unsubstituted or substituted by 1 or 2 substituents independently selected from —C$_{1-3}$alkyl and —C$_{3-7}$cycloalkyl;

and wherein the morpholinyl is further unsubstituted or substituted by phenyl which phenyl is unsubstituted or substituted by a substituent independently selected from —C$_{1-3}$ alkyl and —O—C$_{1-3}$ alkyl;

and wherein the pyrrolidinyl is further unsubstituted or substituted by a triazolyl group which is unsubstituted or substituted by —C$_{1-3}$alkyl;

and wherein the imidazolyl, triazolyl, pyrazolyl, and tetrazolyl groups each are further unsubstituted or substituted by 1, 2 or 3 substituents independently selected from —CH$_2$—C$_{4-7}$cycloalkyl, —CH$_2$—C$_{5-7}$heterocycloalkyl, —CH$_2$-azabicycloheptanyl, —CH$_2$-oxepane, and —CH$_2$-azabicyclohexanyl, and wherein each of —CH$_2$—C$_{4-7}$cycloalkyl, —CH$_2$—C$_{5-7}$heterocycloalkyl, —CH$_2$-azabicycloheptanyl, —CH$_2$-oxepane, or —CH$_2$-azabicyclohexanyl, including the —CH$_2$—, are further unsubstituted or substituted by 1 or 2 substituents independently selected from —C$_{1-3}$ alkyl and F;

or A is

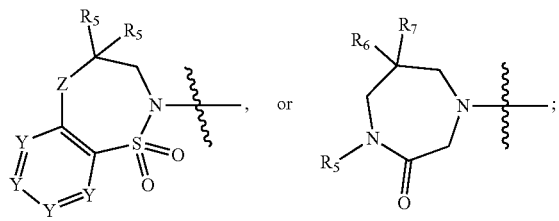

Y is independently selected from N or CH;
Z is O, CH$_2$, NR$_5$, S, S(O) or S(O)$_2$;
R$_5$ is independently selected from hydrogen or —C$_{1-4}$alkyl;
R$_6$ is hydrogen, —C$_{1-5}$alkyl or —(CH$_2$)$_m$—C$_{3-5}$cycloalkyl;
R$_7$ is hydrogen or —C$_{1-4}$alkyl;
or R$_6$ and R$_7$, together with the carbon to which they are attached form a C$_3$-C$_5$-membered cycloalkyl ring;
and, wherein when A is

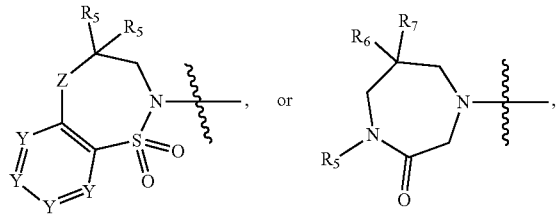

it is unsubstituted or substituted with one, two or three substituents independently selected from halo, —CF$_3$, —C$_{1-4}$alkyl, —CN, —OMe, —C(O)NH$_2$, —OCF$_3$ and —C$_{1-4}$alkylNR$_7$R$_8$;

R$_8$ is —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkyl-heteroaryl or —C$_{1-3}$alkyl-aryl, wherein each of —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkyl-heteroaryl or —C$_{1-3}$alkyl-aryl is unsubstituted or substituted by 1, 2 or 3 substituents independently selected from halo, —CN, —CF$_3$, —OCF$_3$, —OCH$_3$, —C$_{1-3}$alkyl, —OC$_{1-3}$alkyl, —OC$_{3-7}$cycloalkyl, —OC$_{3-7}$hetercycloalkyl, —O-aryl and —O-heteroaryl;

X is independently (CH)$_n$, S, O or N, and wherein the ring containing X is a 5-membered heteroaromatic ring;
m is 0, 1 or 2; and
n is 1 or 2; or a pharmaceutically acceptable salt thereof.

In a second aspect, this invention provides for the use of the compounds of Formula (I) as NRF2 activators.

Accordingly, the present invention is also directed to a method of regulating NRF2 which method comprises contacting a cell with a compound according to Formula (I), or a salt, particularly a pharmaceutically acceptable salt, thereof.

In another aspect, this invention provides for the use of the compounds of Formula (I) for treating and preventing conditions associated with NRF2 imbalance.

In one aspect, the invention is provides a pharmaceutical composition comprising a compound of the invention according to Formula (I), or a salt, particularly a pharmaceutically acceptable salt thereof, and a pharmaceutically acceptable excipient.

Particularly, this invention is directed to a pharmaceutical composition for the treatment of an NRF2 regulated disease or disorder, wherein the composition comprises a compound according to Formula (I), or a salt, particularly a pharmaceutically acceptable salt thereof, and a pharmaceutically acceptable excipient.

In a further aspect, this invention provides for a method of treating a respiratory or non-respiratory disorder, including COPD, asthma, ALI, ARDS, fibrosis, chronic asthma and acute asthma, lung disease secondary to environmental exposures, acute lung infection, chronic lung infection, α1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness, which comprises administering to a human in need thereof, a compound of Formula (I).

In one aspect, this invention relates to a method of treating COPD, which comprises administering to a human in need thereof, a compound of Formula (I), or a salt, particularly a pharmaceutically acceptable salt thereof.

In one aspect, this invention relates to a method of treating heart failure, which comprises administering to a human in need thereof, a compound of Formula (I), or a salt, particularly a pharmaceutically acceptable salt thereof.

In yet another aspect, this invention provides for the use of a compound of Formula (I), or a salt, particularly a pharmaceutically acceptable salt thereof, for the treatment of a respiratory or non-respiratory disorder, including COPD, asthma, ALI, ARDS, fibrosis, chronic asthma and acute asthma, lung disease secondary to environmental exposures, acute lung infection, chronic lung infection, α1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In one aspect, this invention relates to the use of a compound of Formula (I), or a salt, particularly a pharmaceutically acceptable salt thereof, for the treatment of COPD.

In one aspect, this invention relates to the use of a compound of Formula (I), or a salt, particularly a pharmaceutically acceptable salt thereof, for the treatment of heart failure.

In a further aspect, this invention relates to use of a compound of Formula (I), or a salt, particularly a pharmaceutically acceptable salt thereof, in the manufacture of a medicament for use in the treatment of a respiratory or non-respiratory disorder, including COPD, asthma, ALI, ARDS, fibrosis, chronic asthma and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In one aspect, this invention relates to use of a compound of Formula (I), or a salt, particularly a pharmaceutically acceptable salt thereof, in the manufacture of a medicament for the treatment of COPD.

In one aspect, this invention relates to use of a compound of Formula (I), or a salt, particularly a pharmaceutically acceptable salt thereof, in the manufacture of a medicament for the treatment of heart failure.

In a further aspect, this invention relates to a compound of Formula (I), or a salt, particularly a pharmaceutically acceptable salt thereof, for use in medical therapy. This invention relates to a compound of Formula (I), or a salt, particularly a pharmaceutically acceptable salt thereof, for use in therapy, specifically for use in the treatment of a respiratory or non-respiratory disorder, including COPD, asthma, ALI, ARDS, fibrosis, chronic asthma and acute asthma, lung disease secondary to environmental exposures, acute lung infection, chronic lung infection, α1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In one aspect, this invention relates to a compound of Formula (I), or a salt, particularly a pharmaceutically acceptable salt thereof, for use in the treatment of COPD.

In one aspect, this invention relates to a compound of Formula (I), or a salt, particularly a pharmaceutically acceptable salt thereof, for use in the treatment of heart failure.

Other aspects and advantages of the present invention are described further in the following detailed description of the preferred embodiments thereof.

DETAILED DESCRIPTION OF THE INVENTION

The present invention provides for compounds of Formula (I):

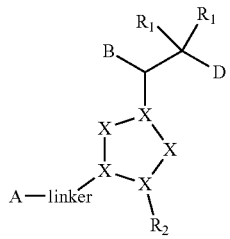

(I)

wherein:
B is benzotriazolyl, phenyl, triazolopyridinyl, —O—(CH$_2$)-triazolyl, or —(CH$_2$)$_2$-triazolyl wherein each of benzotriazolyl, phenyl, triazolopyridinyl, —O—(CH$_2$)-triazolyl, or —(CH$_2$)$_2$-triazolyl is unsubstituted or substituted by 1, 2, or 3 substituents independently selected from —C$_{1-3}$alkyl, —O—C$_{1-3}$alkyl, —CN, —(CH$_2$)$_2$—O—(CH$_2$)$_2$—OR$_3$ and halo;
D is —C(O)OH, —C(O)NR$_3$R$_4$, —C(O)NHSO$_2$CH$_3$, —SO$_2$NHC(O)CH$_3$, -5-(trifluoromethyl)-4H-1,2,4-triazol-2-yl, —NR$_3$—C(O)—R$_4$, —NR$_3$—C(O)—NR$_3$R$_4$; —NR$_3$—C(O)—O—R$_4$ or tetrazolyl;
R$_1$ is independently hydrogen, —C$_{1-3}$alkyl, F, —C$_{3-6}$spirocycloalkyl, oxetane, or the two R$_1$ groups together with the carbon to which they are attached form a cyclopropyl group;
R$_2$ is hydrogen, methyl, —CF$_3$, or halo;
R$_3$ is hydrogen or —C$_{1-3}$alkyl;
R$_4$ is hydrogen, —C$_{1-5}$alkyl, —C$_{3-7}$cycloalkyl, —C$_{4-8}$heterocycloalkyl, —C$_{1-5}$alkoxy, —C$_{1-3}$alkyl-O—C$_{1-3}$alkyl, —C$_{1-3}$alkyl-NH—C$_{1-3}$alkyl, —C$_{1-3}$alkyl-SO$_2$C$_{1-3}$alkyl, —C$_{1-3}$alkyl-C$_{4-8}$heterocycloalkyl, —C$_{1-3}$alkyl-C(O) NR$_4$R$_5$, aryl or heteroaryl, wherein each of —C$_{1-5}$ alkyl, —C$_{3-7}$ cycloalkyl, —C$_{4-7}$ heterocycloalkyl, —C$_{1-5}$alkoxy, —C$_{1-3}$alkyl-O—C$_{1-3}$alkyl, —C$_{1-3}$alkyl-NH—C$_{1-3}$alkyl, —C$_{1-3}$alkyl-C(O)NR$_4$R$_5$, aryl or heteroaryl is unsubstituted or substituted by one or two substituents selected from —OH, —CO$_2$H, —C(O)NR$_4$R$_5$, —C(O)OR$_3$, —N—C (O)—C$_{1-3}$alkyl, F, —CN, —CH—F$_2$, —CF$_3$, —(CH$_2$)$_n$— O—(CH$_2$)$_m$—CH$_3$, —C$_{3-7}$cycloalkyl and a 5-6-membered heteroaryl ring containing 1, 2 or 3 heteroatoms selected from O, N and S;
or R$_3$ and R$_4$ together with the nitrogen atom to which they are attached form a 5-8-membered heterocyclic ring, an 8-11-membered bicyclic heterocyclic ring or a 9-10-membered bridged bicyclic heterocyclic ring, wherein each 5-8-membered ring, 8-11-membered bicyclic ring, or 9-10-membered bridged bicyclic ring optionally includes one —C(O) or one —S(O)$_2$, and wherein each 5-8-membered ring, 8-11-membered bicyclic ring, or 9-10-membered bridged bicyclic ring optionally contains one, two or three oxygen ring atoms, one, two or three sulfur ring atoms or one, two or three nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$alkyl, —C$_{3-7}$cycloalkyl, —C$_{4-7}$heterocycloalkyl, —(CH$_2$)phenyl, halogen, —NR$_3$R$_5$, —CHF$_2$, —CF$_3$, and —(CH$_2$)$_n$—O—(CH$_2$)$_m$—CH$_3$;
Linker is —CH$_2$—, —CH$_2$—N(-cyclopropyl)-CH$_2$—, —CH$_2$—N(CH$_3$)—CH$_2$— or —N—(CH$_3$)—CH$_2$—;
A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;
wherein each of tetrahydrobenzoxazepinyl, tetrahydropyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl is unsubstituted or substituted by 1, 2, or 3 substituents independently selected from —C$_{1-3}$alkyl, —C$_{3-6}$spirocycloalkyl, halo, —CN, —O—C$_{1-3}$alkyl, —CH$_2$—O—CH$_3$, and —OH;
and wherein the piperidinyl is further unsubstituted or substituted by a substituent independently selected from pyrazolyl, —CH$_2$pyrazolyl, and oxadiazolyl, each of which is unsubstituted or substituted by —C$_{1-3}$alkyl, or, when A is piperidinyl, it is unsubstituted or substituted by —SO$_2$R, wherein R is —C$_{1-3}$alkyl, phenyl or —C$_{3-7}$cycloalkyl; and wherein the oxazepane is further unsubstituted or substituted by 1 or 2 substituents independently selected from —C$_{1-3}$alkyl and —C$_{3-7}$cycloalkyl;
and wherein the morpholinyl is further unsubstituted or substituted by phenyl which phenyl is unsubstituted or substituted by a substituent independently selected from —C$_{1-3}$ alkyl and —O—C$_{1-3}$ alkyl;
and wherein the pyrrolidinyl is further unsubstituted or substituted by a triazolyl group which is unsubstituted or substituted by —C$_{1-3}$alkyl;
and wherein the imidazolyl, triazolyl, pyrazolyl, and tetrazolyl groups each are further unsubstituted or substituted by 1, 2 or 3 substituents independently selected from —CH$_2$—C$_{4-7}$cycloalkyl, —CH$_2$—C$_{5-7}$heterocycloalkyl, —CH$_2$-azabicycloheptanyl, —CH$_2$-oxepane, and —CH$_2$-azabicyclohexanyl, and wherein each of —CH$_2$—C$_{4-7}$cycloalkyl, —CH$_2$—C$_{5-7}$heterocycloalkyl, —CH$_2$-azabicycloheptanyl, —CH$_2$-oxepane, or —CH$_2$-azabicyclohexanyl, including the —CH$_2$—, are further unsubstituted or substituted by 1 or 2 substituents independently selected from —C$_{1-3}$ alkyl and F;

or A is

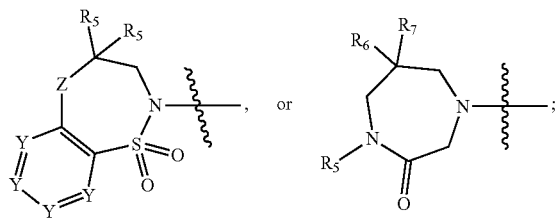

Y is independently selected from N or CH;
Z is O, $CH_2$, $NR_5$, S, S(O) or $S(O)_2$;
$R_5$ is independently selected from hydrogen or —$C_{1-4}$alkyl;
$R_6$ is hydrogen, —$C_{1-5}$alkyl or —$(CH_2)_m$—$C_{3-5}$cycloalkyl;
$R_7$ is hydrogen or —$C_{1-4}$alkyl;
or $R_6$ and $R_7$, together with the carbon to which they are attached form a $C_3$-$C_5$-membered cycloalkyl ring;
and, wherein when A is

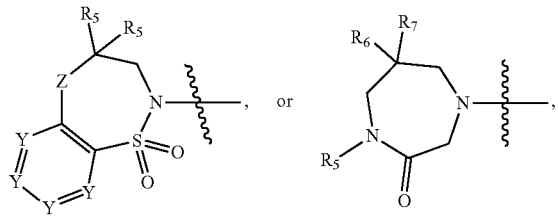

it is unsubstituted or substituted with one, two or three substituents independently selected from halo, —$CF_3$, —$C_{1-4}$alkyl, —CN, —OMe,
—C(O)$NH_2$, —$OCF_3$ and —$C_{1-4}$alkyl$NR_7R_8$;
$R_8$ is —$C_{1-3}$alkyl, aryl, heteroaryl, —C(O)$C_{1-3}$alkyl, —$SO_2C_{1-3}$alkyl, —C(O)aryl, —C(O)heteroaryl, —$SO_2$aryl, —$SO_2$heteroaryl, —$C_{3-7}$cycloalkyl, —$C_{1-3}$alkyl$C_{3-7}$cycloalkyl, —$C_{1-3}$alkyl$C_{3-7}$heterocycloalkyl,
—$C_{1-3}$alkyl-heteroaryl or —$C_{1-3}$alkyl-aryl, wherein each of —$C_{1-3}$alkyl, aryl, heteroaryl, —C(O)$C_{1-3}$alkyl, —$SO_2C_{1-3}$alkyl, —C(O)aryl, —C(O)heteroaryl, —$SO_2$aryl, —$SO_2$heteroaryl, —$C_{3-7}$cycloalkyl, —$C_{1-3}$alkyl$C_{3-7}$cycloalkyl, —$C_{1-3}$alkyl$C_{3-7}$heterocycloalkyl, —$C_{1-3}$alkyl-heteroaryl or —$C_{1-3}$alkyl-aryl is unsubstituted or substituted by 1, 2 or 3 substituents independently selected from halo, —CN, —$CF_3$, —$OCF_3$,
—$OCH_3$, —$C_{1-3}$alkyl, —$OC_{1-3}$alkyl, —$OC_{3-7}$cycloalkyl, —$OC_{3-7}$hetercycloalkyl, —O-aryl and —O-heteroaryl;
X is independently $(CH)_n$, S, O or N, and wherein the ring containing X is a 5-membered heteroaromatic ring;
m is 0, 1 or 2; and
n is 1 or 2; or a pharmaceutically acceptable salt thereof.

"Alkyl" refers to a monovalent saturated hydrocarbon chain having the specified number of carbon member atoms. For example, $C_{1-4}$ alkyl refers to an alkyl group having from 1 to 4 carbon member atoms. Alkyl groups may be straight or branched.

Representative branched alkyl groups have one, two, or three branches. Alkyl includes methyl, ethyl, propyl, (n-propyl and isopropyl), butyl (n-butyl, isobutyl, s-butyl, and t-butyl), pentyl (n-pentyl, tert-pentyl, iso-pentyl), and hexyl (n-hexyl, isohexyl, ter-hexyl).

When used herein, the terms "5-6-membered ring or an 8-10-membered bicyclic ring or a 9-10-membered bridged bicyclic ring" include both saturated and unsaturated ring structures containing the indicated number of carbon atoms. The terms "8-10-membered bicyclic ring or a 9-10-membered bridged bicyclic ring" can be aryl or heteroaryl, and also encompass bicyclic aryl groups containing an aryl ring moiety fused to a cycloalkyl ring moiety.

"Alkoxy" refers to an "alkyl-oxy-" group, containing an alkyl moiety attached through an oxygen linking atom. For example, the term "($C_1$-$C_4$)alkoxy" represents a saturated, straight or branched hydrocarbon moiety having at least 1 and up to 4 carbon atoms attached through an oxygen linking atom. Exemplary "($C_1$-$C_4$)alkoxy" groups include, but are not limited to, methoxy, ethoxy, n-propoxy, isopropoxy, n-butoxy, s-butoxy, and t-butoxy.

"Aryl" refers to a group or moiety comprising an aromatic, monocyclic or bicyclic hydrocarbon radical containing from 5- to 10-carbon ring atoms and having at least one aromatic ring. Examples of "aryl" groups are phenyl, naphthyl, indenyl, and dihydroindenyl (indanyl).

"Cycloalkyl" refers to a monovalent saturated or unsaturated hydrocarbon ring having the specified number of carbon member atoms. For example, $C_{3-6}$cycloalkyl refers to a cycloalkyl group having from 3 to 6 carbon member atoms. Unsaturated cycloalkyl groups have one or more carbon-carbon double bonds within the ring. Cycloalkyl groups are not aromatic. Cycloalkyl includes cyclopropyl, cyclopropenyl, cyclobutyl, cyclobutenyl, cyclopentyl, cyclopentenyl, cyclohexyl, and cyclohexenyl.

A heterocyclic group is a cyclic group having, as ring members, atoms of at least two different elements, which cyclic group may be saturated, partially unsaturated (non aromatic) or fully unsaturated (aromatic). The terms "heterocyclic" or "heterocyclyl" includes heterocycloalkyl and heteroaryl groups. It is to be understood that the terms heterocyclic, heterocyclyl, heteroaryl, and heterocycloalkyl, are intended to encompass stable groups where a ring nitrogen heteroatom is optionally oxidized (e.g., heteroaryl groups containing an N oxide, such as oxo-pyridyl (pyridyl N oxide) and oxo-oxadiazolyl (oxo-4,5-dihydro-1,3,4-oxadiazolyl) or where a ring sulfur heteroatom is optionally oxidized (e.g., heterocycloalkyl groups containing sulfones or sulfoxide moieties, such as tetrahydrothienyl 1 oxide (tetrahydrothienyl sulfoxide, tetrahydrothiophenyl sulfoxide) and tetrahydrothienyl 1,1 dioxide (tetrahydrothienyl sulfone)).

"$C_{4-8}$heterocycloalkyl" refers to a saturated, non-aromatic, monocyclic or bicyclic group containing 4-8 ring atoms, unless otherwise limited in size, containing up to 4 hetero atoms, including, nitrogen, oxygen, and sulfur. Examples are azetidine, thietane, thietane 1-oxide, thietane 1,1-dioxide, tetrahydrofuran, pyrrolidine, tetrahydrothiophene, tetrahydrothiophene 1-oxide, tetrahydrothiophene 1,2-dioxide, piperidine, morpholine, thiomorpholine, thiomorpholine 1-oxide, thiomorpholine 1,1-dioxide, tetrahydropyran, tetrahydrothiopyran, tetrahydrothiopyran 1-oxide, tetrahydrothiopyran 1-1 dioxide, piperidine-2-one, azepan-2-one, pyrrolidin-2-one, azepane, oxepane, oxazepane, thiepane, thiepane 1-oxide, thiepane 1,1-dioxide, and thiazepane.

When used herein, the terms 'halogen' and 'halo' include fluorine, chlorine, bromine and iodine, and fluoro, chloro, bromo, and iodo, respectively.

"Heteroaryl" represents a group or moiety comprising an aromatic monocyclic radical, containing 5- to 6-ring atoms unless otherwise limited in size, including 1 to 4 heteroatoms independently selected from nitrogen, oxygen and sulfur. This term also encompasses 9- to 10-membered bicyclic heterocyclic-aryl groups containing either an aryl ring moiety fused to a heterocycloalkyl ring moiety or a heteroaryl ring moiety fused to a cycloalkyl ring moiety.

Illustrative examples of heteroaryls include, but are not limited to, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl (pyridyl), oxopyridyl (pyridyl-N-oxide), pyridazinyl, pyrazinyl, pyrimidinyl, triazinyl, benzofuranyl, isobenzofuryl, 2,3-dihydrobenzofuryl, 1,3-benzodioxolyl, dihydrobenzodioxinyl, benzothienyl, indolizinyl, indolyl, isoindolyl, dihydroindolyl, benzimidazolyl, dihydrobenzimidazolyl, benzoxazolyl, dihydrobenzoxazolyl, benzothiazolyl, benzoisothiazolyl, dihydrobenzoisothiazolyl, indazolyl, imidazopyridinyl, pyrazolopyridinyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl.

Bicyclic heteroaryl groups include 6,5-fused heteroaryl (9-membered heteroaryl) and 6,6-fused heteroaryl (10-membered heteroaryl) groups. Examples of 6,5-fused heteroaryl (9-membered heteroaryl) groups include benzothienyl, benzofuranyl, indolyl, indolinyl, isoindolyl, isoindolinyl, indazolyl, indolizinyl, isobenzofuryl, 2,3-dihydrobenzofuryl, benzoxazolyl, benzthiazolyl, benzimidazolyl, benzoxadiazolyl, benzthiadiazolyl, benzotriazolyl, 1,3-benzoxathiol-2-on-yl (2-oxo-1,3-benzoxathiolyl), purinyl and imidazopyridinyl.

Examples of 6,6-fused heteroaryl (10-membered heteroaryl) groups include quinolyl, isoquinolyl, phthalazinyl, naphthridinyl (1,5-naphthyridinyl, 1,6-naphthyridinyl, 1,7-naphthyridinyl, 1,8-naphthyridinyl), quinazolinyl, quinoxalinyl, 4H-quinolizinyl, tetrahydroquinolinyl, cinnolinyl, and pteridinyl.

"Oxo" represents a double-bonded oxygen moiety; for example, if attached directly to a carbon atom forms a carbonyl moiety (C=O). "Hydroxy" or "hydroxyl" is intended to mean the radical —OH. As used herein, the term "cyano" refers to the group —CN.

"Substituted" in reference to a group indicates that one or more hydrogen atom attached to a member atom within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e., one that does not spontaneously undergo transformation such as by rearrangement, cyclization, or elimination and that is sufficiently robust to survive isolation from a reaction mixture). When it is stated that a group may contain one or more substituents, one or more (as appropriate) member atoms within the group may be substituted. In addition, a single member atom within the group may be substituted with more than one substituent as long as such substitution is in accordance with the permitted valence of the atom. Suitable substituents are defined herein for each substituted or optionally substituted group.

The term "independently" means that where more than one substituent is selected from a number of possible substituents, those substituents may be the same or different. That is, each substituent is separately selected from the entire group of recited possible substituents.

The invention also includes various isomers of the compounds of Formula (I) and mixtures thereof. "Isomer" refers to compounds that have the same composition and molecular weight but differ in physical and/or chemical properties.

The structural difference may be in constitution (geometric isomers) or in the ability to rotate the plane of polarized light (stereoisomers). The compounds according to Formula (I) contain one or more asymmetric centers, also referred to as chiral centers, and may, therefore, exist as individual enantiomers, diastereomers, or other stereoisomeric forms, or as mixtures thereof. All such isomeric forms are included within the present invention, including mixtures thereof.

Chiral centers may also be present in a substituent such as an alkyl group. Where the stereochemistry of a chiral center present in Formula (I), or in any chemical structure illustrated herein, is not specified the structure is intended to encompass any stereoisomer and all mixtures thereof. Thus, compounds according to Formula (I) containing one or more chiral centers may be used as racemic mixtures, enantiomerically enriched mixtures, or as enantiomerically pure individual stereoisomers.

Individual stereoisomers of a compound according to Formula (I) which contain one or more asymmetric centers may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

For compounds falling within the scope of the invention, the structural conventions used in the Examples are as follows: (a) absolute stereochemistry is defined by the structure; (b) when annotated by "or", then stereochemistry is unknown but resolved; and (c) when annotated by "&" or "and", then stereochemistry is relative, but racemic.

It is to be understood that the references herein to a compound of Formula (I) or a salt thereof includes a compound of Formula (I) as a free base [or acid, as appropriate], or as a salt thereof, for example as a pharmaceutically acceptable salt thereof. Thus, in one embodiment, the invention is directed to a compound of Formula (I). In another embodiment, the invention is directed to a salt of a compound of Formula (I). In a further embodiment, the invention is directed to a pharmaceutically acceptable salt of a compound of Formula (I). In another embodiment, the invention is directed to a compound of Formula (I) or a salt thereof. In a further embodiment, the invention is directed to a compound of Formula (I) or a pharmaceutically acceptable salt thereof.

Compounds of Formula (I) have both a basic amine group and a carboxylic acid group and can consequently be in the form of a zwitterion, also known as an inner salt. Therefore, in an embodiment the compound of Formula (I) is in a zwitterion form.

As used herein, "pharmaceutically acceptable" refers to those compounds (including salts), materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

Pharmaceutically acceptable salts include, amongst others, those described in Berge, J. Pharm. Sci., 1977, 66, 1-19, or those listed in P H Stahl and C G Wermuth, editors, *Handbook of Pharmaceutical Salts; Properties, Selection and Use, Second Edition* Stahl/Wermuth: Wiley-VCH/ VHCA, 2011 (see http://www.wiley.com/WileyCDA/Wiley-Title/productCd-3906390519.html).

The skilled artisan will appreciate that pharmaceutically acceptable salts of the compounds according to Formula (I) may be prepared. These pharmaceutically acceptable salts may be prepared in situ during the final isolation and purification of the compound, or by separately treating the purified compound in its free acid or free base form with a suitable base or acid, respectively.

It will be understood that if a compound of Formula (I) contains two or more basic moieties, the stoichiometry of salt formation may include 1, 2 or more equivalents of acid. Such salts would contain 1, 2 or more acid counterions, for example, a dihydrochloride salt.

Stoichiometric and non-stoichiometric forms of a pharmaceutically acceptable salt of a compound of Formula (I) are included within the scope of the invention, including sub-stoichiometric salts, for example where a counterion contains more than one acidic proton.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicyclate, pamoate (embonate), pantothenate, pectinate, persulfate, phenylacetate, phenylethylbarbitu rate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

Representative pharmaceutically acceptable base addition salts include, but are not limited to, aluminium, 2-amino-2-(hydroxymethyl)-1,3-propanediol (TRIS, tromethamine), arginine, benethamine (N-benzylphenethylamine), benzathine (N,N'-dibenzylethylenediamine), bis-(2-hydroxyethyl) amine, bismuth, calcium, chloroprocaine, choline, clemizole (1-p chlorobenzyl-2-pyrrolildine-1'-ylmethylbenzimidazole), cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, lysine, magnesium, meglumine (N-methylglucamine), piperazine, piperidine, potassium, procaine, quinine, quinoline, sodium, strontium, t-butylamine, and zinc.

As used herein, the term "a compound of Formula (I)" or "the compound of Formula (I)" refers to one or more compounds according to Formula (I). The compound of Formula (I) may exist in solid or liquid form. In the solid state, it may exist in crystalline or noncrystalline form, or as a mixture thereof. The skilled artisan will appreciate that pharmaceutically acceptable solvates may be formed from crystalline compounds wherein solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e., the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of Formula (I) and following of this invention can generally be prepared by carrying out the procedures disclosed in the Schemes and/or in the Examples below, by substituting a readily available isotopically labeled reagent for a non-isotopically labeled reagent.

Representative Embodiments

The present invention provides for compounds of Formula (I):

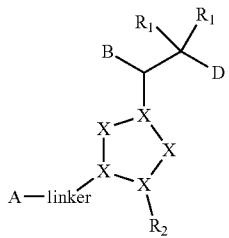

wherein:
B is benzotriazolyl, phenyl, triazolopyridinyl, —O—(CH$_2$)-triazolyl, or —(CH$_2$)$_2$-triazolyl wherein each of benzotriazolyl, phenyl, triazolopyridinyl, —O—(CH$_2$)-triazolyl, or —(CH$_2$)$_2$-triazolyl is unsubstituted or substituted by 1, 2, or 3 substituents independently selected from —C$_{1-3}$alkyl, —O—C$_{1-3}$alkyl, —CN, —(CH$_2$)$_2$—O—(CH$_2$)$_2$—OR$_3$ and halo;
D is —C(O)OH, —C(O)NR$_3$R$_4$, —C(O)NHSO$_2$CH$_3$, —SO$_2$NHC(O)CH$_3$, -5-(trifluoromethyl)-4H-1,2,4-triazol-2-yl, —NR$_3$—C(O)—R$_4$, —NR$_3$—C(O)—NR$_3$R$_4$; —NR$_3$—C(O)—O—R$_4$ or tetrazolyl;
R$_1$ is independently hydrogen, —C$_{1-3}$alkyl, F, —C$_{3-6}$spirocycloalkyl, oxetane, or the two R$_1$ groups together with the carbon to which they are attached form a cyclopropyl group;
R$_2$ is hydrogen, methyl, —CF$_3$, or halo;
R$_3$ is hydrogen or —C$_{1-3}$alkyl;
R$_4$ is hydrogen, —C$_{1-5}$alkyl, —C$_{3-7}$cycloalkyl, —C$_{4-8}$heterocycloalkyl, —C$_{1-5}$alkoxy, —C$_{1-3}$alkyl-O—C$_{1-3}$alkyl, —C$_{1-3}$alkyl-NH—C$_{1-3}$alkyl, —C$_{1-3}$alkyl-SO$_2$C$_{1-3}$alkyl, —C$_{1-3}$alkyl-C$_{4-8}$heterocycloalkyl, —C$_{1-3}$alkyl-C(O)NR$_4$R$_5$, aryl or heteroaryl, wherein each of —C$_1$ alkyl, —C$_{3-7}$ cycloalkyl, —C$_{4-7}$ heterocycloalkyl, —C$_{1-5}$alkoxy, —C$_{1-3}$alkyl-O—C$_{1-3}$alkyl, —C$_{1-3}$alkyl-NH—C$_{1-3}$alkyl, —C$_{1-3}$alkyl-C(O)NR$_4$R$_5$, aryl or heteroaryl is unsubstituted or substituted by one or two substituents selected from —OH, —CO$_2$H, —C(O)NR$_4$R$_5$, —C(O)OR$_3$, —N—C(O)—C$_{1-3}$alkyl, F, —CN, —CH—F$_2$, —CF$_3$, —(CH$_2$)$_n$—O—(CH$_2$)$_m$—CH$_3$, —C$_{3-7}$cycloalkyl and a 5-6-membered heteroaryl ring containing 1, 2 or 3 heteroatoms selected from O, N and S;
or R$_3$ and R$_4$ together with the nitrogen atom to which they are attached form a 5-8-membered heterocyclic ring, an 8-11-membered bicyclic heterocyclic ring or a 9-10-membered bridged bicyclic heterocyclic ring, wherein each 5-8-membered ring, 8-11-membered bicyclic ring, or 9-10-membered bridged bicyclic ring optionally includes one —C(O) or one —S(O)$_2$, and wherein each 5-8-membered ring, 8-11-membered bicyclic ring, or 9-10-membered bridged bicyclic ring optionally contains one, two or three oxygen ring atoms, one, two or three sulfur ring atoms or one, two or three nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$alkyl, —C$_{3-7}$cycloalkyl, —C$_{4-7}$heterocycloalkyl, —(CH$_2$)phenyl, halogen, —NR$_3$R$_5$, —CHF$_2$, —CF$_3$, and —(CH$_2$)$_n$—O—(CH$_2$)$_m$—CH$_3$;
Linker is —CH$_2$—, —CH$_2$—N(-cyclopropyl)-CH$_2$—, —CH$_2$—N(CH$_3$)—CH$_2$— or —N—(CH$_3$)—CH$_2$—;
A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;
wherein each of tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl is unsubstituted or substituted by 1, 2, or 3 substituents independently selected from —C$_{1-3}$alkyl, —C$_{3-6}$spirocycloalkyl, halo, —CN, —O—C$_{1-3}$alkyl, —CH$_2$—O—CH$_3$, and —OH;
and wherein the piperidinyl is further unsubstituted or substituted by a substituent independently selected from pyrazolyl, —CH$_2$pyrazolyl, and oxadiazolyl, each of which is unsubstituted or substituted by —C$_{1-3}$alkyl, or, when A is piperidinyl, it is unsubstituted or substituted by —SO$_2$R, wherein R is —C$_{1-3}$alkyl, phenyl or —C$_{3-7}$cycloalkyl;
and wherein the oxazepane is further unsubstituted or substituted by 1 or 2 substituents independently selected from —C$_{1-3}$alkyl and —C$_{3-7}$cycloalkyl;
and wherein the morpholinyl is further unsubstituted or substituted by phenyl which phenyl is unsubstituted or substituted by a substituent independently selected from —C$_{1-3}$ alkyl and —O—C$_{1-3}$ alkyl;
and wherein the pyrrolidinyl is further unsubstituted or substituted by a triazolyl group which is unsubstituted or substituted by —C$_{1-3}$alkyl;
and wherein the imidazolyl, triazolyl, pyrazolyl, and tetrazolyl groups each are further unsubstituted or substituted by 1, 2 or 3 substituents independently selected from —CH$_2$—C$_{4-7}$cycloalkyl, —CH$_2$—C$_{5-7}$heterocycloalkyl, —CH$_2$-azabicycloheptanyl, —CH$_2$-oxepane, and —CH$_2$-azabicyclohexanyl, and wherein each of —CH$_2$—C$_{4-7}$cycloalkyl, —CH$_2$—C$_{5-7}$heterocycloalkyl, —CH$_2$-azabicycloheptanyl, —CH$_2$-oxepane, or —CH$_2$-azabicyclohexanyl, including the —CH$_2$—, are further unsubstituted or substituted by 1 or 2 substituents independently selected from —C$_{1-3}$ alkyl and F;
or A is

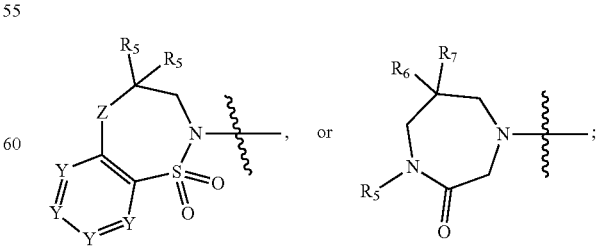

Y is independently selected from N or CH;
Z is O, CH$_2$, NR$_5$, S, S(O) or S(O)$_2$;

R$_5$ is independently selected from hydrogen or —C$_{1-4}$alkyl;
R$_6$ is hydrogen, —C$_{1-5}$alkyl or —(CH$_2$)$_m$—C$_{3-5}$cycloalkyl;
R$_7$ is hydrogen or —C$_{1-4}$alkyl;
or R$_6$ and R$_7$, together with the carbon to which they are attached form a C$_3$-C$_5$-membered cycloalkyl ring;
and, wherein when A is

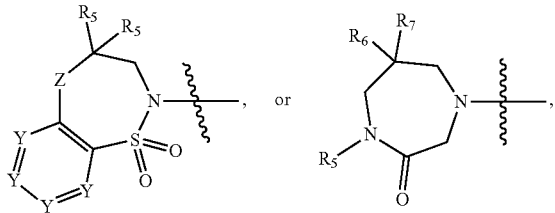

it is unsubstituted or substituted with one, two or three substituents independently selected from halo, —CF$_3$, —C$_{1-4}$alkyl, —CN, —OMe, —C(O)NH$_2$, —OCF$_3$ and —C$_{1-4}$alkylNR$_7$R$_8$;
R$_8$ is —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkyl-heteroaryl or —C$_{1-3}$alkyl-aryl, wherein each of —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkyl-heteroaryl or —C$_{1-3}$alkyl-aryl is unsubstituted or substituted by 1, 2 or 3 substituents independently selected from halo, —CN, —CF$_3$, —OCF$_3$, —OCH$_3$, —C$_{1-3}$alkyl, —OC$_{1-3}$alkyl, —OC$_{3-7}$cycloalkyl, —OC$_{3-7}$hetercycloalkyl, —O-aryl and —O-heteroaryl;
X is independently (CH)$_n$, S, O or N, and wherein the ring containing X is a 5-membered heteroaromatic ring;
m is 0, 1 or 2; and
n is 1 or 2; or a pharmaceutically acceptable salt thereof.

In a second embodiment, the compound of Formula (I) is substituted as follows:
B is benzotriazolyl, phenyl, triazolopyridinyl, —O—(CH$_2$)-triazolyl, or —(CH$_2$)$_2$-triazolyl wherein each of benzotriazolyl, phenyl, triazolopyridinyl, —O—(CH$_2$)-triazolyl, or —(CH$_2$)$_2$-triazolyl is unsubstituted or substituted by 1, 2, or 3 substituents independently selected from —C$_{1-3}$alkyl, —O—C$_{1-3}$alkyl, —CN, —(CH$_2$)$_2$—O—(CH$_2$)$_2$—OR$_3$ and halo;
D is —C(O)OH, —C(O)NR$_3$R$_4$, —C(O)NHSO$_2$CH$_3$, —SO$_2$NHC(O)CH$_3$, 5-(trifluoromethyl)-4H-1,2,4-triazol-2-yl or tetrazolyl;
R$_1$ is independently hydrogen, —C$_{1-3}$alkyl, F, —C$_{3-6}$spirocycloalkyl, oxetane, or the two R$_1$ groups together with the carbon to which they are attached form a cyclopropyl group;
R$_2$ is hydrogen, methyl, —CF$_3$, or halo;
R$_3$ is hydrogen or —C$_{1-3}$alkyl;
R$_4$ is hydrogen, —C$_{1-5}$alkyl, —C$_{3-7}$cycloalkyl, —C$_{4-8}$heterocycloalkyl, —C$_{1-5}$alkoxy, —C$_{1-3}$alkyl-O—C$_{1-3}$alkyl, —C$_{1-3}$alkyl-NH—C$_{1-3}$alkyl, —C$_{1-3}$alkyl-SO$_2$C$_{1-3}$alkyl, —C$_{1-3}$alkyl-C$_{4-8}$heterocycloalkyl, —C$_{1-3}$alkyl-C(O)NR$_4$R$_5$, aryl or heteroaryl, wherein each of —C$_1$ alkyl, —C$_{3-7}$ cycloalkyl, —C$_{4-7}$ heterocycloalkyl, —C$_{1-5}$alkoxy, —C$_{1-3}$alkyl-O—C$_{1-3}$alkyl, —C$_{1-3}$alkyl-NH—C$_{1-3}$alkyl, —C$_{1-3}$alkyl-C(O)NR$_4$R$_5$, aryl or heteroaryl is unsubstituted or substituted by one or two substituents selected from —OH, —CO$_2$H, —C(O)NR$_4$R$_5$,—C(O)OR$_3$, —N═C (O)—C$_{1-3}$alkyl, F, —CN, —CH═F$_2$, —CF$_3$, —(CH$_2$)$_n$—O—(CH$_2$)$_m$—CH$_3$, —C$_{3-7}$cycloalkyl and a 5-6-membered heteroaryl ring containing 1, 2 or 3 heteroatoms selected from O, N and S;
or R$_3$ and R$_4$ together with the nitrogen atom to which they are attached form a 5-8-membered heterocyclic ring, an 8-11-membered bicyclic heterocyclic ring or a 9-10-membered bridged bicyclic heterocyclic ring, wherein each 5-8-membered ring, 8-11-membered bicyclic ring, or 9-10-membered bridged bicyclic ring optionally includes one —C(O) or one —S(O)$_2$, and wherein each 5-8-membered ring, 8-11-membered bicyclic ring, or 9-10-membered bridged bicyclic ring optionally contains one, two or three oxygen ring atoms, one, two or three sulfur ring atoms or one, two or three nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$alkyl, —C$_{3-7}$cycloalkyl, —C$_{4-7}$heterocycloalkyl, —(CH$_2$)phenyl, halogen, —NR$_3$R$_5$, —CHF$_2$, —CF$_3$, and —(CH$_2$)$_n$—O—(CH$_2$)$_m$—CH$_3$;
Linker is —CH$_2$—, —CH$_2$—N(-cyclopropyl)-CH$_2$—, —CH$_2$—N(CH$_3$)—CH$_2$— or —N—(CH$_3$)—CH$_2$—;
A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;
wherein each of tetrahydrobenzoxazepinyl, tetrahydropyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl is unsubstituted or substituted by 1, 2, or 3 substituents independently selected from —C$_{1-3}$alkyl, —C$_{3-6}$spirocycloalkyl, halo, —CN, —O—C$_{1-3}$alkyl, —CH$_2$—O—CH$_3$, and —OH;
and wherein the piperidinyl is further unsubstituted or substituted by a substituent independently selected from pyrazolyl, —CH$_2$pyrazolyl, and oxadiazolyl, each of which is unsubstituted or substituted by —C$_{1-3}$alkyl, or, when A is piperidinyl, it is unsubstituted or substituted by —SO$_2$R, wherein R is —C$_{1-3}$alkyl, phenyl or —C$_{3-7}$cycloalkyl;
and wherein the oxazepane is further unsubstituted or substituted by 1 or 2 substituents independently selected from —C$_{1-3}$alkyl and —C$_{3-7}$cycloalkyl;
and wherein the morpholinyl is further unsubstituted or substituted by phenyl which phenyl is unsubstituted or substituted by a substituent independently selected from —C$_{1-3}$ alkyl and —O—C$_{1-3}$ alkyl;
and wherein the pyrrolidinyl is further unsubstituted or substituted by a triazolyl group which is unsubstituted or substituted by —C$_{1-3}$alkyl;
and wherein the imidazolyl, triazolyl, pyrazolyl, and tetrazolyl groups each are further unsubstituted or substituted by 1, 2 or 3 substituents independently selected from —CH$_2$—C$_{4-7}$cycloalkyl, —CH$_2$—C$_{5-7}$heterocycloalkyl, —CH$_2$-azabicycloheptanyl, —CH$_2$-oxepane, and —CH$_2$-azabicyclohexanyl, and wherein each of —CH$_2$—C$_{4-7}$cycloalkyl, —CH$_2$—C$_{5-7}$heterocycloalkyl, —CH$_2$-azabicycloheptanyl, —CH$_2$-oxepane, or —CH$_2$-azabicyclohexanyl, including the —CH$_2$—, are further unsubstituted or substituted by 1 or 2 substituents independently selected from —C$_{1-3}$ alkyl and F;

$R_5$ is independently selected from hydrogen or —$C_{1-4}$alkyl;
X is independently $(CH)_n$ or S, and wherein the ring containing X is a 5-membered heteroaromatic ring;
m is 0, 1 or 2; and
n is 1;
or a pharmaceutically acceptable salt thereof.

In another embodiment, the compound of Formula (I) is substituted as follows:
B is benzotriazolyl, phenyl, triazolopyridinyl, —O—$(CH_2)$-triazolyl, or —$(CH_2)_2$-triazolyl wherein each of benzotriazolyl, phenyl, triazolopyridinyl, —O—$(CH_2)$-triazolyl, or —$(CH_2)_2$-triazolyl is unsubstituted or substituted by 1, 2, or 3 substituents independently selected from —$C_{1-3}$alkyl, —O—$C_{1-3}$alkyl,
—CN, —$(CH_2)_2$—O—$(CH_2)_2$—$OR_3$ and halo;
D is —C(O)OH, —C(O)$NR_3R_4$, —C(O)$NHSO_2CH_3$, —$SO_2NHC(O)CH_3$, 5-(trifluoromethyl)-4H-1,2,4-triazol-2-yl, or tetrazolyl;
$R_1$ is independently hydrogen, —$C_{1-3}$alkyl, F, —$C_{3-6}$spirocycloalkyl, oxetane, or the two $R_1$ groups together with the carbon to which they are attached form a cyclopropyl group;
$R_2$ is hydrogen, methyl, —$CF_3$, or halo;
$R_3$ is hydrogen or —$C_{1-3}$alkyl;
$R_4$ is hydrogen, —$C_{1-5}$alkyl, —$C_{3-7}$cycloalkyl, —$C_{4-8}$heterocycloalkyl, —$C_{1-5}$alkoxy, —$C_{1-3}$alkyl-O—$C_{1-3}$alkyl, —$C_{1-3}$alkyl-NH—$C_{1-3}$alkyl, —$C_{1-3}$alkyl-$SO_2C_{1-3}$alkyl, —$C_{1-3}$alkyl-$C_{4-8}$heterocycloalkyl, —$C_{1-3}$alkyl-C(O)$NR_4R_5$, aryl or heteroaryl, wherein each of —$C_1$ alkyl, —$C_{3-7}$ cycloalkyl, —$C_{4-7}$ heterocycloalkyl, —$C_{1-5}$alkoxy, —$C_{1-3}$alkyl-O—$C_{1-3}$alkyl, —$C_{1-3}$alkyl-NH—$C_{1-3}$alkyl, —$C_{1-3}$alkyl-C(O)$NR_4R_5$, aryl or heteroaryl is unsubstituted or substituted by one or two substituents selected from —OH, —$CO_2H$, —C(O)$NR_4R_5$,—C(O)$OR_3$, —N—C(O)—$C_{1-3}$alkyl, F, —CN, —CH—$F_2$, —$CF_3$, —$(CH_2)_n$—O—$(CH_2)_m$—$CH_3$, —$C_{3-7}$cycloalkyl and a 5-6-membered heteroaryl ring containing 1, 2 or 3 heteroatoms selected from O, N and S;
or $R_3$ and $R_4$ together with the nitrogen atom to which they are attached form a 5-8-membered heterocyclic ring, an 8-11-membered bicyclic heterocyclic ring or a 9-10-membered bridged bicyclic heterocyclic ring, wherein each 5-8-membered ring, 8-11-membered bicyclic ring, or 9-10-membered bridged bicyclic ring optionally includes one —C(O) or one —$S(O)_2$, and wherein each 5-8-membered ring, 8-11-membered bicyclic ring, or 9-10-membered bridged bicyclic ring optionally contains one, two or three oxygen ring atoms, one, two or three sulfur ring atoms or one, two or three nitrogen ring atoms, and wherein each 5-8-membered ring, 8-11-membered bicyclic ring, or 9-10-membered bridged bicyclic ring is unsubstituted or substituted by one, two or three substituents independently selected from —$C_{1-5}$alkyl, —$C_{3-7}$cycloalkyl, —$C_{4-7}$heterocycloalkyl, —$(CH_2)$phenyl, halogen, —$NR_3R_5$, —$CHF_2$, —$CF_3$, and —$(CH_2)_n$—O—$(CH_2)_m$—$CH_3$;
Linker is —$CH_2$—, —$CH_2$—N(-cyclopropyl)-$CH_2$—, —$CH_2$—N($CH_3$)—$CH_2$— or —N—($CH_3$)—$CH_2$—;
A is

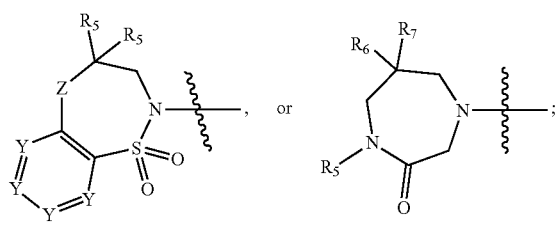

Y is independently selected from N or CH;
Z is O, $CH_2$, $NR_5$, S, S(O) or $S(O)_2$;
$R_5$ is independently selected from hydrogen or —$C_{1-4}$alkyl;
$R_6$ is hydrogen, —$C_{1-5}$alkyl or —$(CH_2)_m$—$C_{3-5}$cycloalkyl;
$R_7$ is hydrogen or —$C_{1-4}$alkyl;
or $R_6$ and $R_7$, together with the carbon to which they are attached form a $C_3$-$C_5$-membered cycloalkyl ring;
and, wherein when A is

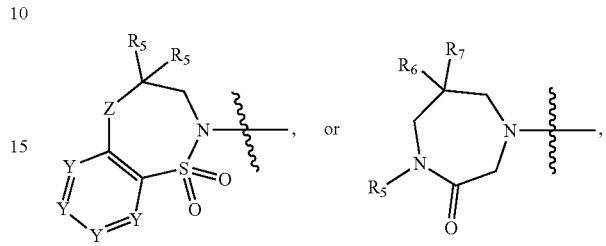

it is unsubstituted or substituted with one, two or three substituents independently selected from halo, —$CF_3$, —$C_{1-4}$alkyl, —CN, —OMe,
—C(O)$NH_2$, —$OCF_3$ and —$C_{1-4}$alkyl$NR_7R_8$;
$R_8$ is —$C_{1-3}$alkyl, aryl, heteroaryl, —C(O)$C_{1-3}$alkyl, —$SO_2C_{1-3}$alkyl, —C(O)aryl, —C(O)heteroaryl, —$SO_2$aryl, —$SO_2$heteroaryl, —$C_{3-7}$cycloalkyl, —$C_{1-3}$alkyl$C_{3-7}$cycloalkyl, —$C_{1-3}$alkyl$C_{3-7}$heterocycloalkyl,
—$C_{1-3}$alkyl-heteroaryl or —$C_{1-3}$alkyl-aryl, wherein each of —$C_{1-3}$alkyl, aryl, heteroaryl, —C(O)$C_{1-3}$alkyl, —$SO_2C_{1-3}$alkyl, —C(O)aryl, —C(O)heteroaryl, —$SO_2$aryl, —$SO_2$heteroaryl, —$C_{3-7}$cycloalkyl, —$C_{1-3}$alkyl$C_{3-7}$cycloalkyl, —$C_{1-3}$alkyl$C_{3-7}$heterocycloalkyl, —$C_{1-3}$alkyl-heteroaryl or —$C_{1-3}$alkyl-aryl is unsubstituted or substituted by 1, 2 or 3 substituents independently selected from halo, —CN, —$CF_3$, —$OCF_3$,
—$OCH_3$, —$C_{1-3}$alkyl, —$OC_{1-3}$alkyl, —$OC_{3-7}$cycloalkyl, —$OC_{3-7}$hetercycloalkyl, —O-aryl and —O-heteroaryl;
X is independently $(CH)_n$ or S, and wherein the ring containing X is a 5-membered heteroaromatic ring;
m is 0, 1 or 2; and
n is 1;
or a pharmaceutically acceptable salt thereof.

In yet another embodiment, the compound of Formula (I) is substituted as follows:
B is benzotriazolyl, phenyl, triazolopyridinyl, —O—$(CH_2)$-triazolyl, or —$(CH_2)_2$-triazolyl wherein each of benzotriazolyl, phenyl, triazolopyridinyl, —O—$(CH_2)$-triazolyl, or —$(CH_2)_2$-triazolyl is unsubstituted or substituted by 1, 2, or 3 substituents independently selected from —$C_{1-3}$alkyl, —O—$C_{1-3}$alkyl,
—CN, —$(CH_2)_2$—O—$(CH_2)_2$—$OR_3$ and halo;
D is —C(O)OH, —C(O)$NR_3R_4$, —C(O)$NHSO_2CH_3$, —$SO_2NHC(O)CH_3$, 5-(trifluoromethyl)-4H-1,2,4-triazol-2-yl, —$NR_3$—C(O)—$R_4$, —$NR_3$—C(O)—$NR_3R_4$; —$NR_3$—C(O)—O—$R_4$ or tetrazolyl;
$R_1$ is independently hydrogen, —$C_{1-3}$alkyl, F, —$C_{3-6}$spirocycloalkyl, oxetane, or the two $R_1$ groups together with the carbon to which they are attached form a cyclopropyl group;
$R_2$ is hydrogen, methyl, —$CF_3$, or halo;
$R_3$ is hydrogen or —$C_{1-3}$alkyl;
$R_4$ is hydrogen, —$C_{1-5}$alkyl, —$C_{3-7}$cycloalkyl, —$C_{4-8}$heterocycloalkyl, —$C_{1-5}$alkoxy, —$C_{1-3}$alkyl-O—$C_{1-3}$alkyl, —$C_{1-3}$alkyl-NH—$C_{1-3}$alkyl, —$C_{1-3}$alkyl-$SO_2C_{1-3}$alkyl, —$C_{1-3}$alkyl-$C_{4-8}$heterocycloalkyl, —$C_{1-3}$alkyl-C(O)$NR_4R_5$, aryl or heteroaryl, wherein each of —$C_1$ alkyl, —$C_{3-7}$ cycloalkyl, —$C_{4-7}$ heterocycloalkyl, —$C_{1-5}$alkoxy, —C$_{1-3}$alkyl-O—C$_{1-3}$alkyl, —C$_{1-3}$alkyl-NH—C$_{1-3}$alkyl, —C$_{1-3}$alkyl-C(O)NR$_4$R$_5$, aryl or heteroaryl is unsubstituted or substituted by one or two substituents selected from —OH, —CO$_2$H, —C(O)NR$_4$R$_5$, —C(O)OR$_3$, —N—C(O)—C$_{1-3}$alkyl, F, —CN, —CH—F$_2$, —CF$_3$, —(CH$_2$)$_n$—O—(CH$_2$)$_m$—CH$_3$, —C$_{3-7}$cycloalkyl and a 5-6-membered heteroaryl ring containing 1, 2 or 3 heteroatoms selected from O, N and S;

or R$_3$ and R$_4$ together with the nitrogen atom to which they are attached form a 5-8-membered heterocyclic ring, an 8-11-membered bicyclic heterocyclic ring or a 9-10-membered bridged bicyclic heterocyclic ring, wherein each 5-8-membered ring, 8-11-membered bicyclic ring, or 9-10-membered bridged bicyclic ring optionally includes one —C(O) or one —S(O)$_2$, and wherein each 5-8-membered ring, 8-11-membered bicyclic ring, or 9-10-membered bridged bicyclic ring optionally contains one, two or three oxygen ring atoms, one, two or three sulfur ring atoms or one, two or three nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$alkyl, —C$_{3-7}$cycloalkyl, —C$_{4-7}$heterocycloalkyl, —(CH$_2$)phenyl, halogen, —NR$_3$R$_5$, —CHF$_2$, —CF$_3$, and —(CH$_2$)$_n$—O—(CH$_2$)$_m$—CH$_3$;

Linker is —CH$_2$—, —CH$_2$—N(-cyclopropyl)-CH$_2$—, —CH$_2$—N(CH$_3$)—CH$_2$— or —N—(CH$_3$)—CH$_2$—;

A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;

wherein each of tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl is unsubstituted or substituted by 1, 2, or 3 substituents independently selected from —C$_{1-3}$alkyl, —C$_{3-6}$spirocycloalkyl, halo, —CN, —O—C$_{1-3}$alkyl, —CH$_2$—O—CH$_3$, and —OH;

and wherein the piperidinyl is further unsubstituted or substituted by a substituent independently selected from pyrazolyl, —CH$_2$pyrazolyl, and oxadiazolyl each of which is unsubstituted or substituted by —C$_{1-3}$alkyl, or, when A is piperidinyl, it is unsubstituted or substituted by —SO$_2$R, wherein R is —C$_{1-3}$alkyl, phenyl or —C$_{3-7}$cycloalkyl;

and wherein the oxazepane is further unsubstituted or substituted by 1 or 2 substituents independently selected from —C$_{1-3}$alkyl and —C$_{3-7}$cycloalkyl;

and wherein the morpholinyl is further unsubstituted or substituted by phenyl which phenyl is unsubstituted or independently substituted by a substituent selected from —C$_{1-3}$ alkyl and —O—C$_{1-3}$ alkyl;

and wherein the pyrrolidinyl is further unsubstituted or substituted by a triazolyl group which is unsubstituted or substituted by —C$_{1-3}$alkyl;

and wherein the imidazolyl, triazolyl, pyrazolyl, and tetrazolyl groups each are further unsubstituted or substituted by 1, 2 or 3 substituents independently selected from —CH$_2$—C$_{4-7}$cycloalkyl, —CH$_2$—C$_{5-7}$heterocycloalkyl, —CH$_2$-azabicycloheptanyl, —CH$_2$-oxepane, and —CH$_2$-azabicyclohexanyl, and wherein each of —CH$_2$—C$_{4-7}$cycloalkyl, —CH$_2$—C$_{5-7}$heterocycloalkyl, —CH$_2$-azabicycloheptanyl, —CH$_2$-oxepane, or —CH$_2$-azabicyclohexanyl, including the —CH$_2$—, are further unsubstituted or substituted by 1 or 2 substituents independently selected from —C$_{1-3}$ alkyl and F;

or A is

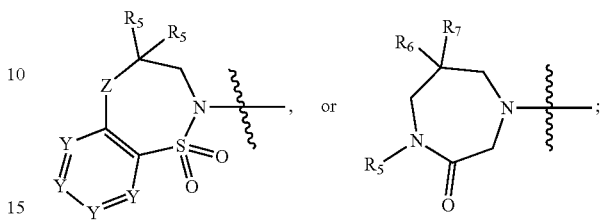

Y is independently selected from N or CH;
Z is O, CH$_2$, NR$_5$, S, S(O) or S(O)$_2$;
R$_5$ is independently selected from hydrogen or —C$_{1-4}$alkyl;
R$_6$ is hydrogen, —C$_{1-5}$alkyl or —(CH$_2$)$_m$—C$_{3-5}$cycloalkyl;
R$_7$ is hydrogen or —C$_{1-4}$alkyl;
or R$_6$ and R$_7$, together with the carbon to which they are attached form a C$_3$-C$_5$-membered cycloalkyl ring;
and, wherein when A is

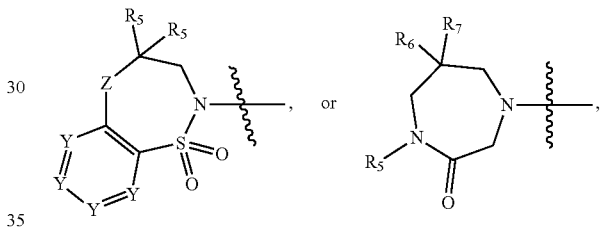

it is unsubstituted or substituted with one, two or three substituents independently selected from halo, —CF$_3$, —C$_{1-4}$alkyl, —CN, —OMe, —C(O)NH$_2$, —OCF$_3$ and —C$_{1-4}$alkylNR$_7$R$_8$;

R$_8$ is —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkyl-heteroaryl or —C$_{1-3}$alkyl-aryl, wherein each of —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkyl-heteroaryl or —C$_{1-3}$alkyl-aryl is unsubstituted or substituted by 1, 2 or 3 substituents independently selected from halo, —CN, —CF$_3$, —OCF$_3$, —OCH$_3$, —C$_{1-3}$alkyl, —OC$_{1-3}$alkyl, —OC$_{3-7}$cycloalkyl, —OC$_{3-7}$hetercycloalkyl, —O-aryl and —O-heteroaryl;

X is independently (CH)$_n$, S, O or N, and wherein the ring containing X is a 5-membered heteroaromatic ring;
m is 0, 1 or 2; and
n is 1;
or a pharmaceutically acceptable salt thereof.

In still another embodiment, the compound of Formula (I) is substituted as follows:
B is benzotriazolyl, phenyl, triazolopyridinyl, —O—(CH$_2$)-triazolyl, or —(CH$_2$)$_2$-triazolyl wherein each of benzotriazolyl, phenyl, triazolopyridinyl, —O—(CH$_2$)-triazolyl, or —(CH$_2$)$_2$-triazolyl is unsubstituted or substituted by 1, 2, or 3 substituents independently selected from —C$_{1-3}$alkyl, —O—C$_{1-3}$alkyl, —CN, —(CH$_2$)$_2$—O—(CH$_2$)$_2$—OR$_3$ and halo;

D is —C(O)OH, —C(O)NHSO$_2$CH$_3$, —SO$_2$NHC(O)CH$_3$, 5-(trifluoromethyl)-4H-1,2,4-triazol-2-yl, or tetrazolyl;

R$_1$ is independently hydrogen, —C$_{1-3}$alkyl, F, —C$_{3-6}$spirocycloalkyl, oxetane, or the two R$_1$ groups together with the carbon to which they are attached form a cyclopropyl group;

R$_2$ is hydrogen, methyl, —CF$_3$, or halo;

R$_3$ is hydrogen or —C$_{1-3}$alkyl;

Linker is —CH$_2$—, —CH$_2$—N(-cyclopropyl)-CH$_2$—, —CH$_2$—N(CH$_3$)—CH$_2$— or —N—(CH$_3$)—CH$_2$—;

A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;

wherein each of tetrahydrobenzoxazepinyl, tetrahydropyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl is unsubstituted or substituted by 1, 2, or 3 substituents independently selected from —C$_{1-3}$alkyl, —C$_{3-6}$spirocycloalkyl, halo, —CN, —O—C$_{1-3}$alkyl, —CH$_2$—O—CH$_3$, and —OH;

and wherein the piperidinyl is further unsubstituted or substituted by a substituent independently selected from pyrazolyl, —CH$_2$pyrazolyl, and oxadiazolyl, each of which is unsubstituted or substituted by —C$_{1-3}$alkyl, or, when A is piperidinyl, it is unsubstituted or substituted by —SO$_2$R, wherein R is —C$_{1-3}$alkyl, phenyl or —C$_{3-7}$cycloalkyl;

and wherein the oxazepane is further unsubstituted or substituted by 1 or 2 substituents independently selected from —C$_{1-3}$alkyl and —C$_{3-7}$cycloalkyl;

and wherein the morpholinyl is further unsubstituted or substituted by phenyl which phenyl is unsubstituted or substituted by a substituent independently selected from —C$_{1-3}$ alkyl and —O—C$_{1-3}$ alkyl;

and wherein the pyrrolidinyl is further unsubstituted or substituted by a triazolyl group which is unsubstituted or substituted by —C$_{1-3}$alkyl;

and wherein the imidazolyl, triazolyl, pyrazolyl, and tetrazolyl groups each are further unsubstituted or substituted by 1, 2 or 3 substituents independently selected from —CH$_2$—C$_{4-7}$cycloalkyl, —CH$_2$—C$_{5-7}$heterocycloalkyl, —CH$_2$-azabicycloheptanyl, —CH$_2$-oxepane, and —CH$_2$-azabicyclohexanyl, and wherein each of —CH$_2$—C$_{4-7}$cycloalkyl, —CH$_2$—C$_{5-7}$heterocycloalkyl, —CH$_2$-azabicycloheptanyl, —CH$_2$-oxepane, or —CH$_2$-azabicyclohexanyl, including the —CH$_2$—, are further unsubstituted or substituted by 1 or 2 substituents independently selected from —C$_{1-3}$ alkyl and F;

or A is

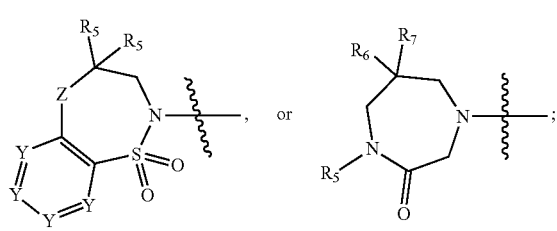

Y is independently selected from N or CH;

Z is O, CH$_2$, NR$_5$, S, S(O) or S(O)$_2$;

R$_5$ is independently selected from hydrogen or —C$_{1-4}$alkyl;

R$_6$ is hydrogen, —C$_{1-5}$alkyl or —(CH$_2$)$_m$—C$_{3-5}$cycloalkyl;

R$_7$ is hydrogen or —C$_{1-4}$alkyl;

or R$_6$ and R$_7$, together with the carbon to which they are attached form a C$_3$-C$_5$-membered cycloalkyl ring;

and, wherein when A is

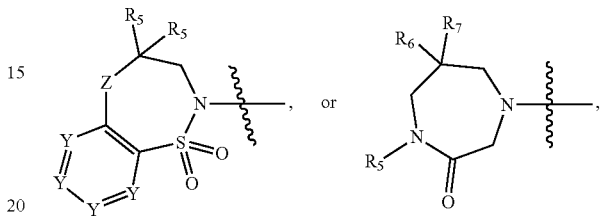

it is unsubstituted or substituted with one, two or three substituents independently selected from halo, —CF$_3$, —C$_{1-4}$alkyl, —CN, —OMe, —C(O)NH$_2$, —OCF$_3$ and —C$_{1-4}$alkylNR$_7$R$_8$;

R$_8$ is —C$_{1-3}$alkyl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkyl-heteroaryl or —C$_{1-3}$alkyl-aryl, wherein each of —C$_{1-3}$alkyl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, or —C$_{1-3}$alkylC$_{3-7}$heterocycloalkyl, is unsubstituted or substituted by 1, 2 or 3 substituents independently selected from halo, —CF$_3$, —OCF$_3$, and —OCH$_3$, and —O-heteroaryl;

X is independently (CH)$_n$, S, O or N, and wherein the ring containing X is a 5-membered heteroaromatic ring;

m is 0, 1 or 2; and n is 1;

or a pharmaceutically acceptable salt thereof.

In still yet another embodiment, the compound of Formula (I) is substituted as follows:

B is benzotriazolyl, phenyl, triazolopyridinyl, —O—(CH$_2$)-triazolyl, or —(CH$_2$)$_2$-triazolyl wherein each of benzotriazolyl, phenyl, triazolopyridinyl, —O—(CH$_2$)-triazolyl, or —(CH$_2$)$_2$-triazolyl is unsubstituted or substituted by 1, 2, or 3 substituents independently selected from —C$_{1-3}$alkyl, —O—C$_{1-3}$alkyl, —CN, —(CH$_2$)$_2$—O—(CH$_2$)$_2$—OR$_3$ and halo;

D is —C(O)OH, —C(O)NHSO$_2$CH$_3$, —SO$_2$NHC(O)CH$_3$, 5-(trifluoromethyl)-4H-1,2,4-triazol-2-yl, or tetrazolyl;

R$_1$ is independently hydrogen, —C$_{1-3}$alkyl, F, —C$_{3-6}$spirocycloalkyl, oxetane, or the two R$_1$ groups together with the carbon to which they are attached form a cyclopropyl group;

R$_2$ is hydrogen, methyl, —CF$_3$, or halo;

R$_3$ is hydrogen or —C$_{1-3}$alkyl;

Linker is —CH$_2$—, —CH$_2$—N(-cyclopropyl)-CH$_2$—, —CH$_2$—N(CH$_3$)—CH$_2$— or —N—(CH$_3$)—CH$_2$—;

A is

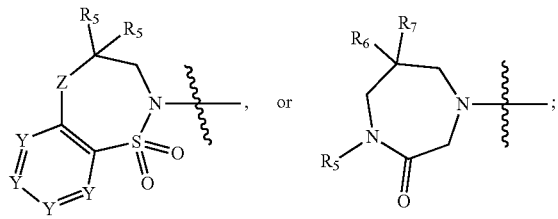

Y is independently selected from N or CH;
Z is O, CH$_2$, NR$_5$, S, S(O) or S(O)$_2$;
R$_5$ is independently selected from hydrogen or —C$_{1-4}$alkyl;
R$_6$ is hydrogen, C$_{1-5}$alkyl or —(CH$_2$)$_m$—C$_{3-5}$cycloalkyl;
R$_7$ is hydrogen or —C$_{1-4}$alkyl;
or R$_6$ and R$_7$, together with the carbon to which they are attached form a C$_3$-C$_5$-membered cycloalkyl ring;
and, wherein when A is

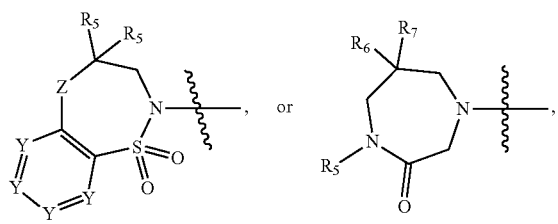

it is unsubstituted or substituted with one, two or three substituents independently selected from halo, —CF$_3$, —C$_{1-4}$alkyl, —CN, —OMe,
—C(O)NH$_2$, —OCF$_3$ and —C$_{1-4}$alkylNR$_7$R$_8$;
R$_8$ is —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl,
—C$_{1-3}$alkyl-heteroaryl or —C$_{1-3}$alkyl-aryl, wherein each of —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkyl-heteroaryl or —C$_{1-3}$alkyl-aryl is unsubstituted or substituted by 1, 2 or 3 substituents independently selected from halo, —CN, —CF$_3$, —OCF$_3$,
—OCH$_3$, —C$_{1-3}$alkyl, —OC$_{1-3}$alkyl, —OC$_{3-7}$cycloalkyl, —OC$_{3-7}$hetercycloalkyl, —O-aryl and —O-heteroaryl;
X is independently (CH)$_n$, S, O or N, and wherein the ring containing X is a 5-membered heteroaromatic ring;
m is 0, 1 or 2; and
n is 1;
or a pharmaceutically acceptable salt thereof.

In another embodiment, the compound of Formula (I) is substituted as follows:
B is benzotriazolyl, phenyl, triazolopyridinyl, —O—(CH$_2$)-triazolyl, or —(CH$_2$)$_2$-triazolyl wherein each of benzotriazolyl, phenyl, triazolopyridinyl, —O—(CH$_2$)-triazolyl, or —(CH$_2$)$_2$-triazolyl is unsubstituted or substituted by 1, 2, or 3 substituents independently selected from —C$_{1-3}$alkyl, —O—C$_{1-3}$alkyl,
—CN, —(CH$_2$)$_2$—O—(CH$_2$)$_2$—OR$_3$ and halo;
D is —C(O)OH, —C(O)NHSO$_2$CH$_3$, —SO$_2$NHC(O)CH$_3$, 5-(trifluoromethyl)-4H-1,2,4-triazol-2-yl, or tetrazolyl;
R$_1$ is independently hydrogen, —C$_{1-3}$alkyl, F, —C$_{3-6}$spirocycloalkyl, oxetane, or the two R$_1$ groups together with the carbon to which they are attached form a cyclopropyl group;
R$_2$ is hydrogen, methyl, —CF$_3$, or halo;
R$_3$ is hydrogen or —C$_{1-3}$alkyl;
Linker is —CH$_2$—, —CH$_2$—N(-cyclopropyl)-CH$_2$—, —CH$_2$—N(CH$_3$)—CH$_2$— or —N—(CH$_3$)—CH$_2$—;
A is

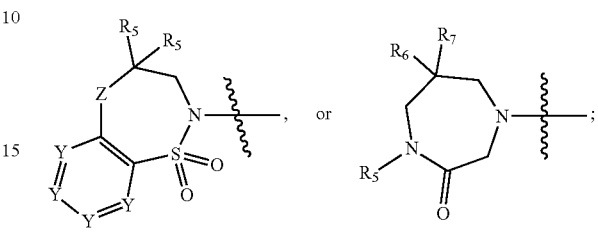

Y is independently selected from N or CH;
Z is O, CH$_2$, NR$_5$, S, S(O) or S(O)$_2$;
R$_5$ is independently selected from hydrogen or —C$_{1-4}$alkyl;
R$_6$ is hydrogen, —C$_{1-5}$alkyl or —(CH$_2$)$_m$—C$_{3-5}$cycloalkyl;
R$_7$ is hydrogen or —C$_{1-4}$alkyl;
or R$_6$ and R$_7$, together with the carbon to which they are attached form a C$_3$-C$_5$-membered cycloalkyl ring;
and, wherein when A is

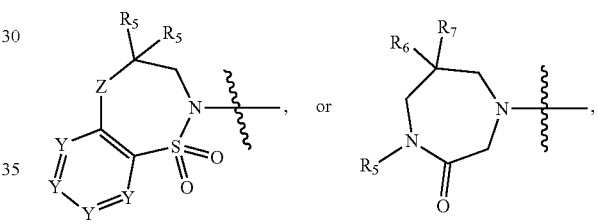

it is unsubstituted or substituted with one, two or three substituents independently selected from halo, —CF$_3$, —C$_{1-4}$alkyl, —CN, —OMe,
—C(O)NH$_2$, —OCF$_3$ and —C$_{1-4}$alkylNR$_7$R$_8$;
R$_8$ is —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl,
—C$_{1-3}$alkyl-heteroaryl or —C$_{1-3}$alkyl-aryl, wherein each of —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkyl-heteroaryl or —C$_{1-3}$alkyl-aryl is unsubstituted or substituted by 1, 2 or 3 substituents independently selected from halo, —CN, —CF$_3$, —OCF$_3$,
—OCH$_3$, —C$_{1-3}$alkyl, —OC$_{1-3}$alkyl, —OC$_{3-7}$cycloalkyl, —OC$_{3-7}$hetercycloalkyl, —O-aryl and —O-heteroaryl;
X is independently (CH)$_n$, S, O or N, and wherein the ring containing X is a 5-membered heteroaromatic ring;
m is 0, 1 or 2; and
n is 1;
or a pharmaceutically acceptable salt thereof.

In a further embodiment, the compound of Formula (I) is substituted as follows:
B is benzotriazolyl, phenyl, triazolopyridinyl, —O—(CH$_2$)-triazolyl, or —(CH$_2$)$_2$-triazolyl wherein each of benzotriazolyl, phenyl, triazolopyridinyl, —O—(CH$_2$)-triazolyl, or —(CH$_2$)$_2$-triazolyl is unsubstituted or substituted by 1, 2, or 3 substituents independently selected from —C$_{1-3}$alkyl, —O—C$_{1-3}$alkyl, —CN, —(CH$_2$)$_2$—O—(CH$_2$)$_2$—OR$_3$ and halo;
D is —C(O)OH;
R$_1$ is independently hydrogen, —C$_{1-3}$alkyl, F, —C$_{3-6}$spirocycloalkyl, oxetane, or the two R$_1$ groups together with the carbon to which they are attached form a cyclopropyl group;
R$_2$ is hydrogen, methyl, —CF$_3$, or halo;
R$_3$ is hydrogen or —C$_{1-3}$alkyl;
Linker is —CH$_2$—, —CH$_2$—N(-cyclopropyl)-CH$_2$—, —CH$_2$—N(CH$_3$)—CH$_2$— or —N—(CH$_3$)—CH$_2$—;
A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;
wherein each of tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl is unsubstituted or substituted by 1, 2, or 3 substituents independently selected from —C$_{1-3}$alkyl, —C$_{3-6}$spirocycloalkyl, halo, —CN, —O—C$_{1-3}$alkyl, —CH$_2$—O—CH$_3$, and —OH;
and wherein the piperidinyl is further unsubstituted or substituted by a substituent independently selected from pyrazolyl, —CH$_2$pyrazolyl, and oxadiazolyl, each of which is unsubstituted or substituted by —C$_{1-3}$alkyl, or, when A is piperidinyl, it is unsubstituted or substituted by —SO$_2$R, wherein R is —C$_{1-3}$alkyl, phenyl or —C$_{3-7}$cycloalkyl;
and wherein the oxazepane is further unsubstituted or substituted by 1 or 2 substituents independently selected from —C$_{1-3}$alkyl and —C$_{3-7}$cycloalkyl;
and wherein the morpholinyl is further unsubstituted or substituted by phenyl which phenyl is unsubstituted or substituted by a substituent independently selected from —C$_{1-3}$ alkyl and —O—C$_{1-3}$ alkyl;
and wherein the pyrrolidinyl is further unsubstituted or substituted by a triazolyl group which is unsubstituted or substituted by —C$_{1-3}$alkyl;
and wherein the imidazolyl, triazolyl, pyrazolyl, and tetrazolyl groups each are further unsubstituted or substituted by 1, 2 or 3 substituents independently selected from —CH$_2$—C$_{4-7}$cycloalkyl, —CH$_2$—C$_{5-7}$heterocycloalkyl, —CH$_2$-azabicycloheptanyl, —CH$_2$-oxepane, and —CH$_2$-azabicyclohexanyl, and wherein each of —CH$_2$—C$_{4-7}$cycloalkyl, —CH$_2$—C$_{5-7}$heterocycloalkyl, —CH$_2$-azabicycloheptanyl, —CH$_2$-oxepane, or —CH$_2$-azabicyclohexanyl, including the —CH$_2$—, are further unsubstituted or substituted by 1 or 2 substituents independently selected from —C$_{1-3}$ alkyl and F;
or A is

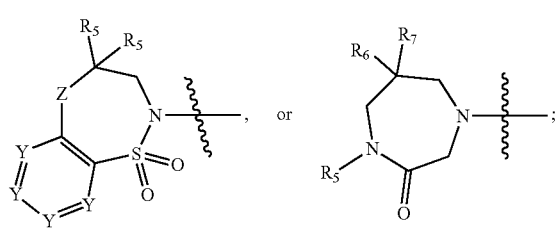

Y is independently selected from N or CH;
Z is O, CH$_2$, NR$_5$, S, S(O) or S(O)$_2$;
R$_5$ is independently selected from hydrogen or —C$_{1-4}$alkyl;
R$_6$ is hydrogen, —C$_{1-5}$alkyl or —(CH$_2$)$_m$—C$_{3-5}$cycloalkyl;
R$_7$ is hydrogen or —C$_{1-4}$alkyl;
or R$_6$ and R$_7$, together with the carbon to which they are attached form a C$_3$-C$_5$-membered cycloalkyl ring;
and, wherein when A is

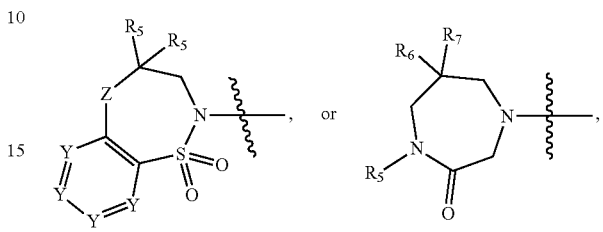

it is unsubstituted or substituted with one, two or three substituents independently selected from halo, —CF$_3$, —C$_{1-4}$alkyl, —CN, —OMe, —C(O)NH$_2$, —OCF$_3$ and —C$_{1-4}$alkylNR$_7$R$_8$;
R$_8$ is —C$_{1-3}$alkyl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkyl-heteroaryl or —C$_{1-3}$alkyl-aryl, wherein each of —C$_{1-3}$alkyl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, or —C$_{1-3}$alkylC$_{3-7}$heterocycloalkyl, is unsubstituted or substituted by 1, 2 or 3 substituents independently selected from halo, —CF$_3$, —OCF$_3$, and —OCH$_3$, and —O-heteroaryl;
X is independently (CH)$_n$ or S, and wherein the ring containing X is a 5-membered heteroaromatic ring;
m is 0, 1 or 2; and
n is 1;
or a pharmaceutically acceptable salt thereof.
In one embodiment, the compound of Formula (I) is substituted as follows:
B is benzotriazolyl which is unsubstituted or substituted by 1, 2, or 3 substituents independently selected from —C$_{1-3}$alkyl;
D is —C(O)OH;
R$_1$ is independently hydrogen or —C$_{1-3}$alkyl;
R$_2$ is methyl or chloro;
Linker is —CH$_2$;
A is

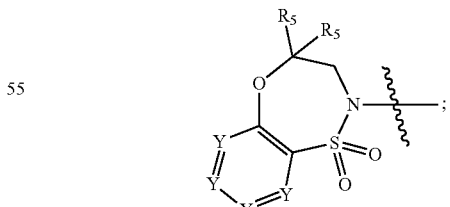

Y is independently selected from N or CH;
R$_5$ is independently hydrogen or —C$_{1-4}$alkyl;
and, wherein A is unsubstituted or substituted with one, two or three substituents independently selected from halo, —CF$_3$, —C$_{1-4}$alkyl, —CN, —OMe, —C(O)NH$_2$, —OCF$_3$, —C$_{1-4}$alkylNR$_7$R$_8$;

R$_7$ is hydrogen or —C$_{1-4}$alkyl;
R$_8$ is —C$_{1-3}$alkyl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkyl-heteroaryl or —C$_{1-3}$alkyl-aryl, wherein each of —C$_{1-3}$alkyl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, or —C$_{1-3}$alkylC$_{3-7}$heterocycloalkyl, is unsubstituted or substituted by 1, 2 or 3 substituents independently selected from halo, —CF$_3$, —OCF$_3$, and —OCH$_3$, and —O-heteroaryl;
X is independently (CH)$_n$ or S, and wherein the ring containing X is a 5-membered heteroaromatic ring; and n is 1;
or a pharmaceutically acceptable salt thereof.

In one embodiment, the compound of Formula (I) is substituted as follows:
B is benzotriazolyl which is unsubstituted or substituted by 1, 2, or 3 substituents independently selected from —C$_{1-3}$alkyl;
D is —C(O)OH;
R$_1$ is independently hydrogen or —C$_{1-3}$alkyl;
R$_2$ is methyl or chloro;
Linker is —CH$_2$;
A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;
wherein each of tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl is unsubstituted or substituted by 1, 2, or 3 substituents independently selected from —C$_{1-3}$alkyl, —C$_{3-6}$spirocycloalkyl, halo, —CN, —O—C$_{1-3}$alkyl, —CH$_2$—O—CH$_3$, and —OH;
and wherein the piperidinyl is further unsubstituted or substituted by a substituent independently selected from pyrazolyl, —CH$_2$pyrazolyl, and oxadiazolyl, each of which is unsubstituted or substituted by —C$_{1-3}$alkyl, or, when A is piperidinyl, it is unsubstituted or substituted by —SO$_2$R, wherein R is —C$_{1-3}$alkyl, phenyl or —C$_{3-7}$cycloalkyl;
and wherein the oxazepane is further unsubstituted or substituted by 1 or 2 substituents independently selected from —C$_{1-3}$alkyl and —C$_{3-7}$cycloalkyl;
and wherein the morpholinyl is further unsubstituted or substituted by phenyl which phenyl is unsubstituted or substituted by a substituent independently selected from —C$_{1-3}$ alkyl and —O—C$_{1-3}$ alkyl;
and wherein the pyrrolidinyl is further unsubstituted or substituted by a triazolyl group which is unsubstituted or substituted by —C$_{1-3}$alkyl;
and wherein the imidazolyl, triazolyl, pyrazolyl, and tetrazolyl groups each are further unsubstituted or substituted by 1, 2 or 3 substituents independently selected from —CH$_2$—C$_{4-7}$cycloalkyl, —CH$_2$—C$_{5-7}$heterocycloalkyl, —CH$_2$-azabicycloheptanyl, —CH$_2$-oxepane, and —CH$_2$-azabicyclohexanyl, and wherein each of —CH$_2$—C$_{4-7}$cycloalkyl, —CH$_2$—C$_{5-7}$heterocycloalkyl, —CH$_2$-azabicycloheptanyl, —CH$_2$-oxepane, or —CH$_2$-azabicyclohexanyl, including the —CH$_2$—, are further unsubstituted or substituted by 1 or 2 substituents independently selected from —C$_{1-3}$ alkyl and F;
X is independently (CH)$_n$ or S, and wherein the ring containing X is a 5-membered heteroaromatic ring; and n is 1;
or a pharmaceutically acceptable salt thereof.

In still yet another embodiment, the compound of Formula (I) is substituted as follows:
B is benzotriazolyl which is unsubstituted or substituted by 1, 2, or 3 substituents independently selected from —C$_{1-3}$alkyl;
D is —C(O)OH;
R, is independently hydrogen or —C$_{1-3}$alkyl;
R$_2$ is methyl or chloro;
Linker is —CH$_2$;
A is

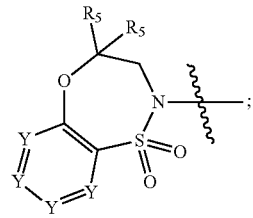

Y is independently selected from N or CH;
R$_5$ is independently hydrogen or —C$_{1-4}$alkyl;
and, wherein A is unsubstituted or substituted with one, two or three substituents independently selected from halo, —CF$_3$, —C$_{1-4}$alkyl and —OMe;
X is independently (CH)$_n$ or S, and wherein the ring containing X is a 5-membered heteroaromatic ring; and n is 1;
or a pharmaceutically acceptable salt thereof.

In one embodiment, the compound of Formula (I) is substituted as follows:
B is benzotriazolyl which is unsubstituted or substituted by 1, 2, or 3 substituents independently selected from —C$_{1-3}$alkyl;
D is —C(O)OH;
R, is independently hydrogen or —C$_{1-3}$alkyl;
R$_2$ is methyl or chloro;
Linker is —CH$_2$;
A is

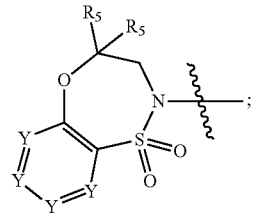

Y is independently selected from N or CH;
R$_5$ is independently selected from hydrogen, methyl or ethyl;
and, wherein A is unsubstituted or substituted with one, two or three substituents independently selected from halo, —CF$_3$, —C$_{1-4}$alkyl and —OMe;-

X is independently (CH)$_n$ or S, and wherein the ring containing X is a 5-membered heteroaromatic ring; and
n is 1;
or a pharmaceutically acceptable salt thereof.

In one embodiment, the compound of Formula (I) is substituted as follows:
B is benzotriazolyl, phenyl, triazolopyridinyl, —O—(CH$_2$)-triazolyl, or —(CH$_2$)$_2$-triazolyl wherein each of benzotriazolyl, phenyl, triazolopyridinyl, —O—(CH$_2$)-triazolyl, or —(CH$_2$)$_2$-triazolyl is unsubstituted or substituted by 1, 2, or 3 substituents independently selected from —C$_{1-3}$alkyl, —O—C$_{1-3}$alkyl,
—CN, —(CH$_2$)$_2$—O—(CH$_2$)$_2$—OR$_3$ and halo;
D is —C(O)OH;
R$_1$ is independently hydrogen, —C$_{1-3}$alkyl, F, —C$_{3-6}$spirocycloalkyl, oxetane, or the two R$_1$ groups together with the carbon to which they are attached form a cyclopropyl group;
R$_2$ is hydrogen, methyl, —CF$_3$, or halo;
R$_3$ is hydrogen or —C$_{1-3}$alkyl;
Linker is —CH$_2$—, —CH$_2$—N(-cyclopropyl)-CH$_2$—, —CH$_2$—N(CH$_3$)—CH$_2$— or —N—(CH$_3$)—CH$_2$—;
A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;
wherein each of tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl is unsubstituted or substituted by 1, 2, or 3 substituents independently selected from —C$_{1-3}$alkyl, —C$_{3-6}$spirocycloalkyl, halo, —CN, —O—C$_{1-3}$alkyl, —CH$_2$—O—CH$_3$, and —OH;
and wherein the piperidinyl is further unsubstituted or substituted by a substituent independently selected from pyrazolyl, —CH$_2$pyrazolyl, and oxadiazolyl, each of which is unsubstituted or substituted by —C$_{1-3}$alkyl, or, when A is piperidinyl, it is unsubstituted or substituted by —SO$_2$R, wherein R is —C$_{1-3}$alkyl, phenyl or —C$_{3-7}$cycloalkyl;
and wherein the oxazepane is further unsubstituted or substituted by 1 or 2 substituents independently selected from —C$_{1-3}$alkyl and —C$_{3-7}$cycloalkyl;
and wherein the morpholinyl is further unsubstituted or substituted by phenyl which phenyl is unsubstituted or substituted by a substituent independently selected from —C$_{1-3}$ alkyl and —O—C$_{1-3}$ alkyl;
and wherein the pyrrolidinyl is further unsubstituted or substituted by a triazolyl group which is unsubstituted or substituted by —C$_{1-3}$alkyl;
and wherein the imidazolyl, triazolyl, pyrazolyl, and tetrazolyl groups each are further unsubstituted or substituted by 1, 2 or 3 substituents independently selected from —CH$_2$—C$_{4-7}$cycloalkyl, —CH$_2$—C$_{5-7}$heterocycloalkyl, —CH$_2$-azabicycloheptanyl, —CH$_2$-oxepane, and —CH$_2$-azabicyclohexanyl, and wherein each of —CH$_2$—C$_{4-7}$cycloalkyl, —CH$_2$—C$_{5-7}$heterocycloalkyl, —CH$_2$-azabicycloheptanyl, —CH$_2$-oxepane, or —CH$_2$-azabicyclohexanyl, including the —CH$_2$—, are further unsubstituted or substituted by 1 or 2 substituents independently selected from —C$_{1-3}$ alkyl and F;

or A is

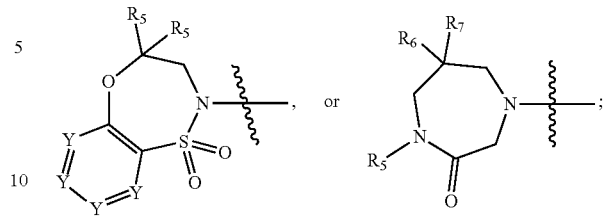

Y is independently selected from N or CH;
R$_5$ is independently selected from hydrogen or —C$_{1-4}$alkyl;
R$_6$ is hydrogen, C$_{1-5}$alkyl or —(CH$_2$)$_m$—C$_{3-5}$cycloalkyl;
R$_7$ is hydrogen or —C$_{1-4}$alkyl;
or R$_6$ and R$_7$, together with the carbon to which they are attached form a C$_3$-C$_5$-membered cycloalkyl ring;
and, wherein when A is

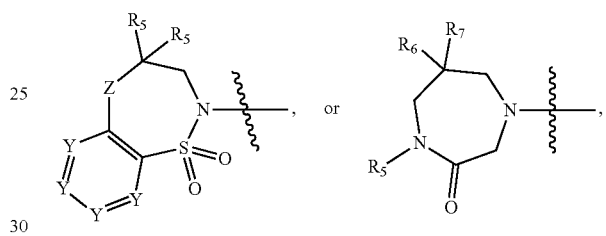

it is unsubstituted or substituted with one, two or three substituents independently selected from halo, —CF$_3$, —C$_{1-4}$alkyl, —CN, —OMe,
—C(O)NH$_2$, —OCF$_3$ and —C$_{1-4}$alkylNR$_7$R$_8$;
R$_8$ is —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkyl-heteroaryl or —C$_{1-3}$alkyl-aryl, wherein each of —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{113}$alkylC$_{3-7}$cycloalkyl, —C$_{1-3}$alkylC$_{3-7}$heterocycloalkyl, —C$_{1-3}$alkyl-heteroaryl or —C$_{1-3}$alkyl-aryl is unsubstituted or substituted by 1, 2 or 3 substituents independently selected from halo, —CN, —CF$_3$, —OCF$_3$,
—OCH$_3$, —C$_{1-3}$alkyl, —OC$_{1-3}$alkyl, —OC$_{3-7}$cycloalkyl, —OC$_{3-7}$hetercycloalkyl, —O-aryl and —O-heteroaryl;
X is independently (CH)$_n$ or O, and wherein the ring containing X is a 5-membered heteroaromatic ring;
m is 0, 1 or 2; and
n is 1;
or a pharmaceutically acceptable salt thereof.

In one embodiment, the compound of Formula (I) is substituted as follows:
B is benzotriazolyl, phenyl, triazolopyridinyl, —O—(CH$_2$)-triazolyl, or —(CH$_2$)$_2$-triazolyl wherein each of benzotriazolyl, phenyl, triazolopyridinyl, —O—(CH$_2$)-triazolyl, or —(CH$_2$)$_2$-triazolyl is unsubstituted or substituted by 1, 2, or 3 substituents independently selected from —C$_{1-3}$alkyl, —O—C$_{1-3}$alkyl,
—CN, —(CH$_2$)$_2$—O—(CH$_2$)$_2$—OR$_3$ and halo;
D is —C(O)OH;
R$_1$ is independently hydrogen, —C$_{1-3}$alkyl, F, —C$_{3-6}$spirocycloalkyl, oxetane, or the two R$_1$ groups together with the carbon to which they are attached form a cyclopropyl group;

$R_2$ is hydrogen, methyl, —$CF_3$, or halo;
$R_3$ is hydrogen or —$C_{1-3}$alkyl;
Linker is —$CH_2$—, —$CH_2$—N(-cyclopropyl)-$CH_2$—, —$CH_2$—N($CH_3$)—$CH_2$— or —N—($CH_3$)—$CH_2$—;
A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;
wherein each of tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl is unsubstituted or substituted by 1, 2, or 3 substituents independently selected from —$C_{1-3}$alkyl, —$C_{3-6}$spirocycloalkyl, halo, —CN, —O—$C_{1-3}$alkyl, —$CH_2$—O—$CH_3$, and —OH;
and wherein the piperidinyl is further unsubstituted or substituted by a substituent independently selected from pyrazolyl, —$CH_2$pyrazolyl, and oxadiazolyl, each of which is unsubstituted or substituted by —$C_{1-3}$alkyl, or, when A is piperidinyl, it is unsubstituted or substituted by —$SO_2R$, wherein R is —$C_{1-3}$alkyl, phenyl or —$C_{3-7}$cycloalkyl;
and wherein the oxazepane is further unsubstituted or substituted by 1 or 2 substituents independently selected from —$C_{1-3}$alkyl and —$C_{3-7}$cycloalkyl;
and wherein the morpholinyl is further unsubstituted or substituted by phenyl which phenyl is unsubstituted or substituted by a substituent independently selected from —$C_{1-3}$ alkyl and —O—$C_{1-3}$ alkyl;
and wherein the pyrrolidinyl is further unsubstituted or substituted by a triazolyl group which is unsubstituted or substituted by —$C_{1-3}$alkyl;
and wherein the imidazolyl, triazolyl, pyrazolyl, and tetrazolyl groups each are further unsubstituted or substituted by 1, 2 or 3 substituents independently selected from —$CH_2$—$C_{4-7}$cycloalkyl, —$CH_2$—$C_{5-7}$heterocycloalkyl, —$CH_2$-azabicycloheptanyl, —$CH_2$-oxepane, and —$CH_2$-azabicyclohexanyl, and wherein each of —$CH_2$—$C_{4-7}$cycloalkyl, —$CH_2$—$C_{5-7}$heterocycloalkyl, —$CH_2$-azabicycloheptanyl, —$CH_2$-oxepane, or —$CH_2$-azabicyclohexanyl, including the —$CH_2$—, are further unsubstituted or substituted by 1 or 2 substituents independently selected from —$C_{1-3}$ alkyl and F;
or A is

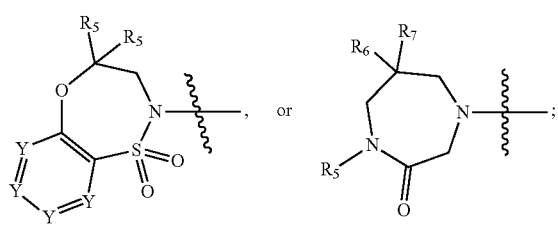

Y is independently selected from N or CH;
$R_5$ is independently selected from hydrogen or —$C_{1-4}$alkyl;
$R_6$ is hydrogen, $C_{1-5}$alkyl or —$(CH_2)_m$—$C_{3-5}$cycloalkyl;
$R_7$ is hydrogen or —$C_{1-4}$alkyl;
or $R_6$ and $R_7$, together with the carbon to which they are attached form a $C_3$-$C_5$-membered cycloalkyl ring;

and, wherein when A is

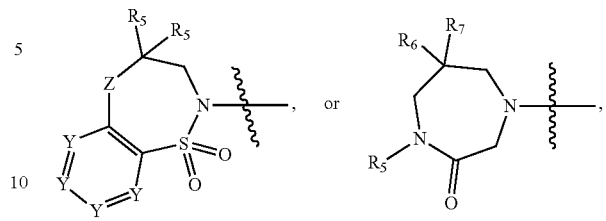

it is unsubstituted or substituted with one, two or three substituents independently selected from halo, —$CF_3$, —$C_{1-4}$alkyl, —CN, —OMe, —C(O)$NH_2$, —$OCF_3$ and —$C_{1-4}$alkyl$NR_7R_8$;
$R_8$ is —$C_{1-3}$alkyl, aryl, heteroaryl, —C(O)$C_{1-3}$alkyl, —$SO_2C_{1-3}$alkyl, —C(O)aryl, —C(O)heteroaryl, —$SO_2$aryl, —$SO_2$heteroaryl, —$C_{3-7}$cycloalkyl, —$C_{1-3}$alkyl$C_{3-7}$cycloalkyl, —$C_{1-3}$alkyl$C_{3-7}$heterocycloalkyl, —$C_{1-3}$alkyl-heteroaryl or —$C_{1-3}$alkyl-aryl, wherein each of —$C_{1-3}$alkyl, aryl, heteroaryl, —C(O)$C_{1-3}$alkyl, —$SO_2C_{1-3}$alkyl, —C(O)aryl, —C(O)heteroaryl, —$SO_2$aryl, —$SO_2$heteroaryl, —$C_{3-7}$cycloalkyl, —$C_{1-3}$alkyl$C_{3-7}$cycloalkyl, —$C_{1-3}$alkyl$C_{3-7}$heterocycloalkyl, —$C_{1-3}$alkyl-heteroaryl or —$C_{1-3}$alkyl-aryl is unsubstituted or substituted by 1, 2 or 3 substituents independently selected from halo, —CN, —$CF_3$, —$OCF_3$, —$OCH_3$, —$C_{1-3}$alkyl, —$OC_{1-3}$alkyl, —$OC_{3-7}$cycloalkyl, —$OC_{3-7}$hetercycloalkyl, —O-aryl and —O-heteroaryl;
X is independently $(CH)_n$, N or S, and wherein the ring containing X is a 5-membered heteroaromatic ring;
m is 0, 1 or 2; and
n is 1;
or a pharmaceutically acceptable salt thereof.

In one embodiment, the compound of Formula (I) is substituted as follows:
B is benzotriazolyl which is unsubstituted or substituted by 1, 2, or 3 substituents independently selected from —$C_{1-3}$alkyl;
D is —C(O)OH;
$R_1$ is independently hydrogen or —$C_{1-3}$alkyl;
$R_2$ is methyl or chloro;
Linker is —$CH_2$;
A is

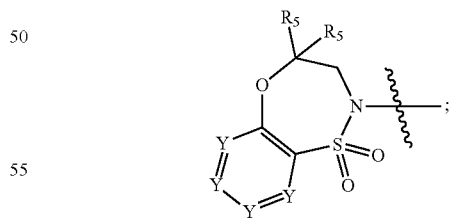

Y is independently selected from N or CH;
$R_5$ is independently hydrogen or —$C_{1-4}$alkyl;
and, wherein when A is unsubstituted or substituted with one, two or three substituents independently selected from halo, —$CF_3$, —$C_{1-4}$alkyl, —CN, —OMe, —C(O)$NH_2$, —$OCF_3$, —$C_{1-4}$alkyl$NR_7R_8$;
$R_7$ is hydrogen or —$C_{1-4}$alkyl;
$R_8$ is —$C_{1-3}$alkyl, aryl, heteroaryl, —C(O)$C_{1-3}$alkyl, —$SO_2C_{1-3}$alkyl, —C(O)aryl, —C(O)heteroaryl, —$SO_2$aryl, —SO₂heteroaryl, —C₃₋₇cycloalkyl, —C₁₋₃alkylC₃₋₇cycloalkyl, —C₁₋₃alkylC₃₋₇heterocycloalkyl,
—C₁₋₃alkyl-heteroaryl or —C₁₋₃alkyl-aryl, wherein each of —C₁₋₃alkyl, aryl, heteroaryl, —C(O)C₁₋₃alkyl, —SO₂C₁₋₃alkyl, —C(O)aryl, —C(O)heteroaryl, —SO₂aryl, —SO₂heteroaryl, —C₃₋₇cycloalkyl, —C₁₋₃alkylC₃₋₇cycloalkyl, —C₁₋₃alkylC₃₋₇heterocycloalkyl, —C₁₋₃alkyl-heteroaryl or —C₁₋₃alkyl-aryl is unsubstituted or substituted by 1, 2 or 3 substituents independently selected from halo, —CN, —CF₃, —OCF₃,
—OCH₃, —C₁₋₃alkyl, —OC₁₋₃alkyl, —OC₃₋₇cycloalkyl, —OC₃₋₇hetercycloalkyl, —O-aryl and —O-heteroaryl;
X is independently (CH)ₙ or O, and wherein the ring containing X is a 5-membered heteroaromatic ring; and
n is 1;
or a pharmaceutically acceptable salt thereof.

In one embodiment, the compound of Formula (I) is substituted as follows:
B is benzotriazolyl which is unsubstituted or substituted by 1, 2, or 3 substituents independently selected from —C₁₋₃alkyl;
D is —C(O)OH;
R₁ is independently hydrogen or —C₁₋₃alkyl;
R₂ is methyl or chloro;
Linker is —CH₂;
A is

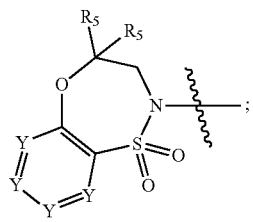

Y is independently selected from N or CH;
R₅ is independently hydrogen or —C₁₋₄alkyl;
and, wherein A is unsubstituted or substituted with one, two or three substituents independently selected from halo, —CF₃, —C₁₋₄alkyl and —OMe;
X is independently (CH)ₙ or O, and wherein the ring containing X is a 5-membered heteroaromatic ring; and
n is 1;
or a pharmaceutically acceptable salt thereof.

In one embodiment, the compound of Formula (I) is substituted as follows:
B is benzotriazolyl which is unsubstituted or substituted by ethyl;
D is —C(O)OH;
R₁ is independently hydrogen or methyl;
R₂ is methyl or chloro;
Linker is —CH₂;
A is

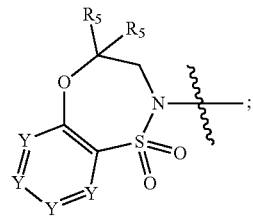

Y is independently selected from N or CH;
R₅ is independently selected from hydrogen, methyl or ethyl;
and, wherein A is unsubstituted or substituted with one, two or three substituents independently selected from halo, —CF₃, —C₁₋₄alkyl and —OMe;
X is independently selected from (CH)ₙ and S, and wherein the ring containing X is a 5-membered heteroaromatic ring; and
n is 1;
or a pharmaceutically acceptable salt thereof.

In one embodiment, the compound of Formula (I) is substituted as follows:
B is benzotriazolyl which is unsubstituted or substituted by ethyl;
D is —C(O)OH;
R, is independently hydrogen or methyl;
R₂ is methyl or chloro;
Linker is —CH₂;
A is

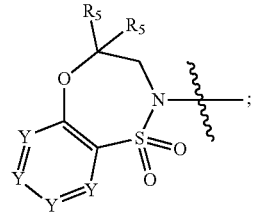

Y is independently selected from N or CH;
R₅ is independently selected from hydrogen, methyl or ethyl;
and, wherein A is unsubstituted;
X is independently selected from (CH)ₙ and S, and wherein the ring containing X is a 5-membered heteroaromatic ring; and
n is 1;
or a pharmaceutically acceptable salt thereof.

In one embodiment, the compound of Formula (I) is substituted as follows:
B is benzotriazolyl which is unsubstituted or substituted by 1, 2, or 3 substituents independently selected from —C₁₋₃alkyl;
D is —C(O)OH;
R₁ is independently hydrogen or —C₁₋₃alkyl;
R₂ is methyl or chloro;
Linker is —CH₂;

A is

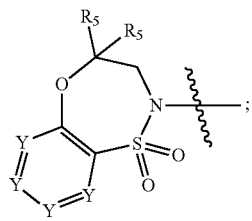

Y is independently selected from N or CH;
R$_5$ is independently selected from hydrogen, methyl or ethyl;
and, wherein A is unsubstituted or substituted with one, two or three substituents independently selected from halo, —CF$_3$, —C$_{1-4}$alkyl and —OMe;
X is independently (CH)$_n$ or O, and wherein the ring containing X is a 5-membered heteroaromatic ring; and
n is 1;
or a pharmaceutically acceptable salt thereof.

In one embodiment, the compound of Formula (I) is substituted as follows:
B is benzotriazolyl which is unsubstituted or substituted by 1, 2, or 3 substituents independently selected from —C$_{1-3}$alkyl;
D is —C(O)OH;
R$_1$ is independently hydrogen or —C$_{1-3}$alkyl;
R$_2$ is methyl or chloro;
Linker is —CH$_2$;
A is

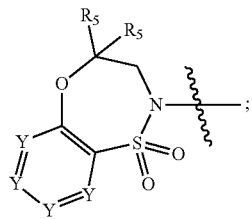

Y is independently selected from N or CH;
R$_5$ is independently selected from hydrogen, methyl or ethyl;
and, wherein A is unsubstituted or substituted with one, two or three substituents independently selected from halo, —CF$_3$, —C$_{1-4}$alkyl and —OMe;
X is independently (CH)$_n$, N or S, and wherein the ring containing X is a 5-membered heteroaromatic ring; and
n is 1;
or a pharmaceutically acceptable salt thereof.

In one embodiment, the compound of Formula (I) is substituted as follows:
B is benzotriazolyl, phenyl, triazolopyridinyl, —O—(CH$_2$)-triazolyl, or —(CH$_2$)$_2$-triazolyl wherein each of benzotriazolyl, phenyl, triazolopyridinyl, —O—(CH$_2$)-triazolyl, or —(CH$_2$)$_2$-triazolyl is unsubstituted or substituted by 1, 2, or 3 substituents independently selected from —C$_{1-3}$alkyl, —O—C$_{1-3}$alkyl,
—CN, —(CH$_2$)$_2$—O—(CH$_2$)$_2$—OR$_3$ and halo;
D is —C(O)OH;
R$_1$ is independently hydrogen, —C$_{1-3}$alkyl, F, —C$_{3-6}$spirocycloalkyl, oxetane, or the two R$_1$ groups together with the carbon to which they are attached form a cyclopropyl group;
R$_2$ is hydrogen, methyl, —CF$_3$, or halo;
R$_3$ is hydrogen or —C$_{1-3}$alkyl;
Linker is —CH$_2$—, —CH$_2$—N(-cyclopropyl)-CH$_2$—, —CH$_2$—N(CH$_3$)—CH$_2$— or —N—(CH$_3$)—CH$_2$—;
A is

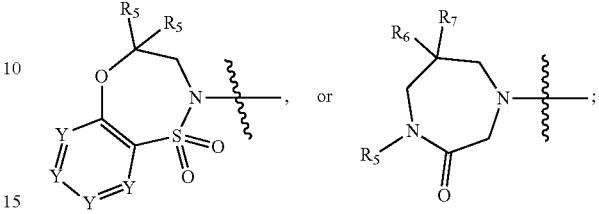

Y is independently selected from N or CH;
R$_5$ is independently selected from hydrogen or —C$_{1-4}$alkyl;
R$_6$ is hydrogen, C$_{1-5}$alkyl or —(CH$_2$)$_m$—C$_{3-5}$cycloalkyl;
R$_7$ is hydrogen or —C$_{1-4}$alkyl;
or R$_6$ and R$_7$, together with the carbon to which they are attached form a C$_3$-C$_5$-membered cycloalkyl ring;
and, wherein when A is

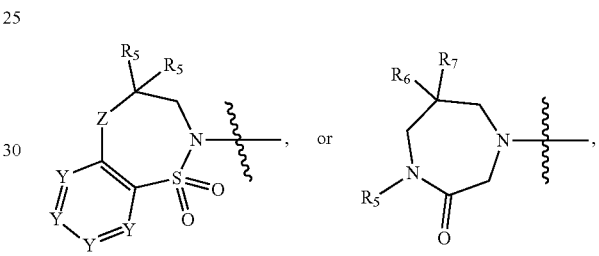

it is unsubstituted or substituted with one, two or three substituents independently selected from halo, —CF$_3$, —C$_{1-4}$alkyl, —CN, —OMe, —C(O)NH$_2$, —OCF$_3$ and —C$_{1-4}$alkylNR$_7$R$_8$;
R$_8$ is —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkyl-heteroaryl or —C$_{1-3}$alkyl-aryl, wherein each of —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkyl-heteroaryl or —C$_{1-3}$alkyl-aryl is unsubstituted or substituted by 1, 2 or 3 substituents independently selected from halo, —CN, —CF$_3$, —OCF$_3$, —OCH$_3$, —C$_{1-3}$alkyl, —OC$_{1-3}$alkyl, —OC$_{3-7}$cycloalkyl, —OC$_{3-7}$hetercycloalkyl, —O-aryl and —O-heteroaryl;
X is independently (CH)$_n$ or O, and wherein the ring containing X is a 5-membered heteroaromatic ring;
m is 0, 1 or 2; and
n is 1;
or a pharmaceutically acceptable salt thereof.

In another embodiment, the compound of Formula (I) is substituted as follows:
B is benzotriazolyl, phenyl, triazolopyridinyl, —O—(CH$_2$)-triazolyl, or —(CH$_2$)$_2$-triazolyl wherein each of benzotriazolyl, phenyl, triazolopyridinyl, —O—(CH$_2$)-triazolyl, or —(CH$_2$)$_2$ triazolyl is unsubstituted or substituted by 1, 2, or 3 substituents independently selected from —C$_{1-3}$alkyl, —O—C$_{1-3}$alkyl, —CN, —(CH$_2$)$_2$—O—(CH$_2$)$_2$—OR$_3$ and halo;

D is —C(O)OH, —C(O)NR$_3$R$_4$, —C(O)NHSO$_2$CH$_3$, —SO$_2$NHC(O)CH$_3$, 5-(trifluoromethyl)-4H-1,2,4-triazol-2-yl, or tetrazolyl;

R$_1$ is independently hydrogen, —C$_{1-3}$alkyl, F, —C$_{3-6}$spirocycloalkyl, oxetane, or the two R$_1$ groups together with the carbon to which they are attached form a cyclopropyl group;

R$_2$ is hydrogen, methyl, CF$_3$, or halo;

R$_3$ is hydrogen or —C$_{1-3}$alkyl R$_4$ is hydrogen, —C$_{1-5}$alkyl, —C$_{3-7}$cycloalkyl, —C$_{4-8}$heterocycloalkyl, —C$_1$alkoxy, —C$_{1-3}$alkyl-O—C$_{1-3}$alkyl, —C$_{1-3}$alkyl-NH—C$_{1-3}$alkyl, —C$_{1-3}$alkyl-SO$_2$C$_{1-3}$alkyl, —C$_{1-3}$alkyl-C$_{4-8}$heterocycloalkyl, —C$_{1-3}$alkyl-C(O)NR$_3$R$_4$, or heteroaryl, wherein each of —C$_{1-5}$ alkyl, —C$_{3-7}$ cycloalkyl, —C$_{4-7}$ heterocycloalkyl, —C$_{1-5}$alkoxy, —C$_{1-3}$alkyl-O—C$_{1-3}$alkyl, —C$_{1-3}$alkyl-NH—C$_{1-3}$alkyl, —C$_{1-3}$alkyl-C(O)NR$_3$R$_4$, or heteroaryl is unsubstituted or substituted by one or two substituents selected from —OH, —C(O), —N—C(O)—C$_{1-3}$alkyl, F, CN, —CH—F$_2$, —CF$_3$, —(CH$_2$)$_n$—O—(CH$_2$)$_m$—CH$_3$, and —C$_{3-7}$cycloalkyl;

or R$_3$ and R$_4$ together with the nitrogen atom to which they are attached form a 5-8-membered heterocyclic ring, an 8-11-membered bicyclic heterocyclic ring or a 9-10-membered bridged bicyclic heterocyclic ring, wherein each 5-8-membered ring, 8-11-membered bicyclic ring, or 9-10-membered bridged bicyclic ring optionally includes one —C(O) or one —S(O)$_2$, and wherein each 5-8-membered ring, 8-11-membered bicyclic ring, or 9-10-membered bridged bicyclic ring optionally contains one, two or three oxygen ring atoms, one, two or three sulfur ring atoms or one, two or three nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$alkyl, —C$_{3-7}$cycloalkyl, —C$_{4-7}$heterocycloalkyl, —(CH$_2$)phenyl, halogen, —NR$_3$R$_4$, —CHF$_2$, —CF$_3$, and —(CH$_2$)$_n$—O—(CH$_2$)$_m$—CH$_3$;

Linker is —CH$_2$—, —CH$_2$—N(-cyclopropyl)-CH$_2$—, —CH$_2$—N(CH$_3$)—CH$_2$— or —N—(CH$_3$)—CH$_2$—;

A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;

wherein each of tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl is unsubstituted or substituted by 1, 2, or 3 substituents independently selected from —C$_{1-3}$alkyl, —C$_{3-6}$spirocycloalkyl, halo, CN, —O—C$_{1-3}$alkyl, —CH$_2$—O—CH$_3$, and OH;

and wherein the piperidinyl is further unsubstituted or substituted by a substituent independently selected from pyrazolyl, —CH$_2$pyrazolyl, and oxadiazolyl each of which is unsubstituted or substituted by —C$_{1-3}$alkyl, or, when A is piperidinyl, it is unsubstituted or substituted by —SO$_2$R, wherein R is C$_{1-3}$alkyl, phenyl or C$_{3-7}$cycloalkyl;

and wherein the oxazepane is further unsubstituted or substituted by 1 or 2 substituents independently selected from —C$_{1-3}$alkyl and —C$_{3-7}$cycloalkyl;

and wherein the morpholinyl is further unsubstituted or substituted by phenyl which phenyl is unsubstituted or independently substituted by a substituent selected from C$_{1-3}$ alkyl and —O—C$_{1-3}$ alkyl;

and wherein the pyrrolidinyl is further optionally substituted by a triazolyl group which is optionally substituted by —C$_{1-3}$alkyl;

and wherein the imidazolyl, triazolyl, pyrazolyl, and tetrazolyl groups each are further unsubstituted or substituted by 1, 2 or 3 substituents independently selected from —CH$_2$—C$_{4-7}$cycloalkyl, —CH$_2$—C$_{5-7}$heterocycloalkyl, —CH$_2$-azabicycloheptanyl, —CH$_2$-oxane, and —CH$_2$-azabicyclohexanyl, and wherein each of —CH$_2$—C$_{4-7}$cycloalkyl, —CH$_2$—C$_{5-7}$heterocycloalkyl, —CH$_2$-azabicycloheptanyl, —CH$_2$-oxepane, or —CH$_2$-azabicyclohexanyl, including the —CH$_2$—, are further unsubstituted or substituted by 1 or 2 substituents independently selected from —C$_{1-3}$ alkyl and F;

or A is

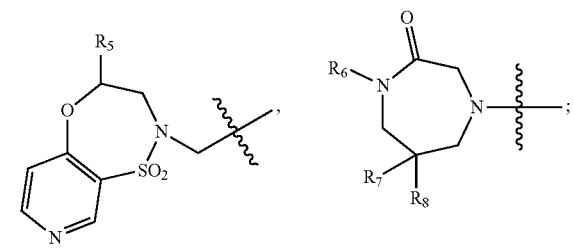

R$_5$ is hydrogen or —C$_{1-4}$alkyl;

R$_6$ is hydrogen, C$_{1-5}$alkyl or —(CH$_2$)$_m$—C$_{3-5}$cycloalkyl;

R$_7$ is hydrogen or —C$_{1-4}$alkyl;

R$_8$ is hydrogen or —C$_{1-4}$alkyl;

X is independently (CH)$_n$, S, O or N;

m is 0, 1 or 2; and n is 1 or 2;

or a pharmaceutically acceptable salt thereof.

In one embodiment, the compound of Formula (I) is substituted as follows:

B is benzotriazolyl, phenyl, triazolopyridinyl, —O—(CH$_2$)-triazolyl, or —(CH$_2$)$_2$-triazolyl wherein each of benzotriazolyl, phenyl, triazolopyridinyl, —O—(CH$_2$)-triazolyl, or —(CH$_2$)$_2$-triazolyl is unsubstituted or substituted by 1, 2, or 3 substituents independently selected from —C$_{1-3}$alkyl, —O—C$_{1-3}$alkyl, —CN, —(CH$_2$)$_2$—O—(CH$_2$)$_2$—OR$_3$ and halo;

D is —C(O)OH;

R$_1$ is independently hydrogen, —C$_{1-3}$alkyl, F, —C$_{3-6}$spirocycloalkyl, oxetane, or the two R$_1$ groups together with the carbon to which they are attached form a cyclopropyl group;

R$_2$ is hydrogen, methyl, CF$_3$, or halo;

R$_3$ is hydrogen or —C$_{1-3}$alkyl;

Linker is —CH$_2$—, —CH$_2$—N(-cyclopropyl)-CH$_2$—, —CH$_2$—N(CH$_3$)—CH$_2$— or —N—(CH$_3$)—CH$_2$—;

A is

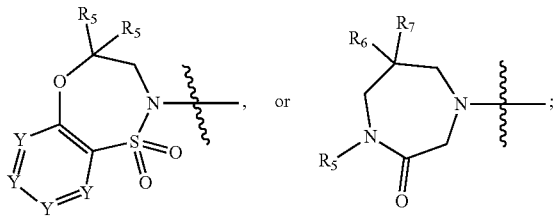

Y is independently selected from N or CH;
R₅ is independently selected from hydrogen or —$C_{1-4}$alkyl;
R₆ is hydrogen, —$C_1$alkyl or —$(CH_2)_m$—$C_{3-5}$cycloalkyl;
R₇ is hydrogen or —$C_{1-4}$alkyl;
or R₆ and R₇, together with the carbon to which they are attached form a $C_3$-$C_5$-membered cycloalkyl ring;
and, wherein when A is

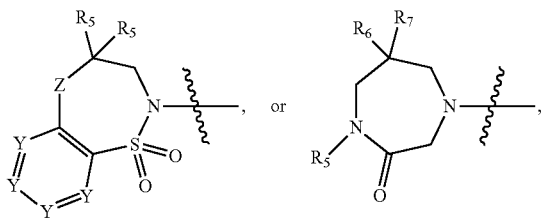

it is unsubstituted or substituted with one, two or three substituents independently selected from halo, —$CF_3$, —$C_{1-4}$alkyl, —CN, —OMe, —C(O)NH₂, —$OCF_3$ and —$C_{1-4}$alkylNR₇R₈;
R₈ is —$C_{1-3}$alkyl, aryl, heteroaryl, —C(O)$C_{1-3}$alkyl, —SO₂$C_{1-3}$alkyl, —C(O)aryl, —C(O)heteroaryl, —SO₂aryl, —SO₂heteroaryl, —$C_{3-7}$cycloalkyl, —$C_{1-3}$alkyl$C_{3-7}$cycloalkyl, —$C_{1-3}$alkyl$C_{3-7}$heterocycloalkyl, —$C_{1-3}$alkyl-heteroaryl or —$C_{1-3}$alkyl-aryl, wherein each of —$C_{1-3}$alkyl, aryl, heteroaryl, —C(O)$C_{1-3}$alkyl, —SO₂$C_{1-3}$alkyl, —C(O)aryl, —C(O)heteroaryl, —SO₂aryl, —SO₂heteroaryl, —$C_{3-7}$cycloalkyl, —$C_{1-3}$alkyl$C_{3-7}$cycloalkyl, —$C_{1-3}$alkyl$C_{3-7}$heterocycloalkyl, —$C_{1-3}$alkyl-heteroaryl or —$C_{1-3}$alkyl-aryl is unsubstituted or substituted by 1, 2 or 3 substituents independently selected from halo, —CN, —$CF_3$, —$OCF_3$, —$OCH_3$, —$C_{1-3}$alkyl, —$OC_{1-3}$alkyl, —$OC_{3-7}$cycloalkyl, —$OC_{3-7}$hetercycloalkyl, —O-aryl and —O-heteroaryl;
X is independently $(CH)_n$ or S, and wherein the ring containing X is a 5-membered heteroaromatic ring;
m is 0, 1 or 2; and
n is 1;
or a pharmaceutically acceptable salt thereof.

It is to be understood that the present invention covers all combinations of the embodiments and particular groups described hereinabove.

Specific examples of compounds of the present invention include the following:
(S)-3-(5-Chloro-4-(((R)-4-ethyl-1,1-dioxido-3,4-dihydro-2H-pyrido[4,3-b][1,4,5]oxathiazepin-2-yl)methyl)thiophen-2-yl)-3-(1-ethyl-4-methyl-1H-benzo[d][1,2,3]triazol-5-yl)propanoic acid;
(S)-3-(5-Chloro-4-(((R)-4-ethyl-1,1-dioxido-3,4-dihydro-2H-pyrido[2,3-b][1,4,5]oxathiazepin-2-yl)methyl)thiophen-2-yl)-3-(1-ethyl-4-methyl-1H-benzo[d][1,2,3]triazol-5-yl)propanoic acid;
(S)-3-(5-Chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-methyl-1H-benzo[d][1,2,3]triazol-5-yl)-2,2-dimethylpropanoic acid;
(R)-3-(5-Chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-methyl-1H-benzo[d][1,2,3]triazol-5-yl)-2,2-dimethylpropanoic acid;
(R)-3-(5-Chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-methyl-1H-benzo[d][1,2,3]triazol-5-yl)propanoic acid;
(R)-3-(5-Chloro-4-(((R)-4-ethyl-1,1-dioxido-3,4-dihydro-2H-pyrido[2,3-b][1,4,5]oxathiazepin-2-yl)methyl)thiophen-2-yl)-3-(1-ethyl-4-methyl-1H-benzo[d][1,2,3]triazol-5-yl)propanoic acid;
(S)-3-(4-(((R)-4-Ethyl-1,1-dioxido-3,4-dihydro-2H-pyrido[2,3-b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoic acid
(S)-3-(4-((4,4-Dimethyl-1,1-dioxido-3,4-dihydro-2H-pyrido[2,3-b][1,4,5]oxathiazepin-2-yl)methyl)-5-methyl-thiophen-2-yl)-3-(1-ethyl-4-methyl-1H-benzo[d][1,2,3]triazol-5-yl)-2,2-dimethylpropanoic acid;
(S)-3-(4-(((R)-4-Ethyl-1,1-dioxido-3,4-dihydro-2H-pyrido[4,3-b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoic acid;
(S)-3-(4-(((R)-4-Ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoic acid;
(R)-3-(4-(((R)-4-Ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoic acid;
(S)-3-(1-Ethyl-4-methyl-1H-benzo[d][1,2,3]triazol-5-yl)-3-(4-((2-((4-ethylpiperidin-1-yl)methyl)-1H-imidazol-1-yl)methyl)-5-methylthiophen-2-yl)-2,2-dimethylpropanoic acid;
(R or S)-3-(4-(((R)-4-Ethyl-1,1-dioxido-3,4-dihydro-2H-benzo[b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoic acid Isomer 1;
(R or S)-3-(4-(((R)-4-Ethyl-1,1-dioxido-3,4-dihydro-2H-benzo[b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoic acid Isomer 2;
(S)-3-(1-Ethyl-4-methyl-1H-benzo[d][1,2,3]triazol-5-yl)-2,2-dimethyl-3-(5-methyl-4-((4,6,6-trimethyl-3-oxo-1,4-diazepan-1-yl)methyl)thiophen-2-yl)propanoic acid;
(S)-3-(1-Ethyl-4-methyl-1H-benzo[d][1,2,3]triazol-5-yl)-2,2-dimethyl-3-(5-methyl-4-(((R)-4-methyl-1,1-dioxido-4,5-dihydropyrido[2,3-f][1,2]thiazepin-2(3H)-yl)methyl)thiophen-2-yl)propanoic acid;
(S)-3-(1-Ethyl-4-methyl-1H-benzo[d][1,2,3]triazol-5-yl)-2,2-dimethyl-3-(5-methyl-4-(((R)-4-methyl-1,1-dioxido-4,5-dihydrobenzo[f][1,2]thiazepin-2(3H)-yl)methyl)thiophen-2-yl)propanoic acid;
(S)-3-(1-Ethyl-4-methyl-1H-benzo[d][1,2,3]triazol-5-yl)-2,2-dimethyl-3-(5-methyl-4-(((S)-4-methyl-1,1-dioxido-4,5-dihydrobenzo[f][1,2]thiazepin-2(3H)-yl)methyl)thiophen-2-yl)propanoic acid;
(S)-3-(1-Ethyl-4-methyl-1H-benzo[d][1,2,3]triazol-5-yl)-2,2-dimethyl-3-(5-methyl-4-(((S)-4-methyl-1,1-dioxido-4,5-dihydropyrido[2,3-f][1,2]thiazepin-2(3H)-yl)methyl)thiophen-2-yl)propanoic acid;

(R or S)-3-(4-(((R)-4-Ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)propanoic acid Isomer 1;

(R or S)-3-(4-(((R)-4-Ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)propanoic acid Isomer 2;

(R)-3-(5-chloro-4-(((R)-4-ethyl-1,1-dioxido-3,4-dihydro-2H-pyrido[4,3-b][1,4,5]oxathiazepin-2-yl)methyl)thiophen-2-yl)-3-(1-ethyl-4-methyl-1H-benzo[d][1,2,3]triazol-5-yl)propanoic acid; (R)-3-(1-Ethyl-4-methyl-1H-benzo[d][1,2,3]triazol-5-yl)-2,2-dimethyl-3-(1-methyl-5-(((S)-4-methyl-1,1-dioxido-4,5-dihydropyrido[2,3-f][1,2]thiazepin-2(3H)-yl)methyl)-1H-pyrazol-3-yl)propanoic acid;

(S)-3-(4-(((R)-4-Ethyl-1,1-dioxido-3,4-dihydro-2H-pyrido[2,3-b][1,4,5]oxathiazepin-2-yl)methyl)-5-methylthiophen-2-yl)-3-(1-ethyl-4-methyl-1H-benzo[d][1,2,3]triazol-5-yl)propanoic acid;

(S)-3-(4-(((R)-4-Ethyl-1,1-dioxido-3,4-dihydro-2H-pyrido[2,3-b][1,4,5]oxathiazepin-2-yl)methyl)-5-methylthiazol-2-yl)-3-(1-ethyl-4-methyl-1H-benzo[d][1,2,3]triazol-5-yl)-2,2-dimethyl-N-(pyridin-3-yl)propanamide;

(S)-3-(4-(((R)-4-Ethyl-1,1-dioxido-3,4-dihydro-2H-pyrido[2,3-b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoic acid (S)-3-(4-(((R)-4-Ethyl-1,1-dioxido-3,4-dihydro-2H-pyrido[4,3-b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoic acid;

(S)-3-(4-(((R)-4-Ethyl-1,1-dioxido-3,4-dihydro-2H-pyrido[4,3-b][1,4,5]oxathiazepin-2-yl)methyl)-5-methylthiazol-2-yl)-3-(1-ethyl-4-methyl-1H-benzo[d][1,2,3]triazol-5-yl)-2,2-dimethyl-N-(pyridin-3-yl)propanamide;

(S)-3-(4-(((R)-4-Ethyl-1,1-dioxido-3,4-dihydro-2H-pyrido[3,2-b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoic acid;

(S)-3-(4-(((R)-4-Ethyl-1,1-dioxido-3,4-dihydro-2H-pyrido[3,2-b][1,4,5]oxathiazepin-2-yl)methyl)-5-methylthiazol-2-yl)-3-(1-ethyl-4-methyl-1H-benzo[d][1,2,3]triazol-5-yl)-2,2-dimethyl-N-(pyridin-3-yl)propanamide;

(S)-3-(1-Ethyl-4-methyl-1H-benzo[d][1,2,3]triazol-5-yl)-2,2-dimethyl-3-(1-methyl-5-(((S)-4-methyl-1,1-dioxido-4,5-dihydropyrido[2,3-f][1,2]thiazepin-2(3H)-yl)methyl)-1H-pyrazol-3-yl)propanoic acid;

(S)-3-(4-(((S)-3-(1H-Pyrazol-1-yl)piperidin-1-yl)methyl)-5-methylthiophen-2-yl)-3-(1-ethyl-4-methyl-1H-benzo[d][1,2,3]triazol-5-yl)-2,2-dimethylpropanoic acid;

(S)-3-(4-(((S)-4-Ethyl-1,1-dioxido-4,5-dihydropyrido[2,3-f][1,2]thiazepin-2(3H)-yl)methyl)-5-methylthiazol-2-yl)-3-(1-ethyl-4-methyl-1H-benzo[d][1,2,3]triazol-5-yl)-2,2-dimethylpropanoic acid;

(S)-3-(4-(((S)-4-Ethyl-1,1-dioxido-4,5-dihydropyrido[2,3-f][1,2]thiazepin-2(3H)-yl)methyl)-5-methylthiazol-2-yl)-3-(1-ethyl-4-methyl-1H-benzo[d][1,2,3]triazol-5-yl)-2,2-dimethyl-N-(pyridin-3-yl)propanamide;

(R)-3-(5-Chloro-4-(((R)-4-ethyl-1,1-dioxido-3,4-dihydro-2H-pyrido[4,3-b][1,4,5]oxathiazepin-2-yl)methyl)thiophen-2-yl)-3-(1-ethyl-4-methyl-1H-benzo[d][1,2,3]triazol-5-yl)-2,2-dimethylpropanoic acid;

(R)-3-(1-Ethyl-4-methyl-1H-benzo[d][1,2,3]triazol-5-yl)-2,2-dimethyl-3-(1-methyl-5-(((S)-4-methyl-1,1-dioxido-8-(trifluoromethyl)-4,5-dihydrobenzo[f][1,2]thiazepin-2(3H)-yl)methyl)-1H-pyrazol-3-yl)propanoic acid;

(R)-3-(5-Chloro-4-(((R)-4-ethyl-1,1-dioxido-3,4-dihydro-2H-pyrido[2,3-b][1,4,5]oxathiazepin-2-yl)methyl)thiophen-2-yl)-3-(1-ethyl-4-methyl-1H-benzo[d][1,2,3]triazol-5-yl)propanoic acid;

(S)-3-(1-Ethyl-4-methyl-1H-benzo[d][1,2,3]triazol-5-yl)-2,2-dimethyl-3-(5-methyl-4-(((S)-4-methyl-1,1-dioxido-4,5-dihydrobenzo[f][1,2]thiazepin-2(3H)-yl)methyl)thiophen-2-yl)propenamide;

(S)-3-(5-Chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-fluoro-1H-benzo[d][1,2,3]triazol-5-yl)-2,2-dimethylpropanoic acid;

(S)-3-(4-(((S)-4-Ethyl-1,1-dioxido-4,5-dihydrobenzo[f][1,2]thiazepin-2(3H)-yl)methyl)-5-methylthiazol-2-yl)-3-(1-ethyl-4-methyl-1H-benzo[d][1,2,3]triazol-5-yl)-2,2-dimethylpropanoic acid;

(S)-3-(4-(((S)-4-Ethyl-1,1-dioxido-4,5-dihydrobenzo[f][1,2]thiazepin-2(3H)-yl)methyl)-5-methylthiazol-2-yl)-3-(1-ethyl-4-methyl-1H-benzo[d][1,2,3]triazol-5-yl)-2,2-dimethyl-N-(pyridin-3-yl)propanamide;

(S)-3-(5-Chloro-4-(((S)-4-methyl-1,1-dioxido-8-(trifluoromethyl)-4,5-dihydrobenzo[f][1,2]thiazepin-2(3H)-yl)methyl)thiophen-2-yl)-3-(1-ethyl-4-fluoro-1H-benzo[d][1,2,3]triazol-5-yl)-2,2-dimethylpropanoic acid;

(S)-3-(1-Ethyl-4-methyl-1H-benzo[d][1,2,3]triazol-5-yl)-2,2-dimethyl-3-(5-methyl-4-(((S)-4-methyl-1,1-dioxido-7-(trifluoromethyl)-4,5-dihydrobenzo[f][1,2]thiazepin-2(3H)-yl)methyl)thiazol-2-yl)propanoic acid;

(S)-3-(1-Ethyl-4-methyl-1H-benzo[d][1,2,3]triazol-5-yl)-2,2-dimethyl-3-(5-methyl-4-(((S)-4-methyl-1,1-dioxido-7-(trifluoromethyl)-4,5-dihydrobenzo[f][1,2]thiazepin-2(3H)-yl)methyl)thiazol-2-yl)-N-(pyridin-3-yl)propanamide;

(R)-3-(4-(((R)-4-Ethyl-1,1-dioxido-3,4-dihydro-2H-pyrido[2,3-b][1,4,5]oxathiazepin-2-yl)methyl)-5-methylthiophen-2-yl)-3-(1-ethyl-4-methyl-1H-benzo[d][1,2,3]triazol-5-yl)propanoic acid;

(R)-3-(4-(((R)-4-Ethyl-1,1-dioxido-3,4-dihydro-2H-pyrido[4,3-b][1,4,5]oxathiazepin-2-yl)methyl)-5-methylthiophen-2-yl)-3-(1-ethyl-4-methyl-1H-benzo[d][1,2,3]triazol-5-yl)propanoic acid;

(S)-3-(4-(((S)-4-Ethyl-1,1-dioxido-8-(trifluoromethyl)-4,5-dihydrobenzo[f][1,2]thiazepin-2(3H)-yl)methyl)-5-methylthiazol-2-yl)-3-(1-ethyl-4-methyl-1H-benzo[d][1,2,3]triazol-5-yl)-2,2-dimethyl-N-(pyridin-3-yl)propanamide;

(S)-3-(4-(((S)-4-Ethyl-1,1-dioxido-8-(trifluoromethyl)-4,5-dihydrobenzo[f][1,2]thiazepin-2(3H)-yl)methyl)-5-methylthiazol-2-yl)-3-(1-ethyl-4-methyl-1H-benzo[d][1,2,3]triazol-5-yl)-2,2-dimethylpropanoic acid;

(S)-3-(1-Ethyl-4-methyl-1H-benzo[d][1,2,3]triazol-5-yl)-2,2-dimethyl-3-(1-methyl-5-(((S)-4-methyl-1,1-dioxido-8-(trifluoromethyl)-4,5-dihydrobenzo[f][1,2]thiazepin-2(3H)-yl)methyl)-1H-pyrazol-3-yl)propanoic acid;

(S)-3-(4-(((R)-4-Ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)-2,2-dimethyl-N-(pyridin-3-yl)propanamide;

(S)-3-(1-Ethyl-4-methyl-1H-benzo[d][1,2,3]triazol-5-yl)-2,2-dimethyl-3-(5-methyl-4-(((S)-4-methyl-1,1-dioxido-4,5-dihydrobenzo[f][1,2]thiazepin-2(3H)-yl)methyl)thiophen-2-yl)-N-(pyridin-3-yl)propanamide;

(R)-3-(5-Chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-fluoro-1H-benzo[d][1,2,3]triazol-5-yl)-2,2-dimethylpropanoic acid;

(S)-3-(5-Chloro-4-(((R)-4-ethyl-1,1-dioxido-3,4-dihydro-2H-pyrido[2,3-b][1,4,5]oxathiazepin-2-yl)methyl)thiophen-2-yl)-3-(1-ethyl-4-methyl-1H-benzo[d][1,2,3]triazol-5-yl)-2,2-dimethylpropanoic acid;
(S)-3-(4-(((S)-4-Ethyl-1,1-dioxido-8-(trifluoromethyl)-4,5-dihydrobenzo[f][1,2]thiazepin-2(3H)-yl)methyl)-5-methylthiophen-2-yl)-3-(1-ethyl-4-methyl-1H-benzo[d][1,2,3]triazol-5-yl)-2,2-dimethylpropanoic acid;
(S)-3-(5-Chloro-4-(((R)-4-ethyl-1,1-dioxido-3,4-dihydro-2H-pyrido[4,3-b][1,4,5]oxathiazepin-2-yl)methyl)thiophen-2-yl)-3-(1-ethyl-4-methyl-1H-benzo[d][1,2,3]triazol-5-yl)-2,2-dimethylpropanoic acid;
(R)-3-(5-Chloro-4-(((S)-4-methyl-1,1-dioxido-8-(trifluoromethyl)-4,5-dihydrobenzo[f][1,2]thiazepin-2(3H)-yl)methyl)thiophen-2-yl)-3-(1-ethyl-4-fluoro-1H-benzo[d][1,2,3]triazol-5-yl)-2,2-dimethylpropanoic acid;
(R)-3-(4-(((R)-4-Ethyl-1,1-dioxido-3,4-dihydro-2H-pyrido[2,3-b][1,4,5]oxathiazepin-2-yl)methyl)-5-methylthiophen-2-yl)-5-(1-ethyl-1H-1,2,3-triazol-4-yl)-2,2-dimethylpentanoic acid;
(S)-3-(4-(((R)-4-Ethyl-1,1-dioxido-3,4-dihydro-2H-pyrido[2,3-b][1,4,5]oxathiazepin-2-yl)methyl)-5-methylthiophen-2-yl)-5-(1-ethyl-1H-1,2,3-triazol-4-yl)-2,2-dimethylpentanoic acid;
(S)-3-(4-(((R)-2-Ethyl-2,3-dihydropyrido[2,3-f][1,4]oxazepin-4(5H)-yl)methyl)-5-methylthiophen-2-yl)-3-(1-ethyl-4-methyl-1H-benzo[d][1,2,3]triazol-5-yl)-2,2-dimethylpropanoic acid;
(R)-5-(1-Ethyl-1H-1,2,3-triazol-4-yl)-2,2-dimethyl-3-(5-methyl-4-(((S)-4-methyl-1,1-dioxido-4,5-dihydropyrido[2,3-f][1,2]thiazepin-2(3H)-yl)methyl)thiophen-2-yl)pentanoic acid;
(S)-5-(1-Ethyl-1H-1,2,3-triazol-4-yl)-2,2-dimethyl-3-(5-methyl-4-(((S)-4-methyl-1,1-dioxido-4,5-dihydropyrido[2,3-f][1,2]thiazepin-2(3H)-yl)methyl)thiophen-2-yl)pentanoic acid;
(S)-3-(4-(((R)-4-Ethyl-1,1-dioxido-3,4-dihydro-2H-benzo[b][1,4,5]oxathiazepin-2-yl)methyl)-5-methylthiophen-2-yl)-5-(1-ethyl-1H-1,2,3-triazol-4-yl)-2,2-dimethylpentanoic acid;
(R)-3-(4-(((R)-4-Ethyl-1,1-dioxido-3,4-dihydro-2H-benzo[b][1,4,5]oxathiazepin-2-yl)methyl)-5-methylthiophen-2-yl)-5-(1-ethyl-1H-1,2,3-triazol-4-yl)-2,2-dimethylpentanoic acid; and
(S)-3-(4-(((R)-4-Ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)-2,2-dimethyl-N-(1H-tetrazol-5-yl)propanamide, 0.10Formic acid salt;
or a pharmaceutically acceptable salt thereof.

Compound Preparation

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

The synthesis of the compounds of the general Formula (I) and pharmaceutically acceptable derivatives and salts thereof may be accomplished as outlined below in Schemes 1-20. In the following description, the groups are as defined above for compounds of Formula (I) unless otherwise indicated. Abbreviations are as defined in the Examples section. Starting materials are commercially available or are made from commercially available starting materials using methods known to those skilled in the art.

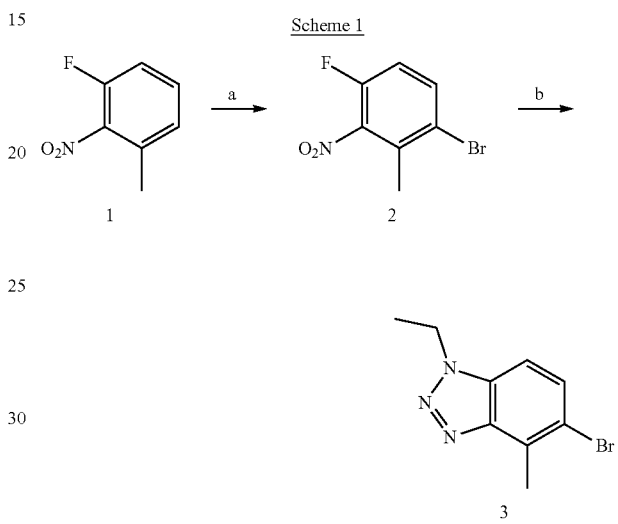

Conditions: a) NBS, TFA, H$_2$SO$_4$; b) i) MeNH$_2$ (or) EtNH$_2$ THF; ii) Zn, HOAc; iii) NaNO$_2$, H$_2$SO$_4$ Scheme 1 shows a general scheme for the preparation of 5-bromo-4-methyl-1-methyl-1H-benzo[d][1,2,3]triazole. Starting with commercially available 1-fluoro-3-methyl-2-nitrobenzene, bromination with NBS provides intermediate 2. Displacement of the fluoride using an appropriate amine followed by zinc metal reduction of the nitro to the aniline and diazotization and cyclization provides the required triazole 3.

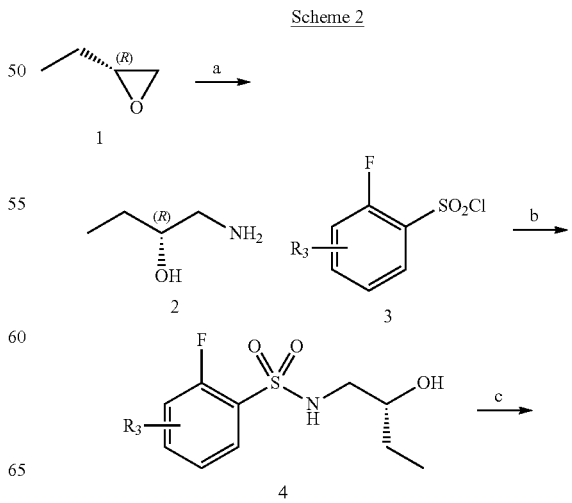

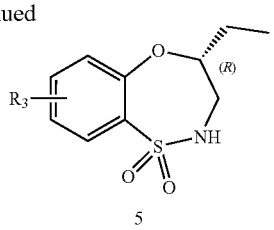

5

Conditions: a) NH₄OH; b) K₂CO₃, THF/H₂O; c) t-BuOK, DMSO

Scheme 2 represents a general scheme for the preparation of sulfonamide 5. In this, (R)-2-ethyloxirane and substituted 2-fluorobenzene-1-sulfonyl chloride depicted as starting material are commercially available. Reaction conditions are as described above in the scheme; however, the skilled artisan will appreciate that certain modifications in the reaction conditions and/or reagents used are possible. Epoxide ring opening of (R)-2-ethyloxirane yields a single enantiomerically pure 2. Sulfonamide formation under basic condition with appropriate amino alcohol to give intermediate 4, followed by displacement of fluoride 3 with potassium tert-butoxide provides the required intermediate 5.

Scheme 3

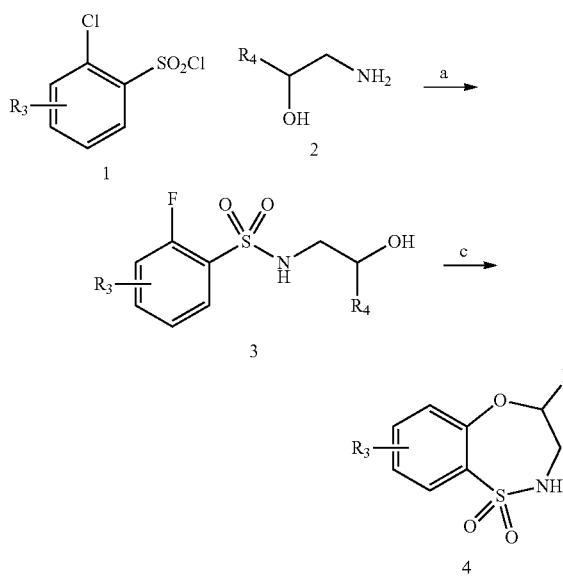

R4 = (R) ethyl, or di-methyl
Conditions: a) K₂CO₃, THF/H₂O; b) t-BuOK, DMSO

Scheme 3 represents a general scheme for the preparation of sulfonamide 4. In this, amino alcohol 2 and substituted 2-cholorobenzene-1-sulfonyl chloride depicted as starting material are commercially available or may be synthesized from readily available materials. Reaction conditions are as described above in the scheme; however, the skilled artisan will appreciate that certain modifications in the reaction conditions and/or reagents used are possible. Sulfonamide formation under basic condition with appropriate amino alcohol and commercially available 2-chloro-pyridine-3-sulfonyl chloride to give intermediate 3, followed by displacement of chloride with potassium tert-butoxide provides the required intermediate 4.

Scheme 4

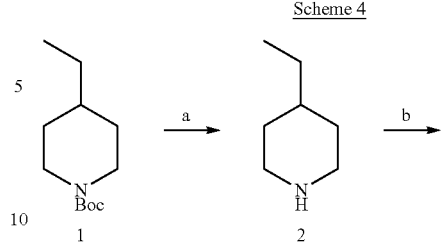

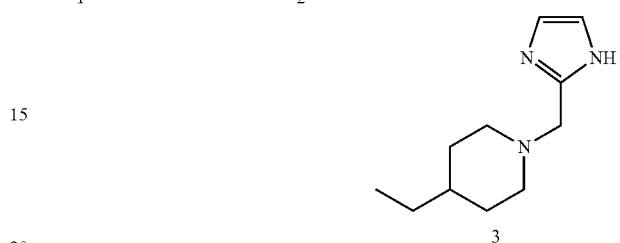

Conditions: a) TFA, DCM; b) IH-imidazole-2-carbaldehyde, titanium(IV) isopropoxide, NaCNBH₃, ethanol Scheme 4 represents a general scheme for the preparation of 1-((1H-imidazol-2-yl)methyl)-4-ethylpiperidine used in the invention. Substituted 1-tert-butyl 4-ethylpiperidine-1-carboxylate depicted as starting material is commercially available. Reaction conditions are as described above in the scheme; however, the skilled artisan will appreciate that certain modifications in the reaction conditions and/or reagents used are possible. Deprotection under acid condition followed by reductive amination reaction provides the required intermediate 3.

Scheme 5

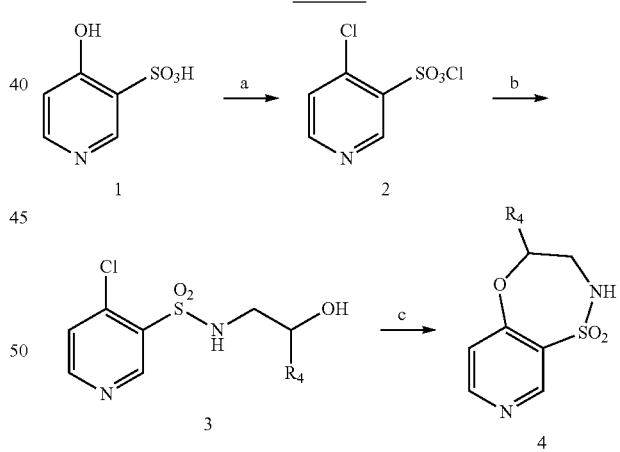

Conditions: a) POCl₃, PCl₅; b) H₂NCH₂CH(R₄)OH, K₂CO₃, THF/H₂O; c) t-BuOK, DMSO

Scheme 5 represents a general scheme for the preparation of 3,4-dihydro-2H-pyrido[4,3-b][1,4,5]oxathiazepine 1,1-dioxide, 4-methyl-3,4-dihydro-2H-pyrido[4,3-b][1,4,5]oxathiazepine 1,1-dioxide, and 4-ethyl-3,4-dihydro-2H-pyrido[4,3-b][1,4,5]oxathiazepine 1,1-dioxide used in the invention. In this, 4-hydroxypyridine-3-sulfonic acid depicted as starting material is commercially available. Reaction with the appropriate aminoalcohol followed by displacement of the fluoride provides the required intermediate 4.

Scheme 6

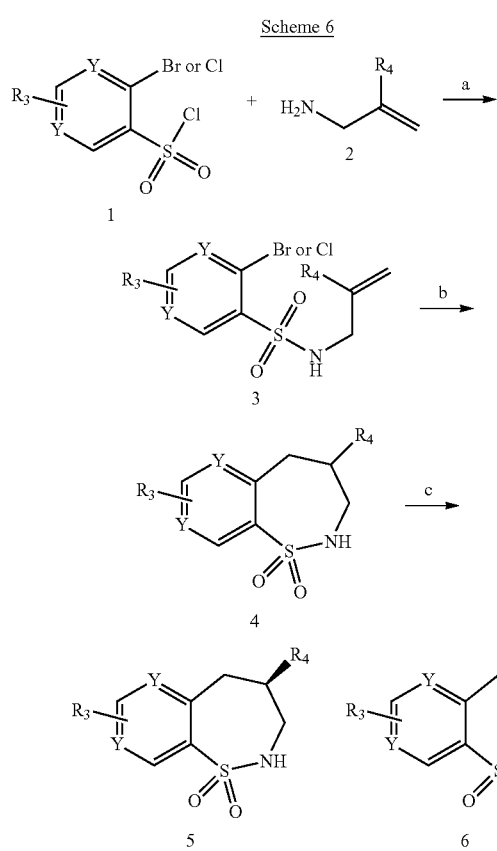

Conditions: a) Et₃N, DCM; b) AIBN, Bu₃SnH, toluene; c) Chiral SFC

Scheme 6 represents a general scheme for the preparation of compounds according to Formula (I). Substituted 2-bromo or chloro benzene-sulfonyl chloride 1 is either commercially available or may be synthesized from readily available materials. Reaction conditions are as described above in the scheme; however, the skilled artisan will appreciate that certain modifications in the reaction conditions and/or reagents used are possible. Sulfonamide formation with the appropriate amine 2 and sulfonyl chloride 1 to give compound 3, is followed by radical cyclization with AIBN to yield the cyclic sulfonamide. Resolution of compound 4 via Chiral SFC produces each enantiomerically pure isomer 5 and 6.

Scheme 7

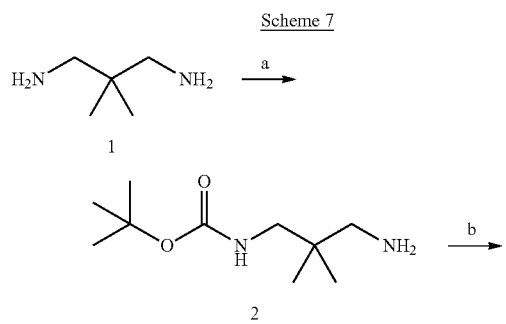

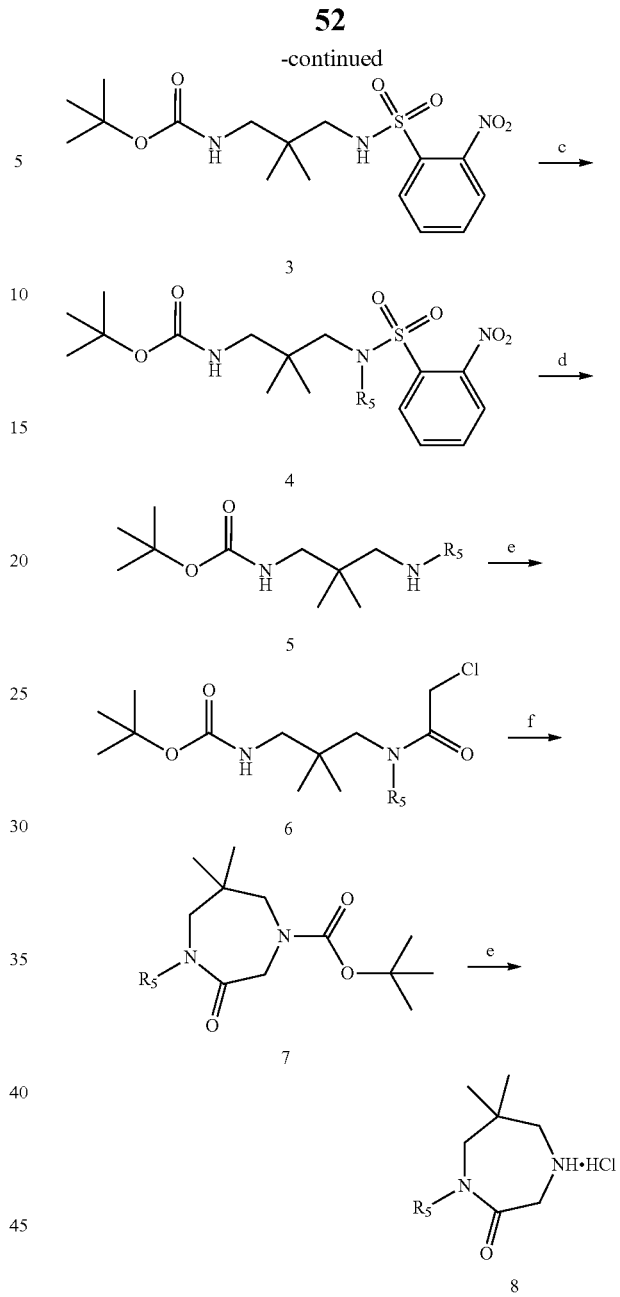

Conditions: a) (Boc)₂O, DCM; b) K₂CO₃, 2-nitrobenzene-1-sulfonyl chloride, DCM; c) R₅I, K₂CO₃, DMF, 90° C.; d) PhSH, K₂CO₃, DMF; e) Et₃N, 2-chloroacetyl chloride, DCM; f) NaH, DMF; g) HCl, dioxane, DCM Scheme 7 represents a general scheme for the preparation of compounds according to Formula (I). 2,2-Dimethylpropane-1,3-diamine 1 is commercially available. Reaction conditions are as described above in the scheme; however, the skilled artisan will appreciate that certain modifications in the reaction conditions and/or reagents used are possible. Mono-amine protection of 1 with Boc group followed by sulfonamide formation with 2-nitrobenzene-1-sulfonyl chloride under basic condition to give compound 3. Treatment of compound 3 with appropriate available iodo at high temperature to give compound 4, followed by deprotection to give amine 5. Compound 5 was reacted with 2-chloroacetyl chloride in the presence of triethylamine to give compound 6. Cyclization was successful with NaH to give lactam 7. Deprotection the Boc group with HCl to give lactam 8 as hydrochloride salt.

Scheme 8

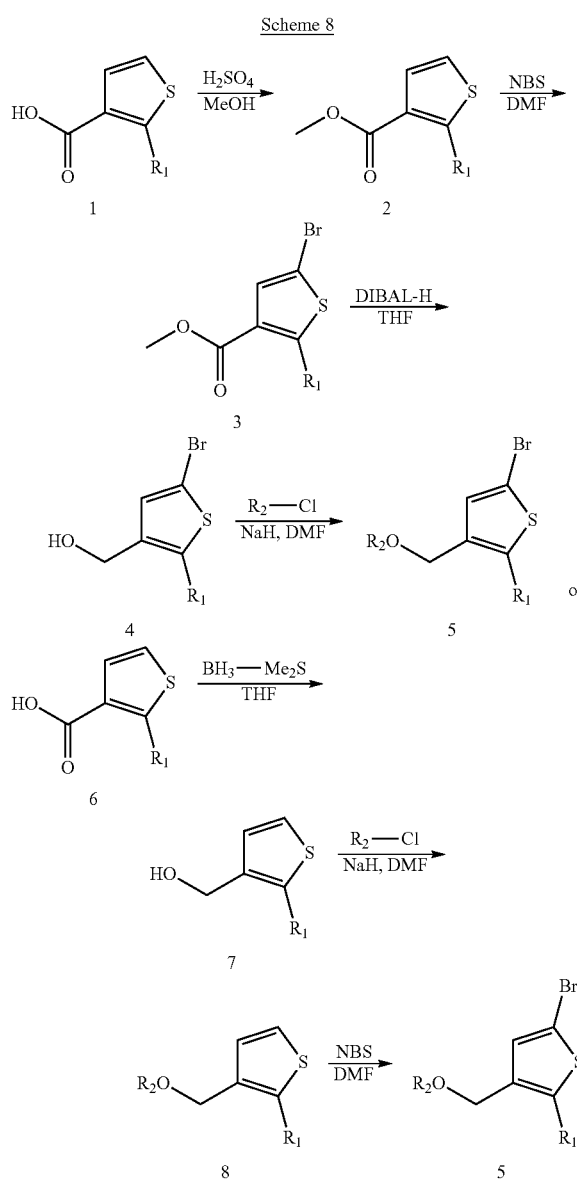

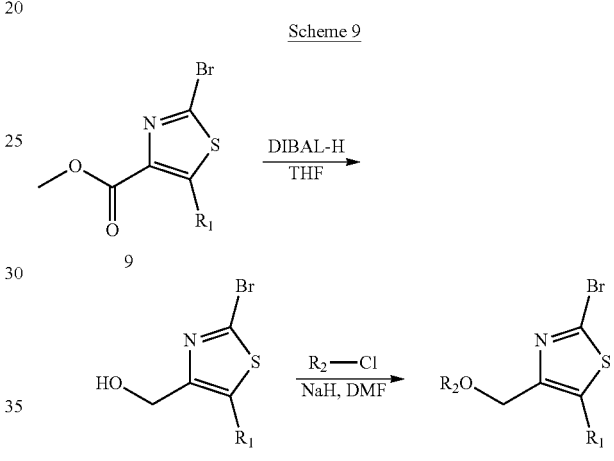

Scheme 8 shows a general scheme for the preparation of substituted thiophenes. In Scheme 8, $R_1$ is $CH_3$ or Cl. $R_2$ is a protecting group linked to an oxygen such as para-methoxy benzyl or tert-butyldimethylsilyl. Starting with the commercially available carboxylic acid methylation with $H_2SO_4$ and methanol provides intermediate 2. Bromination of 2 can be achieved using NBS to provide intermediate 3. Reduction of the carboxylic acid ester group of 3 can be performed with a reducing agent such as DIBAL-H to provide intermediate 4. Alkylation of the alcohol using a strong base and a suitable protecting group provides intermediate 5. An alternate route to substituted thiophenes would start with the reduction of commercially available carboxylic acid 6 with a suitable reducing agent like $BH_3 \cdot Me_2S$ to provide the intermediate 7. Alkylation of the alcohol using a strong base and a suitable protecting group provides intermediate 8. Bromination of 8 can be achieved using NBS to provide intermediate 5.

Scheme 9 shows a general scheme for the preparation of substituted thiazoles. $R_1$ and $R_2$ are defined previously. Starting with the commercially available carboxylic acid ester 9, reduction of the carboxylic acid ester group is achieved with a reducing agent such as DIBAL-H to provide intermediate 10. Alkylation of the alcohol using a strong base and a suitable protecting group provides intermediate 11.

Scheme 10

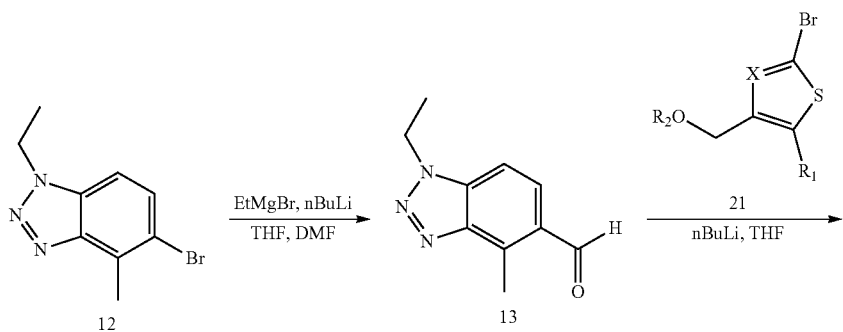

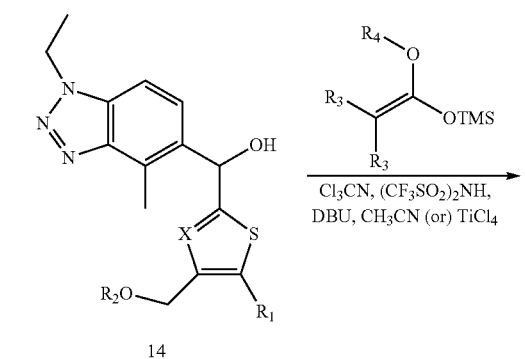
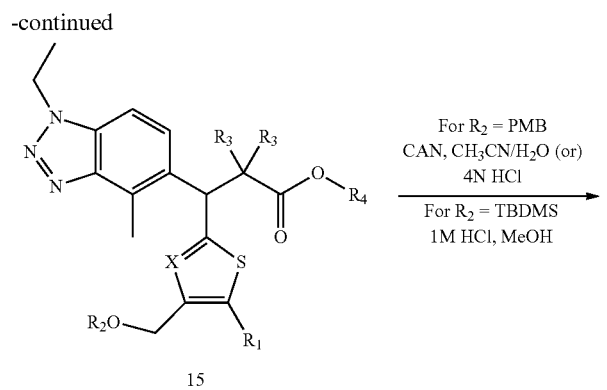
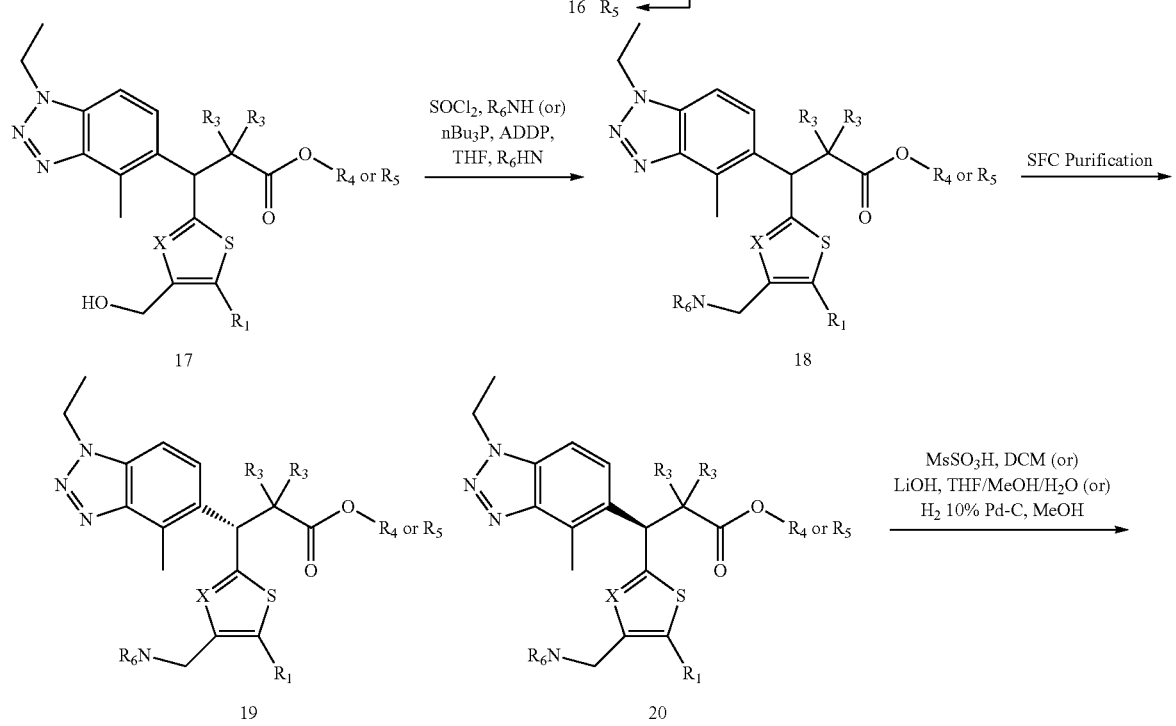
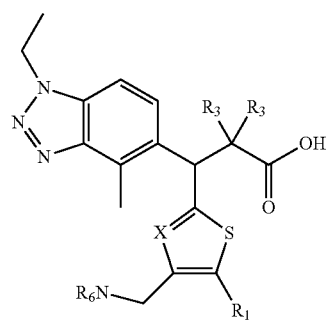

Scheme 10 represents a general scheme for the preparation of compounds according to Formula (I). In Scheme 3 $R_1$ and $R_2$ are previously defined. $R_3$ is either H or $CH_3$. $R_4$ is alkyl. $R_5$ is benzyl. X is either C or N. $R_6$ are amines as depicted in Schemes 2-7. Starting with 5-bromo-4-methyl-1-methyl-1H-benzo[d][1,2,3]triazole 12, whose preparation is depicted in Scheme 1, formylation of the bromide is performed using a metal-halogen exchange reaction which is quenched with DMF to provide 13. A metal halogen exchange reaction is then performed on 21, whose preparation is depicted in Schemes 8 and 9, after which, aldehyde 5 is added to provide the secondary benzylic alcohol 14.

Intermediate 15, arises from treatment of alcohol 14 with the appropriate silylketene acetal in the presence of a Lewis acid or via one-pot Bronsted base/Bronsted acid system. At this point, the alkyl ester 15 can be converted to the benzyl ester 16 via hydrolysis of the alkyl ester with base and quenching the carboxylic acid salt with benzyl bromide. One skilled in the art could also envisage using a substituted benzyl group such as para-methoxy benzyl bromide or dimethoxy benzyl bromide. The alcohol can be deprotected with either ceric ammonium nitrate or 4N HCl, where $R_2$=PMB, to provide 17. In the case where $R_2$=TBDMS, 1N HCl in Methanol can be used to deprotect the alcohol to also provide 17. Activation of the benzylic alcohol to a benzylic chloride using a chlorinating reagent like thionyl chloride, and subsequent displacement of the chloride with a suitable electrophile such as a secondary amine or a sulfonamide affords 18. Alternatively the benzylic alcohol may also be displaced by a suitably acidic nucleophile, such as a sulfonamide, under Mitsunobu conditions using tri-n-butyl phosphine and ADDP, to afford 18. The pure enantiomers of 18 can be separated using chiral SFC chromatography to provide 19 and 20. Alternatively, chiral SFC chromatography could be performed on the compounds 15 or 16 or 17 to provide pure enantiomers which could then be carried on through the above scheme as pure enantiomers. The ester groups on 19 and 20 can be removed under acidic or basic conditions to provide 21. In the case where the ester is benzylic, hydrogenation conditions could also be employed.

Scheme 11

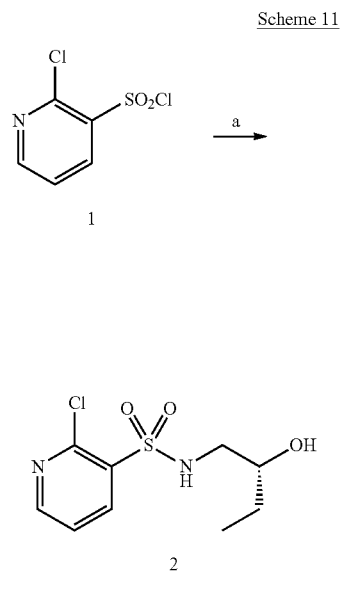

Conditions: a) (R)—H$_2$NCH$_2$CH(Et)OH, H$_2$CO$_3$, THF/H$_2$O; b) t-BuOK, DMSO Scheme 11 represents a general scheme for the preparation of (R)-4-ethyl-3,4-dihydro-2H-pyrido[2,3-b][1,4,5]oxathiazepine 1,1-dioxide, used in the invention. In this, the 2-chloropyridine-3-sulfonyl chloride depicted as starting material is commercially available. Reaction with the appropriate amino alcohol followed by displacement of the chloride with the alcohol in the presence of a base provides the required intermediate 3.

Scheme 12

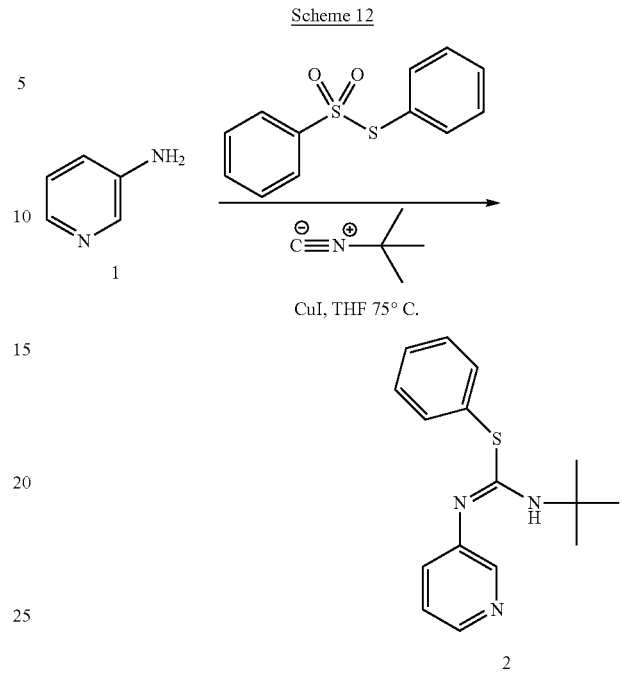

Scheme 12 represents a scheme for the preparation of phenyl (E)-N-(tert-butyl)-N'-(pyridin-3-yl)carbamimidothioate, used in the invention. In this, pyridin-3-amine depicted as starting material is commercially available. The reaction with 2-isocyano-2-methylpropane and S-phenyl benzenesulfonothioate in 2-methyltetrahydrofuran is heated with copper(I) iodide and provides the required intermediate 2.

Scheme 13

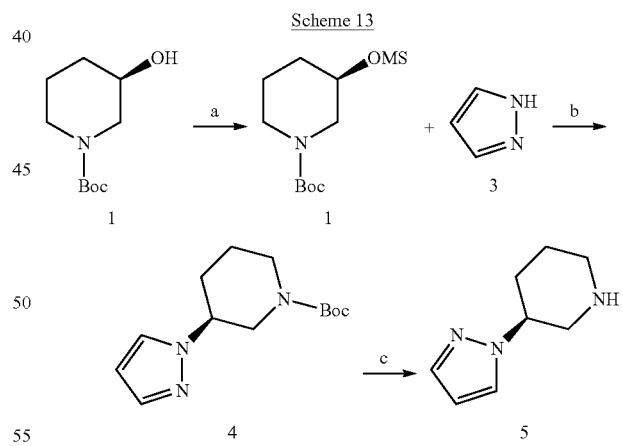

Conditions: a) TEA, MsCl; b) NaH, DMF 0° C. to 50° C., c) 4M HCl/1,4 dioxane

Scheme 13 shows a general scheme for the preparation of (S)-3-(1H-pyrazol-1-yl)piperidine. Starting with the commercially available (R)-tert-butyl 3-hydroxypiperidine-1-carboxylate 1, the alcohol is converted to the mesylate with methanesulfonic acid to provide intermediate 2. Alkylation of commercially available 1H-pyrazole 3 using a strong base and 2 provides intermediate 4. Deprotection of the amine is achieved using 4N HCl in 1,4 dioxane to provide 5.

Scheme 14
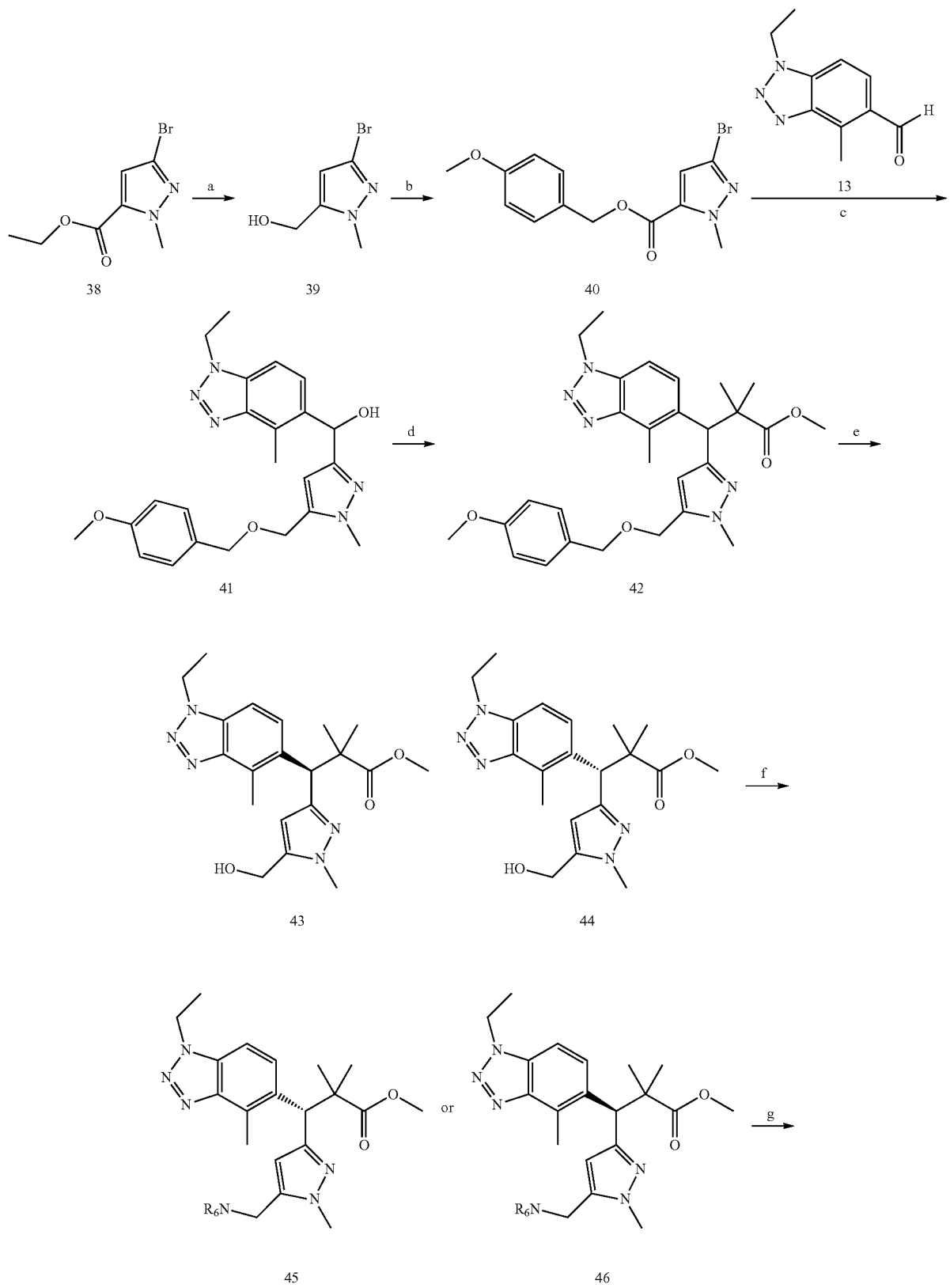

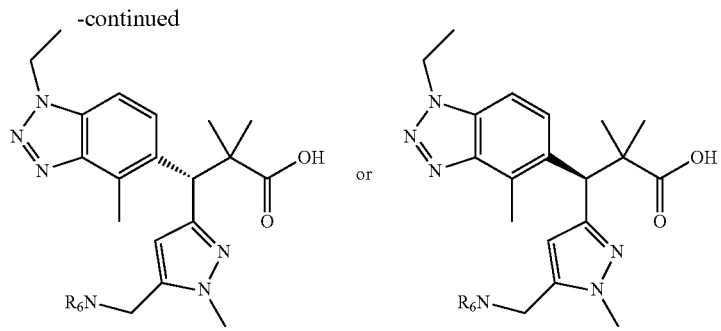

Conditions: a) DIBAL-H, THF, 0° C.; b) PMB-Cl, NaH, DMF 0° C., c) EtMgBr, nBuLi, THF, -40° C., d), silylketene acetal, 2,2,2-trichloroacetonitrile, DBU, Lewis acid, Chiral resolution, e) CAN or 4N HCl, f) nBu₃Ph, ADDP, HNR₆, g). LiOH THF/MeOH/H₂O Scheme 14 represents a general scheme for the preparation of compounds according to Formula (I). R₆ is as previously defined. The commercially available carboxylic acid ester 38 is reduced with a suitable reducing agent like DIBAL-H to provide the intermediate 39. Intermediate 40 is prepared by alkylation of 39 using a strong base and para-methoxybenzyl chloride. A metal halogen exchange reaction is then performed on 40, after which aldehyde 13, is added to provide the secondary benzylic alcohol 41. Intermediate 42, arises from treatment of alcohol 41 with the appropriate silylketene acetal in the presence of a Lewis acid or via one-pot Bronsted base/Bronsted acid system. The protected alcohol can be deprotected with either ceric ammonium nitrate or 4N HCl, to provide the racemic alcohol which can be resolved with chiral SFC or HPLC to provide single enantiomers which could then be carried on through the above scheme as single enantiomers 43 and 44. Activation of the benzylic alcohol of either isomer to a benzylic chloride using a chlorinating reagent like thionyl chloride, and subsequent displacement of the chloride with a suitable electrophile such as a secondary amine or a sulfonamide affords 45 or 46. Alternatively the benzylic alcohol may also be displaced by a suitably acidic nucleophile, such as a sulfonamide, under Mitsunobu conditions using tri-n-butyl phosphine and ADDP, to afford 45 or 46. The ester groups on 45 and 46 can be removed under acidic or basic conditions to provide 47 or 48.

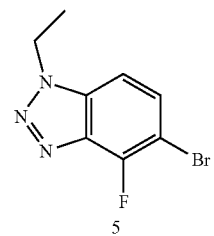

Conditions: a) EtNH₂, EtOH, 0° C. b) NBS, DMF; c) Raney Ni, NH₂NH₂-H₂O, EtOH, 0° C., d) NaNO₂, H₂SO₄, Scheme 15 shows a general scheme for the preparation of 5-bromo-1-ethyl-4-fluoro-1H-benzo[d][1,2,3]triazole. Starting with commercially available 1,3-difluoro-2-nitrobenzene, a fluoride is displaced with an appropriate amine to afford intermediate 2. Bromination with NBS provides intermediate 3. Zinc metal reduction of the nitro to the aniline provides 4 and diazotization and cyclization affords the required triazole 5.

Scheme 15

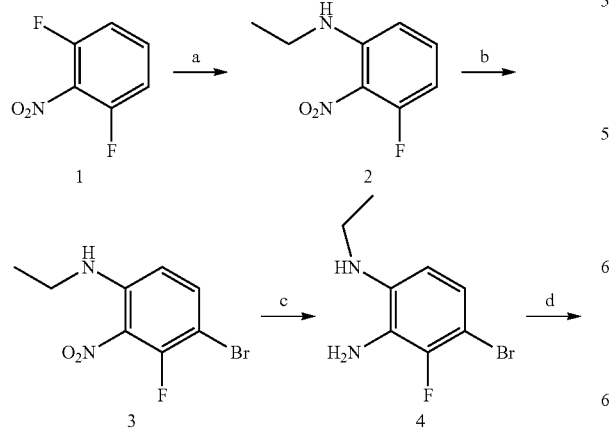

Scheme 16

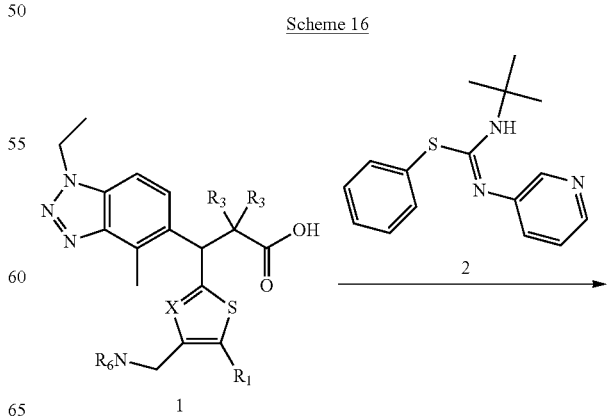

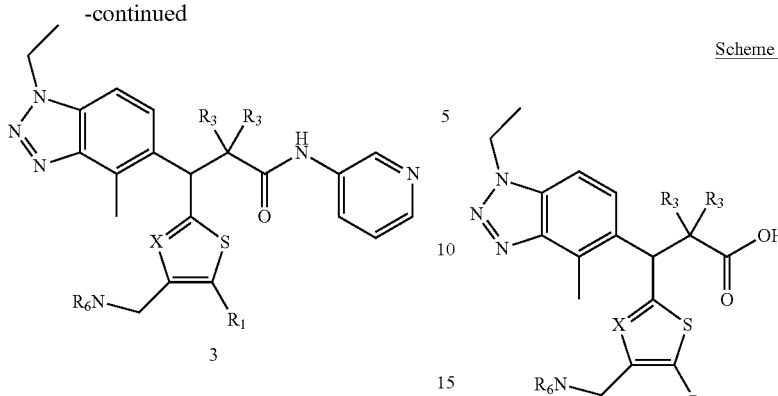

Scheme 16 represents a general scheme for the preparation of compounds according to Formula (I). Carboxylic acid 1 and phenyl (E)-N-(tert-butyl)-N'-(pyridin-3-yl)carbamimidothioate, was heated with a catalyst such as ferric acetylacetonate to provide the required compound 3. One skilled in the art could envisage performing this amide coupling reaction by other methods including, but not limited to the activation of the carboxylic acid with a chlorinating reagent like thionyl chloride, and subsequent displacement of the chloride with a suitable amine. Alternatively, the amide could be formed by activation of the carboxylic acid with amide coupling reagents and subsequent displacement of the activated carboxylic acid with a suitable amine.

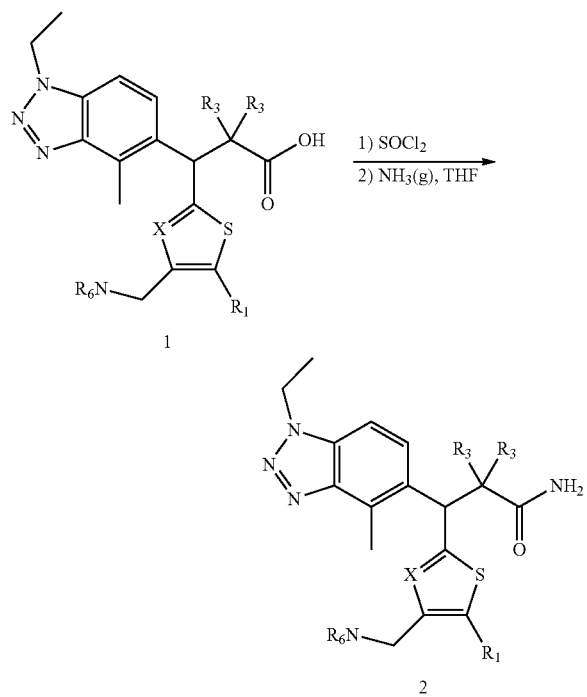

Scheme 17 represents a general scheme for the preparation of compounds according to Formula (I). Carboxylic acid 1 is activated with a chlorinating reagent like thionyl chloride followed by the subsequent displacement of the chloride with a source of ammonia such as ammonia gas to provide 2.

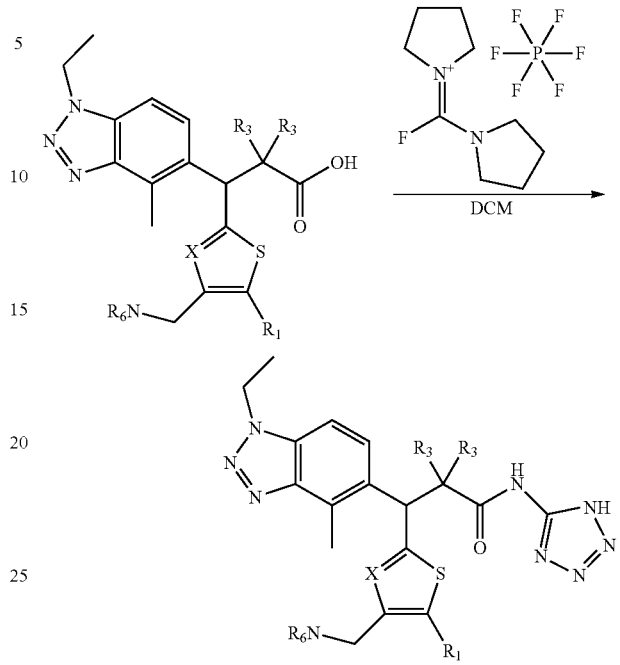

Scheme 18 represents a general scheme for the preparation of compounds according to Formula (I). Carboxylic acid 1 is activated with the coupling agent 1-(fluoro(pyrrolidin-1-yl)methylene)pyrrolidin-1-ium hexafluorophosphate(V) (BTFFH) in DCM followed by heating with the commercially available amine 1H-tetrazol-5-amine. One skilled in the art could envisage performing this amide coupling reaction by other methods including, but not limited to, the activation of the carboxylic acid with a chlorinating reagent like thionyl chloride, and subsequent displacement of the chloride with a suitable amine. Alternatively, the amide could be formed by the method in Scheme X.

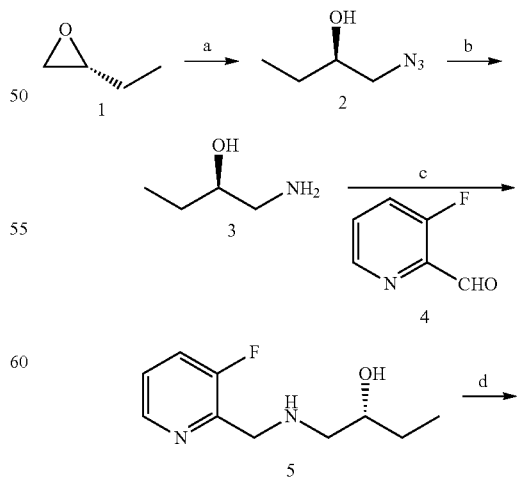

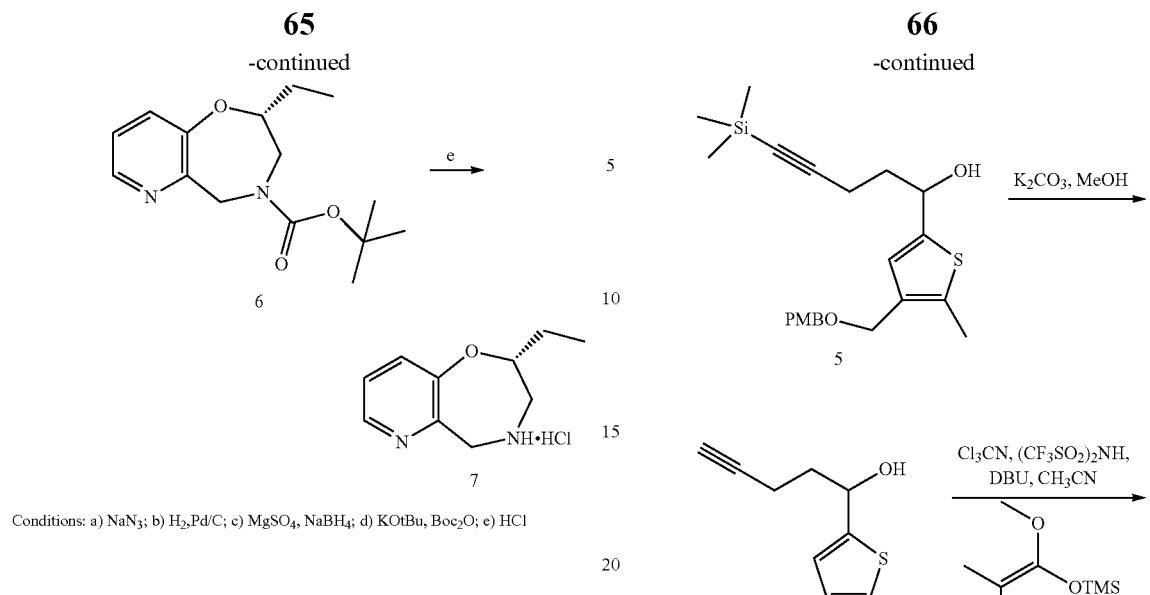

Conditions: a) NaN₃; b) H₂,Pd/C; c) MgSO₄, NaBH₄; d) KOtBu, Boc₂O; e) HCl

Scheme 19 represents a general scheme for the preparation of (R)-2-Ethyl-2,3,4,5-tetrahydropyrido[2,3-f][1,4] oxazepine, hydrochloride 7, used in the invention. Reaction conditions are as described above in the scheme; however, the skilled artisan will appreciate that certain modifications in the reaction conditions and/or reagents used are possible. The (R)-1-azidobutan-2-ol 2 is prepared from the commercially available (R)-2-ethyloxirane 1 and an azide source such as sodium azide. The azide can be reduced using hydrogenation conditions and a catalyst such as palladium on carbon to provide 3. A skilled artisan will appreciate that 3 can be prepared directly from the reaction of (R)-2-ethyloxirane and an ammonia source such as ammonium hydroxide. A reductive amination reaction is then performed using the commercially available 3-fluoropicolinaldehyde and 3, using sodium borohydride. Displacement of the fluoride with potassium-t-butoxide followed by amidation of the amine with Boc-anhydride provides 6. The carbamate is deprotected with a suitable acid, such as HCl, to provide the intermediate 7.

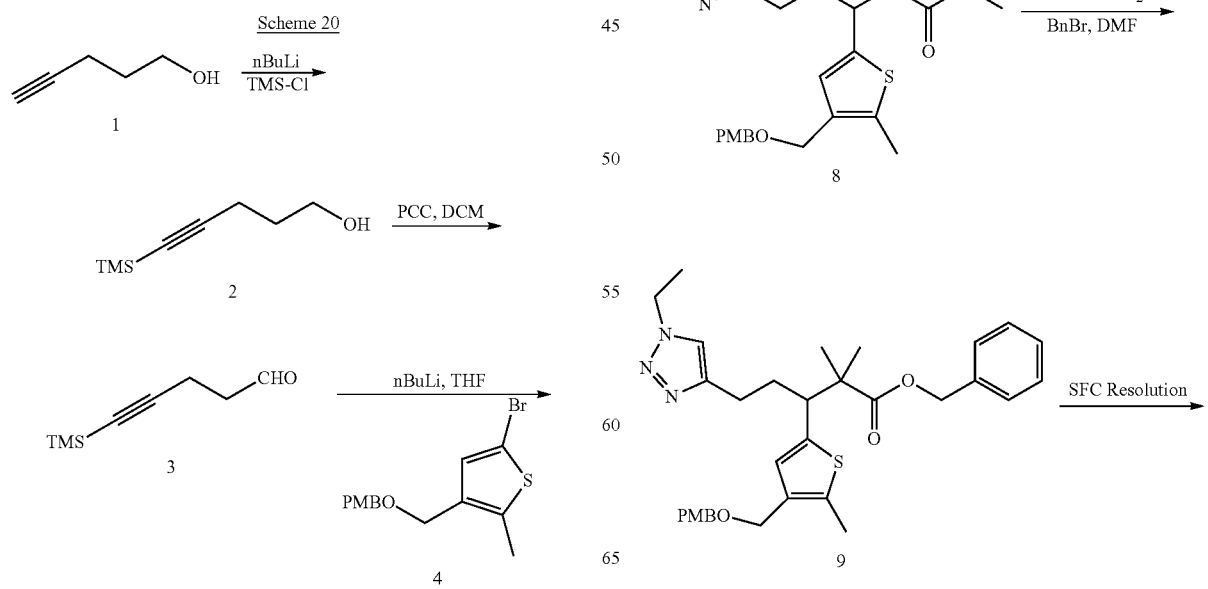

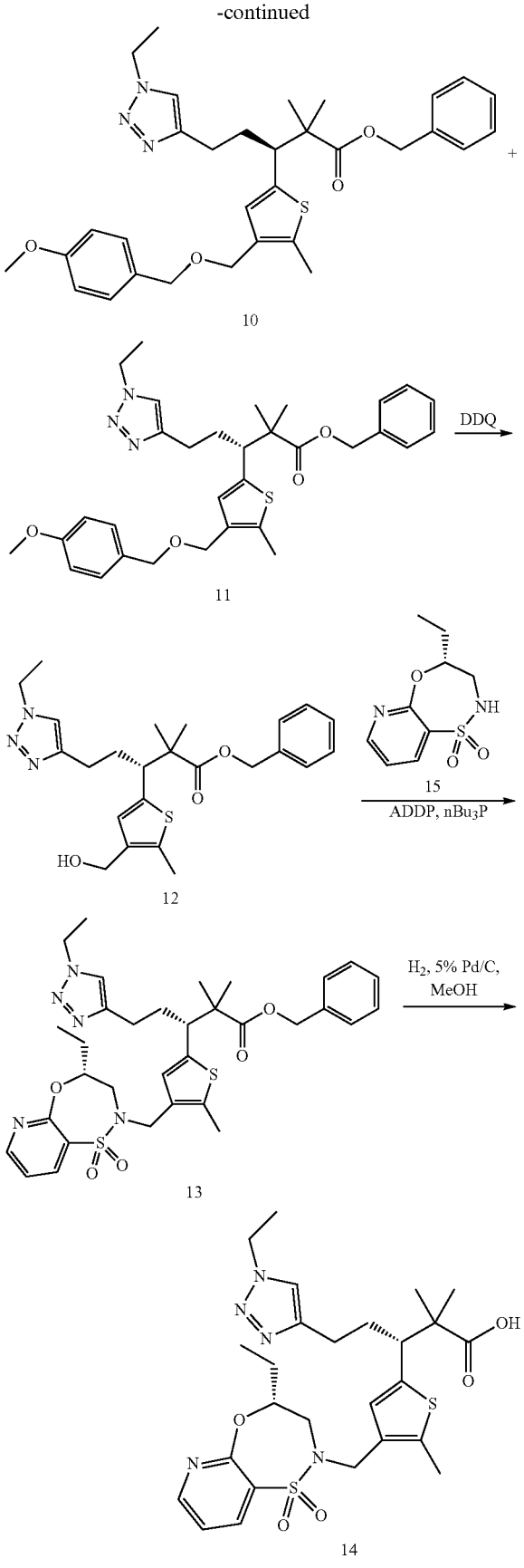

Scheme 20 represents a general scheme for the preparation of compounds according to Formula (I). Intermediate 2 is prepared by the substitution of the alkyne with trimethylsilyl chloride and nBuLi. Intermediate 3 is prepared by the oxidation of the aceylenic alcohol with PCC in DCM. One skilled in the art could also envisage using other suitable alcohol oxidation methods to perform this conversion. A metal halogen exchange reaction is then performed on 4, after which aldehyde 3 is added to provide the secondary benzylic alcohol 5. Deprotection of the alkyene is performed using $K_2CO_3$ in MeOH to afford 6.

Intermediate 7, arises from treatment of alcohol 6 with the appropriate silylketene acetal via a one-pot Bronsted base/Bronsted acid system. Intermediate 7 is subjected to a click reaction using sodium azide and ethyl iodide with a copper catalyst to afford the triazole 8. At this point, the alkyl ester 8 can be converted to the benzyl ester 9 via hydrolysis of the alkyl ester with base and quenching the carboxylic acid salt with benzyl bromide. One skilled in the art could also envisage using a substituted benzyl group such as paramethoxy benzyl bromide or dimethoxy benzyl bromide as a protecting group. Racemic compound 9 is resolved with chiral SFC or HPLC to provide single enantiomers which are then carried on separately through the above scheme as single enantiomers 10 and 11. The protected benzyl alcohol of either isomer is deprotected with DDQ to provide 12. One skilled in the art could also envisage using other suitable oxidative or acidic methods to perform this reaction. The benzylic alcohol of either isomer is displaced by sulfonamide 15 under Mitsunobu conditions using tri-n-butyl phosphine and ADDP, to afford 13. Alternatively, activation of the benzylic alcohol of either isomer to a benzylic chloride using a chlorinating reagent like thionyl chloride, and subsequent displacement of the chloride with a suitable nucleophile such as a secondary amine or a sulfonamide affords 13. The benzyl ester on 13 can be removed under hydrogenation conditions using Pd on carbon to provide 14. Alternatively, the ester can be removed under acidic or basic hydrolysis conditions to provide 14.

Biological Activity

As stated above, the compounds according to Formula I are NRF2 activators, and are useful in the treatment or prevention of human diseases that exhibit oxidative stress components such as respiratory and non-respiratory disorders, including COPD, asthma, ALI, ARDS, fibrosis, chronic and acute asthma, lung disease secondary to environmental exposures, acute lung infection, chronic lung infection, α1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Nonalcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

The biological activity of the compounds according to Formula I can be determined using any suitable assay for determining the activity of a candidate compound as a NRF2 activator, as well as tissue and in vivo models.

The biological activity of the compounds of Formula (I) are demonstrated by the following tests.

BEAS-2B NQO1 MTT Assay

NAD(P)H:quinone oxidoreductase 1 (NQO1), also called DT diaphorase, is a homodimeric FAD-containing enzyme that catalyzes obligatory NAD(P)H-dependent two-electron reductions of quinones and protects cells against the toxic and neoplastic effects of free radicals and reactive oxygen species arising from one-electron reductions. The transcription of NQO1 is finely regulated by NRF2, and thus NQO1 activity is a good marker for NRF2 activation. On day one, frozen BEAS-2B cells (ATCC) were thawed in a water bath, counted, and re-suspended at a concentration of 250,000 cells/mL. Fifty microliters of cells were plated in 384 well black clear-bottomed plates. Plates were incubated at 37° C., 5% $CO_2$ overnight. On day two, plates were centrifuged and 50 nL of compound or controls were added to the cells. Plates were then incubated at 37° C., 5% $CO_2$ for 48 hours. On day four, medium was aspirated from the plate and crude cell lysates were made by adding 13 uL of 1× Cell Signaling Technologies lysis buffer with 1 Complete, Mini, EDTA-free Protease Inhibitor Tablet (Roche) for each 10 mL of lysis buffer. After lysis plates were incubated for 20 minutes at room temperature. Two microliters of lysate were removed for use in Cell Titer Glo assay (Promega) and MTT cocktail was prepared (Prochaska et. al. 1998) for measurement of NQO1 activity. Fifty microliters of MTT cocktail is added to each well, plate is centrifuged, and analyzed on an Envision plate reader (Perkin Elmer) using Absorbance 570 nm label for 30 minutes. Product formation was measured kinetically and the $pEC_{50}$ of NQO1 specific activity induction was calculated by plotting the change in absorbance (Delta OD/min) versus the log of compound concentration followed by 3-parameter fitting.

$pEC_{50}$ is the negative log of the $EC_{50}$.

All examples described herein possessed NQO1 specific enzyme activity in BEAS-2B cells with $EC_{50}$s between >10 μM-<1 nM unless otherwise noted (see table below). $EC_{50}$s<1 nM (+++++), $EC_{50}$s 1 nM-10 nM (++++), $EC_{50}$s 10 nM-100 nM (+++), $EC_{50}$s 100 nM-1 uM (++), $EC_{50}$s 1 uM-10 uM (+), $EC_{50}$s>10 uM (−), or were not determined (ND).

| Ex # | $EC_{50}$ |
|---|---|
| 1 | ++ |
| 2 | + |
| 3 | +++++ |
| 4 | ++ |
| 5 | +++ |
| 6 | +++ |
| #7 | +++++ |
| 8 | ++++ |
| #9 | +++++ |
| #10 | +++++ |
| 11 | +++ |
| 12 | ++++ |
| #13 | ++++ |
| 14 | +++ |
| 15 | ++++ |
| 16 | ++++ |
| 17 | ++++ |
| #18 | +++++ |
| #19 | +++++ |
| 20 | +++ |
| 21 | ++ |
| 22 | +++ |

* in some determinations $EC_{50}$ values were > 10 uM
in some determinations $EC_{50}$ values were < 170 pM

| Ex # | $EC_{50}$ |
|---|---|
| 23 | + |
| 24 | ++ |
| 25 | ++ |
| 26 | ++++ |
| 27 | +++++ |
| 28 | ++ |
| 29 | ++++ |
| 30 | ++ |
| 31 | ++ |
| 32 | ++ |
| 33 | +++++ |
| 34 | ++ |
| 35 | ++ |
| 36 | ++ |
| 37 | ++ |
| 38 | +++ |
| 39 | +++ |
| 40 | +++ |
| 41 | +++++ |
| 42 | +++ |
| 43 | +++ |
| 44 | +++++ |
| 45 | +++ |
| 46 | +++ |
| 47 | +++ |
| 48 | +++ |
| *49 | +++++ |
| 50 | ++++ |
| 51 | ++++ |
| 52 | ++++ |
| 53 | +++++ |
| 54 | +++++ |
| *55 | +++++ |
| 56 | +++++ |
| 57 | +++++ |
| 58 | ++++ |
| 59 | ++++ |
| 60 | ++++ |
| 61 | ++++ |
| 62 | ++++ |
| 63 | ++++ |
| 64 | +++++ |
| 65 | +++ |

Methods of Use

The compounds of the invention are NRF2 activators, and are useful in the treatment or prevention of respiratory and non-respiratory disorders, including COPD, asthma, ALI, ARDS, fibrosis, chronic asthma and acute asthma, lung disease secondary to environmental exposures, acute lung infection, chronic lung infection, α1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

Accordingly, in another aspect the invention is directed to methods of treating such conditions.

The methods of treatment of the invention comprise administering a safe and effective amount of a compound according to Formula I or a pharmaceutically-acceptable salt thereof to a patient in need thereof.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human or other animal.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical dosages for oral administration range from 1 mg to 1000 mg per person per day. Preferred dosages are 1-500 mg once daily, more preferred is 1-100 mg per person per day. IV dosages range form 0.1-000 mg/day, preferred is 0.1-500 mg/day, and more preferred is 0.1-100 mg/day. Inhaled daily dosages range from 10 ug-10 mg/day, with preferred 10 ug-2 mg/day, and more preferred 50uug-500 ug/day.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, ethers, esters, thioesters, carbonates, and carbamates, are well known to those skilled in the art.

Compositions

The compounds of the invention will normally, but not necessarily, be formulated into pharmaceutical compositions prior to administration to a patient. Accordingly, in another aspect the invention is directed to pharmaceutical compositions comprising a compound of the invention and one or more pharmaceutically-acceptable excipient.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 1 mg to 1000 mg.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

In another aspect, the invention is directed to a dosage form adapted for administration to a patient parenterally including subcutaneous, intramuscular, intravenous or intradermal. Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In another aspect, the invention is directed to a dosage form adapted for administration to a patient by inhalation. For example, the compound of the invention may be inhaled into the lungs as a dry powder, an aerosol, a suspension, or a solution.

Dry powder compositions for delivery to the lung by inhalation typically comprise a compound of the invention as a finely divided powder together with one or more pharmaceutically acceptable excipients as finely divided powders. Pharmaceutically acceptable excipients particularly suited for use in dry powders are known to those skilled in the art and include lactose, starch, mannitol, and mono-, di-, and polysaccharides.

The dry powder compositions for use in accordance with the present invention are administered via inhalation devices. As an example, such devices can encompass capsules and cartridges of for example gelatin, or blisters of, for example, laminated aluminum foil. In various embodiments, each capsule, cartridge or blister may contain doses of composition according to the teachings presented herein. Examples of inhalation devices can include those intended for unit dose or multi-dose delivery of composition, including all of the devices set forth herein. As an example, in the case of multi-dose delivery, the formulation can be pre-metered (e.g., as in Diskus®, see GB2242134, U.S. Pat. Nos. 6,032,666, 5,860,419, 5,873,360, 5,590,645, 6,378,519 and 6,536,427 or Diskhaler, see GB 2178965, 2129691 and 2169265, U.S. Pat. Nos. 4,778,054, 4,811,731, 5,035,237) or metered in use (e.g., as in Turbuhaler, see EP 69715, or in the devices described in U.S. Pat. No. 6,321,747). An example of a unit-dose device is Rotahaler (see GB 2064336). In one embodiment, the Diskus® inhalation device comprises an elongate strip formed from a base sheet having a plurality of recesses spaced along its length and a lid sheet peelably sealed thereto to define a plurality of containers, each container having therein an inhalable formulation containing the compound optionally with other excipients and additive taught herein. The peelable seal is an engineered seal, and in one embodiment the engineered seal is a hermetic seal. Preferably, the strip is sufficiently flexible to be wound into a roll. The lid sheet and base sheet will preferably have leading end portions which are not sealed to one another and at least one of the leading end portions is constructed to be attached to a winding means. Also, preferably the engineered seal between the base and lid sheets extends over their whole width. The lid sheet may preferably be peeled from the base sheet in a longitudinal direction from a first end of the base sheet.

A dry powder composition may also be presented in an inhalation device which permits separate containment of two different components of the composition. Thus, for example, these components are administrable simultaneously but are stored separately, e.g., in separate pharmaceutical compositions, for example as described in WO 03/061743 A1 WO 2007/012871 A1 and/or WO2007/068896, as well as U.S. Pat. Nos. 8,113,199, 8,161,968, 8,511,304, 8,534,281, 8,746,242 and 9,333,310.

In one embodiment an inhalation device permitting separate containment of components is an inhaler device having two peelable blister strips, each strip containing pre-metered doses in blister pockets arranged along its length, e.g., multiple containers within each blister strip, e.g., as found in ELLIPTA®. Said device has an internal indexing mechanism which, each time the device is actuated, peels opens a pocket of each strip and positions the blisters so that each newly exposed dose of each strip is adjacent to the manifold which communicates with the mouthpiece of the device. When the patient inhales at the mouthpiece, each dose is simultaneously drawn out of its associated pocket into the manifold and entrained via the mouthpiece into the patient's respiratory tract. A further device that permits separate containment of different components is DUOHALER™ of Innovata. In addition, various structures of inhalation devices provide for the sequential or separate delivery of the pharmaceutical composition(s) from the device, in addition to simultaneous delivery.

Aerosols may be formed by suspending or dissolving a compound of the invention in a liquefied propellant. Suitable propellants include halocarbons, hydrocarbons, and other liquefied gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of the invention will typically be administered to a patient via a metered dose inhaler (MDI). Such devices are known to those skilled in the art.

The aerosol may contain additional pharmaceutically acceptable excipients typically used with multiple dose inhalers such as surfactants, lubricants, cosolvents and other excipients to improve the physical stability of the formulation, to improve valve performance, to improve solubility, or to improve taste.

Suspensions and solutions comprising a compound of the invention may also be administered to a patient via a nebulizer. The solvent or suspension agent utilized for nebulization may be any pharmaceutically acceptable liquid such as water, aqueous saline, alcohols or glycols, e.g., ethanol, isopropyl alcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically acceptable excipients may be added to the suspension or solution. The compound of the invention may be stabilized by the addition of an inorganic acid, e.g., hydrochloric acid, nitric acid, sulfuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of the invention. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

The compounds of Formula (I) and pharmaceutically acceptable salts thereof may be used in combination with one or more other agents which may be useful in the prevention or treatment of allergic disease, inflammatory disease, autoimmune disease, for example; antigen immunotherapy, anti-histamines, corticosteroids, (eg fluticasone propionate, fluticasone furoate, beclomethasone dipropionate, budesonide, ciclesonide, mometasone furoate, triamcinolone, flunisolide), NSAIDs, leukotriene modulators (e.g. montelukast, zafirlukast, pranlukast), iNOS inhibitors, tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g. sodium 3-(3-(tert-butylthio)-1-(4-(6-ethoxypyridin-3-yl)benzyl)-5-((5-methylpyridin-2-yl)methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-IgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents).

Suitably, for the treatment of asthma, compounds or pharmaceutical formulations of the invention may be administered together with an anti-inflammatory agent such as, for example, a corticosteroid, or a pharmaceutical formulation thereof. For example, a compound of the invention may be formulated together with an anti-inflammatory agent, such as a corticosteroid, in a single formulation, such as a dry powder formulation for inhalation. Alternatively, a pharmaceutical formulation comprising a compound of the invention may be administered in conjunction with a pharmaceutical formulation comprising an anti-inflammatory agent, such as a corticosteroid, either simultaneously or sequentially. In one embodiment, a pharmaceutical formulation comprising a compound of the invention and a pharmaceutical formulation comprising an anti-inflammatory agent, such as a corticosteroid, may each be held in device suitable for the simultaneous administration of both formulations via inhalation.

Suitable corticosteroids for administration together with a compound of the invention include, but are not limited to, fluticasone furoate, fluticasone propionate, beclomethasone diproprionate, budesonide, ciclesonide, mometasone furoate, triamcinolone, flunisolide and prednisilone. In one embodiment of the invention a corticosteroid for administration together with a compound of the invention via inhalation includes fluticasone furoate, fluticasone propionate, beclomethasone diproprionate, budesonide, ciclesonide, mometasone furoate, and, flunisolide.

Suitably, for the treatment of COPD, compounds or pharmaceutical formulations of the invention may be administered together with one or more bronchodilators, or pharmaceutical formulations thereof. For example, a compound of the invention may be formulated together with one or more bronchodilators in a single formulation, such as a dry powder formulation for inhalation. Alternatively, a pharmaceutical formulation comprising a compound of the invention may be administered in conjunction with a pharmaceutical formulation comprising one or more bronchodilators, either simultaneously or sequentially. In a further alternative, a formulation comprising a compound of the invention and a bronchodilator may be administered in conjunction with a pharmaceutical formulation comprising a further bronchodilator. In one embodiment, a pharmaceutical formulation comprising a compound of the invention and a pharmaceutical formulation comprising one or more bronchodilators may each be held in device suitable for the simultaneous administration of both formulations via inhalation. In a further embodiment, a pharmaceutical formulation comprising a compound of the invention together with a bronchodilator and a pharmaceutical formulation comprising a further bronchodilator may each be held in one or more devices suitable for the simultaneous administration of both formulations via inhalation.

Suitable bronchodilators for administration together with a compound of the invention include, but are not limited to, $\beta_2$-adrenoreceptor agonists and anticholinergic agents. Examples of $\beta_2$-adrenoreceptor agonists, include, for example, vilanterol, salmeterol, salbutamol, formoterol, salmefamol, fenoterol carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt of salbutamol or the fumarate salt of formoterol. Suitable anticholinergic agents include umeclidinium (for example, as the bromide), ipratropium (for example, as the bromide), oxitropium (for example, as the bromide) and tiotropium (for example, as the bromide). In one embodiment of the invention, a compound of the invention may be administered together with a $\beta_2$-adrenoreceptor agonist, such as vilanterol, and an anticholinergic agent, such as, umeclidinium.

The compounds may also be used in combination with agents for aiding transplantation including Cyclosporines, Tacrolimus, Mycophenolate mofetil, Prednisone, Azathioprine, Sirolimus, Daclizumab, Basiliximab, or OKT3.

They may also be used in combination with agents for Diabetes: metformin (biguanides), meglitinides, sulfonylureas, DPP-4 inhibitors, Thiazolidinediones, Alpha-glucosidase inhibitors, Amylin mimetics, Incretin mimetics, and insulin.

The compounds may be used in combination with antihypertensives such as diuretics, ACE inhibitors, ARBS, calcium channel blockers, and beta blockers.

One embodiment of the invention encompasses combinations comprising one or two other therapeutic agents. It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimize the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical formulation and thus pharmaceutical formulations comprising a combination as defined above together with a pharmaceutically acceptable diluent or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation. Appropriate doses of known therapeutic agents will readily be appreciated by those skilled in the art.

The invention thus provides, in a further aspect, a pharmaceutical composition comprising a combination of a compound of the invention together with another therapeutically active agent.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

All temperatures are given in degrees Celsius, all solvents are highest available purity and all reactions run under anhydrous conditions in an argon (Ar) or nitrogen ($N_2$) atmosphere where necessary.

Analtech Silica Gel GF and E. Merck Silica Gel 60 F-254 thin layer plates were used for thin layer chromatography. Both flash and gravity chromatography were carried out on E. Merck Kieselgel 60 (230-400 mesh) silica gel. The CombiFlash® system used for purification in this application was purchased from Isco, Inc. CombiFlash® purification was carried out using prepacked silica gel columns, a detector with UV wavelength at 254 nm and a variety of solvents or solvent combinations.

Preparative HPLC was performed using a Gilson Preparative System with variable wavelength UV detection or an Agilent Mass Directed AutoPrep (MDAP) system with both mass and variable wavelength UV detection or Waters Preparative System with UV/PDA detection or an Shimadzu PREP LC 20AP. A variety of reverse phase columns, e.g., Luna 5 m C18(2) 100 A, SunFire C18, XBridge C18, Atlantics T3 were used in the purification with the choice of column support dependent upon the conditions used in the purification. The compounds are eluted using a gradient of $CH_3CN$ and water. Neutral conditions used an $CH_3CN$ and water gradient with no additional modifier, acidic conditions used an acid modifier, 0.1% TFA (added to both the $CH_3CN$ and water) or 0.1% formic acidand basic conditions used a basic modifier, 0.1% $NH_4OH$ (added to the water) or 10 mM ammonium bicarbonate.

Analytical HPLC was run using an Agilent system, Shimadzu/Sciex LCMS with variable wavelength UV detection using reverse phase chromatography with a $CH_3CN$ and water gradient with a 0.02 or 0.1% TFA modifier (added to each solvent). LC-MS was determined using either a PE Sciex Single Quadrupole 150EX LC-MS, or Waters ZQ Single Quadrupole LC-MS or Agilent 1200 series SL (dectectors: Agilent 6140 single quadrupole and Agilent 1200 MWD SL) instruments. The compound is analyzed using a reverse phase column, e.g., Thermo Hypersil Gold C18, eluted using a gradient of $CH_3CN$ and water with a low percentage of an acid modifier such as 0.02% TFA or 0.1% formic acid or a base modifier such as 5 mM ammonium bicarbonate (adjusted to pH 10 with aqueous ammonia). When specified "acid method" refers to 0.1% formic acid in water and $CH_3CN$ gradient (1.8 min. 0.9 mL/min flow) with a Waters Acquity UPLC HSS C18; 1.8μ; 2.1×50 mm at 50° C.; "basic method" refers to 95:5 $H_2O$+0.1% $NH_4OH$: $CH_3CN$ (pH=9.4) and water gradient (1.8 min. 0.9 mL/min flow) with a Waters Acquity UPLC BEH C18; 1.7; 2.1×50 mm at 50° C. and "overnight basic method" refers to 95:5 $H_2O$+0.1% $NH_4OH$:$CH_3CN$ (pH=9.4) and water gradient (16 min. 0.8 mL/min flow) with a Waters Acquity UPLC BEH C18; 1.71; 2.1×50 mm at 50° C.

Preparative Chiral SFC was performed using a Thar/Waters Preparative SFC System with single wavelength UV detection system or PDA detector. A variety of chiral SFC columns, e.g. Chiralpak IA, IC, AY, AD. OD, OJ, C2 were used in the purification. The compounds are eluted using supercritical fluid $CO_2$ and co-solvents, such as MeOH, EtOH, IPA, and combination of these solvent in different ratio based on the compound selectivity. Modifiers (0.1% of TFA, $NH_4OH$, DEA) would be used as needed.

Analytical Chiral SFC was run using a Thar/Waters SFC system with variable wavelength UV detection or PDA detector. A variety of chiral SFC columns, e.g. Chiralpak IA, IB, IC, ID, AY, AD, AS, CCL4 were used in the purification. The compounds are eluted using supercritical fluid $CO_2$ and co-solvents, such as MeOH, EtOH, IPA, and combination of these solvent in different ratio based on the compound selectivity. Modifiers (0.1% of TFA, $NH_4OH$, DEA) would be used as needed.

Celite® is a filter aid composed of acid-washed diatomaceous silica, and is a registered trademark of Manville Corp., Denver, Colo. Isolute® is a functionalized silica gel based sorbent, and is a registered trademark of Biotage AB Corp., Sweden.

Nuclear magnetic resonance spectra were recorded at 400 MHz using a Bruker AVANCE 400 or Brucker DPX400 or Varian MR400 400 MHz spectrometer. $CDCl_3$ is deuteriochloroform, DMSO-$D_6$ is hexadeuteriodimethylsulfoxide, and MeOD is tetradeuteriomethanol, $CD_2Cl_2$ is deuteriodichloromethane. Chemical shifts are reported in parts per million (6) downfield from the internal standard tetramethylsilane (TMS) or calibrated to the residual proton signal in the NMR solvent (e.g., $CHCl_3$ in $CDCl_3$). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz.

Heating of reaction mixtures with microwave irradiations was carried out on a Biotage Initiator® or CEM microwave reactor, typically employing the high absorbance setting.

Cartridges or columns containing polymer based functional groups (acid, base, metal chelators, etc) can be used as part of compound workup. The "amine" columns or cartridges are used to neutralize or basify acidic reaction mixtures or products. These include $NH_2$ Aminopropyl SPE-ed SPE Cartridges available from Applied Separations and diethylamino SPE cartridges available from United Chemical Technologies, Inc.

Table of Abbreviations

[Rh(cod)Cl]$_2$ or [RhCl(cod)]$_2$: di-μ-chlorido-bis[η$^2$,η$^2$-(cyclocta-1,5-diene)rhodium
® T3P: 2,4,6-tripropyl-1,3,5,2,4,6-trioxatriphosphorinane 2,4,6-trioxide
|C: degree Celsius
AcOH: acetic acid
ADDP: (E)-diazene-1,2-diylbis(piperidin-1-ylmethanone)
aq = aqueous
BINAP: 2,2'-bis(diphenylphosphino)-1,1'-binaphthalene
CDI: Carbonyl dimidazole
$CH_2Cl_2$: dichloromethane
$CH_3CN$: acetonitrile
$CHCl_3$: chloroform
$Cs_2CO_3$: cesium carbonate
DBU: 1,8-diazabicyclo[5.4.0]undec-7-ene
DCE: dichloroethane
DCM: dichloromethane
DIPEA or DIEA: diisopropylethyl amine
DME: dimethyl ether
DMF: N,N-dimethylformamide
DMF-DMA or DMF-dimethyl acetal: N,N-dimethylformaide-dimethyl acetal
DMSO: dimethyl sulfoxide
EDC: 1-ethyl-3-(3-dimethylaminopropyl)carbodiimide
$Et_2O$: diethyl ether
$Et_3N$: triethylamine
EtOAc: ethyl acetate
EtOH: ethanol
g: gram(s)
h: hour(s)
HATU: O-(7-azabenzotriazol-1-yl)-N,N,N',N'-tetramethyluronium hexafluorophosphate
HBTU: N,N,N',N'-tetramethyl-O-(1H-benzotriazol-1-yl)uronium hexafluorophosphate
HCl: hydrochloric acid
HOAt: 1-hydroxy-7-azabenzotriazole
HPLC: high performance liquid chromatography
IPA: isopropyl alcohol
$K_2CO_3$: potassium carbonate
KOAc: potassium acetate
LAH: lithium aluminum hydride
LC: liquid chromatography
LC-MS: liquid chromatography-mass spectroscopy
$LiBH_4$: lithium borohydride
LiHMDS: lithium hexamethyldisilazane
LiOH: lithium hydroxide
M: molar
MeCN: acetonitrile
MeI: methyl iodide
MeOH: methanol
mg: milligram(s)

Table of Abbreviations (continued)

MgCl₂: magnesium chloride
MgSO₄: magnesium sulfate
MHz: megahertz
min: minute(s)
mL: milliliter(s)
mmol: millimole(s)
MS: mass spectroscopy
N₂: nitrogen gas
Na₂CO₃: sodium carbonate
Na₂SO₄: sodium sulfate
NaBH₃CN or NaCNBH₃: sodium cyanoborohydride
NaCl: sodium chloride
NaH: sodium hydride
NaHCO₃: sodium bicarbonate
NaHMDS: sodium hexamethyldisilazane
NaHSO₄: sodium bisulfate
NaOAc: sodium acetate
NaOH: sodium hydroxide
NBS: N-bromosuccinimide
nBuLi: n-butyl lithium
NH₄Cl: ammonium chloride
NMR: nuclear magnetic resonance
P(tBu)₃: tri-t-butyl phosphine
Pd(PhP₃)₄: tetrakistriphenylphosphine palladium
Pd/C: palladium on carbon
Pd₂(dba)₃: tris(dibenzylideneacetone)-dipalladium(0)
PdCl₂(dppf) or Pd(dppf)Cl₂: [1,1'-bis(diphenylphosphino)-ferrocene] dichloropalladium(II)
Petrol: petroleum ether
PS-PPh₃: polymer supported triphenylphosphine
PtO₂: platinum(IV) oxide
RT: room temperature
T3P: 2,4,6-tripropyl-1,3,5,2,4,6-trioxatriphosphorinane-2,4,6-trioxide solution
TEA: triethylamine
TFA: trifluoroacetic acid
TFFH: tetrafluoroformamidinium hexafluorophosphate
THF: tetrahydrofuran
triflic anhydride: trifluoromethanesulfonic anhydride
TsOH: p-toluenesulfonic acid
wt %: weight percent

Intermediates

Intermediate 1: (S)-tert-Butyl 3-(1H-pyrazol-1-yl)piperidine-1-carboxylate

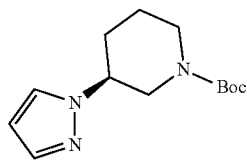 [SMILES: CC(C)(C)OC(=O)N1CCC[C@H](n2cccn2)C1]

To a solution of 60% NaH in mineral oil (20.04 g, 501 mmol) in N,N-dimethylformamide (DMF)(250 mL), at 00° C. was added 1H-pyrazole (34.1 g, 501 mmol) in N,N-dimethylformamide(DMF) (250 mL) dropwise over a period of 30 min and stirred for 30 min at the same temperature. (R)-tert-butyl 3-((methylsulfonyl)oxy)piperidine-1-carboxylate (70 g, 251 mmol) in N,N-dimethylformamide (DMF) (250 mL), was then added at 00° C. dropwise for 30 min and then stirred for 30 min at 00° C. The reaction mixture was heated to 50° C. and stirred overnight. The reaction mixture was cooled to 00° C., quenched with ice cold water and extracted with EtOAc (2×10000 mL). The organic layer was washed with cold water (2×500 mL), dried over anhydrous Na₂SO₄, evaporated under reduced pressure.

The residue was purified by flash chromatography, eluting with 0-5% EtOAc in petroleum ether to provide the title compound. (14 g, 55.7 mmol, 22.23% yield), LCMS m/z 252 (M+H)⁺, 4.32 min (ret. time).

Intermediate 2: (S)-3-(1H-Pyrazol-1-yl)piperidine Hydrochloride

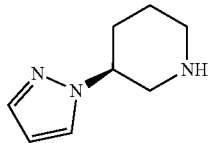 [SMILES: c1cnn([C@H]2CCCNC2)c1]

To a solution of (S)-tert-butyl 3-(1H-pyrazol-1-yl)piperidine-1-carboxylate (14 g, 55.7 mmol) in 1,4-dioxane (140 mL) was added 4M HCl(1,4-dioxane) (100 mL, 400 mmol) slowly at 10° C. and stirred for 2 h at 27° C. The reaction mixture was concentrated under reduced pressure to afford the title compound. (11 g, 47.1 mmol, 85% yield), LCMS m/z 152 (M+H)⁺, 1.48 min (ret. time).

Intermediate 3: N-(2,4-Dimethoxybenzyl)-2-methylenebutan-1-amine

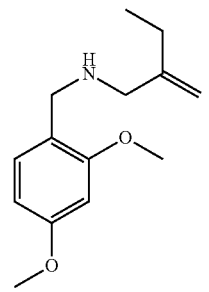 [SMILES: C=C(CC)CNCc1ccc(OC)cc1OC]

To a solution of 2-methylenebutanal (50 g, 594 mmol) in toluene (500 mL) was added (2,4-dimethoxyphenyl)methanamine (99 g, 594 mmol) and stirred at 110° C. for 48 hr. The reaction mixture was concentrated and dissolved in ethanol (300 mL). NaBH₄ (45.0 g, 1189 mmol) was added at 0° C. and the reaction stirred at ambient temperature for 6 hr. The reaction mixture was evaporated under reduced pressure, quenched with water (400 mL) and extracted with DCM (2×800 mL). The organic layer was dried over anhydrous Na₂SO₄ and filtered. The filtrate was evaporated under reduced pressure and the crude product was purified by column chromatography eluting with EtOAc: Hexane (15:85), to afford the title compound (75 g, 185 mmol, 31.1% yield), LCMS m/z 236 (M+H)⁺, 1.51 min (ret. time).

Intermediate 4: 2-Chloropyridine-3-sulfonyl chloride

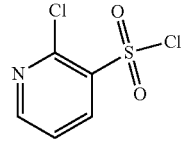 [SMILES: O=S(=O)(Cl)c1cccnc1Cl]

Step A: Thionyl chloride (159 mL, 2178 mmol) was added drop wise over 60 min to water (450 mL) at 0° C. The solution was allowed to stirred at ambient temperature for 17 h then copper(I) chloride (0.554 g, 5.60 mmol) was added to the mixture at −3° C. and the resulting yellow green solution was stirred for 1 hour at −3° C.

Step B: 37% HCl (503 mL, 6129 mmol) was added with vigorous stirring to 2-chloropyridin-3-amine (40 g, 311 mmol) at −5° C. and a solution of sodium nitrite (37.8 g, 548 mmol) in water (82 mL) was added drop wise over 45 min, the temperature of the reaction mixture was maintained at −5° C. and stirred for 10 min.

Step C: The mixture obtained from step B was added to the solution obtained from step A over 30 min at −3° C. The reaction mixture was maintained at 0° C. for 75 min with vigorous stirring. The solid was filtered and dried to give the title compound (20 g, 92 mmol, 29.5% yield) as brown color solid. LCMS m/z 212.02 (M+H), 2.058 min (ret. time)

Intermediate 5: 2-Chloro-N-(2,4-dimethoxybenzyl)-N-(2-methylenebutyl)pyridine-3-sulfonamide

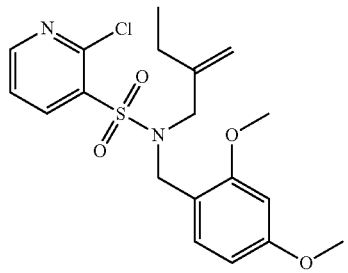 [SMILES: C=C(CC)CN(Cc1ccc(OC)cc1OC)S(=O)(=O)c1cccnc1Cl]

To a solution of N-(2,4-dimethoxybenzyl)-2-methylenebutan-1-amine (30 g, 83 mmol) in dichloromethane (DCM) (300 mL) was added 2-chloropyridine-3-sulfonyl chloride (17.57 g, 83 mmol) and TEA (23.10 mL, 166 mmol) at 0° C. The reaction mixture was stirred at ambient temperature for 16 h. The reaction mixture was quenched with ice water, and extracted with DCM (2×300 mL). The organic layer was washed with cold water (2×300 mL), and brine (200 mL). The organic layer was dried over anhydrous $Na_2SO_4$ and filtered. The filtrate was evaporated under reduced pressure and the crude compound was purified by column chromatography eluting with EtOAc: Hexane (11:89) as solvent to afford the title compound. (28 g, 53.5 mmol, 64.5% yield). LCMS m/z 411 (M+H)$^+$, 2.73 min (ret. time).

Intermediate 6: 2-Chloro-N-(2-methylenebutyl)pyridine-3-sulfonamide N60160-98-A2

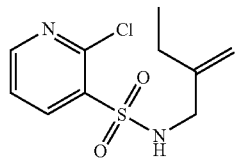 [SMILES: C=C(CC)CNS(=O)(=O)c1cccnc1Cl]

To a solution of 2-chloro-N-(2,4-dimethoxybenzyl)-N-(2-methylenebutyl)pyridine-3-sulfonamide (28 g, 53.1 mmol) in dichloromethane (DCM) (280 mL) was added anisole (9 mL, 82 mmol) and TFA (30 mL, 389 mmol) at 0° C. The reaction mixture was stirred at ambient temperature for 16 h. The reaction mixture was concentrated under vacuum, quenched with saturated $NaHCO_3$, and extracted with DCM (2×250 mL). The organic layer was dried over anhydrous $Na_2SO_4$ and filtered. The filtrate was evaporated under reduced pressure and purified by column chromatography eluting with EtOAc: Hexane (12:88) as solvent to afford the title compound. (13 g, 38.0 mmol, 71.6% yield), LCMS m/z 260 (M+H)+, 1.97 min (ret. time).

Intermediate 7: 4-Ethyl-2,3,4,5-tetrahydropyrido[2,3-f][1,2]thiazepine 1,1-dioxide

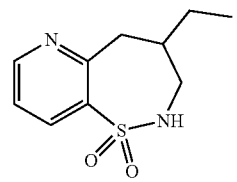

To a solution of 2-chloro-N-(2-methylenebutyl)pyridine-3-sulfonamide (14 g, 46.2 mmol) in benzene (90 mL) was added AIBN (3.79 g, 23.09 mmol) and tributylstannane (40.3 g, 139 mmol) at 65° C. The reaction was stirred at 85° C. for 16 h. The reaction mixture was evaporated under reduced pressure and purified by column chromatography eluting with EtOAc: Hexane (14:86) as solvent to afford the title compound (14 g, 28.2 mmol, 61.1% yield) LCMS m/z 227 (M+H)$^+$, 1.74 min (ret. time). This batch compound was combined with other batches of this compound prepared by the same method, and purified by column chromatography eluting with using EtOAc: Hexane (12:88) as solvent. The solvents were concentrated and the compound was cooled to 0° C. and washed with pentane (40 mL) and diethyl ether (15 mL) to afford the title compound. (5.1 g, 97% pure) LCMS m/z 227 (M+H)$^+$, 1.55 min (ret. time).

Intermediate 8: (S)-4-Ethyl-2,3,4,5-tetrahydropyrido[2,3-f][1,2]thiazepine 1,1-dioxide and Intermediate 9: (R)-4-ethyl-2,3,4,5-tetrahydropyrido[2,3-f][1,2]thiazepine 1,1-dioxide

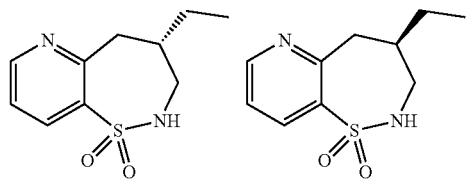

The compound was resolved by chiral SFC (Column: Chiralpak AS-H (30×250 mm), 5p; Co-solvent: 20% EtOH; Flowrate: 100 g/min; Back pressure: 100Bar, 80% $CO_2$) to provide (S)-4-ethyl-2,3,4,5-tetrahydropyrido[2,3-f][1,2]thiazepine 1,1-dioxide (2.29 g, 45% yield). LCMS m/z 227 (M+H)+, 1.94 min (ret. time), (chiral SFC ret. time: 4.07 min) and (R)-4-ethyl-2,3,4,5-tetrahydropyrido[2,3-f][1,2]thiazepine 1,1-dioxide (2.3 g, 46% yield). LCMS m/z 227 (M+H)+, 1.98 min (ret. time), (chiral SFC ret. time: 4.53 min).

Intermediate 10: (R)-2-Fluoro-N-(2-hydroxybutyl)benzenesulfonamide

To a solution of (R)-1-aminobutan-2-ol (14.66 g, 164 mmol) in tetrahydrofuran (THF) (200 mL) and water (60 mL) at ambient temperature was added K$_2$CO$_3$ (14.20 g, 103 mmol) and 2-fluorobenzene-1-sulfonyl chloride (20 g, 103 mmol). It was stirred for 16 h. The reaction mixture was diluted with water (100 mL) and extracted with EtOAc (2×100 mL). The combined organic layer was washed with brine solution (200 mL) and dried over anhydrous Na$_2$SO$_4$, filtered and concentrated to give the title compound (14 g, 53.8 mmol, 52.3% yield) as a gummy liquid. LC-MS m/z 494.83 (2M–H)+, 1.660 min (ret. time).

Intermediate 11: (R)-4-Ethyl-3,4-dihydro-2H-benzo[b][1,4,5]oxathiazepine 1,1-dioxide

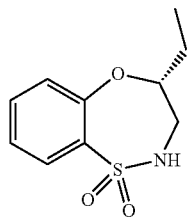

To a solution of (R)-2-fluoro-N-(2-hydroxybutyl)benzenesulfonamide (14 g, 56.6 mmol) in dimethyl sulfoxide (DMSO) (140 mL) at 0° C. was added potassium tert-butoxide (6.35 g, 56.6 mmol). It was then heated at 80° C. for 4 h. The reaction mixture was cooled and neutralized with 1N HCl, diluted with ice water (500 mL) and extracted with EtOAc (2×400 mL). The combined organic layer was washed with chilled brine solution (200 mL) and dried over anhydrous Na$_2$SO$_4$, filtered and concentrated. The crude residue was purified on flash column chromatography eluting with 50% EtOAc in hexane. Desired fractions were concentrated to give the title compound (11.12 g, 48.9 mmol, 86% yield) as a white solid. LC-MS m/z 228.05 (M+H)$^+$, 1.84 min (ret. time).

Example 1

(S)-3-(5-Chloro-4-(((R)-4-ethyl-1,1-dioxido-3,4-dihydro-2H-pyrido[4,3-b][1,4,5]oxathiazepin-2-yl)methyl)thiophen-2-yl)-3-(1-ethyl-4-methyl-1H-benzo[d][1,2,3]triazol-5-yl)propanoic acid

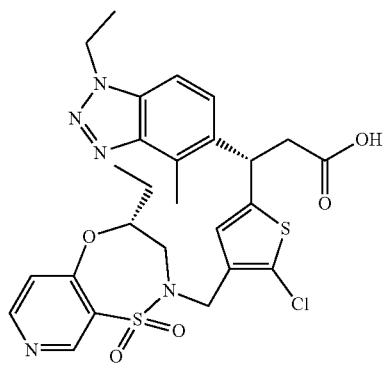 [SMILES: CC[C@@H]1CN(Cc2cc([C@@H](CC(=O)O)c3ccc4c(nnn4CC)c3C)sc2Cl)S(=O)(=O)c2cnccc2O1]

(R)-1-Aminobutan-2-ol

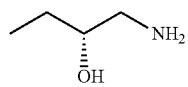

To a solution of ammonium hydroxide (113 ml, 2912 mmol) was added (R)-2-ethyloxirane (21 g, 291 mmol) and the resulting reaction mixture was stirred at 25° C. for 20 h. The reaction mixture was evaporated under vacuum on lyophilization to give the title compound (16 g, 180 mmol, 61.6% yield). It was carried to next step without further purification.

4-Chloropyridine-3-sulfonyl chloride

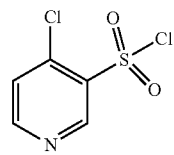 [SMILES: O=S(=O)(Cl)c1cnccc1Cl]

To a suspension of 4-hydroxypyridine-3-sulfonic acid (17.5 g, 100 mmol) at 0° C. was added PCl$_5$ (72.8 g, 350 mmol) and POCl$_3$ (18.62 ml, 200 mmol). It was heated at 120° C. for 1 h. The reaction mixture was cooled to ambient temperature and concentrated. It was diluted with EtOAc and poured over ice. Solid NaHCO$_3$ was added and extracted with EtOAc. The organic layer was dried over anhydrous Na$_2$SO$_4$ and filtered. The filtrate was concentrated to give the title compound (18 g, 84 mmol, 84% yield) as pale yellow liquid. LC/MS m/z=211.96 (M+H)$^+$, 1.94 min (ret. time).

(R)-4-Chloro-N-(2-hydroxybutyl)pyridine-3-sulfonamide

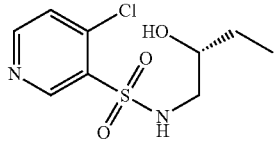 [SMILES: CC[C@@H](O)CNS(=O)(=O)c1cnccc1Cl]

To a suspension of 4-chloropyridine-3-sulfonyl chloride (18 g, 85 mmol) in mixture of tetrahydrofuran (THF) (120 mL) and water (60 mL) at 0° C. was added $K_2CO_3$ (14.08 g, 102 mmol) and (R)-1-aminobutan-2-ol (7.57 g, 85 mmol). The reaction mixture was stirred at ambient temperature for 16 h. The reaction mixture was concentrated, quenched with ice water, extracted with DCM twice. The combined organic layer was dried over anhydrous $Na_2SO_4$, filtered and concentrated. The crude product was purified with flash column chromatography eluting with MeOH: DCM (2:98) to give the title compound (17 g, 64.2 mmol, 76% yield) as a liquid. LC/MS m/z=265.15 $(M+H)^+$, 1.39 min (ret. time).

(R)-4-Ethyl-3,4-dihydro-2H-pyrido[4,3-b][1,4,5]oxathiazepine 1,1-dioxide

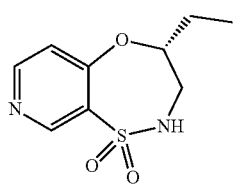

To a solution of (R)-4-chloro-N-(2-hydroxybutyl)pyridine-3-sulfonamide (17 g, 64.2 mmol) in tetrahydrofuran (THF) (200 mL) at 0° C. was added $KO_tBu$ (14.41 g, 128 mmol). It was stirred for 5 min, and then the reaction mixture was refluxed at 80° C. for 6 h. The reaction mixture was concentrated and quenched with 1N HCl, extracted with EtOAc twice. The organic layer was dried over anhydrous $Na_2SO_4$, filtered and concentrated. The crude product was purified via flash column chromatography eluting with EtOAc:Pet. ether (55:45) under vacuum to get a gum. The gummy residue was washed with n-pentane and diethyl ether to afford the title compound (7.52 g, 32.3 mmol, 50.3% yield) as white solid. LC/MS m/z=229.06 $(M+H)^+$, 1.46 min (ret. time).

Methyl 2-chlorothiophene-3-carboxylate

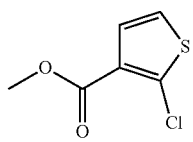

To a solution of 2-chlorothiophene-3-carboxylic acid (5 g, 30.8 mmol) dissolved in methanol (60 mL) was added sulfuric acid (10.65 mL, 200 mmol) slowly at ambient temperature and the mixture was refluxed for 18 h. Saturated aqueous $NaHCO_3$ was added to the reaction mixture until pH=8. The mixture was extracted with EtOAc (3×). The combined organics were dried and evaporated to afford the title compound. (5 g, 28.3 mmol, 92% yield), LC/MS m/z=176(M+H)+, 0.78 (ret. time).

Methyl 5-bromo-2-chlorothiophene-3-carboxylate

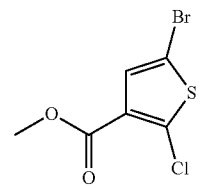

A solution of methyl 2-chlorothiophene-3-carboxylate (10 g, 56.6 mmol) in N,N-dimethylformamide (DMF) (40 mL) was cooled in an ice bath to 0° C. N-Bromosuccinimide (11.08 g, 62.3 mmol) was added portion wise and stirred at 0° C. for 10 min. The reaction was warmed to ambient temperature and stirred for 30 min. It was then heated to 50° C. for 30 min and at ambient temperature for 2 h. The reaction was then cooled and quenched with water and diluted with diethyl ether. The aqueous layer was then extracted with diethyl ether (2×). The combined organics were washed with water (2×) and dried with $MgSO_4$. The residue was purified by flash chromatography eluting with 0-5% acetone/hexane to provide the title compound. (7.56 g, 52% yield). $^1$H NMR (400 MHz, CHLOROFORM-d) δ 7.37 (s, 1H), 3.90 (s, 3H).

(5-Bromo-2-chlorothiophen-3-yl)methanol

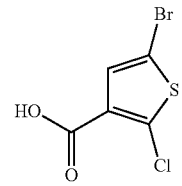

A solution of methyl 5-bromo-2-chlorothiophene-3-carboxylate (7.56 g, 29.6 mmol) in tetrahydrofuran (THF) (250 mL) under nitrogen was cooled in ice bath. To the solution was added DIBAL-H (59.2 mL, 59.2 mmol) and stirred for 1 h at 0° C. The reaction was then quenched with 1N HCl and 6N HCl at 0° C. until the solution was acidic and gelatinous solids had broken up. The layers were separated and the aqueous layer was extracted with EtOAc (3×). The combined organics were washed with water, brine and dried with $MgSO_4$ and concentrated. The residue was purified by flash chromatography eluting with 0-20% EtOAc/hexane to provide the title compound. (5.75 g, 85% yield). $^1$H NMR (400 MHz, CHLOROFORM-d) δ 7.04 (s, 1H), 4.61 (s, 2H), 1.69 (br. s., 1H).

5-Bromo-2-chloro-3-(((4-methoxybenzyl)oxy)methyl)thiophene

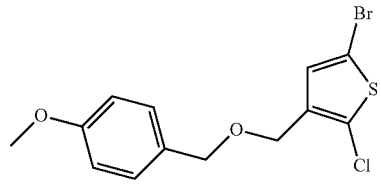 [SMILES: COc1ccc(COCc2cc(Br)sc2Cl)cc1]

(5-Bromo-2-chlorothiophen-3-yl)methanol (5.75 g, 25.3 mmol) was dissolved in N,N-dimethylformamide (DMF) (50 mL) under argon and cooled in an ice-bath. 60% sodium hydride (2.022 g, 50.5 mmol) was added portion wise and the reaction was stirred at 23° C. for 1 h. The reaction was cooled again to 10° C. and 1-(chloromethyl)-4-methoxybenzene (5.54 mL, 37.9 mmol) was added and stirred at 23° C. for 14 h. The reaction was quenched with water (25 mL) and stirred for 5 min. The reaction was diluted with water (100 mL) and EtOAc (300 mL) and extracted with additional EtOAc (2×200 mL). The combined EtOAc layers were washed with water (4×100 mL) and then saturated aqueous NaCl (2×100 mL), dried over $Na_2SO_4$ and concentrated. The residue was purified by flash chromatography eluting with 0-10% EtOAc/hexane to provide the title compound. (6.7 g, 76% yield). $^1$H NMR (400 MHz, CHLOROFORM-d) δ 7.28-7.31 (m, 2H), 7.01 (s, 1H), 6.92 (d, J=8.03 Hz, 2H), 4.49 (s, 2H), 4.44 (s, 2H), 3.84 (s, 3H).

1-Ethyl-4-methyl-1H-benzo[d][1,2,3]triazole-5-carbaldehyde

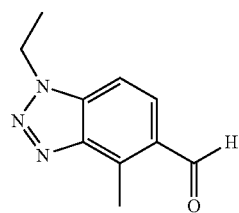

To a solution of 1M ethylmagnesium bromide in THF (7.84 mL, 7.84 mmol) in toluene (60 mL) at −40° C., in an oven dried 500 mL flask under argon, was added dropwise via syringe 1.6M nBuLi in hexane (10.77 mL, 17.24 mmol) and stirred for 1 h. To this solution was added 5-bromo-1-ethyl-4-methyl-1H-benzo[d][1,2,3]triazole (4.09 g, 15.67 mmol) in tetrahydrofuran (THF) (20 mL) via addition funnel and stirred for 1 h. The reaction was transferred to an ice/NaCl bath and stirred at −15° C. DMF (7.28 mL, 94 mmol) was added dropwise via addition funnel and stirred at −15° C. for 1 h and then at ambient temperature for 45 min. The reaction was quenched with saturated $NH_4Cl$, and diluted with water. The layers were separated and the aqueous layer was extracted with EtOAc (3x). The combined organics were washed with water (2x), brine and dried with $MgSO_4$. The residue was purified by flash chromatography eluting with 0-30% EtOAc/hexane to provide the title compound. (2.63 g, 89% yield). LC/MS m/z=190 (M+H)+, 0.60 min (ret time).

(5-Chloro-4-(((4-methoxybenzyl)oxy)methyl)thiophen-2-yl)(1-ethyl-4-methyl-1H-benzo[d][1,2,3]triazol-5-yl)methanol

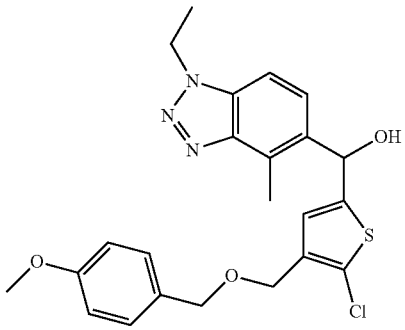 [SMILES: CCn1nnc2c(C)c(C(O)c3cc(COCc4ccc(OC)cc4)c(Cl)s3)ccc21]

5-Bromo-2-chloro-3-(((4-methoxybenzyl)oxy)methyl)thiophene (4.2 g, 12.08 mmol) was dissolved in dry tetrahydrofuran (THF) (5 mL) in an oven dried and argon flushed flask and stirred with molecular sieves for 2 h. In a separate flask, 1-ethyl-4-methyl-1H-benzo[d][1,2,3]triazole-5-carbaldehyde (2.74 g, 14.50 mmol) was also dissolved in dry tetrahydrofuran (THF) (5 mL) in an oven dried and argon flushed flask and stirred with activated molecular sieves as well for 2 h. After this, the thiophene reaction flask was cooled to −78° C. and n-butyllithium (1.6M in hexanes) (8.31 mL, 13.29 mmol) was added to the reaction mixture and stirred for 30 min. To this solution was added the aldehyde solution and was stirred in a dry ice-acetone bath cooling for 2 h. The reaction was then diluted with water (25 mL) and EtOAc (75 mL). The aqueous layer was extracted with an additional portion of EtOAc (50 mL) and the combined EtOAc layers were washed with water (50 mL) and saturated aqueous NaCl (50 mL), dried over $Na_2SO_4$ and concentrated. The residue was purified by flash chromatography eluting with 0-50% EtOAc/hexane to provide the title compound. (4.5 g, 81% yield). LC/MS m/z=458 (M+H)+, 1.16 min (ret time).

(S)-Methyl 3-(5-chloro-4-(((4-methoxybenzyl)oxy)methyl)thiophen-2-yl)-3-(1-ethyl-4-methyl-1H-benzo[d][1,2,3]triazol-5-yl)propanoate and (R)-methyl 3-(5-chloro-4-(((4-methoxybenzyl)oxy)methyl)thiophen-2-yl)-3-(1-ethyl-4-methyl-1H-benzo[d][1,2,3]triazol-5-yl)propanoate

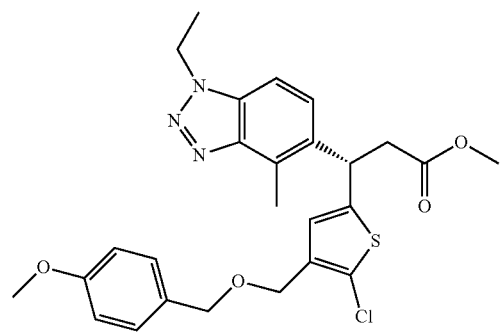

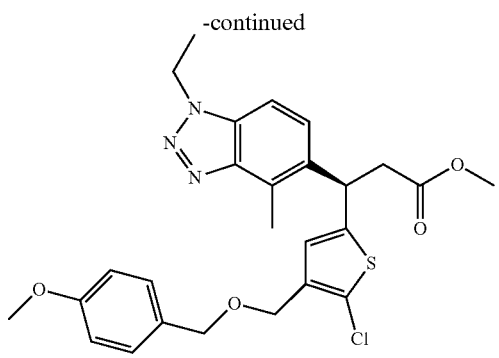

(5-chloro-4-(((4-methoxybenzyl)oxy)methyl)thiophen-2-yl)(1-ethyl-4-methyl-1H-benzo[d][1,2,3]triazol-5-yl)methanol (1 g, 2.184 mmol) and tert-butyl((1-methoxyvinyl)oxy)dimethylsilane (1.430 mL, 6.55 mmol) were dissolved in dry dichloromethane (DCM) (30 mL), and cooled at 0° C. Titanium tetrachloride (2.184 mL, 2.184 mmol) dissolved in dichloromethane (DCM) (30 mL) was also cooled to 0° C. and added dropwise to the reaction mixture. The reaction was stirred at 0° C. and was allowed to warm slowly to ambient temperature and stirred for 24 h. A 5% aqueous NaHSO₄ solution was added and the organic layers were separated, dried with MgSO₄, filtered and then concentrated to afford methyl 3-(5-chloro-4-(((4-methoxybenzyl)oxy)methyl)thiophen-2-yl)-3-(1-ethyl-4-methyl-1H-benzo[d][1,2,3]triazol-5-yl)propanoate (500 mg, 0.973 mmol, 44.5% yield). This compound was resolved by chiral SFC (Column: Chiralpak IA 20×250 mm, 5u; Co-solvent: 25% EtOH; Flowrate: 50 g/min; Back pressure: 100Bar) to give (S)-Methyl 3-(5-chloro-4-(((4-methoxybenzyl)oxy)methyl)thiophen-2-yl)-3-(1-ethyl-4-methyl-1H-benzo[d][1,2,3]triazol-5-yl)propanoate (0.244 g, 21% yield). LC/MS m/z=514 (M+H)+, 1.30 min (ret time) and (R)-methyl 3-(5-chloro-4-(((4-methoxybenzyl)oxy)methyl)thiophen-2-yl)-3-(1-ethyl-4-methyl-1H-benzo[d][1,2,3]triazol-5-yl)propanoate (0.234 g, 20% yield). LC/MS m/z=514 (M+H)+, 1.31 min (ret time).

(S)-Methyl 3-(5-chloro-4-(hydroxymethyl)thiophen-2-yl)-3-(1-ethyl-4-methyl-1H-benzo[d][1,2,3]triazol-5-yl)propanoate

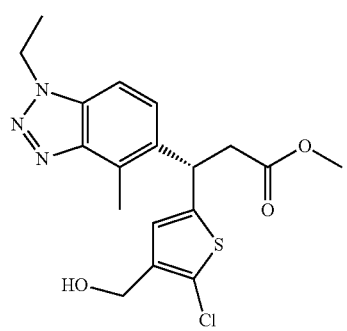 [SMILES: CCn1nnc2c(C)c([C@H](CC(=O)OC)c3cc(CO)c(Cl)s3)ccc21]

(S)-methyl 3-(5-chloro-4-(((4-methoxybenzyl)oxy)methyl)thiophen-2-yl)-3-(1-ethyl-4-methyl-1H-benzo[d][1,2,3]triazol-5-yl)propanoate (230 mg, 0.447 mmol) was dissolved in 4N hydrochloric acid (10 mL, 40.0 mmol) and let stir for 1 h. The compound was then purified by flash chromatography eluting with 0-50% EtOAc/hexane to provide the title compound. (0.144 g, 65% yield). LC/MS m/z=394 (M+H)+, 1.02 min (ret time).

(S)-Methyl 3-(5-chloro-4-(((R)-4-ethyl-1,1-dioxido-3,4-dihydro-2H-pyrido[4,3-b][1,4,5]oxathiazepin-2-yl)methyl)thiophen-2-yl)-3-(1-ethyl-4-methyl-1H-benzo[d][1,2,3]triazol-5-yl)propanoate

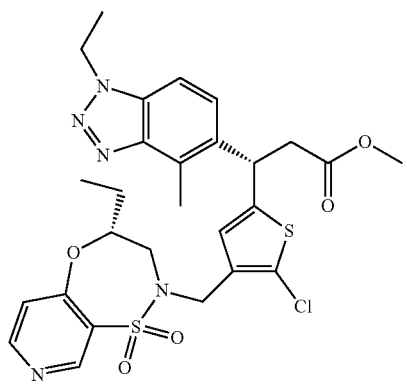 [SMILES: CC[C@@H]1CN(Cc2cc([C@@H](CC(=O)OC)c3ccc4c(nnn4CC)c3C)sc2Cl)S(=O)(=O)c2cnccc2O1]

To a solution of (S)-methyl 3-(5-chloro-4-(hydroxymethyl)thiophen-2-yl)-3-(1-ethyl-4-methyl-1H-benzo[d][1,2,3]triazol-5-yl)propanoate (48 mg, 0.122 mmol), (R)-4-ethyl-3,4-dihydro-2H-pyrido[4,3-b][1,4,5]oxathiazepine 1,1-dioxide (55.6 mg, 0.244 mmol) and (E)-diazene-1,2-diylbis(piperidin-1-ylmethanone) (61.5 mg, 0.244 mmol) in tetrahydrofuran (THF) (4 mL) was added tributylphosphine (0.061 mL, 0.244 mmol) and stirred for 1.5 h. The solvent was concentrated and the residue was purified by reverse phase preparative HPLC under neutral conditions to provide the title compound (0.058 g, 79% yield). LC/MS m/z=604 (M+H)+, 1.16 min (ret. time).

(S)-3-(5-Chloro-4-(((R)-4-ethyl-1,1-dioxido-3,4-dihydro-2H-pyrido[4,3-b][1,4,5]oxathiazepin-2-yl)methyl)thiophen-2-yl)-3-(1-ethyl-4-methyl-1H-benzo[d][1,2,3]triazol-5-yl)propanoic acid

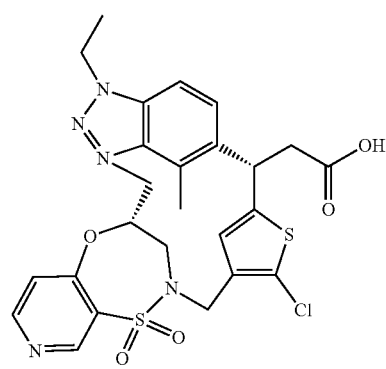

To a solution of (S)-methyl 3-(5-chloro-4-(((R)-4-ethyl-1,1-dioxido-3,4-dihydro-2H-pyrido[4,3-b][1,4,5]oxathiazepin-2-yl)methyl)thiophen-2-yl)-3-(1-ethyl-4-methyl-1H-benzo[d][1,2,3]triazol-5-yl)propanoate (58 mg, 0.096 mmol) dissolved in tetrahydrofuran (THF) (2.000 mL), water (1 mL) and methanol (2.000 mL) was added lithium hydroxide (11.50 mg, 0.480 mmol) and stirred at ambient temperature for 1 h. The reaction was acidified with a 10% formic acid solution and concentrated. The residue was purified by reverse phase preparative HPLC under formic acid conditions to provide the title compound (0.047 g, 83% yield). LC/MS m/z=590 (M+H)+, 1.06 min (ret. time).

Example 2

(S)-3-(5-Chloro-4-(((R)-4-ethyl-1,1-dioxido-3,4-dihydro-2H-pyrido[2,3-b][1,4,5]oxathiazepin-2-yl)methyl)thiophen-2-yl)-3-(1-ethyl-4-methyl-1H-benzo[d][1,2,3]triazol-5-yl)propanoic acid

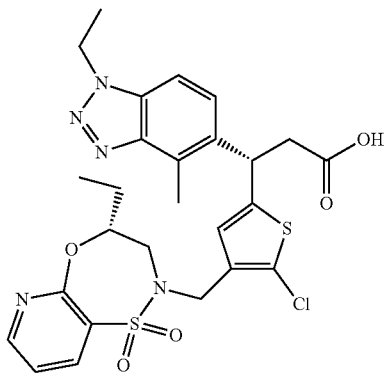 [SMILES: CC[C@@H]1CN(Cc2cc([C@@H](CC(=O)O)c3ccc4c(nnn4CC)c3C)sc2Cl)S(=O)(=O)c2cccnc2O1]

(R)-2-Chloro-N-(2-hydroxybutyl)pyridine-3-sulfonamide

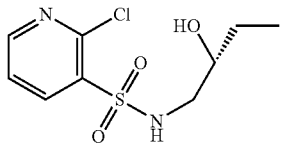 [SMILES: CC[C@@H](O)CNS(=O)(=O)c1cccnc1Cl]

To a solution of 2-chloropyridine-3-sulfonyl chloride (15 g, 70.7 mmol) in tetrahydrofuran (THF) (100 mL) was added (R)-1-aminobutan-2-ol (6.31 g, 70.7 mmol), potassium carbonate (9.78 g, 70.7 mmol) and water (30 mL). The reaction mixture was stirred for 2 h at ambient temperature. The reaction mixture was quenched with water (20 mL) and extracted with EtOAc (3×20 mL). The combined organic layer was dried over anhydrous Na$_2$SO$_4$, filtered and concentrated to give the title compound (14 g, 43.6 mmol, 61.7% yield). LC/MS m/z=262.95 (M−H)$^+$, 2.627 min (ret. time).

(R)-4-Ethyl-3,4-dihydro-2H-pyrido[2,3-b][1,4,5]oxathiazepine 1,1-dioxide

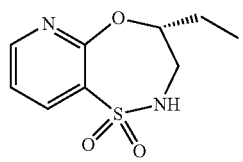

To a solution of (R)-2-chloro-N-(2-hydroxybutyl)pyridine-3-sulfonamide (13 g, 49.1 mmol) in tetrahydrofuran (THF) (130 mL) at 5° C. was added potassium tert-butoxide (16.53 g, 147 mmol), then was heated to 75° C. for 3 h. The reaction mixture was cooled to ambient temperature and then quenched with ice water (200 mL) and neutralized with 1N HCl (10 mL) solution. It was extracted with ethyl acetate (4×100 mL). The combined organic layer was washed with ice cold water (30 mL), washed with brine solution (30 mL), dried over anhydrous Na$_2$SO$_4$, filtered and concentrated. The crude residue was purified with flash column chromatography eluting with EtOAc: hexane (4:6) to give the title compound (4.9 g, 20.77 mmol, 42.3% yield) as an off-white solid. LC/MS m/z=229.08 (M+H)$^+$, 2.555 min (ret. time).

(S)-Methyl 3-(5-chloro-4-(((R)-4-ethyl-1,1-dioxido-3,4-dihydro-2H-pyrido[2,3-b][1,4,5]oxathiazepin-2-yl)methyl)thiophen-2-yl)-3-(1-ethyl-4-methyl-1H-benzo[d][1,2,3]triazol-5-yl)propanoate

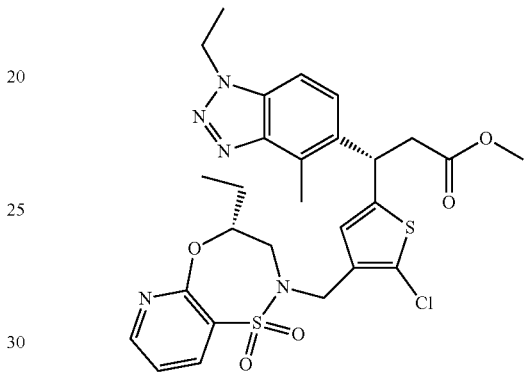

To a solution of (S)-methyl 3-(5-chloro-4-(hydroxymethyl)thiophen-2-yl)-3-(1-ethyl-4-methyl-1H-benzo[d][1,2,3]triazol-5-yl)propanoate (48 mg, 0.122 mmol), (R)-4-ethyl-3,4-dihydro-2H-pyrido[2,3-b][1,4,5]oxathiazepine 1,1-dioxide (55.6 mg, 0.244 mmol) and (E)-diazene-1,2-diylbis(piperidin-1-ylmethanone) (61.5 mg, 0.244 mmol) in tetrahydrofuran (THF) (4 mL) was added tributylphosphane (0.061 mL, 0.244 mmol) and the reaction stirred for 1.5 h. The solvent was concentrated and the residue was purified by reverse phase preparative HPLC under neutral conditions to provide the title compound (0.065 g, 88% yield). LC/MS m/z=604 (M+H)+, 1.17 min (ret. time).

(S)-3-(5-Chloro-4-(((R)-4-ethyl-1,1-dioxido-3,4-dihydro-2H-pyrido[2,3-b][1,4,5]oxathiazepin-2-yl)methyl)thiophen-2-yl)-3-(1-ethyl-4-methyl-1H-benzo[d][1,2,3]triazol-5-yl)propanoic acid

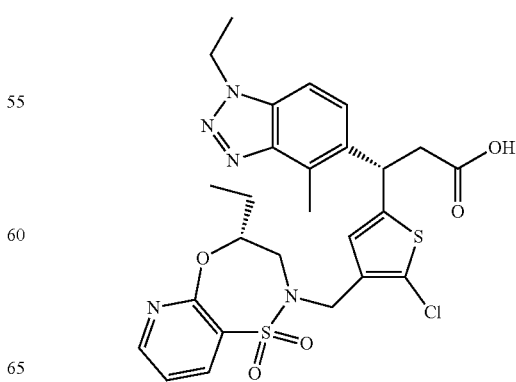

To a solution of (S)-methyl 3-(5-chloro-4-(((R)-4-ethyl-1,1-dioxido-3,4-dihydro-2H-pyrido[2,3-b][1,4,5]oxathiazepin-2-yl)methyl)thiophen-2-yl)-3-(1-ethyl-4-methyl-1H-benzo[d][1,2,3]triazol-5-yl)propanoate (65 mg, 0.108 mmol) dissolved in tetrahydrofuran (THF) (2.000 mL), water (1 mL) and methanol (2.000 mL) was added lithium hydroxide (12.88 mg, 0.538 mmol) and stirred at ambient temperature for 1 h. The reaction was acidified with a 10% formic acid solution and concentrated. The residue was purified by reverse phase preparative HPLC under formic acid conditions to provide the title compound (0.054 g, 85% yield). LC/MS m/z=590 (M+H)+, 1.06 min (ret. time).

Example 3

(S)-3-(5-Chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-methyl-1H-benzo[d][1,2,3]triazol-5-yl)-2,2-dimethylpropanoic acid

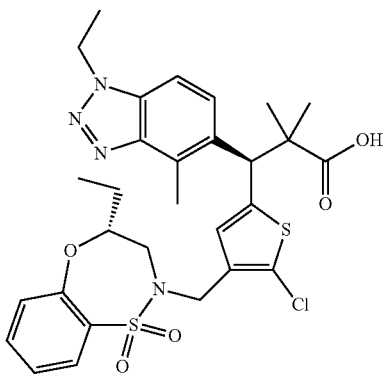 [SMILES: CC[C@@H]1CN(Cc2cc([C@@H](c3ccc4c(nnn4CC)c3C)C(C)(C)C(=O)O)sc2Cl)S(=O)(=O)c2ccccc2O1]

(2-Chlorothiophen-3-yl)methanol

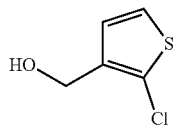

To a solution of 2-chlorothiophene-3-carboxylic acid (2.5 g, 15.38 mmol) in tetrahydrofuran (THF) (12.07 mL), was added borane-methyl sulfide complex (2.92 mL, 30.8 mmol) at 0° C. The reaction was warmed to 23° C. and stirred for 14 h. Afterwards, additional borane-methyl sulfide complex (0.730 mL, 7.69 mmol) was added to the reaction mixture and stirred for several hours. The reaction was cooled in an ice water bath and was quenched slowly with methanol (6.04 mL). When most of the bubbling ended the solvents were removed in vacuo and the residue was dissolved in EtOAc (10 mL) and washed with saturated aqueous NaHCO$_3$. The aqueous layer was extracted with EtOAc (50 mL) and the combined EtOAc layers were washed with water (5 mL) and saturated aqueous NaCl, dried over Na$_2$SO$_4$ and concentrated to afford the title compound (2.2 g, 95% yield)$^1$H NMR (400 MHz, CHLOROFORM-d) δ 6.98-7.19 (m, 2H), 4.67 (d, J=4.52 Hz, 2H), 1.65-1.81 (m, 1H).

2-Chloro-3-(((4-methoxybenzyl)oxy)methyl)thiophene

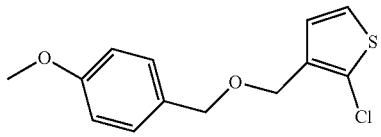 [SMILES: COc1ccc(COCc2ccsc2Cl)cc1]

To a solution of (2-chlorothiophen-3-yl)methanol (2.2 g, 14.80 mmol) dissolved in N,N-dimethylformamide (DMF) (24.47 mL) under argon and cooled in an ice-bath was added 60% sodium hydride (1.184 g, 29.6 mmol) portion wise. The reaction was stirred at 23° C. for 1 h then cooled again to 10° C. with the ice bath. 1-(chloromethyl)-4-methoxybenzene (3.48 g, 22.21 mmol) was added and the reaction was stirred at 23° C. for 14 h. The reaction was quenched with water (25 mL) and stirred for 5 min. The reaction was diluted with water (100 mL) and EtOAc (300 mL) and the product was extracted with an additional EtOAc (2×200 mL). The combined EtOAc layers were washed with water (4×100 mL) and then saturated aqueous NaCl (2×100 mL), dried with Na$_2$SO$_4$ and concentrated. The residue was purified by flash chromatography eluting with 0-10% EtOAc/hexane to provide the title compound. (3.5 g, 84% yield).1H NMR (400 MHz, CHLOROFORM-d) δ ppm 7.26-7.34 (m, 2H), 7.03 (d, J=5.52 Hz, 1H) 7.11 (d, J=5.52 Hz, 1H), 6.91 (d, J=8.28 Hz, 2H), 4.44-4.64 (m, 4H), 3.84 (s, 3H).

5-Bromo-2-chloro-3-(((4-methoxybenzyl)oxy)methyl)thiophene

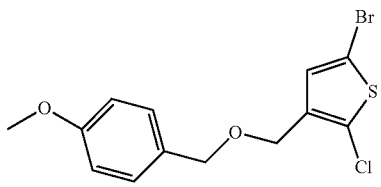 [SMILES: COc1ccc(COCc2cc(Br)sc2Cl)cc1]

A solution of 2-chloro-3-(((4-methoxybenzyl)oxy)methyl)thiophene (3.3 g, 12.28 mmol) in N,N-dimethylformamide (DMF) (20 mL) was cooled to 0° C. N-bromosuccinimide (2.404 g, 13.51 mmol) was added portion wise and stirred at 0° C. for 10 min. The reaction was warmed to ambient temperature and stirred for 30 min. It was then heated to 50° C. for 30 min and at ambient temperature for 2 h. The reaction was then cooled and diethyl ether and water were added. The aqueous layer was then extracted with diethyl ether (2×). The combined organics were washed with water (2×) and dried with MgSO$_4$. The residue was purified by flash chromatography eluting with 0-5% acetone/hexane to provide the title compound. (2.40 g, 56% yield). H NMR (400 MHz, CHLOROFORM-d) δ 7.26-7.32 (m, 2H), 7.01 (s, 1H), 6.92 (d, J=8.28 Hz, 2H), 4.49 (s, 2H), 4.44 (s, 2H), 3.84 (s, 3H).

Methyl 3-(5-chloro-4-(((4-methoxybenzyl)oxy)methyl)thiophen-2-yl)-3-(1-ethyl-4-methyl-1H-benzo[d][1,2,3]triazol-5-yl)-2,2-dimethylpropanoate

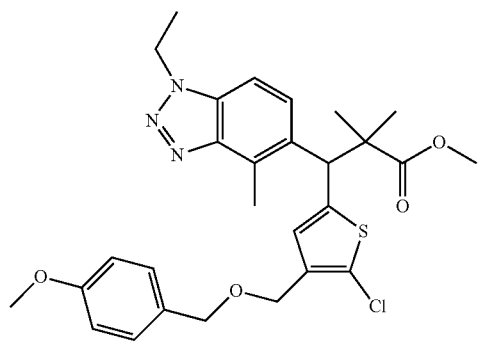

2,2,2-Trichloroacetonitrile (252 mg, 1.747 mmol) was added to a solution of (5-chloro-4-(((4-methoxybenzyl)oxy)methyl)thiophen-2-yl)(1-ethyl-4-methyl-1H-benzo[d][1,2,3]triazol-5-yl)methanol (400 mg, 0.873 mmol) in acetonitrile (10 mL). 2,3,4,6,7,8,9,10-octahydropyrimido[1,2-a]azepine (6.65 mg, 0.044 mmol) was then added and the reaction mixture was stirred at ambient temperature for 40 min. ((1-methoxy-2-methylprop-1-en-1-yl)oxy)trimethylsilane (381 mg, 2.184 mmol) was dissolved in acetonitrile, followed by 1,1,1-trifluoro-N-((trifluoromethyl)sulfonyl)methanesulfonamide (24.56 mg, 0.087 mmol) and the solution stirred at ambient temperature for 1 h. The reaction mixture was partitioned between saturated NH₄Cl and ethyl acetate. The water layer was extracted with ethyl acetate (2×100 mL). The combined organic phases were dried with MgSO₄ and concentrated to get crude product. The crude residue was purified by flash chromatography eluting with 0-60% EtOAc/hexane to provide the title compound. (0.450 g, 95% yield). LC/MS m/z=542/543/544 m/z (M+H)+, 1.38 min (ret time).

(S)-Benzyl 3-(5-chloro-4-(((4-methoxybenzyl)oxy)methyl)thiophen-2-yl)-3-(1-ethyl-4-methyl-1H-benzo[d][1,2,3]triazol-5-yl)-2,2-dimethylpropanoate and (R)-benzyl 3-(5-chloro-4-(((4-methoxybenzyl)oxy)methyl)thiophen-2-yl)-3-(1-ethyl-4-methyl-1H-benzo[d][1,2,3]triazol-5-yl)-2,2-dimethylpropanoate

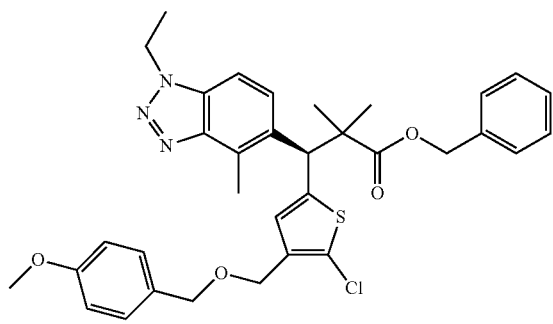

-continued

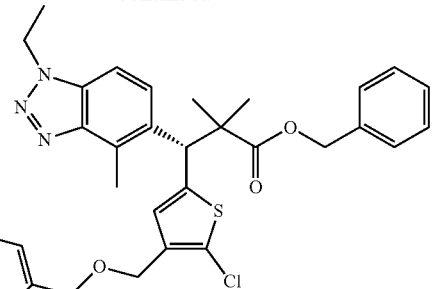

To a solution of methyl 3-(5-chloro-4-(((4-methoxybenzyl)oxy)methyl)thiophen-2-yl)-3-(1-ethyl-4-methyl-1H-benzo[d][1,2,3]triazol-5-yl)-2,2-dimethylpropanoate (800 mg, 1.476 mmol) dissolved in tetrahydrofuran (THF) (2.000 mL), methanol (2 mL) and water (1.000 mL) in a microwave reaction vial was added lithium hydroxide (177 mg, 7.38 mmol) and stirred at 100° C. for 2 h on the microwave. The solvents were concentrated and the residue was dried on high vacuum. The residue was then dissolved in DMF and benzyl bromide (0.702 mL, 5.90 mmol) was added to the reaction mixture and allowed to stir. The product was purified by flash chromatography eluting with 0-50% EtOAc/hexane to provide benzyl 3-(5-chloro-4-(((4-methoxybenzyl)oxy)methyl)thiophen-2-yl)-3-(1-ethyl-4-methyl-1H-benzo[d][1,2,3]triazol-5-yl)-2,2-dimethylpropanoate (800 mg, 88% yield). This compound was resolved by chiral SFC (Column: Chiralpak AY 20×250 mm, 5u; Co-solvent: 25% EtOH; Flowrate: 50 g/min; Back pressure: 100Bar) to give the (S)-Benzyl 3-(5-chloro-4-(((4-methoxybenzyl)oxy)methyl)thiophen-2-yl)-3-(1-ethyl-4-methyl-1H-benzo[d][1,2,3]triazol-5-yl)-2,2-dimethylpropanoate (0.362 g, 39% yield). LC/MS m/z=618 (M+H)+, 1.54 min (ret time), (chiral SFC ret. time: 3.43 min). and (R)-benzyl 3-(5-chloro-4-(((4-methoxybenzyl)oxy)methyl)thiophen-2-yl)-3-(1-ethyl-4-methyl-1H-benzo[d][1,2,3]triazol-5-yl)-2,2-dimethylpropanoate (0.380 g, 41% yield). LC/MS m/z=618 (M+H)+, 1.54 min (ret time), (chiral SFC ret. time: 5.77 min).

(S)-Benzyl 3-(5-chloro-4-(hydroxymethyl)thiophen-2-yl)-3-(1-ethyl-4-methyl-1H-benzo[d][1,2,3]triazol-5-yl)-2,2-dimethylpropanoate

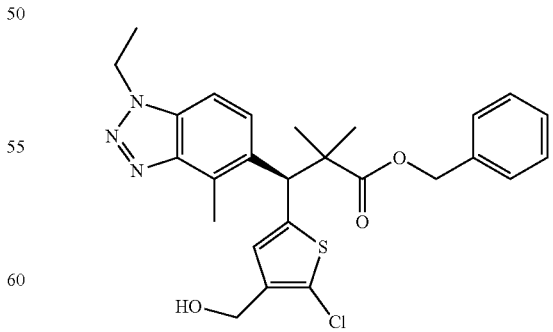

To a solution of (S)-benzyl 3-(5-chloro-4-(((4-methoxybenzyl)oxy)methyl)thiophen-2-yl)-3-(1-ethyl-4-methyl-1H-benzo[d][1,2,3]triazol-5-yl)-2,2-dimethylpropanoate (362 mg, 0.586 mmol) dissolved in acetonitrile (9.00 mL) was added ceric ammonium nitrate (963 mg, 1.757 mmol) and water (1 mL) and stirred for 2 h. The reaction was diluted with EtOAc (100 mL) and water (50 mL), and the phases were separated. The aqueous layer was extracted with EtOAc (50 mL) and the combined EtOAc layers were washed with water (50 mL) and saturated aqueous NaCl. The reaction was dried with Na₂SO₄ and concentrated. The residue was purified by flash chromatography eluting with 0-100% EtOAc/hexane to provide the title compound. (0.150 g, 51% yield). LC/MS m/z=498 (M+H)+, 1.12 min (ret time).

(S)-Benzyl 3-(5-chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-methyl-1H-benzo[d][1,2,3]triazol-5-yl)-2,2-dimethylpropanoate

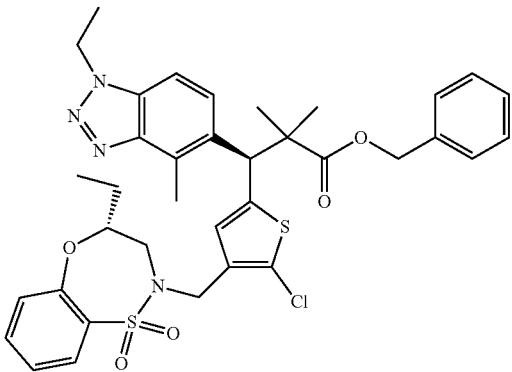 [SMILES: CC[C@@H]1CN(Cc2cc([C@@H](c3ccc4c(nnn4CC)c3C)C(C)(C)C(=O)OCc3ccccc3)sc2Cl)S(=O)(=O)c2ccccc2O1]

To a solution of (S)-benzyl 3-(5-chloro-4-(hydroxymethyl)thiophen-2-yl)-3-(1-ethyl-4-methyl-1H-benzo[d][1,2,3]triazol-5-yl)-2,2-dimethylpropanoate (50 mg, 0.100 mmol), (R)-4-ethyl-3,4-dihydro-2H-benzo[b][1,4,5]oxathiazepine 1,1-dioxide (45.6 mg, 0.201 mmol) and (E)-diazene-1,2-diylbis(piperidin-1-ylmethanone) (50.7 mg, 0.201 mmol) in tetrahydrofuran (THF) (4 mL) was added tributylphosphine (0.050 mL, 0.201 mmol) and stirred for 1 h 15 min. The reaction was then concentrated and the residue was purified by reverse phase preparative HPLC under neutral conditions to provide the title compound (0.050 g, 70% yield). LC/MS m/z=707 (M+H)+, 1.54 min (ret. time).

(S)-3-(5-Chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-methyl-1H-benzo[d][1,2,3]triazol-5-yl)-2,2-dimethylpropanoic acid

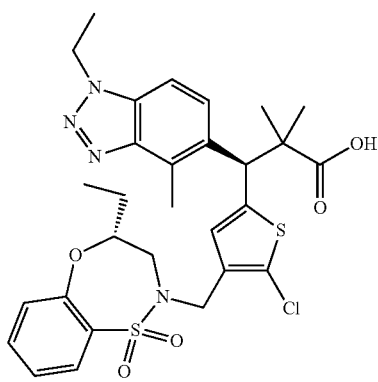 [SMILES: CC[C@@H]1CN(Cc2cc([C@@H](c3ccc4c(nnn4CC)c3C)C(C)(C)C(=O)O)sc2Cl)S(=O)(=O)c2ccccc2O1]

To a solution of (S)-benzyl 3-(5-chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-methyl-1H-benzo[d][1,2,3]triazol-5-yl)-2,2-dimethylpropanoate (50 mg, 0.071 mmol) dissolved in tetrahydrofuran (THF) (2 mL) water (1.000 mL) and methanol (2.000 mL) in a microwave reaction vial, was added lithium hydroxide (8.46 mg, 0.353 mmol) and stirred at 100° C. for 1 h on the microwave. A solution of 10% formic acid and added dropwise to the reaction until it had reached acidic conditions Reaction was condensed, and the residue was purified by reverse phase preparative HPLC under formic acid conditions to provide the title compound (0.015 g, 34% yield). LC/MS m/z=617 (M+H)+, 1.27 min (ret. time).

Example 4

(R)-3-(5-Chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-methyl-1H-benzo[d][1,2,3]triazol-5-yl)-2,2-dimethylpropanoic acid

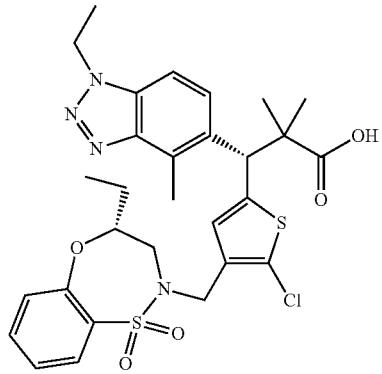 [SMILES: CC[C@@H]1CN(Cc2cc([C@H](c3ccc4c(nnn4CC)c3C)C(C)(C)C(=O)O)sc2Cl)S(=O)(=O)c2ccccc2O1]

(R)-2-Fluoro-N-(2-hydroxybutyl)benzenesulfonamide

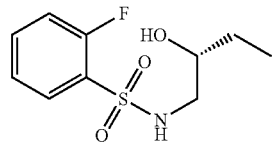 [SMILES: CC[C@@H](O)CNS(=O)(=O)c1ccccc1F]

To a solution of (R)-1-aminobutan-2-ol (14.66 g, 164 mmol) in tetrahydrofuran (THF) (200 mL) and water (60 mL) at ambient temperature was added K₂CO₃ (14.20 g, 103 mmol) and 2-fluorobenzene-1-sulfonyl chloride (20 g, 103 mmol). It was stirred for 16 h. The reaction mixture was diluted with water (100 mL) and extracted with EtOAc (2×100 mL). The combined organic layer was washed with brine solution (200 mL) and dried over anhydrous Na₂SO₄, filtered and concentrated to give the title compound (14 g, 53.8 mmol, 52.3% yield) as a gummy liquid. LC/MS m/z=494.83 (2M−H)+, 1.660 min (ret. time).

101

(R)-4-Ethyl-3,4-dihydro-2H-benzo[b][1,4,5]oxathiazepine 1,1-dioxide

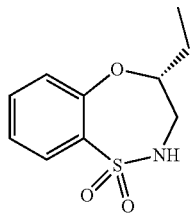

To a solution of (R)-2-fluoro-N-(2-hydroxybutyl)benzenesulfonamide (14 g, 56.6 mmol) in dimethyl sulfoxide (DMSO) (140 mL) at 0° C. was added potassium tert-butoxide (6.35 g, 56.6 mmol). It was then heated at 80° C. for 4 h. The reaction mixture was cooled and neutralized with 1N HCl, diluted with ice water (500 mL) and extracted with EtOAc (2×400 mL). The combined organic layer was washed with chilled brine solution (200 mL) and dried over anhydrous $Na_2SO_4$, filtered and concentrated. The crude residue was purified via flash column chromatography eluting with 50% EtOAc in hexane to give the title compound (11.12 g, 48.9 mmol, 86% yield) as a white solid. LC/MS m/z=228.05 (M+H)+, 1.84 min (ret. time).

(R)-Benzyl 3-(5-chloro-4-(hydroxymethyl)thiophen-2-yl)-3-(1-ethyl-4-methyl-1H-benzo[d][1,2,3]triazol-5-yl)-2,2-dimethylpropanoate

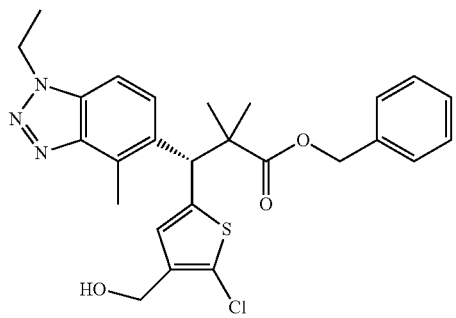 [SMILES: CCn1nnc2c(C)c([C@@H](c3cc(CO)c(Cl)s3)C(C)(C)C(=O)OCc3ccccc3)ccc21]

(R)-benzyl 3-(5-chloro-4-(((4-methoxybenzyl)oxy)methyl)thiophen-2-yl)-3-(1-ethyl-4-methyl-1H-benzo[d][1,2,3]triazol-5-yl)-2,2-dimethylpropanoate (250 mg, 0.404 mmol) was dissolved in acetonitrile (5.00 mL) combined with ceric ammonium nitrate (222 mg, 0.404 mmol) and water (1 mL) and stirred 1 h. Additional ceric ammonium nitrate (111 mg, 0.202 mmol) was added and the reaction was allowed to stir for an additional 1 h. The reaction was then diluted with EtOAc (100 mL) and water (50 mL), and the phases were separated. The aqueous layer was extracted again with EtOAc (50 mL) and the combined EtOAc layers were washed with water (50 mL) and saturated aqueous NaCl. The reaction was dried with $Na_2SO_4$ and concentrated. The residue was purified by flash chromatography eluting with 0-100% EtOAc/hexane to provide the title compound. (0.126 g, 62% yield). LC/MS m/z=498 (M+H)+, 1.20 min (ret time).

102

(R)-Benzyl 3-(5-chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-methyl-1H-benzo[d][1,2,3]triazol-5-yl)-2,2-dimethylpropanoate

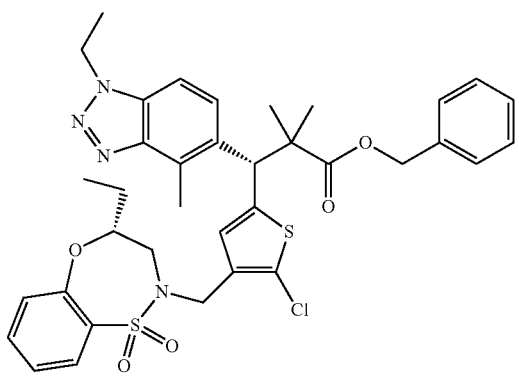 [SMILES: CC[C@@H]1CN(Cc2cc([C@H](c3ccc4c(nnn4CC)c3C)C(C)(C)C(=O)OCc3ccccc3)sc2Cl)S(=O)(=O)c2ccccc2O1]

To a solution of (R)-benzyl 3-(5-chloro-4-(hydroxymethyl)thiophen-2-yl)-3-(1-ethyl-4-methyl-1H-benzo[d][1,2,3]triazol-5-yl)-2,2-dimethylpropanoate (61 mg, 0.122 mmol), and (R)-4-ethyl-3,4-dihydro-2H-benzo[b][1,4,5]oxathiazepine 1,1-dioxide (55.7 mg, 0.245 mmol) and (E)-diazene-1,2-diylbis(piperidin-1-ylmethanone) (61.8 mg, 0.245 mmol) in tetrahydrofuran (THF) (4 mL) was added tributylphosphine (0.061 mL, 0.245 mmol) and stirred for 1 h 15 min. The reaction was then concentrated, and the residue was purified by reverse phase preparative HPLC under neutral conditions to provide the title compound (0.090 g, 104% yield). LC/MS m/z=707 (M+H)+, 1.51 min (ret. time).

(R)-3-(5-Chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-methyl-1H-benzo[d][1,2,3]triazol-5-yl)-2,2-dimethylpropanoic acid

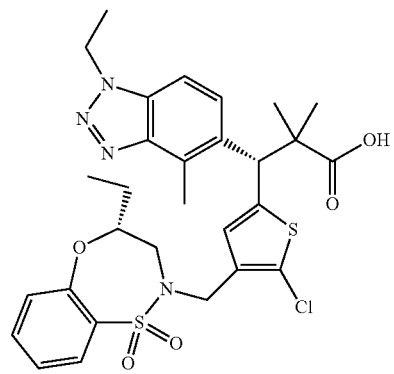 [SMILES: CC[C@@H]1CN(Cc2cc([C@H](c3ccc4c(nnn4CC)c3C)C(C)(C)C(=O)O)sc2Cl)S(=O)(=O)c2ccccc2O1]

To a solution of (R)-benzyl 3-(5-chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-methyl-1H-benzo[d][1,2,3]triazol-5-yl)-2,2-dimethylpropanoate (90 mg, 0.127 mmol) dissolved in tetrahydrofuran (THF) (2 mL), water (1.000 mL) and methanol (2.000 mL) in a microwave reaction vial was added lithium hydroxide (15.24 mg, 0.636 mmol) and stirred at 100° C. for 2 h on the microwave. A solution of 10% formic acid and added dropwise to the reaction until it was acidic. The reaction was then concentrated, and the residue was purified by reverse phase preparative HPLC under neutral conditions to provide the title compound (0.020 g, 25% yield). LC/MS m/z=617 (M+H)+, 1.24 min (ret. time).

Example 5

(R)-3-(5-Chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-methyl-1H-benzo[d][1,2,3]triazol-5-yl)propanoic acid

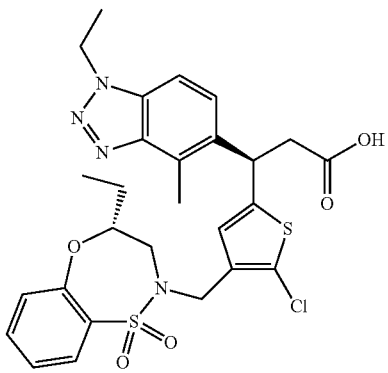 [SMILES: CC[C@@H]1CN(Cc2cc([C@H](CC(=O)O)c3ccc4c(nnn4CC)c3C)sc2Cl)S(=O)(=O)c2ccccc2O1]

(R)-Methyl 3-(5-chloro-4-(hydroxymethyl)thiophen-2-yl)-3-(1-ethyl-4-methyl-1H-benzo[d][1,2,3]triazol-5-yl)propanoate

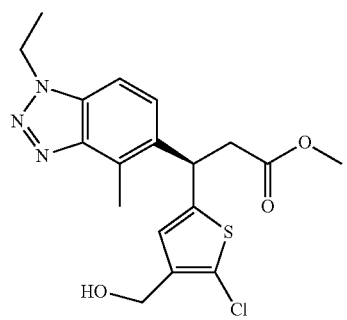 [SMILES: CCn1nnc2c(C)c([C@@H](CC(=O)OC)c3cc(CO)c(Cl)s3)ccc21]

(R)-methyl 3-(5-chloro-4-(((4-methoxybenzyl)oxy)methyl)thiophen-2-yl)-3-(1-ethyl-4-methyl-1H-benzo[d][1,2,3]triazol-5-yl)propanoate (220 mg, 0.428 mmol) was dissolved in 4N hydrochloric acid (10 mL, 40.0 mmol) and stirred for 1 h. The reaction was concentrated and the residue was purified by flash chromatography eluting with 0-50% EtOAc/hexanes to provide the title compound. (0.145 g, 86% yield). LC/MS m/z=394 (M+H)+, 1.02 min (ret time).

(R)-Methyl 3-(5-chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-methyl-1H-benzo[d][1,2,3]triazol-5-yl)propanoate

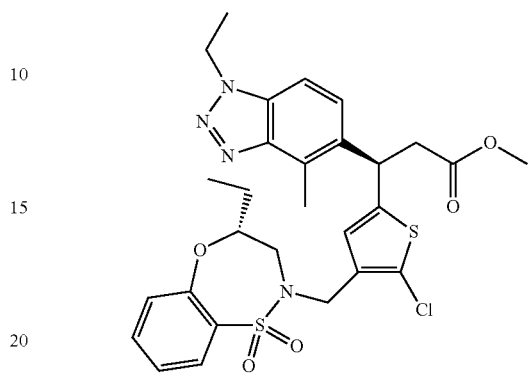

To a solution of (S)-methyl 3-(5-chloro-4-(hydroxymethyl)thiophen-2-yl)-3-(1-ethyl-4-methyl-1H-benzo[d][1,2,3]triazol-5-yl)propanoate (48 mg, 0.122 mmol), (R)-4-ethyl-3,4-dihydro-2H-benzo[b][1,4,5]oxathiazepine 1,1-dioxide (55.4 mg, 0.244 mmol) and (E)-diazene-1,2-diylbis(piperidin-1-ylmethanone) (61.5 mg, 0.244 mmol) in tetrahydrofuran (THF) (4 mL) was added tributylphosphine (0.061 mL, 0.244 mmol) stirred for 1 h 15 min. The reaction was then concentrated and the residue was purified by reverse phase preparative HPLC under neutral conditions to provide the title compound (0.061 g, 83% yield). LC/MS m/z=603 (M+H)+, 1.34 min (ret. time).

(R)-3-(5-Chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-methyl-1H-benzo[d][1,2,3]triazol-5-yl)propanoic acid

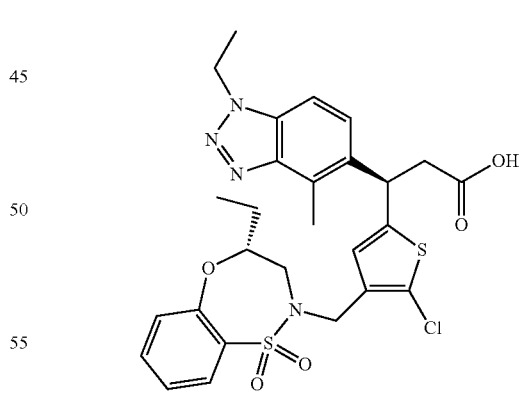

To a solution of (R)-methyl 3-(5-chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-methyl-1H-benzo[d][1,2,3]triazol-5-yl)propanoate (61 mg, 0.101 mmol) dissolved in tetrahydrofuran (THF) (2.000 mL), water (1 mL) and methanol (2.000 mL) was added lithium hydroxide (12.11 mg, 0.506 mmol) and the reaction mixture stirred at ambient temperature for 1 h. A solution of 10% formic acid was added dropwise to the reaction until the solution was acidic. The solvents were concentrated and the residue was purified by reverse phase preparative HPLC under formic acid conditions to provide the title compound (0.028 g, 47% yield). LC/MS m/z=589 (M+H)+, 1.24 min (ret. time).

Example 6

(R)-3-(5-Chloro-4-(((R)-4-ethyl-1,1-dioxido-3,4-dihydro-2H-pyrido[2,3-b][1,4,5]oxathiazepin-2-yl)methyl)thiophen-2-yl)-3-(1-ethyl-4-methyl-1H-benzo[d][1,2,3]triazol-5-yl)propanoic acid

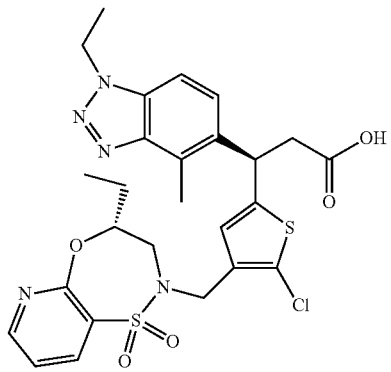 [SMILES: CC[C@@H]1CN(Cc2cc([C@H](CC(=O)O)c3ccc4c(nnn4CC)c3C)sc2Cl)S(=O)(=O)c2cccnc2O1]

(R)-Methyl 3-(5-chloro-4-(((R)-4-ethyl-1,1-dioxido-3,4-dihydro-2H-pyrido[2,3-b][1,4,5]oxathiazepin-2-yl)methyl)thiophen-2-yl)-3-(1-ethyl-4-methyl-1H-benzo[d][1,2,3]triazol-5-yl)propanoate

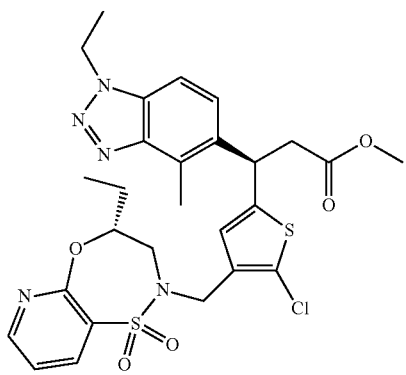 [SMILES: CC[C@@H]1CN(Cc2cc([C@H](CC(=O)OC)c3ccc4c(nnn4CC)c3C)sc2Cl)S(=O)(=O)c2cccnc2O1]

To a solution of (R)-methyl 3-(5-chloro-4-(hydroxymethyl)thiophen-2-yl)-3-(1-ethyl-4-methyl-1H-benzo[d][1,2,3]triazol-5-yl)propanoate (48 mg, 0.122 mmol), (R)-4-ethyl-3,4-dihydro-2H-pyrido[2,3-b][1,4,5]oxathiazepine 1,1-dioxide (55.6 mg, 0.244 mmol) and (E)-diazene-1,2-diylbis(piperidin-1-ylmethanone) (61.5 mg, 0.244 mmol) in tetrahydrofuran (THF) (4 mL) was added tributylphosphine (0.061 mL, 0.244 mmol) and stirred for 1 h 15 min. The reaction was then concentrated and the residue was purified by reverse phase preparative HPLC under neutral conditions to provide the title compound (0.063 g, 86% yield). LC/MS m/z=604 (M+H)+, 1.17 min (ret. time).

(R)-3-(5-Chloro-4-(((R)-4-ethyl-1,1-dioxido-3,4-dihydro-2H-pyrido[2,3-b][1,4,5]oxathiazepin-2-yl)methyl)thiophen-2-yl)-3-(1-ethyl-4-methyl-1H-benzo[d][1,2,3]triazol-5-yl)propanoic Acid

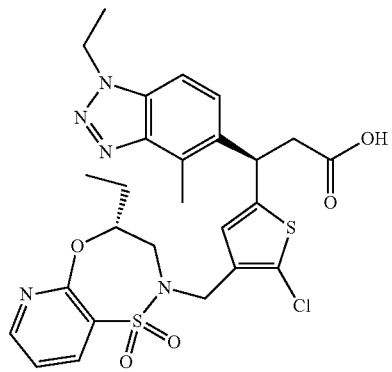 [SMILES: CC[C@@H]1CN(Cc2cc([C@H](CC(=O)O)c3ccc4c(nnn4CC)c3C)sc2Cl)S(=O)(=O)c2cccnc2O1]

To a solution of (R)-methyl 3-(5-chloro-4-(((R)-4-ethyl-1,1-dioxido-3,4-dihydro-2H-pyrido[2,3-b][1,4,5]oxathiazepin-2-yl)methyl)thiophen-2-yl)-3-(1-ethyl-4-methyl-1H-benzo[d][1,2,3]triazol-5-yl)propanoate (63 mg, 0.104 mmol) dissolved in tetrahydrofuran (THF) (2.000 mL), water (1 mL) and methanol (2.000 mL) was added lithium hydroxide (12.49 mg, 0.521 mmol) and stirred at ambient temperature for 2 h. A solution of 10% formic acid was added dropwise to the reaction until the solution was acidic. The solvents were concentrated and the residue was purified by reverse phase preparative HPLC under formic acid conditions to provide the title compound (0.024 g, 39% yield). LC/MS m/z=590 (M+H)+, 1.08 min (ret. time).

Example 7

(S)-3-(4-(((R)-4-Ethyl-1,1-dioxido-3,4-dihydro-2H-pyrido[2,3-b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoic acid

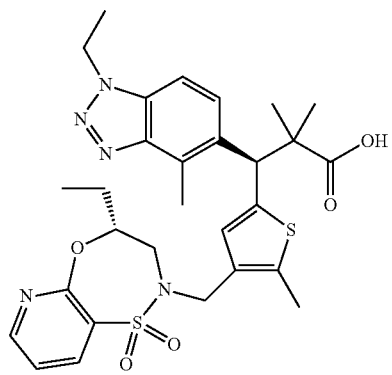 [SMILES: CC[C@@H]1CN(Cc2cc([C@@H](c3ccc4c(nnn4CC)c3C)C(C)(C)C(=O)O)sc2C)S(=O)(=O)c2cccnc2O1]

107

(5-Bromo-2-methylthiophen-3-yl)methanol

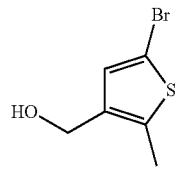

A solution of ethyl 5-bromo-2-methylthiophene-3-carboxylate (3.915 g, 15.72 mmol) in tetrahydrofuran (THF) (79 mL) was cooled in ice bath. To this was added DIBAL-H (40.9 mL, 40.9 mmol) and stirred for 3 h at 0° C. Another portion of DIBAL-H (7.86 mL, 7.86 mmol) was added and stirred for 30 min followed by the addition of another portion of DIBAL-H (3.93 mL, 3.93 mmol) and stirred for 30 min. The reaction was quenched with 140 mL 1N HCl at 0° C. The solution was extracted with EtOAc (3×). The organic layers were washed with 1N HCl, brine and dried MgSO$_4$ and concentrated. The residue was purified by flash chromatography eluting with 100% DCM to provide the title compound. (3.30 g, 97% yield). LC/MS m/z=189/190 (M-OH)+, 0.75 min (ret time).

((5-Bromo-2-methylthiophen-3-yl)methoxy)(tert-butyl)dimethylsilane

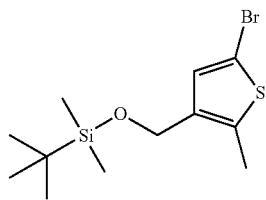 [SMILES: Cc1sc(Br)cc1CO[Si](C)(C)C(C)(C)C]

A solution of (5-bromo-2-methylthiophen-3-yl)methanol (3.30 g, 14.50 mmol) in N,N-dimethylformamide (DMF) (72.5 mL) was cooled to 0° C. and to it was added imidazole (2.96 g, 43.5 mmol) followed by TBDMS-Cl (3.28 g, 21.75 mmol). The reaction was stirred at 0° C. for 1 h and warmed to ambient temperature and stirred for 2 h. The solvent was concentrated and the residue was suspended in water. The aqueous layer was extracted with DCM (3×). The combined organics were washed with water, brine and dried with MgSO$_4$. The crude compound was purified by flash chromatography eluting with 100% hexane to provide the title compound. (4.513 g, 95% yield). $^1$H NMR (400 MHz, CHLOROFORM-d) δ 6.89 (s, 1H), 4.53 (s, 2H), 2.31 (s, 3H), 0.91 (s, 9H), 0.08 (s, 6H).

108

(4-(((Tert-butyldimethylsilyl)oxy)methyl)-5-methyl-thiophen-2-yl)(1-ethyl-4-methyl-1H-benzo[d][1,2,3]triazol-5-yl)methanol

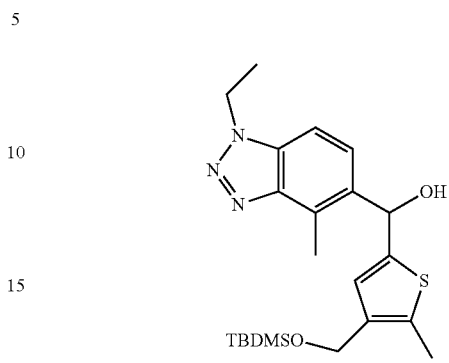

A solution of ((5-bromo-2-methylthiophen-3-yl)methoxy)(tert-butyl)dimethylsilane (3.49 g, 10.86 mmol) in tetrahydrofuran (THF) (45 mL) was cooled to −78° C. 1M n-butyllithium in THF (10.52 mL, 16.83 mmol) was added dropwise and stirred for 1.5 h. 1-ethyl-4-methyl-1H-benzo[d][1,2,3]triazole-5-carbaldehyde (2.466 g, 13.03 mmol) in tetrahydrofuran (THF) (15 mL) was then added dropwise and stirred at −78° C. for 1 h. The reaction was quenched with water (3 mL) and allowed to warm to ambient temperature. It was then diluted with EtOAc and the organic layer was washed with water (3×). The aqueous layer was back extracted with EtOAc (2×) and the combined organic layers were washed with brine and dried with MgSO$_4$. The crude residue was purified by flash chromatography eluting with 0-35% EtOAc/hexane and again with 0-15% EtOAc/DCM. Impure chromatography fractions were repurified eluting with 0-20% EtOAc/DCM. All product batches were combined to provide the title compound. (2.97 g, 63% yield). LC/MS m/z=432 (M+H)+, 1.40 min (ret. time).

Methyl 3-(4-(((tert-butyldimethylsilyl)oxy)methyl)-5-methylthiophen-2-yl)-3-(1-ethyl-4-methyl-1H-benzo[d][1,2,3]triazol-5-yl)-2,2-dimethylpropanoate

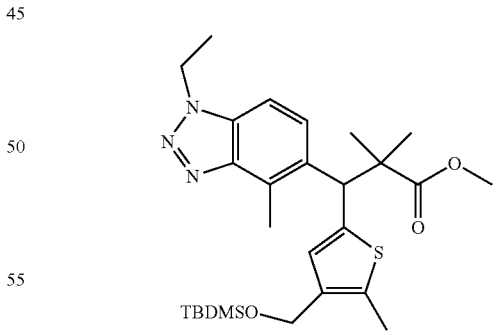

To a solution of (4-(((tert-butyldimethylsilyl)oxy)methyl)-5-methylthiophen-2-yl)(1-ethyl-4-methyl-1H-benzo[d][1,2,3]triazol-5-yl)methanol (2.97 g, 6.88 mmol) in acetonitrile (60 mL) at 0° C., was added 2,2,2-trichloroacetonitrile (1.035 mL, 10.32 mmol) in acetonitrile (12 mL), via addition funnel, dropwise and stirred for 10 min. DBU (0.052 mL, 0.344 mmol) in acetonitrile (5 mL), was then added dropwise, via addition funnel, and stirred for 1 h. The reaction was warmed to ambient temperature for 10 min and re-cooled. Afterwards, ((1-methoxy-2-methylprop-1-en-1-yl)oxy)trimethylsilane (1.677 mL, 8.26 mmol) was added dropwise, via syringe, in acetonitrile (12 mL) followed by dropwise addition of 1,1,1-trifluoro-N-((trifluoromethyl)sulfonyl)methanesulfonamide (0.193 g, 0.688 mmol) in acetonitrile (15 mL) and stirred at ambient temperature for 2 h. The reaction was quenched with saturated. NaHCO$_3$ and the aqueous layer was extracted with EtOAc (4×). The combined organics were washed with brine and dried with MgSO$_4$ and concentrated. The residue was purified by flash chromatography eluting with 0-20% EtOAc/hexanes. Impure chromatography fractions were repurified eluting with 0-15% EtOAc/hexanes. All product batches were combined to provide the title compound. (2.83 g, 80% yield). LC/MS m/z=516 (M+H)+, 1.60 min (ret. time).

(S)-Benzyl 3-(1-ethyl-4-methyl-1H-benzo[d][1,2,3]triazol-5-yl)-3-(4-(hydroxymethyl)-5-methylthiophen-2-yl)-2,2-dimethylpropanoate and (R)-benzyl 3-(1-ethyl-4-methyl-1H-benzo[d][1,2,3]triazol-5-yl)-3-(4-(hydroxymethyl)-5-methylthiophen-2-yl)-2,2-dimethylpropanoate

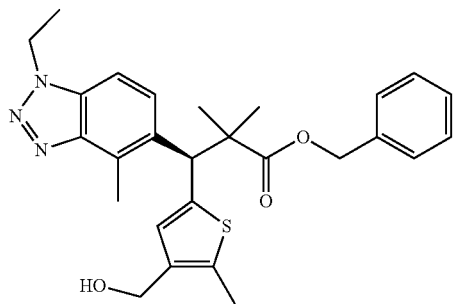

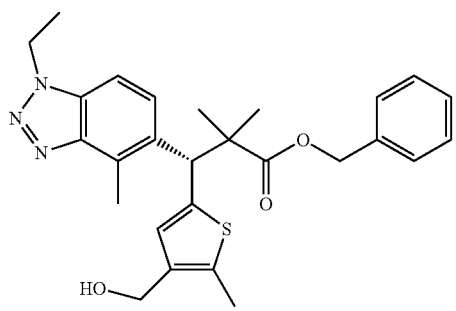

This reaction was divided equally into three individual microwave reactions. To a solution of methyl 3-(4-(((tert-butyldimethylsilyl)oxy)methyl)-5-methylthiophen-2-yl)-3-(1-ethyl-4-methyl-1H-benzo[d][1,2,3]triazol-5-yl)-2,2-dimethylpropanoate (2.83 g, 5.49 mmol) in tetrahydrofuran (THF) (15 mL) methanol (15.00 mL) and water (15.00 mL) was added LiOH (0.526 g, 21.95 mmol) and heated on a microwave to 150° C. for 2 h. The reactions were combined and the solvents were concentrated and pumped on high vacuum overnight. The lithium salt was dissolved in N,N-dimethylformamide (DMF) (20 mL) and benzyl bromide (0.653 mL, 5.49 mmol) in N,N-dimethylformamide (DMF) (5 mL) was added dropwise and stirred for 3 h. Additional benzyl bromide (0.065 mL, 0.549 mmol) was then added and stirred for 5 h. Additional benzyl bromide (0.163 mL, 1.372 mmol) was added and stirred for 40 min. The reaction was quenched with 20 mL of 1N HCl and the aqueous layer was extracted with EtOAc. The organic layer was washed with water (2×). The combined aqueous layers were extracted with EtOAc. The combined organics were washed with water and brine and dried with MgSO$_4$ and concentrated. The residue was purified by flash chromatography eluting with 0-50% EtOAc/hexanes to provide benzyl 3-(1-ethyl-4-methyl-1H-benzo[d][1,2,3]triazol-5-yl)-3-(4-(hydroxymethyl)-5-methylthiophen-2-yl)-2,2-dimethylpropanoate (1.58 g, 58% yield). This compound was resolved by chiral SFC (Column: Chiralpak AY 20×250 mm, 5u; Co-solvent: 20% EtOH; Flowrate: 50 g/min; Back pressure: 100Bar) to give (S)-benzyl 3-(1-ethyl-4-methyl-1H-benzo[d][1,2,3]triazol-5-yl)-3-(4-(hydroxymethyl)-5-methylthiophen-2-yl)-2,2-dimethylpropanoate (0.682 g, 26% yield) and (R)-benzyl 3-(1-ethyl-4-methyl-1H-benzo[d][1,2,3]triazol-5-yl)-3-(4-(hydroxymethyl)-5-methylthiophen-2-yl)-2,2-dimethylpropanoate (0.694 g, 26% yield).

(S)-Benzyl 3-(4-(((R)-4-ethyl-1,1-dioxido-3,4-dihydro-2H-pyrido[2,3-b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoate

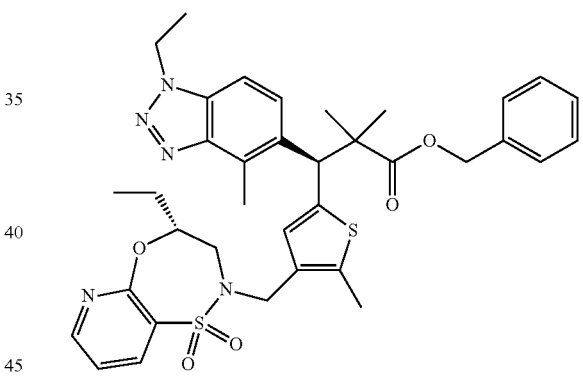

To a solution of (S)-benzyl 3-(1-ethyl-4-methyl-1H-benzo[d][1,2,3]triazol-5-yl)-3-(4-(hydroxymethyl)-5-methylthiophen-2-yl)-2,2-dimethylpropanoate (50 mg, 0.105 mmol) in tetrahydrofuran (THF) (2 mL) was added (R)-4-ethyl-3,4-dihydro-2H-pyrido[2,3-b][1,4,5]oxathiazepine 1,1-dioxide (56.4 mg, 0.247 mmol) and (E)-diazene-1,2-diylbis(piperidin-1-ylmethanone) (ADDP) (62.3 mg, 0.247 mmol). The reaction was degassed with vacuum and flushed with nitrogen. Tri-n-butylphosphine (0.061 mL, 0.247 mmol) was then added and the reaction was stirred at ambient temperature for 1 h. The solvents were concentrated and the residue was purified by reverse phase preparative HPLC under neutral conditions to provide the title compound (0.062 g, 86% yield). LC/MS m/z=688 (M+H)+, 1.38 min (ret. time).

(S)-3-(4-(((R)-4-Ethyl-1,1-dioxido-3,4-dihydro-2H-pyrido[2,3-b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoic Acid

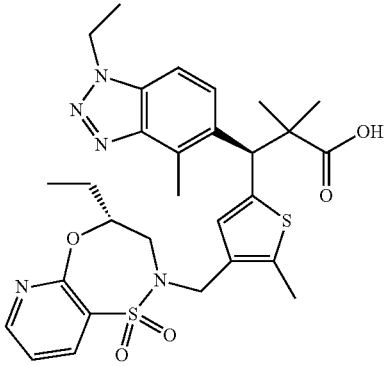 [SMILES: CC[C@@H]1CN(Cc2cc([C@@H](c3ccc4c(nnn4CC)c3C)C(C)(C)C(=O)O)sc2C)S(=O)(=O)c2cccnc2O1]

A solution of (S)-benzyl 3-(4-(((R)-4-ethyl-1,1-dioxido-3,4-dihydro-2H-pyrido[2,3-b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoate (62 mg, 0.090 mmol) in methanol (6 mL) was run through an H-Cube at full H$_2$ pressure with a 10% Pd/C cartridge for 20 min. The system was flushed with methanol and the solvent was concentrated and the residue was purified by reverse phase preparative HPLC under formic acid conditions to provide the title compound (0.028 g, 52% yield). LC/MS m/z=598 (M+H)+, 1.07 min (ret. time).

Example 8

(S)-3-(4-((4,4-Dimethyl-1,1-dioxido-3,4-dihydro-2H-pyrido[2,3-b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoic Acid

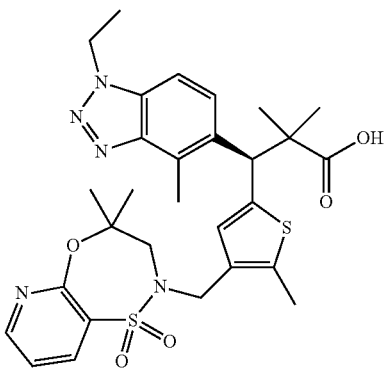 [SMILES: CCn1nnc2c(C)c([C@H](c3cc(CN4CC(C)(C)Oc5ncccc5S4(=O)=O)c(C)s3)C(C)(C)C(=O)O)ccc21]

2-Chloro-N-(2-hydroxy-2-methylpropyl)pyridine-3-sulfonamide

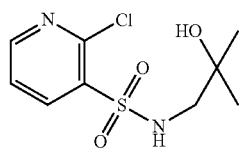 [SMILES: CC(C)(O)CNS(=O)(=O)c1cccnc1Cl]

To a solution of 2-chloropyridine-3-sulfonyl chloride (9 g, 42.4 mmol) in tetrahydrofuran (THF) (150 mL) was added 1-amino-2-methylpropan-2-ol (3.78 g, 42.4 mmol), potassium carbonate (5.87 g, 42.4 mmol) and water (45 mL). The reaction mixture was stirred at ambient temperature for 2 h. The reaction mixture was quenched with water (20 mL) and extracted with EtOAc (3×20 mL). The combined organic layer was dried over anhydrous Na$_2$SO$_4$, filtered and concentrated to give the title compound (9 g, 33.1 mmol, 78% yield) as off-whit solid. LC/MS m/z=265.00 (M+H)$^+$, 1.372 min (ret. time).

4,4-Dimethyl-3,4-dihydro-2H-pyrido[2,3-b][1,4,5]oxathiazepine 1,1-dioxide

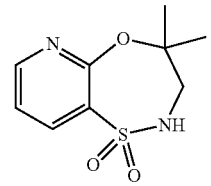

To a solution of 2-chloro-N-(2-hydroxy-2-methylpropyl)pyridine-3-sulfonamide (9 g, 34.0 mmol) in dimethyl sulfoxide (DMSO) (90 mL) at 10° C. was added potassium tert-butoxide (11.44 g, 102 mmol), then heated to 75° C. for 1 h. The reaction mixture was cooled to ambient temperature and poured into water (400 mL). It was neutralized with 1N HCl and the obtained solid was filtered, washed with water and dried well to give the title compound (4.96 g, 21.70 mmol, 63.8% yield) as light yellow solid. LC/MS m/z=229.01 (M+H)$^+$, 2.192 min (ret. time).

(S)-Benzyl 3-(4-((4,4-dimethyl-1,1-dioxido-3,4-dihydro-2H-pyrido[2,3-b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoate

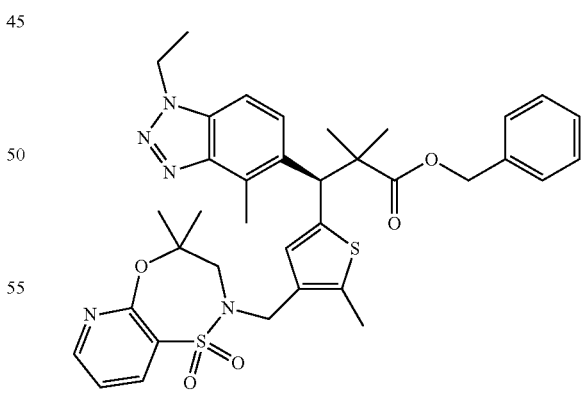

To a solution of (S)-benzyl 3-(1-ethyl-4-methyl-1H-benzo[d][1,2,3]triazol-5-yl)-3-(4-(hydroxymethyl)-5-methylthiophen-2-yl)-2,2-dimethylpropanoate (50 mg, 0.105 mmol) in tetrahydrofuran (THF) (2 mL) was added 4,4-dimethyl-3,4-dihydro-2H-pyrido[2,3-b][1,4,5]oxathiazepine 1,1-dioxide (56.4 mg, 0.247 mmol) and (E)-diazene-1,2-diylbis(piperidin-1-ylmethanone) (ADDP) (62.3 mg, 0.247 mmol).

The reaction was degassed with vacuum and flushed with nitrogen. Tri-n-butylphosphine (0.061 mL, 0.247 mmol) was then added and the reaction was stirred at ambient temperature for 3 days. The solvents were concentrated and the residue was purified by reverse phase preparative HPLC under neutral conditions to provide the title compound (0.048 g, 66% yield). LC/MS m/z=688 (M+H)+, 1.31 min (ret. time).

(S)-3-(4-((4,4-Dimethyl-1,1-dioxido-3,4-dihydro-2H-pyrido[2,3-b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoic Acid

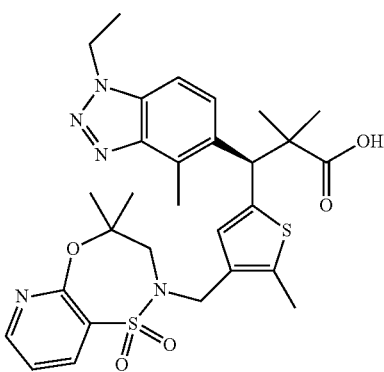 [SMILES: CCn1nnc2c(C)c([C@H](c3cc(CN4CC(C)(C)Oc5ncccc5S4(=O)=O)c(C)s3)C(C)(C)C(=O)O)ccc21]

A solution of (S)-benzyl 3-(4-((4,4-dimethyl-1,1-dioxido-3,4-dihydro-2H-pyrido[2,3-b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoate (48 mg, 0.070 mmol) in methanol (6 mL) was run through a H-Cube at full H$_2$ pressure with a 10% Pd/C cartridge for 20 min. The system was flushed with methanol and the solvent was concentrated and the residue was purified by reverse phase preparative HPLC under formic acid conditions to provide the title compound (0.025 g, 60% yield). LC/MS m/z=598 (M+H)+, 1.03 min (ret. time).

Example 9

(S)-3-(4-(((R)-4-Ethyl-1,1-dioxido-3,4-dihydro-2H-pyrido[4,3-b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoic Acid

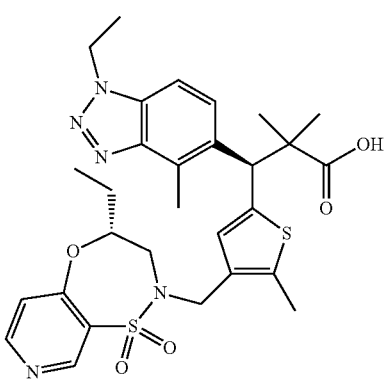 [SMILES: CC[C@@H]1CN(Cc2cc([C@@H](c3ccc4c(nnn4CC)c3C)C(C)(C)C(=O)O)sc2C)S(=O)(=O)c2cnccc2O1]

(S)-Benzyl 3-(4-(((R)-4-ethyl-1,1-dioxido-3,4-dihydro-2H-pyrido[4,3-b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoate

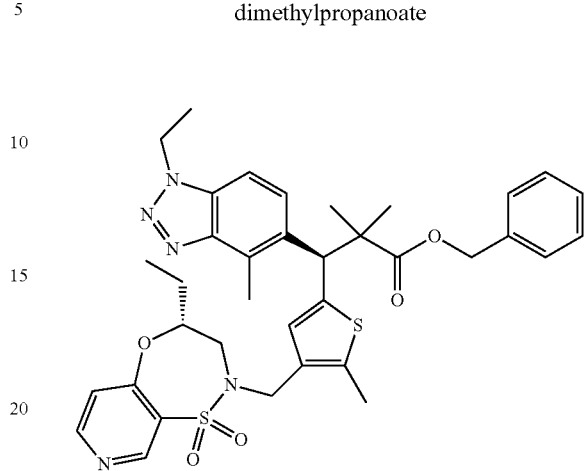

To a solution of (S)-benzyl 3-(1-ethyl-4-methyl-1H-benzo[d][1,2,3]triazol-5-yl)-3-(4-(hydroxymethyl)-5-methylthiophen-2-yl)-2,2-dimethylpropanoate (50 mg, 0.105 mmol) in tetrahydrofuran (THF) (2 mL) was added (R)-4-ethyl-3,4-dihydro-2H-pyrido[4,3-b][1,4,5]oxathiazepine 1,1-dioxide (47.8 mg, 0.209 mmol) and (E)-diazene-1,2-diylbis(piperidin-1-ylmethanone) (ADDP) (52.8 mg, 0.209 mmol). The reaction was degassed with vacuum and flushed with nitrogen. Tri-n-butylphosphine (0.052 mL, 0.209 mmol) was added and the reaction was stirred at ambient temperature for 3 h. The solvents were concentrated and the residue was purified by reverse phase preparative HPLC under neutral conditions to provide the title compound (0.060 g, 83% yield). LC/MS m/z=688 (M+H)+, 1.37 min (ret. time).

(S)-3-(4-(((R)-4-Ethyl-1,1-dioxido-3,4-dihydro-2H-pyrido[4,3-b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoic Acid

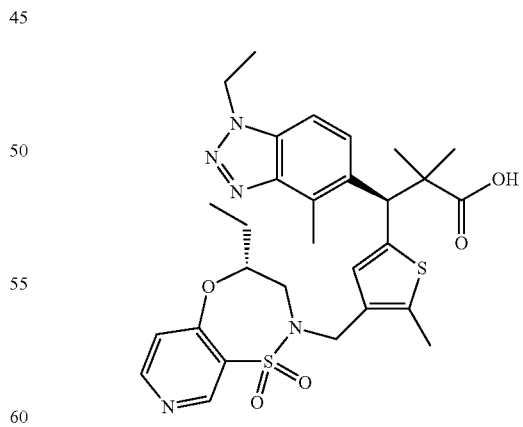

A solution of (S)-benzyl 3-(4-(((R)-4-ethyl-1,1-dioxido-3,4-dihydro-2H-pyrido[4,3-b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoate (60 mg, 0.087 mmol) in methanol (6 mL) and was run through a H-Cube at full H$_2$ pressure with a 10% Pd/C cartridge for 15 min. The system was flushed with methanol and the solvent was concentrated and the residue was purified by reverse phase preparative HPLC under formic acid conditions to provide the title compound (0.037 g, 71% yield). LC/MS m/z=598 (M+H)+, 1.06 min (ret. time).

Example 10

(S)-3-(4-(((R)-4-Ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoic Acid

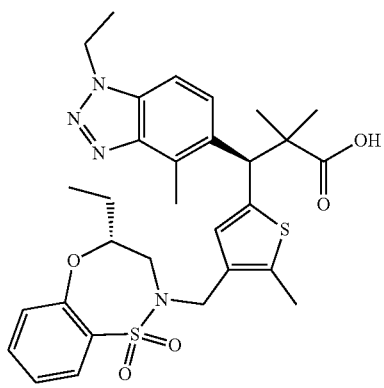 [SMILES: CC[C@@H]1CN(Cc2cc([C@@H](c3ccc4c(nnn4CC)c3C)C(C)(C)C(=O)O)sc2C)S(=O)(=O)c2ccccc2O1]

(S)-Benzyl 3-(4-(((R)-4-ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoate

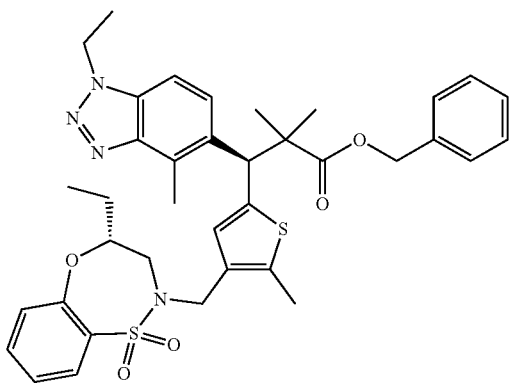 [SMILES: CC[C@@H]1CN(Cc2cc([C@@H](c3ccc4c(nnn4CC)c3C)C(C)(C)C(=O)OCc3ccccc3)sc2C)S(=O)(=O)c2ccccc2O1]

To a solution of (S)-benzyl 3-(1-ethyl-4-methyl-1H-benzo[d][1,2,3]triazol-5-yl)-3-(4-(hydroxymethyl)-5-methylthiophen-2-yl)-2,2-dimethylpropanoate (101 mg, 0.211 mmol) in tetrahydrofuran (THF) (4 mL) was added (R)-4-ethyl-3,4-dihydro-2H-benzo[b][1,4,5]oxathiazepine 1,1-dioxide (114 mg, 0.502 mmol) and (E)-diazene-1,2-diylbis(piperidin-1-ylmethanone) (ADDP) (127 mg, 0.503 mmol). Tri-n-butylphosphine (0.124 mL, 0.504 mmol) was then added and stirred at ambient temperature for 1 h. The solvents were concentrated and the residue was purified by reverse phase preparative HPLC under neutral conditions to provide the title compound (0.134 g, 92% yield). LC/MS m/z=687 (M+H)+, 1.46 min (ret. time).

(S)-3-(4-(((R)-4-Ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoic Acid

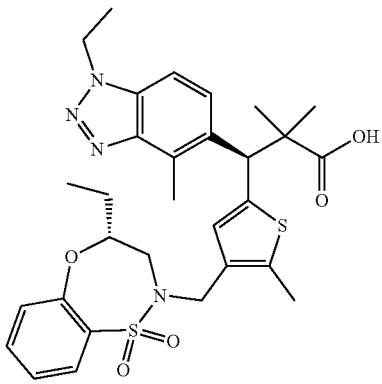 [SMILES: CC[C@@H]1CN(Cc2cc([C@@H](c3ccc4c(nnn4CC)c3C)C(C)(C)C(=O)O)sc2C)S(=O)(=O)c2ccccc2O1]

A solution of (S)-benzyl 3-(4-(((R)-4-ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoate (134 mg, 0.195 mmol) in methanol (8 mL) was subjected to 10% Pd/C using 30×4 mm cartridge on H-Cube using full $H_2$ mode.

After 45 min the pressure was increased to 20 bar and run for 5 h. The solvents were concentrated and the residue was dissolved in methanol (8.00 mL). The flask was flushed with nitrogen and 10% palladium on carbon (20.76 mg, 0.020 mmol) was added. The flask was evacuated and purged with hydrogen in balloon. This procedure was repeated three times and the reaction stirred under $H_2$ for 18 h. The completed reaction was filtered through Celite and washed with MeOH. The solvent was concentrated and the residue was purified by reverse phase preparative HPLC under neutral conditions to provide the title compound (0.080 g, 70% yield). LC/MS m/z=597 (M+H)+, 1.21 min (ret. time).

Example 11

(R)-3-(4-(((R)-4-Ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoic Acid

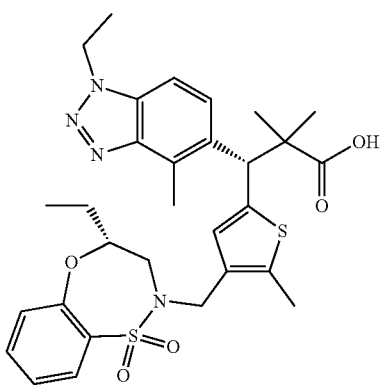 [SMILES: CC[C@@H]1CN(Cc2cc([C@H](c3ccc4c(nnn4CC)c3C)C(C)(C)C(=O)O)sc2C)S(=O)(=O)c2ccccc2O1]

117

(S)-Methyl 3-(1-ethyl-4-methyl-1H-benzo[d][1,2,3]triazol-5-yl)-3-(4-(hydroxymethyl)-5-methylthiophen-2-yl)-2,2-dimethylpropanoate and (R)-methyl 3-(1-ethyl-4-methyl-1H-benzo[d][1,2,3]triazol-5-yl)-3-(4-(hydroxymethyl)-5-methylthiophen-2-yl)-2,2-dimethylpropanoate

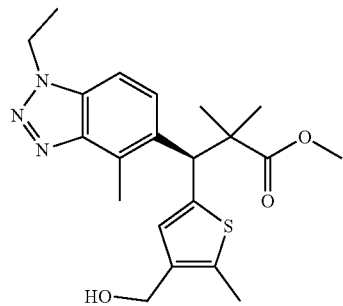

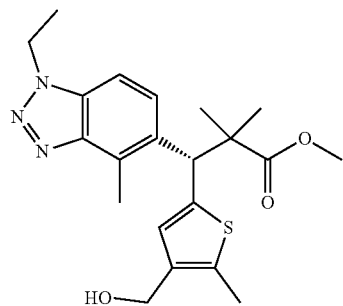

To a solution of methyl 3-(4-(((tert-butyldimethylsilyl)oxy)methyl)-5-methylthiophen-2-yl)-3-(1-ethyl-4-methyl-1H-benzo[d][1,2,3]triazol-5-yl)-2,2-dimethylpropanoate (0.413 g, 0.785 mmol) in methanol (30 mL) at 0° C., was added 1M HCl (0.942 mL, 0.942 mmol) and stirred for 1 h. The solvent was concentrated and the residue was purified by reverse phase preparative HPLC under neutral conditions to provide methyl 3-(1-ethyl-4-methyl-1H-benzo[d][1,2,3]triazol-5-yl)-3-(4-(hydroxymethyl)-5-methylthiophen-2-yl)-2,2-dimethylpropanoate (0.333 g, 55% yield) This compound was resolved by chiral SFC (Column: Chiralpak AY 20×250 mm, 5u; Co-solvent: 20% EtOH; Flowrate: 50 g/min; Back pressure: 100Bar) to provide (S)-methyl 3-(1-ethyl-4-methyl-1H-benzo[d][1,2,3]triazol-5-yl)-3-(4-(hydroxymethyl)-5-methylthiophen-2-yl)-2,2-dimethylpropanoate (0.047 g, 15% yield). LC/MS m/z=402 (M+H)+, 0.99 min (ret. time) and (R)-methyl 3-(1-ethyl-4-methyl-1H-benzo[d][1,2,3]triazol-5-yl)-3-(4-(hydroxymethyl)-5-methylthiophen-2-yl)-2,2-dimethylpropanoate (0.046 g, 14% yield). LC/MS m/z=402 (M+H)+, 0.99 min (ret. time).

118

(R)-Methyl 3-(4-(((R)-4-ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoate

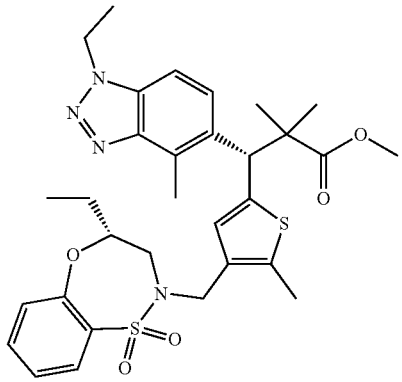 [SMILES: CC[C@@H]1CN(Cc2cc([C@H](c3ccc4c(nnn4CC)c3C)C(C)(C)C(=O)OC)sc2C)S(=O)(=O)c2ccccc2O1]

To a solution of (R)-methyl 3-(1-ethyl-4-methyl-1H-benzo[d][1,2,3]triazol-5-yl)-3-(4-(hydroxymethyl)-5-methylthiophen-2-yl)-2,2-dimethylpropanoate (46 mg, 0.115 mmol) in tetrahydrofuran (THF) (2 mL) was added (R)-4-ethyl-3,4-dihydro-2H-benzo[b][1,4,5]oxathiazepine 1,1-dioxide (52.1 mg, 0.229 mmol) and (E)-diazene-1,2-diylbis(piperidin-1-ylmethanone) (ADDP) (57.8 mg, 0.229 mmol). Tri-n-butylphosphine (0.057 mL, 0.229 mmol) was then added and stirred at ambient temperature for 4 h. The solvent was concentrated and the residue was purified by reverse phase preparative HPLC under neutral conditions to provide the title compound. (0.061 g, 87% yield). LC/MS m/z=611 (M+H)+, 1.38 min (ret. time).

(R)-3-(4-(((R)-4-Ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoic Acid

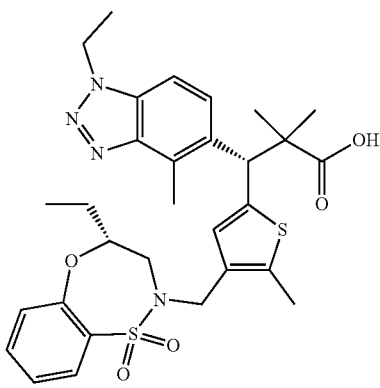 [SMILES: CC[C@@H]1CN(Cc2cc([C@H](c3ccc4c(nnn4CC)c3C)C(C)(C)C(=O)O)sc2C)S(=O)(=O)c2ccccc2O1]

To a solution of (R)-methyl 3-(4-(((R)-4-ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoate (51 mg, 0.083 mmol) in tetrahydrofuran (THF) (1 mL) methanol (1.000 mL) and water (1.000 mL) was added LiOH (8.00 mg, 0.334 mmol) and stirred at ambient temperature. The reaction was then transferred to a microwave reaction vessel and heated on a microwave to 120° C. for 3 h. The solvent was concentrated and the residue was redissolved in acetonitrile and acidified with formic acid. The residue was purified by reverse phase preparative HPLC under formic acid conditions to provide the title compound. (0.034 g, 69% yield). LC/MS m/z=597 (M+H)+, 1.17 min (ret. time).

Example 12

(S)-3-(1-Ethyl-4-methyl-1H-benzo[d][1,2,3]triazol-5-yl)-3-(4-((2-((4-ethylpiperidin-1-yl)methyl)-1H-imidazol-1-yl)methyl)-5-methylthiophen-2-yl)-2,2-dimethylpropanoic acid

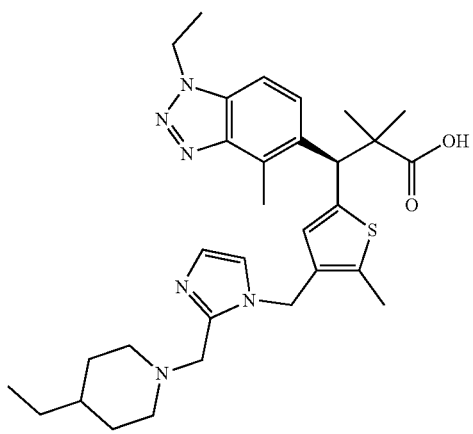 [SMILES: CCC1CCN(Cc2nccn2Cc2cc([C@@H](c3ccc4c(nnn4CC)c3C)C(C)(C)C(=O)O)sc2C)CC1]

tert-Butyl 4-ethylidenepiperidine-1-carboxylate

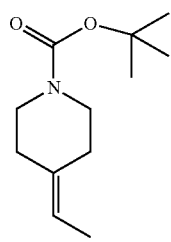

Under nitrogen, ethyltriphenylphosphonium bromide (19.10 g, 51.4 mmol) was added portionwise to the 1M LiHMDS (51.4 mL, 51.4 mmol) in THF at 0° C. and stirred for 1 hr. A solution of benzyl 4-oxopiperidine-1-carboxylate (10 g, 42.9 mmol) in tetrahydrofuran (THF) (20 mL) was added and stirred for 2 h. The reaction was quenched with brine, and extracted with EtOAc (2×100 mL). The combined organic layers were washed with brine, dried and concentrated. The residue was purified by eluting with PE/EA=10/1 to give the title compound (8.0 g, 32.6 mmol, 76% yield), LC/MS m/z=247.0 (M+H)+, 2.27 min (ret. time)

4-Ethylpiperidine

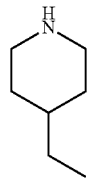

The mixture of benzyl 4-ethylidenepiperidine-1-carboxylate (8000 mg, 32.6 mmol), Pd/C (1735 mg, 16.31 mmol) in methanol (100 mL) was hydrogenated at room atmosphere for 5 h. The reaction was filtered and concentrated to give the title compound. (2500 mg, 22.08 mmol, 67.7% yield), LC/MS m/z=114 (M+H)+, 1.23 min (ret. time)

1-((1H-Imidazol-2-yl)methyl)-4-ethylpiperidine

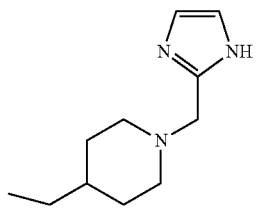

To a mixture of 4-ethylpiperidine (2500 mg, 22.08 mmol) and 1H-imidazole-2-carbaldehyde (2122 mg, 22.08 mmol) was added titanium(IV) isopropoxide (7.77 mL, 26.5 mmol) dropwise. After stirring at 25° C. for 2 h. ethanol (120 mL) and sodium cyanotrihydroborate (1388 mg, 22.08 mmol) were added and stirred for another 8 h. The reaction was quenched with water (2 ml), was filtered and concentrated. The residue was purified by reversed phase the title compound. (3000 mg, 14.74 mmol, 66.8% yield), LC/MS m/z=194 (M+H)+, 1.63 min (ret. time)

(S)-Benzyl 3-(1-ethyl-4-methyl-1H-benzo[d][1,2,3]triazol-5-yl)-3-(4-((2-((4-ethylpiperidin-1-yl)methyl)-1H-imidazol-1-yl)methyl)-5-methylthiophen-2-yl)-2,2-dimethylpropanoate

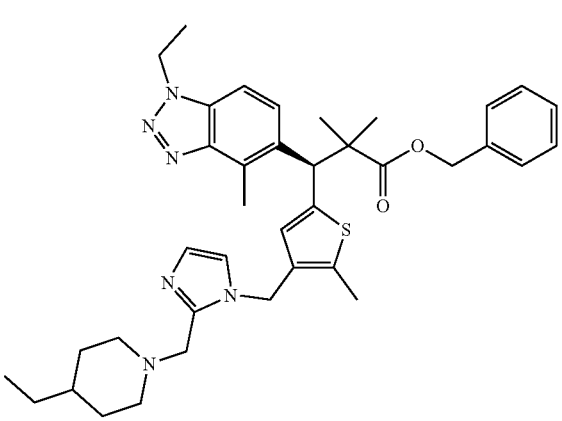 [SMILES: CCC1CCN(Cc2nccn2Cc2cc([C@@H](c3ccc4c(nnn4CC)c3C)C(C)(C)C(=O)OCc3ccccc3)sc2C)CC1]

To a solution of (S)-benzyl 3-(1-ethyl-4-methyl-1H-benzo[d][1,2,3]triazol-5-yl)-3-(4-(hydroxymethyl)-5-methylthiophen-2-yl)-2,2-dimethylpropanoate (60 mg, 0.126 mmol) in dichloromethane (DCM) (3 mL) was added thionyl chloride (0.018 mL, 0.251 mmol) and stirred at ambient temperature for 30 min. The solvent was removed and the residue was dissolved in acetonitrile (3.00 mL) in a 10 mL microwave reaction vessel. To this solution was added 1-((1H-imidazol-2-yl)methyl)-4-ethylpiperidine, Trifluoroacetic acid salt (42.5 mg, 0.138 mmol) and DIEA (0.088 mL, 0.502 mmol). The reaction was heated on microwave to 120° C. for 1 h. The compound was purified by reverse phase preparative HPLC under trifluoroacetic acid conditions to provide the title compound. (0.028 g, 34% yield). LC/MS m/z=653 (M+H)+, 1.12 min (ret. time).

(S)-3-(1-Ethyl-4-methyl-1H-benzo[d][1,2,3]triazol-5-yl)-3-(4-((2-((4-ethylpiperidin-1-yl)methyl)-1H-imidazol-1-yl)methyl)-5-methylthiophen-2-yl)-2,2-dimethylpropanoic Acid

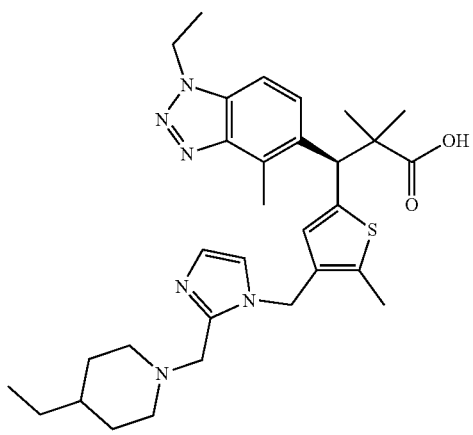 [SMILES: CCC1CCN(Cc2nccn2Cc2cc([C@@H](c3ccc4c(nnn4CC)c3C)C(C)(C)C(=O)O)sc2C)CC1]

To a solution of (S)-benzyl 3-(1-ethyl-4-methyl-1H-benzo[d][1,2,3]triazol-5-yl)-3-(4-((2-((4-ethylpiperidin-1-yl)methyl)-1H-imidazol-1-yl)methyl)-5-methylthiophen-2-yl)-2,2-dimethylpropanoate (28 mg, 0.043 mmol) in tetrahydrofuran (THF) (1 mL) methanol (1.000 mL) and water (1.000 mL) was added LiOH (5.14 mg, 0.214 mmol) and stirred at ambient temperature for 1 h. The reaction was then transferred to a microwave reaction vessel and heated on a microwave to 120° C. for 4.5 h. Afterwards, additional LiOH (2.054 mg, 0.086 mmol) was added and heated on a microwave to 120° C. for 2.5 h. The solvent was concentrated and the residue was purified by reverse phase preparative HPLC under formic acid conditions to provide the title compound. (0.007 g, 29% yield). LC/MS m/z=563 (M+H)+, 0.91 min (ret. time).

Example 13

(R or S)-3-(4-(((R)-4-Ethyl-1,1-dioxido-3,4-dihydro-2H-benzo[b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoic Acid Isomer 1

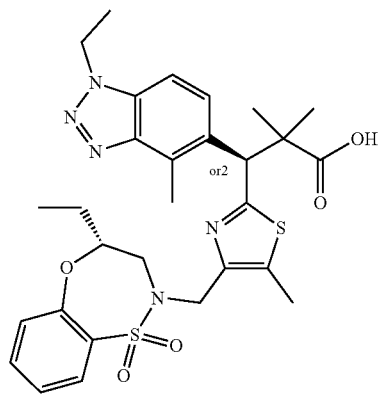 [SMILES: CC[C@@H]1CN(Cc2nc([C@@H](c3ccc4c(nnn4CC)c3C)C(C)(C)C(=O)O)sc2C)S(=O)(=O)c2ccccc2O1]

(2-Bromo-5-methylthiazol-4-yl)methanol

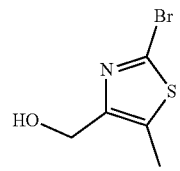

A solution of methyl 2-bromo-5-methylthiazole-4-carboxylate (1.00 g, 4.24 mmol) in tetrahydrofuran (THF) (21.18 mL) was cooled in ice bath. To this was added DIBAL-H (10.59 mL, 10.59 mmol) and stirred for 2 h at 0° C. Additional DIBAL-H (8.47 mL, 8.47 mmol) was added and stirred for 1 h at 0° C. The reaction was quenched with 1N HCl (10 mL) and stirred at 0° C. for 15 minutes. Another 1N HCl (10 mL) was added at ambient temperature and the aqueous layer was extracted with EtOAc (4x). The combined organic layers were washed with 1N HCl, brine, dried with MgSO4 and concentrated to provide the title compound. (0.497 g, 56% yield). LC/MS m/z=208/209 (M+H)+, 0.047 min (ret. time).

2-Bromo-4-(((4-methoxybenzyl)oxy)methyl)-5-methylthiazole

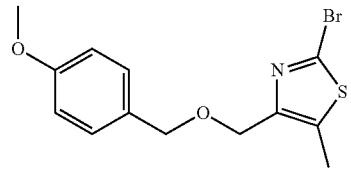 [SMILES: COc1ccc(COCc2nc(Br)sc2C)cc1]

A solution of (2-bromo-5-methylthiazol-4-yl)methanol (0.497 g, 2.389 mmol) in N,N-dimethylformamide (DMF)

(10 mL) under nitrogen was cooled to 0° C. 60% NaH (0.191 g, 4.78 mmol) was added to the solution portion wise and stirred at 0° C. for 30 min. A solution of 1-(chloromethyl)-4-methoxybenzene (0.561 g, 3.58 mmol) in N,N-dimethylformamide (DMF) (5 mL) was then added dropwise and reaction was allowed to warm to ambient temperature over 2.5 h. The reaction was then quenched with water and the solvents were concentrated. The residue was dissolved in EtOAc and washed with water. The aqueous layer was extracted with EtOAc (3×) and the combined organics were washed with water, brine and dried with $MgSO_4$ and concentrated. The residue was purified by flash chromatography eluting with 0-20% EtOAc/hexanes to provide the title compound. (0.237 g, 26% yield). LC/MS m/z=327/329 (M+H)+, 1.05 min (ret. time).

(1-Ethyl-4-methyl-1H-benzo[d][1,2,3]triazol-5-yl)(4-(((4-methoxybenzyl)oxy)methyl)-5-methylthiazol-2-yl)methanol

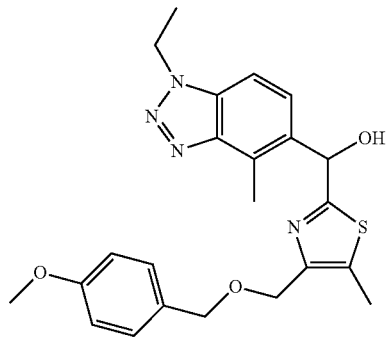

A solution of 2-bromo-4-(((4-methoxybenzyl)oxy)methyl)-5-methylthiazole (0.237 g, 0.722 mmol) in tetrahydrofuran (THF) (5 mL) was cooled to −78° C. 1.6 M n-butyllithium in hexanes (0.700 mL, 1.119 mmol) was added dropwise and stirred for 1.5 h. 1-ethyl-4-methyl-1H-benzo[d][1,2,3]triazole-5-carbaldehyde (0.164 g, 0.866 mmol) in tetrahydrofuran (THF) (3 mL) was then added dropwise and stirred at −78° C. for 1 h. The reaction was quenched with water (1 mL) and allowed to warm to ambient temperature. It was then diluted with EtOAc and washed with water (3×). The combined aqueous layers were extracted with EtOAc (2×). The combined organic layers were washed with brine and dried with $MgSO_4$. The residue was purified by flash chromatography eluting with 0-80% EtOAc/hexanes to provide the title compound. (0.236 g, 74% yield). LC/MS m/z=439 (M+H)+, 0.97 min (ret. time).

Methyl 3-(1-ethyl-4-methyl-1H-benzo[d][1,2,3]triazol-5-yl)-3-(4-(((4-methoxybenzyl)oxy)methyl)-5-methylthiazol-2-yl)-2,2-dimethylpropanoate

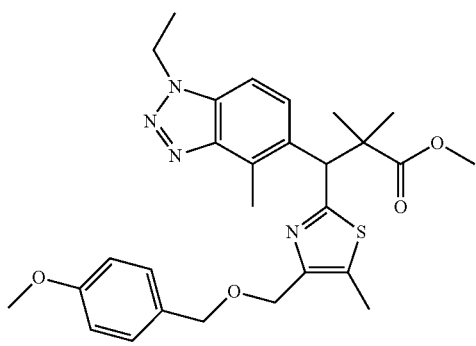

To a solution of (1-ethyl-4-methyl-1H-benzo[d][1,2,3]triazol-5-yl)(4-(((4-methoxybenzyl)oxy)methyl)-5-methylthiazol-2-yl)methanol (0.236 g, 0.538 mmol) in acetonitrile (6 mL) at 0° C., was added 2,2,2-trichloroacetonitrile (0.081 mL, 0.807 mmol) in acetonitrile (2 mL), dropwise, via addition funnel and stirred for 10 min. DBU (4.06 µl, 0.027 mmol) in acetonitrile (1 mL), was then added dropwise, via addition funnel, and stirred for 1 h. The reaction was warmed to ambient temperature for 10 min and recooled. Afterwards, ((1-methoxy-2-methylprop-1-en-1-yl)oxy)trimethylsilane (0.131 mL, 0.646 mmol) was added dropwise, via syringe, in acetonitrile (2 mL) followed by dropwise addition of 1,1,1-trifluoro-N-((trifluoromethyl)sulfonyl)methanesulfonamide (0.015 g, 0.054 mmol) in acetonitrile (3 mL) and stirred at ambient temperature for 1.5 h. The reaction was quenched with saturated. $NaHCO_3$ and aqueous layer was extracted with EtOAc (4×). The combined organics were washed with brine and dried with $MgSO_4$ and concentrated. The residue was purified by flash chromatography eluting with 0-50% EtOAc/hexane to provide the title compound. (0.236 g, 84% yield). LC/MS m/z=523 (M+H)+, 1.26 min (ret. time).

(R or S)-Benzyl 3-(1-ethyl-4-methyl-1H-benzo[d][1,2,3]triazol-5-yl)-3-(4-(((4-methoxybenzyl)oxy)methyl)-5-methylthiazol-2-yl)-2,2-dimethylpropanoate Isomer 1 and (R or S)-benzyl 3-(1-ethyl-4-methyl-1H-benzo[d][1,2,3]triazol-5-yl)-3-(4-(((4-Methoxybenzyl)oxy)methyl)-5-methylthiazol-2-yl)-2,2-dimethylpropanoate Isomer 2

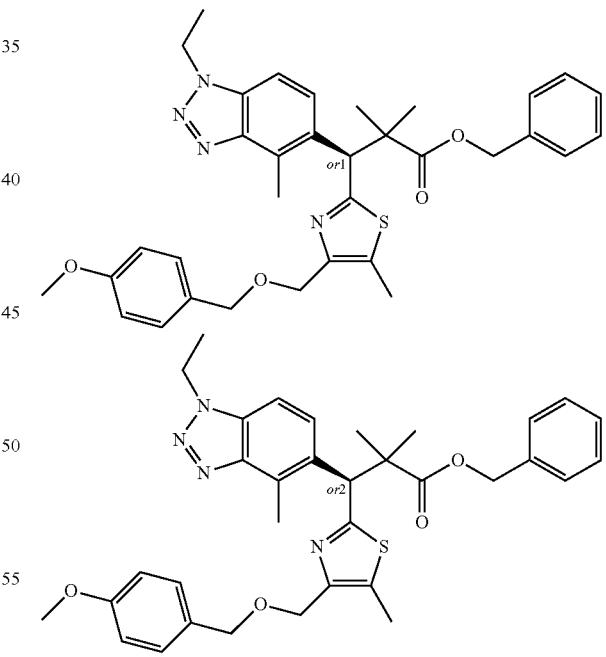

To a solution of methyl 3-(1-ethyl-4-methyl-1H-benzo[d][1,2,3]triazol-5-yl)-3-(4-(((4-methoxybenzyl)oxy)methyl)-5-methylthiazol-2-yl)-2,2-dimethylpropanoate (0.236 g, 0.452 mmol) in tetrahydrofuran (THF) (3 mL), methanol (3.00 mL) and water (3.00 mL) in a 20 mL microwave reaction vessel was added LiOH (0.054 g, 2.258 mmol) and heated on a microwave to 100° C. for 1 h 35 min. The solvents were concentrated and pumped dry on high vacuum. The lithium salt was dissolved in DMF and benzyl bromide (0.215 mL, 1.806 mmol) was added and stirred at ambient temperature for 1.5 h. The solvents were concentrated and the residue was purified by flash chromatography eluting with 0-50% EtOAc/hexane to provide Benzyl 3-(1-ethyl-4-methyl-1H-benzo[d][1,2,3]triazol-5-yl)-3-(4-(((4-methoxybenzyl)oxy)methyl)-5-methylthiazol-2-yl)-2,2-dimethylpropanoate as a mixture of isomers (0.236 g, 84% yield). This compound was resolved by chiral SFC (Column: Chiralpak AY 20×250 mm, 5u; Co-solvent: 30% IPA; Flow-rate: 50 g/min; Back pressure: 100Bar, Temperature: 30° C.) to provide single enantiomerically pure (R or S)-benzyl 3-(1-ethyl-4-methyl-1H-benzo[d][1,2,3]triazol-5-yl)-3-(4-(((4-methoxybenzyl)oxy)methyl)-5-methylthiazol-2-yl)-2,2-dimethylpropanoate Isomer 1 (0.094 g, 34% yield). LC/MS m/z=599 (M+H)+, 1.44 min (ret. time), (chiral SFC ret. time: 2.8 min) and single enantiomerically pure (R or S)-benzyl 3-(1-ethyl-4-methyl-1H-benzo[d][1,2,3]triazol-5-yl)-3-(4-(((4-methoxybenzyl)oxy)methyl)-5-methylthiazol-2-yl)-2,2-dimethylpropanoate Isomer 2 (0.096 g, 35% yield). LC/MS m/z=599 (M+H)+, 1.44 min (ret. time), (chiral SFC ret. time: 3.85 min).

(R or S)-Benzyl 3-(1-ethyl-4-methyl-1H-benzo[d][1,2,3]triazol-5-yl)-3-(4-(hydroxymethyl)-5-methylthiazol-2-yl)-2,2-dimethylpropanoate Isomer 1

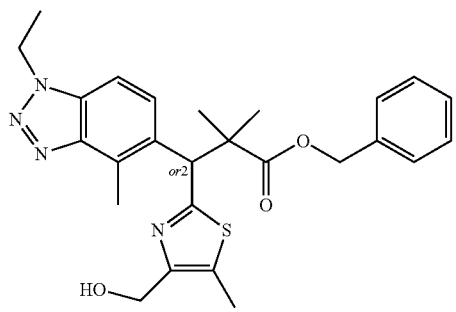 [SMILES: CCn1nnc2c(C)c(C(c3nc(CO)c(C)s3)C(C)(C)C(=O)OCc3ccccc3)ccc21]

To a solution of (R or S)-benzyl 3-(1-ethyl-4-methyl-1H-benzo[d][1,2,3]triazol-5-yl)-3-(4-(((4-methoxybenzyl)oxy)methyl)-5-methylthiazol-2-yl)-2,2-dimethylpropanoate Isomer 1 (94 mg, 0.157 mmol) in acetonitrile (2 mL) was added ceric ammonium nitrate (258 mg, 0.471 mmol) and stirred at ambient temperature for 1 h. The reaction was diluted with ethyl acetate and washed with water. The water was back extracted with ethyl acetate and the combined organics were washed with water, brine and dried with MgSO$_4$. The solvent was concentrated and the residue was purified by flash chromatography eluting with 0-50% EtOAc/hexane to provide the title compound. (0.066 g, 88% yield). LC/MS m/z=479 (M+H)+, 1.08 min (ret. time).

(R or S)-Benzyl 3-(4-(((R)-4-ethyl-1,1-dioxido-3,4-dihydro-2H-benzo[b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoate Isomer 1

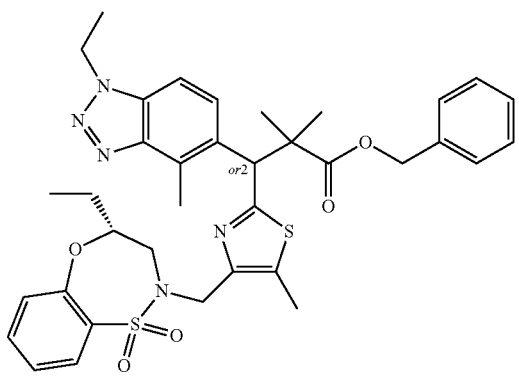 [SMILES: CC[C@@H]1CN(Cc2nc(C(c3ccc4c(nnn4CC)c3C)C(C)(C)C(=O)OCc3ccccc3)sc2C)S(=O)(=O)c2ccccc2O1]

To a solution of (R or S)-benzyl 3-(1-ethyl-4-methyl-1H-benzo[d][1,2,3]triazol-5-yl)-3-(4-(hydroxymethyl)-5-methylthiazol-2-yl)-2,2-dimethylpropanoate Isomer 1 (66 mg, 0.138 mmol) in tetrahydrofuran (THF) (2 mL) was added (R)-4-ethyl-3,4-dihydro-2H-benzo[b][1,4,5]oxathiazepine 1,1-dioxide (62.7 mg, 0.276 mmol) and (E)-diazene-1,2-diylbis(piperidin-1-ylmethanone) (ADDP) (69.6 mg, 0.276 mmol). Tri-n-butylphosphine (0.068 mL, 0.276 mmol) was then added and stirred at ambient temperature for 23 h. The solvent was concentrated and the residue was purified by reverse phase preparative HPLC under neutral conditions to provide the title compound. (0.077 g, 81% yield). LC/MS m/z=687 (M+H)+, 1.47 min (ret. time).

(R or S)-3-(4-(((R)-4-Ethyl-1,1-dioxido-3,4-dihydro-2H-benzo[b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoic Acid

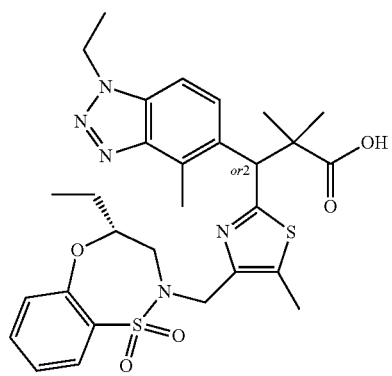 [SMILES: CC[C@@H]1CN(Cc2nc(C(c3ccc4c(nnn4CC)c3C)C(C)(C)C(=O)O)sc2C)S(=O)(=O)c2ccccc2O1]

To a solution of (R or S)-benzyl 3-(4-(((R)-4-ethyl-1,1-dioxido-3,4-dihydro-2H-benzo[b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoate Isomer 1 (77 mg, 0.112 mmol) in tetrahydrofuran (THF) (2 mL), methanol (2.000 mL), and water (2.000 mL) in a 10 mL microwave reaction tube, was added LiOH (13.40 mg, 0.560 mmol) and heated on a microwave to 120° C. for 1.5 h. The solvents were concentrated and the residue was suspended in acetonitrile and acidified with formic acid. The solvent was concentrated and the residue was purified by reverse phase preparative HPLC under formic acid conditions to provide the title compound. (0.042 g, 62% yield). LC/MS m/z=598 (M+H)+, 1.19 min (ret. time).

Example 14

(R or S)-3-(4-(((R)-4-Ethyl-1,1-dioxido-3,4-di-hydro-2H-benzo[b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoic Acid Isomer 2

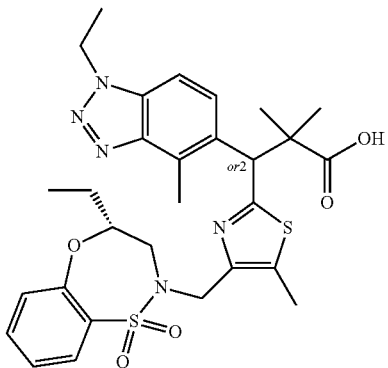 [SMILES: CC[C@@H]1CN(Cc2nc(C(c3ccc4c(nnn4CC)c3C)C(C)(C)C(=O)O)sc2C)S(=O)(=O)c2ccccc2O1]

(R or S)-Benzyl 3-(1-ethyl-4-methyl-1H-benzo[d][1,2,3]triazol-5-yl)-3-(4-(hydroxymethyl)-5-methylthiazol-2-yl)-2,2-dimethylpropanoate Isomer 2

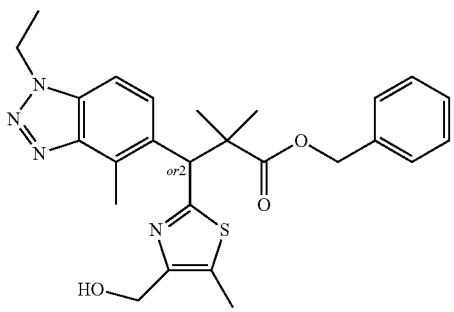 [SMILES: CCn1nnc2c(C)c(C(c3nc(CO)c(C)s3)C(C)(C)C(=O)OCc3ccccc3)ccc21]

To a solution of (R or S)-benzyl 3-(1-ethyl-4-methyl-1H-benzo[d][1,2,3]triazol-5-yl)-3-(4-(((4-methoxybenzyl)oxy)methyl)-5-methylthiazol-2-yl)-2,2-dimethylpropanoate Isomer 2 (96 mg, 0.160 mmol) in acetonitrile (2 mL) was added ceric ammonium nitrate (264 mg, 0.481 mmol) and stirred at ambient temperature for 1 h. The reaction was diluted with ethyl acetate and washed with water. The aqueous layer was back extracted with ethyl acetate and the combined organics were washed with water, brine and dried with MgSO4. The solvent was concentrated and the residue was purified by flash chromatography eluting with 0-55% EtOAc/hexane to provide the title compound. (0.061 g, 79% yield). LC/MS m/z=479 (M+H)+, 0.94 min (ret. time).

(R or S)-Benzyl 3-(4-(((R)-4-ethyl-1,1-dioxido-3,4-dihydro-2H-benzo [b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoate Isomer 2

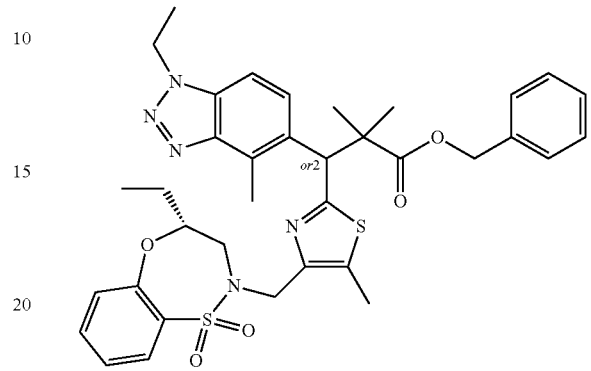

To a solution of (R or S)-benzyl 3-(1-ethyl-4-methyl-1H-benzo[d][1,2,3]triazol-5-yl)-3-(4-(hydroxymethyl)-5-methylthiazol-2-yl)-2,2-dimethylpropanoate Isomer 2 (61 mg, 0.127 mmol) in tetrahydrofuran (THF) (2 mL) was added (R)-4-ethyl-3,4-dihydro-2H-benzo[b][1,4,5]oxathiazepine 1,1-dioxide (57.9 mg, 0.255 mmol) and (E)-diazene-1,2-diylbis(piperidin-1-ylmethanone) (ADDP) (64.3 mg, 0.255 mmol). Tri-n-butylphosphine (0.063 mL, 0.255 mmol) was added and the reaction was stirred at ambient temperature for 23 h The solvent was concentrated and the residue was purified by reverse phase preparative HPLC under neutral conditions to provide the title compound. (0.078 g, 89% yield). LC/MS m/z=688 (M+H)+, 1.45 min (ret. time).

(R or S)-3-(4-(((R)-4-Ethyl-1,1-dioxido-3,4-di-hydro-2H-benzo[b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoic Acid Isomer 2

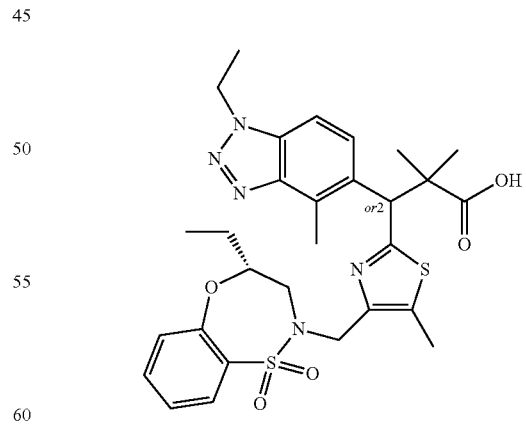

To a solution of (R or S)-benzyl 3-(4-(((R)-4-ethyl-1,1-dioxido-3,4-dihydro-2H-benzo[b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoate Isomer 2 (78 mg, 0.113 mmol) in tetrahydrofuran (THF) (2 mL), methanol (2.000 mL), and water (2.000 mL) in a 10 mL microwave reaction tube, was added LiOH (13.58 mg, 0.567 mmol) and heated on a microwave to 120° C. for 1.5 h. The solvent was concentrated and the residue was suspended in acetonitrile and acidified with formic acid. The solvent was concentrated and the residue was purified by reverse phase preparative HPLC under formic acid conditions to provide the title compound. (0.052 g, 78% yield). LC/MS m/z=598 (M+H)+, 1.20 min (ret. time).

Example 15

(S)-3-(1-Ethyl-4-methyl-1H-benzo[d][1,2,3]triazol-5-yl)-2,2-dimethyl-3-(5-methyl-4-((4,6,6-trimethyl-3-oxo-1,4-diazepan-1-yl)methyl)thiophen-2-yl)propanoic Acid

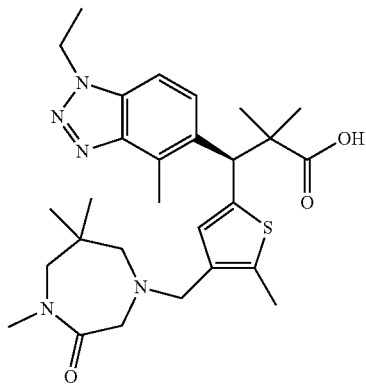 [SMILES: CCn1nnc2c(C)c([C@H](c3cc(CN4CC(=O)N(C)CC(C)(C)C4)c(C)s3)C(C)(C)C(=O)O)ccc21]

tert-Butyl (2,2-dimethyl-3-(N-methyl-2-nitrophenylsulfonamido)propyl)carbamate

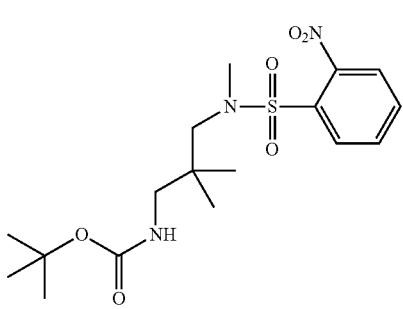 [SMILES: CN(CC(C)(C)CNC(=O)OC(C)(C)C)S(=O)(=O)c1ccccc1[N+](=O)[O-]]

To a solution of tert-butyl (2,2-dimethyl-3-(2-nitrophenylsulfonamido)propyl)carbamate (10 g, 25.8 mmol) in N,N-dimethylformamide (DMF) (100 mL) at 0° C. was added potassium carbonate (5.35 g, 38.7 mmol) portion wise. It was stirred at ambient temperature for 12 h. It was quenched with water (10 mL) and extracted with DCM (2×50 mL). The combined organic layer was washed with brine solution (10 mL) and dried over anhydrous Na₂SO₄, filtered and concentrated. The crude residue was purified with flash column chromatography using EtOAc: hexane (3:7) as solvent. The eluted fractions were concentrated under vacuum to give the title compound (8 g, 19.68 mmol, 76% yield) as gummy liquid. LC/MS m/z=402.50 (M+H)+, 2.502 min (ret. time).

tert-Butyl (2,2-dimethyl-3-(methylamino)propyl)carbamate

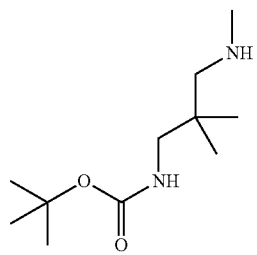

To a solution of tert-butyl (2,2-dimethyl-3-(N-methyl-2-nitrophenylsulfonamido)propyl)carbamate (8 g, 19.93 mmol) in N,N-dimethylformamide (DMF) at 0° C. was added K₂CO₃ (2.75 g, 19.93 mmol) and thiophenol (2.052 mL, 19.93 mmol). It was stirred at ambient temperature for 6 h. It was quenched with water (10 mL) and then acidified with 1N HCl. It was extracted with ethyl acetate (2×10 mL). The aqueous layer was basified with 1N NaOH and extracted with ethyl acetate (2×20 mL).

The second organic layer was washed with brine (10 mL) and concentrated to give the title compound (4 g, 18.49 mmol, 93% yield) as a gummy liquid. ¹H NMR (400 MHz, CDCl₃) b ppm 0.93 (s, 6H), 1.43 (s, 9H), 2.86 (d, J=6.80 Hz, 2H), 3.16 (s, 3H), 3.18-3.23 (m, 2H), 5.91 (br s, 1H).

tert-Butyl (3-(2-chloro-N-methylacetamido)-2,2-dimethylpropyl)carbamate

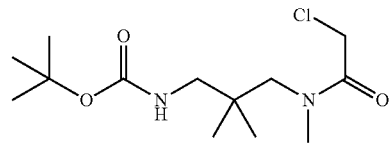 [SMILES: CN(CC(C)(C)CNC(=O)OC(C)(C)C)C(=O)CCl]

To a solution of tert-butyl (2,2-dimethyl-3-(methylamino)propyl)carbamate (4 g, 18.49 mmol) in dichloromethane (DCM) (40 mL) at 0° C. was added chloroacetyl chloride (1.777 mL, 22.19 mmol). It was stirred at ambient temperature for 12 h under nitrogen. The reaction mixture was quenched with saturated sodium bicarbonate solution (20 mL) and extracted with DCM (2×20 mL). The organic layer was concentrated. The crude residue was purified with flash column chromatography using EtOAc: hexane (4:6) as solvent to give the title compound (4.5 g, 13.60 mmol, 73.6% yield) as gummy liquid. LC/MS m/z=193.0 (M-Boc)+, 3.426 min (ret. time).

tert-Butyl 4,6,6-trimethyl-3-oxo-1,4-diazepane-1-carboxylate

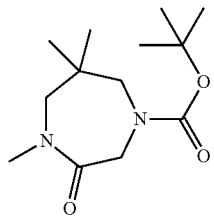 [SMILES: CN1CC(C)(C)CN(C(=O)OC(C)(C)C)CC1=O]

To a solution of tert-butyl (3-(2-chloro-N-methylacetamido)-2,2-dimethylpropyl)carbamate (4.2 g, 14.34 mmol) in N,N-dimethylformamide (DMF) (40 mL) at 0° C. was added NaH (0.516 g, 21.52 mmol) portionwise. It was stirred at ambient temperature for 6 h. It was quenched with cold water (100 mL) and extracted with DCM (2×50 mL). The combined organic layer was washed with brine solution (10 mL), dried over anhydrous Na$_2$SO$_4$, filtered and concentrated. It was purified with flash column chromatography using EtOAc:hexane (4:6) as solvent to give the title compound (1.9 g, 7.31 mmol, 50.9% yield) as an off-white solid. LC/MS m/z=257.16 (M+H)+, 1.907 min (ret. time).

1,6,6-Trimethyl-1,4-diazepan-2-one, hydrochloride

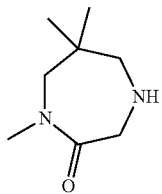

To a solution of tert-butyl 4,6,6-trimethyl-3-oxo-1,4-diazepane-1-carboxylate (1.345 g, 5.25 mmol) in 1,4-dioxane (5 mL) was added 4 M HCl in 1,4 dioxane (3.00 mL, 12.00 mmol) and stirred at ambient temperature for 19 h 45 min. Additional 4M HCl in 1,4 dioxane (1.312 mL, 5.25 mmol) was added and continued stirring for 47 h. The solvents were concentrated and dried to give the title compound (0.924 g, 4.80 mmol, 91%). LCMS m/z 156 (M+H)+, 1.17 min (ret time)$^1$H NMR (400 MHz, DMSO-d$_6$) δ 9.80 (br. s., 1H), 5.24 (br. s., 3H), 3.81 (br. s., 2H), 2.96 (br. s., 2H), 2.91 (s, 2H), 0.99 (s, 6H).

(S)-Benzyl 3-(1-ethyl-4-methyl-1H-benzo[d][1,2,3]triazol-5-yl)-2,2-dimethyl-3-(5-methyl-4-((4,6,6-trimethyl-3-oxo-1,4-diazepan-1-yl)methyl)thiophen-2-yl)propanoate

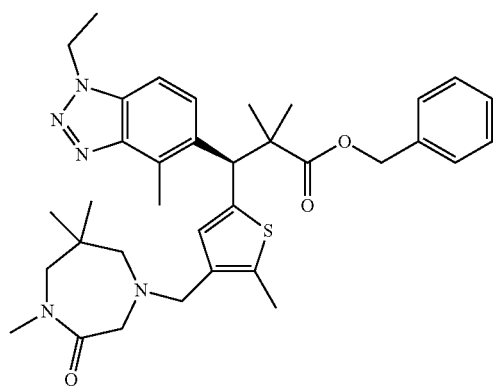 [SMILES: CCn1nnc2c(C)c([C@H](c3cc(CN4CC(=O)N(C)CC(C)(C)C4)c(C)s3)C(C)(C)C(=O)OCc3ccccc3)ccc21]

To a solution of (S)-benzyl 3-(1-ethyl-4-methyl-1H-benzo[d][1,2,3]triazol-5-yl)-3-(4-(hydroxymethyl)-5-methylthiophen-2-yl)-2,2-dimethylpropanoate (60 mg, 0.126 mmol) in dichloromethane (DCM) (3 mL) was added thionyl chloride (0.018 mL, 0.251 mmol) and stirred at ambient temperature for 30 min. The solvent was removed and the residue was dissolved in acetonitrile (3.00 mL) in a 10 mL microwave reaction vessel. To this solution was added 1,6,6-trimethyl-1,4-diazepan-2-one hydrochloride (26.6 mg, 0.138 mmol) and DIEA (0.088 mL, 0.502 mmol). The reaction was heated on microwave to 120° C. for 1 h.

The solvent was concentrated and the residue was purified by reverse phase preparative HPLC under neutral conditions to provide the title compound. (0.067 g, 87% yield). LC/MS m/z=616 (M+H)+, 1.04 min (ret. time).

(S)-3-(1-Ethyl-4-methyl-1H-benzo[d][1,2,3]triazol-5-yl)-2,2-dimethyl-3-(5-methyl-4-((4,6,6-trimethyl-3-oxo-1,4-diazepan-1-yl)methyl)thiophen-2-yl)propanoic Acid

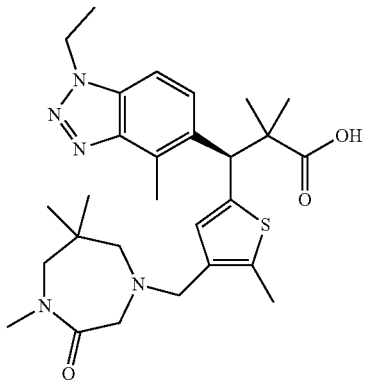 [SMILES: CCn1nnc2c(C)c([C@H](c3cc(CN4CC(=O)N(C)CC(C)(C)C4)c(C)s3)C(C)(C)C(=O)O)ccc21]

To a solution of (S)-benzyl 3-(1-ethyl-4-methyl-1H-benzo[d][1,2,3]triazol-5-yl)-2,2-dimethyl-3-(5-methyl-4-((4,6,6-trimethyl-3-oxo-1,4-diazepan-1-yl)methyl)thiophen-2-yl) propanoate (67 mg, 0.109 mmol) in tetrahydrofuran (THF) (2 mL), methanol (2.000 mL), and water (2.000 mL), in a 10 mL microwave reaction vial was added LiOH (13.03 mg, 0.544 mmol) and heated on microwave at 120° C. for 1 h. The solvent was concentrated and the residue was suspended in acetonitrile and acidified with formic acid. The solvent was concentrated and the residue was purified by reverse phase preparative HPLC under formic acid conditions to provide the title compound. (0.042 g, 73% yield). LC/MS m/z=526 (M+H)+, 0.79 min (ret. time).

Example 16

(S)-3-(1-Ethyl-4-methyl-1H-benzo[d][1,2,3]triazol-5-yl)-2,2-dimethyl-3-(5-methyl-4-(((R)-4-methyl-1,1-dioxido-4,5-dihydropyrido[2,3-f][1,2]thiazepin-2(3H)-yl)methyl)thiophen-2-yl)propanoic Acid

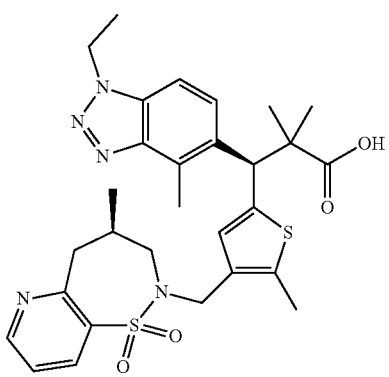 [SMILES: CCn1nnc2c(C)c([C@H](c3cc(CN4C[C@H](C)Cc5ncccc5S4(=O)=O)c(C)s3)C(C)(C)C(=O)O)ccc21]

(S)-Benzyl 3-(1-ethyl-4-methyl-1H-benzo[d][1,2,3]triazol-5-yl)-2,2-dimethyl-3-(5-methyl-4-(((R)-4-methyl-1,1-dioxido-4,5-dihydropyrido[2,3-f][1,2]thiazepin-2(3H)-yl)methyl)thiophen-2-yl)propanoate

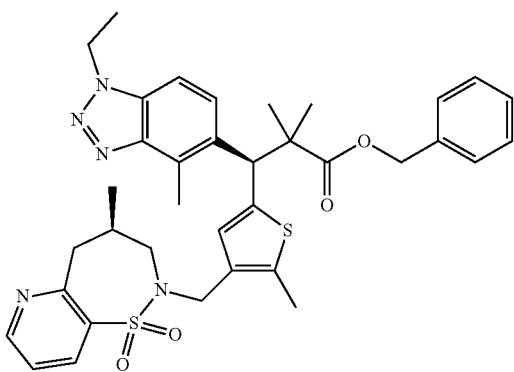 [SMILES: CCn1nnc2c(C)c([C@H](c3cc(CN4C[C@H](C)Cc5ncccc5S4(=O)=O)c(C)s3)C(C)(C)C(=O)OCc3ccccc3)ccc21]

To a solution of (S)-benzyl 3-(1-ethyl-4-methyl-1H-benzo[d][1,2,3]triazol-5-yl)-3-(4-(hydroxymethyl)-5-methylthiophen-2-yl)-2,2-dimethylpropanoate (50 mg, 0.105 mmol) in tetrahydrofuran (THF) (2 mL) was added (R)-4-methyl-2,3,4,5-tetrahydropyrido[2,3-f][1,2]thiazepine 1,1-dioxide (44.4 mg, 0.209 mmol) and (E)-diazene-1,2-diylbis(piperidin-1-ylmethanone) (ADDP) (52.8 mg, 0.209 mmol). Tri-n-butylphosphine (0.052 mL, 0.209 mmol) was added and the reaction was stirred at ambient temperature for 2 h. The solvent was concentrated and the residue was purified by reverse phase preparative HPLC under neutral conditions to provide the title compound. (0.053 g, 75% yield). LC/MS m/z=672 (M+H)+, 1.39 min (ret. time).

(S)-3-(1-Ethyl-4-methyl-1H-benzo[d][1,2,3]triazol-5-yl)-2,2-dimethyl-3-(5-methyl-4-(((R)-4-methyl-1,1-dioxido-4,5-dihydropyrido[2,3-f][1,2]thiazepin-2(3H)-yl)methyl)thiophen-2-yl)propanoic Acid

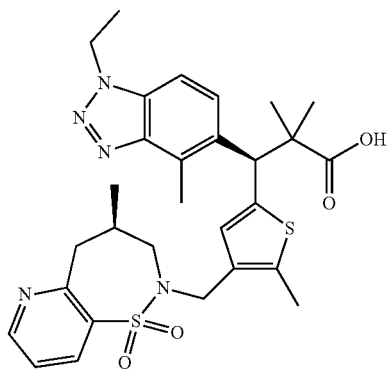 [SMILES: CCn1nnc2c(C)c([C@H](c3cc(CN4C[C@H](C)Cc5ncccc5S4(=O)=O)c(C)s3)C(C)(C)C(=O)O)ccc21]

To a solution of (S)-benzyl 3-(1-ethyl-4-methyl-1H-benzo[d][1,2,3]triazol-5-yl)-2,2-dimethyl-3-(5-methyl-4-(((R)-4-methyl-1,1-dioxido-4,5-dihydropyrido[2,3-f][1,2]thiazepin-2(3H)-yl)methyl)thiophen-2-yl)propanoate (53 mg, 0.079 mmol) in tetrahydrofuran (THF) (2 mL), methanol (2.000 mL), and water (2.000 mL) in a 10 mL microwave reaction tube, was added LiOH (9.45 mg, 0.394 mmol) and heated on a microwave to 120° C. for 3 h. The solvent was concentrated and the residue was suspended in acetonitrile and acidified with formic acid. The solvent was concentrated and the residue was purified by reverse phase preparative HPLC under formic acid conditions to provide the title compound. (0.037 g, 81% yield). LC/MS m/z=582 (M+H)+, 1.10 min (ret. time).

Example 17

(S)-3-(1-Ethyl-4-methyl-1H-benzo[d][1,2,3]triazol-5-yl)-2,2-dimethyl-3-(5-methyl-4-(((R)-4-methyl-1,1-dioxido-4,5-dihydrobenzo[f][1,2]thiazepin-2(3H)-yl)methyl)thiophen-2-yl)propanoic Acid

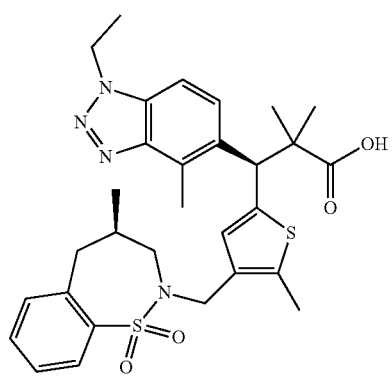 [SMILES: CCn1nnc2c(C)c([C@H](c3cc(CN4C[C@H](C)Cc5ccccc5S4(=O)=O)c(C)s3)C(C)(C)C(=O)O)ccc21]

(S)-Benzyl 3-(1-ethyl-4-methyl-1H-benzo[d][1,2,3]triazol-5-yl)-2,2-dimethyl-3-(5-methyl-4-(((R)-4-methyl-1,1-dioxido-4,5-dihydrobenzo[f][1,2]thiazepin-2(3H)-yl)methyl)thiophen-2-yl)propanoate
N40237-20-A1

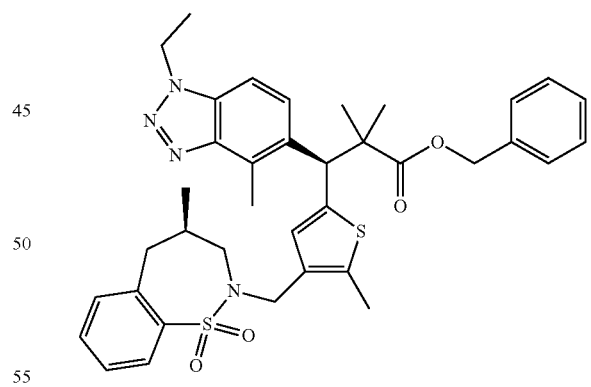

To a solution of (S)-benzyl 3-(1-ethyl-4-methyl-1H-benzo[d][1,2,3]triazol-5-yl)-3-(4-(hydroxymethyl)-5-methylthiophen-2-yl)-2,2-dimethylpropanoate (50 mg, 0.105 mmol) in tetrahydrofuran (THF) (2 mL) was added (R)-4-methyl-2,3,4,5-tetrahydrobenzo[f][1,2]thiazepine 1,1-dioxide (44.2 mg, 0.209 mmol) and (E)-diazene-1,2-diylbis(piperidin-1-ylmethanone) (ADDP) (52.8 mg, 0.209 mmol). Tri-n-butylphosphine (0.052 mL, 0.209 mmol) was added and stirred at ambient temperature for 2 h. The solvent was concentrated and the residue was purified by reverse phase preparative HPLC under neutral conditions to provide the title compound. (0.055 g, 78% yield). LC/MS m/z=670 (M+H)+, 1.52 min (ret. time).

(S)-3-(1-Ethyl-4-methyl-1H-benzo[d][1,2,3]triazol-5-yl)-2,2-dimethyl-3-(5-methyl-4-(((R)-4-methyl-1,1-dioxido-4,5-dihydrobenzo[f][1,2]thiazepin-2(3H)-yl)methyl)thiophen-2-yl)propanoic Acid

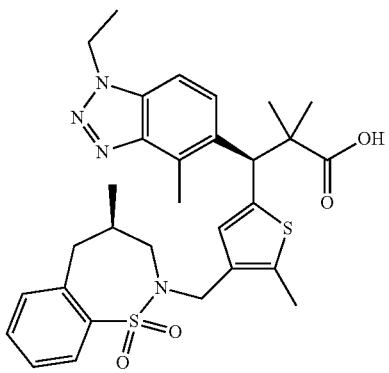 [SMILES: CCn1nnc2c(C)c([C@H](c3cc(CN4C[C@H](C)Cc5ccccc5S4(=O)=O)c(C)s3)C(C)(C)C(=O)O)ccc21]

To a solution of (S)-benzyl 3-(1-ethyl-4-methyl-1H-benzo[d][1,2,3]triazol-5-yl)-2,2-dimethyl-3-(5-methyl-4-(((R)-4-methyl-1,1-dioxido-4,5-dihydrobenzo[f][1,2]thiazepin-2(3H)-yl)methyl)thiophen-2-yl)propanoate (55 mg, 0.082 mmol) in tetrahydrofuran (THF) (2 mL), methanol (2.000 mL), and water (2.000 mL) in a 10 mL microwave reaction tube, was added LiOH (9.82 mg, 0.410 mmol) and heated on a microwave to 120° C. for 3 h and at 150° C. for 1 h. Additional LiOH (9.82 mg, 0.410 mmol) was added and the reaction was heated on a microwave at 150° C. for 1 h. The solvent was concentrated and the residue was suspended in acetonitrile and acidified with formic acid. The solvent was concentrated and the residue was purified by reverse phase preparative HPLC under formic acid conditions to provide the title compound. (0.037 g, 78% yield). LC/MS m/z=581 (M+H)+, 1.24 min (ret. time).

Example 18

(S)-3-(1-Ethyl-4-methyl-1H-benzo[d][1,2,3]triazol-5-yl)-2,2-dimethyl-3-(5-methyl-4-(((S)-4-methyl-1,1-dioxido-4,5-dihydrobenzo[f][1,2]thiazepin-2(3H)-yl)methyl)thiophen-2-yl)propanoic Acid

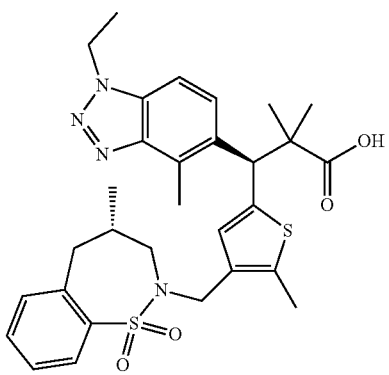 [SMILES: CCn1nnc2c(C)c([C@H](c3cc(CN4C[C@@H](C)Cc5ccccc5S4(=O)=O)c(C)s3)C(C)(C)C(=O)O)ccc21]

2-Bromo-N-(2-methylallyl)benzenesulfonamide

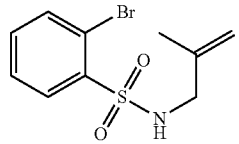

To a solution of 2-bromobenzene-1-sulfonyl chloride (25 g, 98 mmol) in dichloromethane (DCM) (250 mL) at 0° C. was added TEA (13.64 mL, 98 mmol) and 2-methylprop-2-en-1-amine (6.96 g, 98 mmol) and stirred for 10 min. Then it was stirred at ambient temperature for 16 h. The reaction mixture was quenched with ice cold water and extracted with DCM (2×200 mL). The combined organic layer was washed with ice cold water (2×100 mL), washed with brine solution(100 mL), dried over anhydrous Na$_2$SO$_4$. It was filtered and concentrated to give the title compound (20 g, 68.3 mmol, 69.8% yield). LC/MS m/z=289.81 (M+H)$^+$, 2.20 min (ret. time).

4-Methyl-2,3,4,5-tetrahydrobenzo[f][1,2]thiazepine 1,1-dioxide

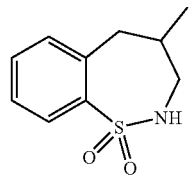

To a solution of 2-bromo-N-(2-methylallyl)benzenesulfonamide (16 g, 55.1 mmol) in toluene (160 mL) at ambient temperature was added AIBN (1.811 g, 11.03 mmol). The reaction mixture was heated to 75° C. and added tri-n-butyltin hydride (29.4 mL, 110 mmol). It was heated at 110° C. for 18 h. The reaction mixture was cooled to ambient temperature, diluted with ice water (500 mL) and extracted with EtOAc (2×300 mL). The combined organic layer was washed with chilled brine solution (200 mL) and dried over anhydrous Na$_2$SO$_4$, filtered and concentrated. The crude residue was purified via flash column chromatography eluting with 15% ethyl acetate in hexane to give the title compound (8.51 g, 39.9 mmol, 72.3% yield) as a white solid. LC/MS m/z=211.11 (M+H)+, 1.826 min (ret. time).

(S)-4-Methyl-2,3,4,5-tetrahydrobenzo[f][1,2]thiazepine 1,1-dioxide and (R)-4-methyl-2,3,4,5-tetrahydrobenzo[f][1,2]thiazepine 1,1-dioxide

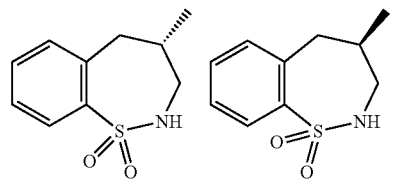

4-Methyl-2,3,4,5-tetrahydrobenzo[f][1,2]thiazepine 1,1-dioxide (4000 mg, 18.93 mmol) was resolved by Chiral SFC (Column: Chiralpak AY 20×250 mm, 5u; co-solvent: 20% EtOH; Flow rate: 50 mg/min; Back pressure: 100Bar) to give single enantiomerically pure (S)-4-methyl-2,3,4,5-tetrahydrobenzo[f][1,2]thiazepine 1,1-dioxide (2.2996 g, 10.88 mmol, 57.5% yield) (chiral SFC ret. time: 1.85 min) LC-MS m/z 211.9 (M+H)+, 0.72 min (ret. time) and single enantiomerically pure (R)-4-methyl-2,3,4,5-tetrahydrobenzo[f][1,2]thiazepine 1,1-dioxide (2.2195 g, 10.50 mmol, 55.5% yield) (chiral SFC ret. time: 2.5 min) LC/MS m/z=211.9 (M+H)+, 0.72 min (ret. time).

(S)-Benzyl 3-(1-ethyl-4-methyl-1H-benzo[d][1,2,3]triazol-5-yl)-2,2-dimethyl-3-(5-methyl-4-(((S)-4-methyl-1,1-dioxido-4,5-dihydrobenzo[f][1,2]thiazepin-2(3H)-yl)methyl)thiophen-2-yl)propanoate

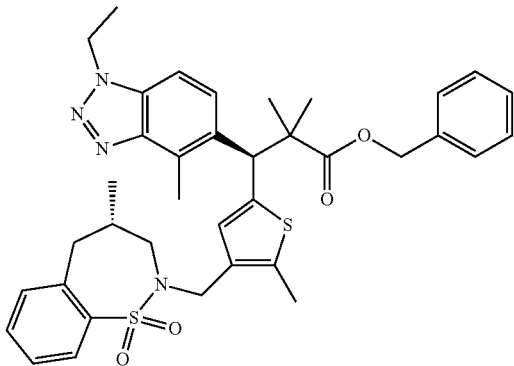 [SMILES: CCn1nnc2c(C)c([C@H](c3cc(CN4C[C@@H](C)Cc5ccccc5S4(=O)=O)c(C)s3)C(C)(C)C(=O)OCc3ccccc3)ccc21]

To a solution of (S)-benzyl 3-(1-ethyl-4-methyl-1H-benzo[d][1,2,3]triazol-5-yl)-3-(4-(hydroxymethyl)-5-methylthiophen-2-yl)-2,2-dimethylpropanoate (50 mg, 0.105 mmol) in tetrahydrofuran (THF) (2 mL) was added (S)-4-methyl-2,3,4,5-tetrahydrobenzo[f][1,2]thiazepine 1,1-dioxide (44.2 mg, 0.209 mmol) and (E)-diazene-1,2-diylbis(piperidin-1-ylmethanone) (ADDP) (52.8 mg, 0.209 mmol). Tri-n-butylphosphine (0.052 mL, 0.209 mmol) was added and stirred at ambient temperature for 22 h. The solvent was concentrated and the residue was purified by reverse phase preparative HPLC under neutral conditions to provide the title compound. (0.049 g, 69% yield). LC/MS m/z=671 (M+H)+, 1.51 min (ret. time).

(S)-3-(1-Ethyl-4-methyl-1H-benzo[d][1,2,3]triazol-5-yl)-2,2-dimethyl-3-(5-methyl-4-(((S)-4-methyl-1,1-dioxido-4,5-dihydrobenzo[f][1,2]thiazepin-2(3H)-yl)methyl)thiophen-2-yl)propanoic Acid

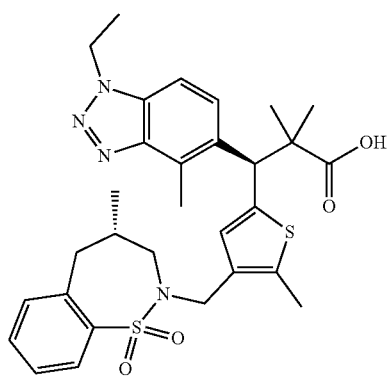 [SMILES: CCn1nnc2c(C)c([C@H](c3cc(CN4C[C@@H](C)Cc5ccccc5S4(=O)=O)c(C)s3)C(C)(C)C(=O)O)ccc21]

To a solution of (S)-benzyl 3-(1-ethyl-4-methyl-1H-benzo[d][1,2,3]triazol-5-yl)-2,2-dimethyl-3-(5-methyl-4-(((S)-4-methyl-1,1-dioxido-4,5-dihydrobenzo[f][1,2]thiazepin-2(3H)-yl)methyl)thiophen-2-yl)propanoate (49 mg, 0.073 mmol) in tetrahydrofuran (THF) (2 mL) methanol (2.000 mL), and water (2.000 mL) in a 10 mL microwave reaction tube was added LiOH (8.75 mg, 0.365 mmol) and heated on a microwave to 120° C. for 3 h. The solvent was concentrated and the residue was suspended in acetonitrile and acidified with formic acid. The solvent was concentrated and the residue was purified by reverse phase preparative HPLC under formic acid conditions to provide the title compound. (0.032 g, 75% yield). LC/MS m/z=581 (M+H)+, 1.24 min (ret. time).

Example 19

(S)-3-(1-Ethyl-4-methyl-1H-benzo[d][1,2,3]triazol-5-yl)-2,2-dimethyl-3-(5-methyl-4-(((S)-4-methyl-1,1-dioxido-4,5-dihydropyrido[2,3-f][1,2]thiazepin-2(3H)-yl)methyl)thiophen-2-yl)propanoic Acid

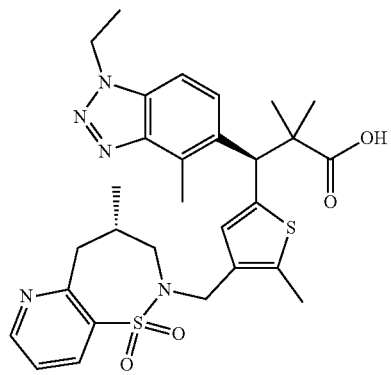 [SMILES: CCn1nnc2c(C)c([C@H](c3cc(CN4C[C@@H](C)Cc5ncccc5S4(=O)=O)c(C)s3)C(C)(C)C(=O)O)ccc21]

2-Chloropyridine-3-sulfonyl Chloride

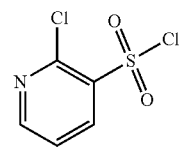 [SMILES: O=S(=O)(Cl)c1cccnc1Cl]

Step a: Thionyl chloride (159 mL, 2178 mmol) was added drop wise over 60 min to water (450 mL) at 0° C. The solution was allowed to stirred at ambient temperature for 17 h then copper(I) chloride (0.554 g, 5.60 mmol) was added to the mixture at −3° C. and the resulting yellow green solution was stirred at −3° C. for 1 h.

Step b: HCl (503 mL, 6129 mmol) was added with vigorous stirring to 2-chloropyridin-3-amine (40 g, 311 mmol) at −5° C. and a solution of sodium nitrite (37.8 g, 548 mmol) in water (82 mL) was added drop wise over 45 min, the temperature of the reaction mixture was maintained at −5° C. and stirred for 10 min.

Step c: The mixture obtained from step b was added to the solution obtained from step a over 30 min at −3° C. Reaction mixture was maintained at 0° C. for 75 min with vigorous stirring. The solid was filtered and dried to give the title compound (20 g, 92 mmol, 29.5% yield) as brown color solid. LC/MS m/z=212.02 (M+H)⁺, 2.058 min (ret. time).

2-Chloro-N-(2-methylallyl)pyridine-3-sulfonamide

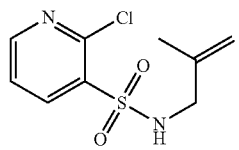

To a solution of 2-chloropyridine-3-sulfonyl chloride (20 g, 94 mmol) in dichloromethane (DCM) (200 mL) was added 2-methylprop-2-en-1-amine (7.38 g, 104 mmol) and TEA (26.3 mL, 189 mmol). It was stirred for 1 h at ambient temperature. The reaction mixture was quenched with water (100 mL) and extracted with DCM (3×80 mL). The combined organic layer was washed with brine solution (80 mL), dried over anhydrous $Na_2SO_4$, filtered and concentrated. The crude residue was purified by column chromatography eluting with 25% ethyl acetate in n-hexane to give the title compound (16 g, 63.5 mmol, 67.4% yield). LC/MS m/z=246.97 (M+H)+, 1.800 min (ret. time).

4-Methyl-2,3,4,5-tetrahydropyrido[2,3-f][1,2]thiazepine 1,1-dioxide

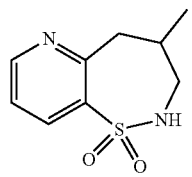

To a solution of 2-chloro-N-(2-methylallyl)pyridine-3-sulfonamide (15 g, 60.8 mmol) in toluene (150 mL) was added AIBN (1.997 g, 12.16 mmol) and heated to 75° C. then added tri-n-butyltin hydride (48.7 mL, 182 mmol) and the reaction mixture was heated to 110° C. for 20 h. The reaction mixture was concentrated. The residue was diluted with ethyl acetate (200 mL) water was added and extracted. The organic layer was washed with brine solution (80 mL), dried over anhydrous $Na_2SO_4$, filtered and concentrated. The crude residue was purified by column chromatography eluting with 25% ethyl acetate in n-hexane to give the title compound (4.27 g, 19.80 mmol, 32.6% yield) LC/MS m/z=213.07 (M+H)⁺, 1.372 min (ret. time).

(S)-4-Methyl-2,3,4,5-tetrahydropyrido[2,3-f][1,2] thiazepine 1,1-dioxide and (R)-4-methyl-2,3,4,5-tetrahydropyrido[2,3-f][1,2]thiazepine 1,1-dioxide

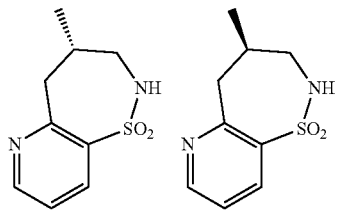

4-methyl-2,3,4,5-tetrahydropyrido[2,3-f][1,2]thiazepine 1,1-dioxide (4.27 g, 20.12 mmol) was resolved by Chiral SFC (Column: Chiralpak IC 20×150 mm, 5u; co-solvent: 20% IPA; flowrate: 50 g/min; Back pressure: 100Bar) to give single enantiomerically pure (S)-4-methyl-2,3,4,5-tetrahydropyrido[2,3-f][1,2]thiazepine 1,1-dioxide (1.96 g, 9.23 mmol, 45.9% yield) LC-MS m/z 213.0 (M+H)+, 0.43 min (ret. time) (chiral SFC ret. time: 2.95 min) and single enantiomerically pure (R)-4-methyl-2,3,4,5-tetrahydropyrido[2,3-f][1,2]thiazepine 1,1-dioxide (1.96 g, 9.23 mmol, 45.9% yield) LC/MS m/z=213.0 (M+H)+, 0.44 min (ret. time) (chiral SFC ret. time: 4.09 min).

(S)-Benzyl 3-(1-ethyl-4-methyl-1H-benzo[d][1,2,3] triazol-5-yl)-2,2-dimethyl-3-(5-methyl-4-(((S)-4-methyl-1,1-dioxido-4,5-dihydropyrido[2,3-f][1,2] thiazepin-2(3H)-yl)methyl)thiophen-2-yl)propanoate

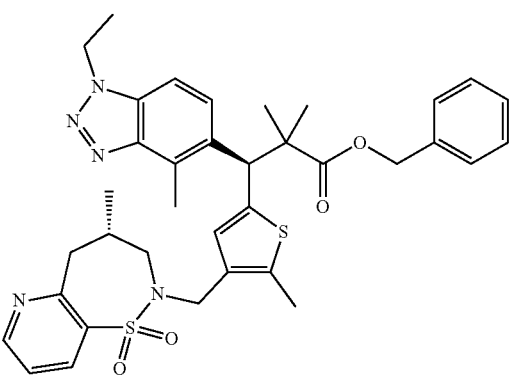 [SMILES: CCn1nnc2c(C)c([C@H](c3cc(CN4C[C@@H](C)Cc5ncccc5S4(=O)=O)c(C)s3)C(C)(C)C(=O)OCc3ccccc3)ccc21]

To a solution of (S)-benzyl 3-(1-ethyl-4-methyl-1H-benzo[d][1,2,3]triazol-5-yl)-3-(4-(hydroxymethyl)-5-methylthiophen-2-yl)-2,2-dimethylpropanoate (59 mg, 0.124 mmol) in tetrahydrofuran (THF) (2 mL) was added (S)-4-methyl-2,3,4,5-tetrahydropyrido[2,3-f][1,2]thiazepine 1,1-dioxide (52.4 mg, 0.247 mmol) and (E)-diazene-1,2-diylbis(piperidin-1-ylmethanone) (ADDP) (62.3 mg, 0.247 mmol). Tri-n-butylphosphine (0.061 mL, 0.247 mmol) was added and the reaction was stirred at ambient temperature for 2 h. The solvent was concentrated and the residue was purified by reverse phase preparative HPLC under neutral conditions to provide the title compound. (0.011 g, 13% yield). LC/MS m/z=672 (M+H)+, 1.39 min (ret. time).

(S)-3-(1-Ethyl-4-methyl-1H-benzo[d][1,2,3]triazol-5-yl)-2,2-dimethyl-3-(5-methyl-4-(((S)-4-methyl-1,1-dioxido-4,5-dihydropyrido[2,3-f][1,2]thiazepin-2(3H)-yl)methyl)thiophen-2-yl)propanoic Acid

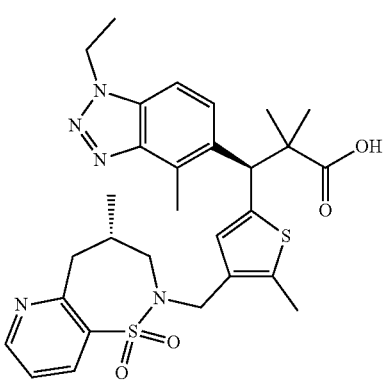 [SMILES: CCn1nnc2c(C)c([C@H](c3cc(CN4C[C@@H](C)Cc5ncccc5S4(=O)=O)c(C)s3)C(C)(C)C(=O)O)ccc21]

To a solution of (S)-benzyl 3-(1-ethyl-4-methyl-1H-benzo[d][1,2,3]triazol-5-yl)-2,2-dimethyl-3-(5-methyl-4-(((S)-4-methyl-1,1-dioxido-4,5-dihydropyrido[2,3-f][1,2]thiazepin-2(3H)-yl)methyl)thiophen-2-yl)propanoate (11 mg, 0.016 mmol) in tetrahydrofuran (THF) (1 mL), methanol (1.000 mL), and water (1.000 mL) in a 10 mL microwave reaction tube was added LiOH (1.960 mg, 0.082 mmol) and heated on a microwave to 120° C. for 3 h and at 150° C. for 2 h. Additional LiOH (3.92 mg, 0.164 mmol) was added and the reaction was heated on a microwave to 150° C. for 1.5 h. The solvent was concentrated and the residue was suspended in acetonitrile and acidified with formic acid. The solvent was concentrated and the residue was purified by reverse phase preparative HPLC under formic acid conditions to provide the title compound. (0.03 g, 35% yield). LC/MS m/z=582 (M+H)+, 1.10 min (ret. time).

Example 20

(R or S)-3-(4-(((R)-4-Ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)propanoic acid Isomer 1

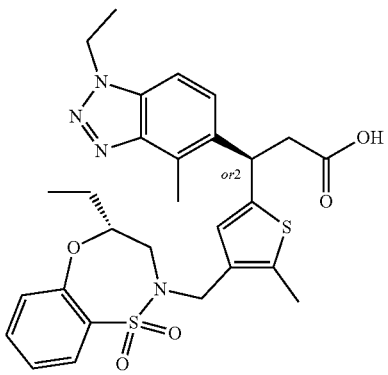 [SMILES: CC[C@@H]1CN(Cc2cc([C@H](CC(=O)O)c3ccc4c(nnn4CC)c3C)sc2C)S(=O)(=O)c2ccccc2O1]

Ethyl 5-bromo-2-methylthiophene-3-carboxylate

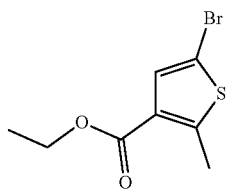

To a solution of ethyl 2-methylthiophene-3-carboxylate (10.00 g, 58.7 mmol) in N,N-dimethylformamide (DMF) (60 mL) was added acetic acid (40 mL). The reaction warmed up after adding acetic acid to DMF solution so it was cooled in ice bath. NBS (10.46 g, 58.7 mmol) was then added and the reaction was stirred at ambient temperature for 20 h. The reaction was diluted with water and extracted with EtOAc (3×). The combined organics were washed with water, saturated NaHSO₃, brine, dried with MgSO₄ and concentrated. The residue was redissolved in EtOAc and washed with water (4×), brine, dried with MgSO₄ and concentrated. The solvent was concentrated and the residue was purified by flash chromatography eluting with 0-5% EtOAc/hexane to provide the title compound. (12.32 g, 73% yield). LC/MS m/z=248/250 (M+H)+, 1.21 min (ret. time).

(5-Bromo-2-methylthiophen-3-yl)methanol

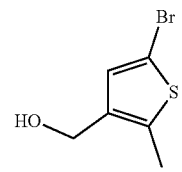

A solution of ethyl 5-bromo-2-methylthiophene-3-carboxylate (12.32 g, 43.0 mmol) in tetrahydrofuran (THF) (215 mL) under nitrogen was cooled in an ice bath. To this was added 1M DIBAL-H in THF (112 mL, 112 mmol) and stirred for 3 h at 0° C. Additional 1M DIBAL-H in THF (21.51 mL, 21.51 mmol) was added and reaction was stirred at 0° C. for 1 h and ambient temperature for 1 h. The reaction was cooled to 0° C. and additional 1M DIBAL-H in THF (32.3 mL, 32.3 mmol) was added and stirred at ambient temperature for 18 h. The reaction was cooled in an ice bath and additional 1M DIBAL-H in THF (23.23 mL, 23.23 mmol) was added and stirred at 0° C. for 3.5 h. Additional 1M DIBAL-H in THF (13 mL, 13.00 mmol) was added and stirred for 1 h at 0° C. and 1 h at ambient temperature. The reaction was cooled in an ice bath and additional 1M DIBAL-H in hexane (20 mL, 20.00 mmol) was added and stirred for 1 h at 0° C. Additional 1M DIBAL-H in DCM (25 mL, 25.00 mmol) was added and stirred for 15 min. Additional 1M DIBAL-H in DCM (25 mL, 25.00 mmol) was added and stirred for 15 min and at −78° C. for 18 h. The reaction was quenched with 1N HCl and 6N HCl and stirred at 0° C. The mixture was transferred to separatory funnel and layers were separated. Aqueous layer was extracted with EtOAc (3×). The combined organics were washed with water, brine, dried with MgSO₄ and concentrated. The residue was purified by flash chromatography eluting with 0-12% EtOAc/hexane to provide the title compound. (10.09 g, 100% yield). LC/MS m/z=189/191 (M+H—OH)+, 0.071 min (ret. time).

5-Bromo-3-(((4-methoxybenzyl)oxy)methyl)-2-methylthiophene

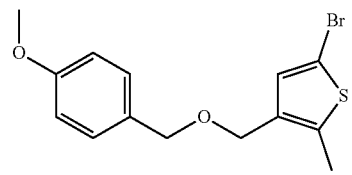 [SMILES: COc1ccc(COCc2cc(Br)sc2C)cc1]

A solution of (5-bromo-2-methylthiophen-3-yl)methanol (10.03 g, 42.6 mmol) in N,N-dimethylformamide (DMF) (100 mL) under nitrogen was cooled to 0° C. 60% NaH (2.56 g, 63.9 mmol) was added to the solution portion wise over 1 h and stirred at 0° C. for 1 h until most of gas evolution had subsided. A solution of 1-(chloromethyl)-4-methoxybenzene (8.68 g, 55.4 mmol) in N,N-dimethylformamide (DMF) (20 mL) was then added dropwise and reaction was allowed to stir for 2 h at 0° C. and at ambient temperature for 2.5 h. The reaction was quenched with water and ice and then diluted with water. The aqueous layer was extracted with EtOAc (4×). The combined organics were washed with water (4×), brine, and dried with MgSO₄. The residue was purified by flash chromatography eluting with 0-50% EtOAc/hexane to provide the title compound. (10.51 g, 68% yield). LC/MS m/z=327/329 (M+H)+, 1.35 min (ret. time).

(1-Ethyl-4-methyl-1H-benzo[d][1,2,3]triazol-5-yl)(4-(((4-methoxybenzyl)oxy)methyl)-5-methylthiophen-2-yl)methanol

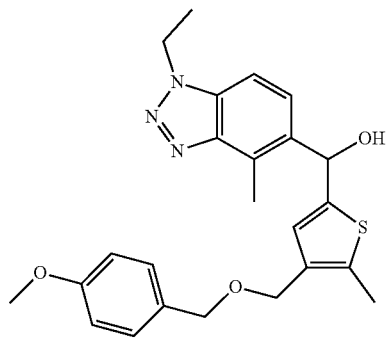

A solution of 5-bromo-3-(((4-methoxybenzyl)oxy)methyl)-2-methylthiophene (6.28 g, 19.19 mmol) in tetrahydrofuran (THF) (150 mL) in an oven dried flask, under nitrogen, was cooled to −78° C. 1.6 M n-butyllithium in hexanes (17.99 mL, 28.8 mmol) was added dropwise via syringe and stirred for 1.5 h. 1-ethyl-4-methyl-1H-benzo[d][1,2,3]triazole-5-carbaldehyde (3.63 g, 19.19 mmol) in tetrahydrofuran (THF) (90 mL) was then added dropwise over 1.5 h and stirred at −78° C. for 1 h. The reaction was quenched with water (30 mL) and allowed to warm to ambient temperature. The reaction was diluted with EtOAc and the organic layer was washed with water (2×). The organic layer was back extracted with EtOAc (2×). The combined organic layers were washed with brine and dried with MgSO₄. The residue was purified by flash chromatography eluting with 0-50% EtOAc/hexane to provide the title compound. (6.78 g, 81% yield). LC/MS m/z=438 (M+H)+, 1.07 min (ret. time).

Methyl 3-(4-(chloromethyl)-5-methylthiophen-2-yl)-3-(1-ethyl-4-methyl-1H-benzo[d][1,2,3]triazol-5-yl)propanoate, (R)-methyl 3-(1-ethyl-4-methyl-1H-benzo[d][1,2,3]triazol-5-yl)-3-(4-(((4-methoxybenzyl)oxy)methyl)-5-methylthiophen-2-yl)propanoate and (S)-methyl 3-(1-ethyl-4-methyl-1H-benzo[d][1,2,3]triazol-5-yl)-3-(4-(((4-methoxybenzyl)oxy)methyl)-5-methylthiophen-2-yl)propanoate

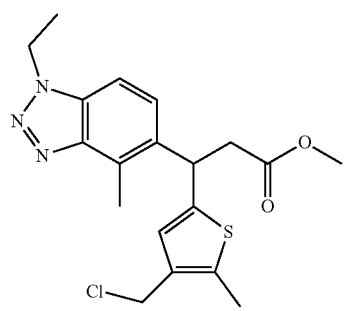

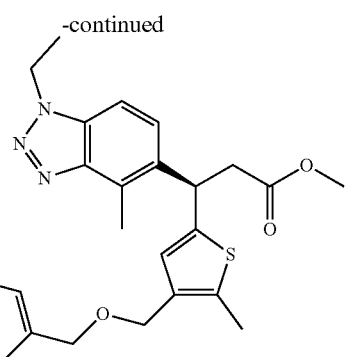

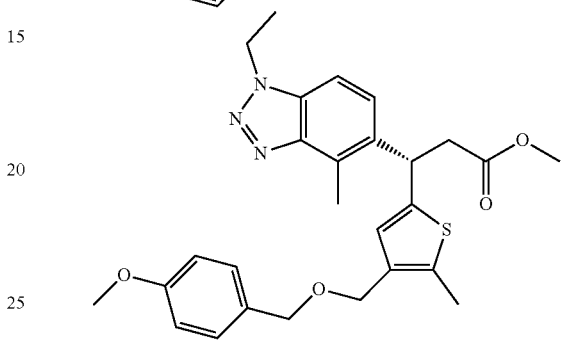

To a solution of (1-ethyl-4-methyl-1H-benzo[d][1,2,3]triazol-5-yl)(4-(((4-methoxybenzyl)oxy)methyl)-5-methylthiophen-2-yl) methanol (0.500 g, 1.143 mmol) and tert-butyl((1-methoxyvinyl)oxy)dimethylsilane (0.757 mL, 3.43 mmol) in dichloromethane (DCM) (50 mL) in an oven dried flask, under nitrogen atmosphere, at 0° C., was added a solution of 1M titanium tetrachloride in DCM (1.143 mL, 1.143 mmol) in dichloromethane (DCM) (15 mL) over 1 h and stirred at 0° C. for 30 min. The reaction was quenched with 5% NaHSO₄ (20 mL) while cooled. The layers were separated in separatory funnel and aqueous layer was washed with DCM (3×). Emulsions formed and extraction had to be filtered. The combined organics were washed with water (2×), brine, dried with MgSO₄ and concentrated. The residue was purified by flash chromatography eluting with 0-50% EtOAc/hexane to provide Methyl 3-(4-(chloromethyl)-5-methylthiophen-2-yl)-3-(1-ethyl-4-methyl-1H-benzo[d][1,2,3]triazol-5-yl)propanoate (0.68 g, 15% yield). 1H NMR (400 MHz, CHLOROFORM-d) δ 7.29-7.38 (m, 2H), 6.65 (s, 1H), 5.09 (t, J=7.78 Hz, 1H), 4.64 (q, J=7.11 Hz, 2H), 4.43 (s, 2H), 3.59 (s, 3H), 3.14-3.23 (m, 1H), 2.99-3.09 (m, 1H), 2.88 (s, 3H), 2.34 (s, 3H), 1.61 (t, J=7.28 Hz, 3H), and methyl 3-(1-ethyl-4-methyl-1H-benzo[d][1,2,3]triazol-5-yl)-3-(4-(((4-methoxybenzyl)oxy)methyl)-5-methylthiophen-2-yl)propanoate (0.367 g, 65% yield).

Methyl 3-(1-ethyl-4-methyl-1H-benzo[d][1,2,3]triazol-5-yl)-3-(4-(((4-methoxybenzyl)oxy)methyl)-5-methylthiophen-2-yl)propanoate was resolved by chiral SFC (Column: Chiralpak IA 20×250 mm, 5u; Co-solvent: 30% MeOH; Flowrate: 50 g/min; Back pressure: 100Bar) to give single enantiomerically pure (R)-methyl 3-(1-ethyl-4-methyl-1H-benzo[d][1,2,3]triazol-5-yl)-3-(4-(((4-methoxybenzyl)oxy)methyl)-5-methylthiophen-2-yl)propanoate (0.138 g, 24% yield). LC/MS m/z=494 (M+H)+, 1.23 min (ret. time), (chiral SFC ret. time: 1.82 min) and single enantiomerically pure (S)-methyl 3-(1-ethyl-4-methyl-1H-benzo[d][1,2,3]triazol-5-yl)-3-(4-(((4-methoxybenzyl)oxy)methyl)-5-methylthiophen-2-yl)propanoate (0.137 g, 24% yield). LC/MS m/z=494 (M+H)+, 1.25 min (ret. time), (chiral SFC ret. time: 2.41 min).

(R or S)-Methyl 3-(4-(((R)-4-ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)propanoate Isomer 1 and (R or S)-methyl 3-(4-(((R)-4-ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)propanoate Isomer 2

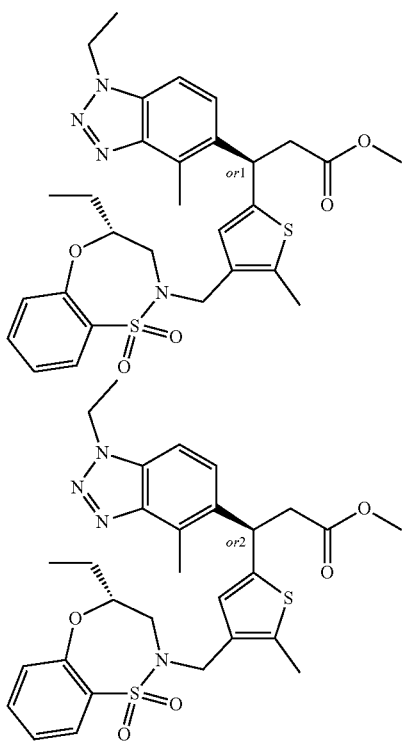

To a solution of (R)-4-ethyl-3,4-dihydro-2H-benzo[b][1,4,5]oxathiazepine 1,1-dioxide (0.047 g, 0.208 mmol) in N,N-dimethylformamide (DMF) (3 mL) under nitrogen and cooled to 0° C., was added 60% NaH (10.41 mg, 0.260 mmol) portion wise. The reaction was then warmed to ambient temperature and stirred for 1 h. Methyl 3-(4-(chloromethyl)-5-methylthiophen-2-yl)-3-(1-ethyl-4-methyl-1H-benzo[d][1,2,3]triazol-5-yl)propanoate (0.068 g, 0.174 mmol) in N,N-dimethylformamide (DMF) (3.00 mL) was then added dropwise to reaction and stirred for 30 min. Reaction was quenched with saturated. NaHCO₃, diluted with water and EtOAc and the aqueous layer was extracted with EtOAc (3×). The combined organic layers were washed with water (2×), brine and dried with MgSO₄ and concentrated. The residue was resolved by chiral SFC (Column: Chiralpak IA 20×250 mm, 5u; Co-solvent: 30% EtOH; Flowrate: 50 g/min; Back pressure: 100Bar) to give single enantiomerically pure (R or S)-methyl 3-(4-(((R)-4-ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)propanoate Isomer 1 (0.037 g, 36% yield). LC/MS m/z=583 (M+H)+, 1.24 min (ret. time), (chiral SFC ret. time: 2.07 min) and single enantiomerically pure (R or S)-methyl 3-(4-(((R)-4-ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)propanoate Isomer 2 N40237-70-P2 (0.038 g, 35% yield). LC/MS m/z=583 (M+H)+, 1.24 min (ret. time), (chiral SFC ret. time: 3.97 min).

(R or S)-3-(4-(((R)-4-Ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)propanoic Acid Isomer 1

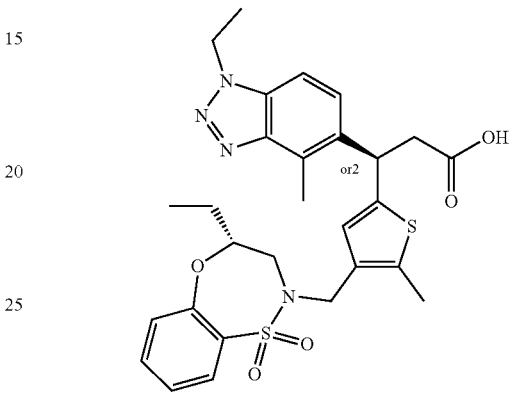

To a solution of (R or S)-methyl 3-(4-(((R)-4-ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)propanoate Isomer 1 (37 mg, 0.063 mmol) in tetrahydrofuran (THF) (2 mL), methanol (2 mL), and water (1.00 mL) was added lithium hydroxide (7.60 mg, 0.317 mmol) and stirred at ambient temperature for 19 h. The reaction was acidified with formic acid and the solvents were concentrated. The residue was purified by reverse phase preparative HPLC under formic acid conditions to provide the title compound. (0.026 g, 72% yield). LC/MS m/z=569 (M+H)+, 1.13 min (ret. time).

Example 21

(R or S)-3-(4-(((R)-4-Ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)propanoic Acid Isomer 2

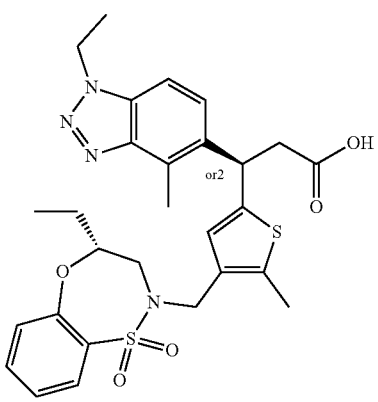 [SMILES: CC[C@@H]1CN(Cc2cc([C@H](CC(=O)O)c3ccc4c(nnn4CC)c3C)sc2C)S(=O)(=O)c2ccccc2O1]

To a solution of (R or S)-methyl 3-(4-(((R)-4-ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)propanoate Isomer 2 (38 mg, 0.062 mmol) in tetrahydrofuran (THF) (2 mL), methanol (2 mL), and water (1.00 mL) was added lithium hydroxide (7.42 mg, 0.310 mmol) and stirred at ambient temperature for 19 h. The reaction was acidified with formic acid and the solvents were concentrated. The residue was purified by reverse phase preparative HPLC under formic acid conditions to provide the title compound. (0.027 g, 77% yield). LC/MS m/z=569 (M+H)+, 1.13 min (ret. time).

Example 22

(R)-3-(5-chloro-4-(((R)-4-ethyl-1,1-dioxido-3,4-dihydro-2H-pyrido[4,3-b][1,4,5]oxathiazepin-2-yl)methyl)thiophen-2-yl)-3-(1-ethyl-4-methyl-1H-benzo[d][1,2,3]triazol-5-yl)propanoic Acid

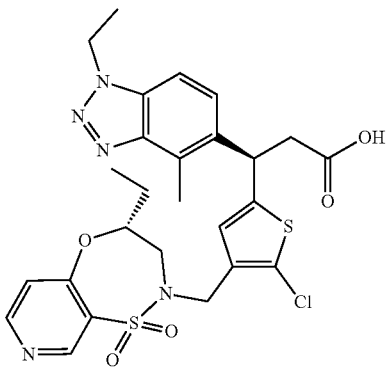 [SMILES: CC[C@@H]1CN(Cc2cc([C@H](CC(=O)O)c3ccc4c(nnn4CC)c3C)sc2Cl)S(=O)(=O)c2cnccc2O1]

(R)-Methyl 3-(5-chloro-4-(((R)-4-ethyl-1,1-dioxido-3,4-dihydro-2H-pyrido[4,3-b][1,4,5]oxathiazepin-2-yl)methyl)thiophen-2-yl)-3-(1-ethyl-4-methyl-1H-benzo[d][1,2,3]triazol-5-yl)propanoate

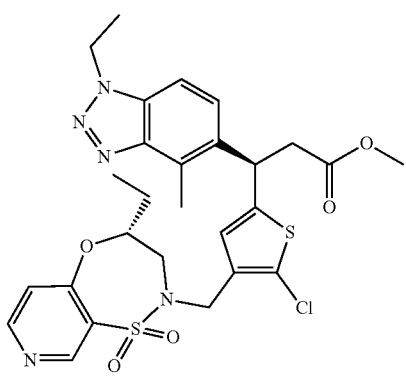 [SMILES: CC[C@@H]1CN(Cc2cc([C@H](CC(=O)OC)c3ccc4c(nnn4CC)c3C)sc2Cl)S(=O)(=O)c2cnccc2O1]

To a solution of (R)-methyl 3-(5-chloro-4-(hydroxymethyl)thiophen-2-yl)-3-(1-ethyl-4-methyl-1H-benzo[d][1,2,3]triazol-5-yl)propanoate (48 mg, 0.122 mmol), and (R)-4-ethyl-3,4-dihydro-2H-pyrido[4,3-b][1,4,5]oxathiazepine 1,1-dioxide (55.6 mg, 0.244 mmol) and (E)-diazene-1,2-diylbis(piperidin-1-ylmethanone) (61.5 mg, 0.244 mmol) in tetrahydrofuran (THF) (4 mL) was added tributylphosphine (0.061 mL, 0.244 mmol) and stirred for 1 h 15 min. The reaction was then concentrated, and the residue was purified by reverse phase preparative HPLC under neutral conditions to provide the title compound. (0.065 g, 78% yield). LC/MS m/z=604 (M+H)+, 1.14 min (ret. time).

(R)-3-(5-Chloro-4-(((R)-4-ethyl-1,1-dioxido-3,4-dihydro-2H-pyrido[4,3-b][1,4,5]oxathiazepin-2-yl)methyl)thiophen-2-yl)-3-(1-ethyl-4-methyl-1H-benzo[d][1,2,3]triazol-5-yl)propanoic Acid

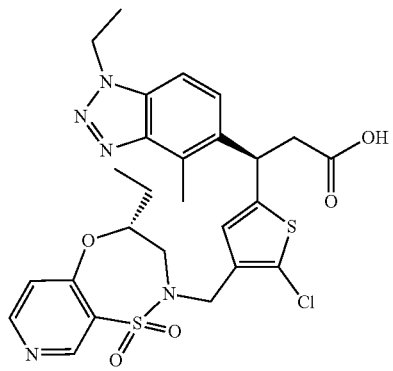 [SMILES: CC[C@@H]1CN(Cc2cc([C@H](CC(=O)O)c3ccc4c(nnn4CC)c3C)sc2Cl)S(=O)(=O)c2cnccc2O1]

To a solution of (R)-methyl 3-(5-chloro-4-(((R)-4-ethyl-1,1-dioxido-3,4-dihydro-2H-pyrido[4,3-b][1,4,5]oxathiazepin-2-yl)methyl)thiophen-2-yl)-3-(1-ethyl-4-methyl-1H-benzo[d][1,2,3]triazol-5-yl)propanoate (65 mg, 0.108 mmol) in tetrahydrofuran (THF) (2.000 mL), water (1 mL) and methanol (2.000 mL) was added lithium hydroxide (12.88 mg, 0.538 mmol) and stirred at ambient temperature for 1 h. A solution of 10% formic acid was then added dropwise to the reaction until it was acidic. The reaction was then concentrated, and the residue was purified by reverse phase preparative HPLC under formic acid conditions to provide the title compound. (0.039 g, 61% yield). LC/MS m/z=604 (M+H)+, 1.14 min (ret. time).

Example 23

(R)-3-(1-Ethyl-4-methyl-1H-benzo[d][1,2,3]triazol-5-yl)-2,2-dimethyl-3-(1-methyl-5-(((S)-4-methyl-1,1-dioxido-4,5-dihydropyrido[2,3-f][1,2]thiazepin-2(3H)-yl)methyl)-1H-pyrazol-3-yl)propanoic Acid

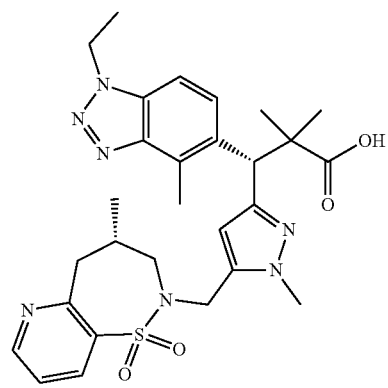 [SMILES: CCn1nnc2c(C)c([C@@H](c3cc(CN4C[C@@H](C)Cc5ncccc5S4(=O)=O)n(C)n3)C(C)(C)C(=O)O)ccc21]

149

Ethyl 3-bromo-1-methyl-1H-pyrazole-5-carboxylate

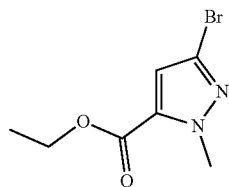

A solution of ethyl 1-methyl-1H-pyrazole-5-carboxylate (8.20 g, 53.2 mmol) in tetrahydrofuran (THF) (53.2 mL) in an oven dried 500 mL flask, flushed with nitrogen, was cooled to −15° C. 1M 2,2,6,6-tetramethyl-piperdinylmagnesiumchloride lithium chloride complex in THF/toluene (58.5 mL, 58.5 mmol) was then added dropwise and stirred for 18 h at −15° C. The reaction was cooled to −20'C and 1,2-dibromo-1,1,2,2-tetrachloroethane (20.78 g, 63.8 mmol) was added portion wise as a solid. The reaction was stirred at −20'C for 30 min and was allowed to warm to 20° C. over 1.5 h and stirred for an additional 1 h. The reaction was quenched with portion wise addition of 40 mL brine, and diluted with EtOAc. Emulsions formed so the reaction was filtered, the layers were separated and the aqueous layer was extracted with EtOAc (2×). Saturated aqueous $NH_4Cl$ was added to bring the aqueous layer to neutral pH and break up emulsions. The aqueous layer was then extracted with EtOAc (2×). The combined organic layers were washed with water, brine and dried with $MgSO_4$ and concentrated. The residue was purified by flash chromatography eluting with 0-10% EtOAc/hexanes to provide the title compound. (2.00 g, 14% yield). LC/MS m/z 233/235 (M+H)+, 0.85 min (ret time).

(3-Bromo-1-methyl-1H-pyrazol-5-yl)methanol

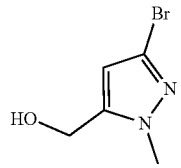

A solution of ethyl 3-bromo-1-methyl-1H-pyrazole-5-carboxylate (2.00 g, 8.58 mmol) in tetrahydrofuran (THF) (42.9 mL) under nitrogen, was cooled in an ice bath. To it was added 1M DIBAL-H in THF (25.7 mL, 25.7 mmol) and stirred for 1 hour at 0° C. The reaction was quenched with 1N HCl (38.6 mL, 38.6 mmol). The reaction was transferred to separatory funnel and the layers were separated. The aqueous layer was extracted with EtOAc (4×). The combined organics were washed with water. Emulsions formed which were filtered and the layers were separated. The aqueous layer was extracted with EtOAc. The combined organics were washed with brine, dried with $MgSO_4$ and concentrated. The residue was purified by flash chromatography eluting with 0-50% EtOAc/hexanes to provide the title compound. (1.21 g, 73% yield). LC/MS m/z=191/193 (M+H)+, 0.37 min (ret. time).

150

3-Bromo-5-(((4-methoxybenzyl)oxy)methyl)-1-methyl-1H-pyrazole

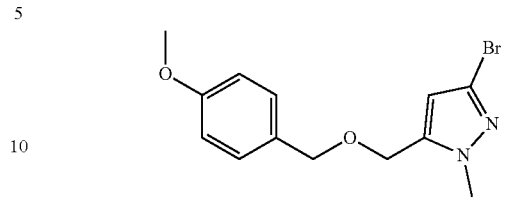

A solution of (3-bromo-1-methyl-1H-pyrazol-5-yl)methanol (1.21 g, 6.33 mmol) in N,N-dimethylformamide (DMF) (15 mL) under nitrogen was cooled to 0° C. 60% NaH (0.380 g, 9.50 mmol) was added to the solution portion wise over 30 min and stirred at 0° C. for 1.5 h until most of frothing had subsided. A solution of 1-(chloromethyl)-4-methoxybenzene (1.488 g, 9.50 mmol) in N,N-dimethylformamide (DMF) (5 mL) was then added dropwise and the reaction was allowed to stir for 2 h at 0° C. Additional 1-(chloromethyl)-4-methoxybenzene (0.248 g, 1.584 mmol) in N,N-dimethylformamide (DMF) (2 mL) was added and the reaction stirred at 0° C. for 1 h. Additional 60% NaH (0.063 g, 1.584 mmol) was added and the reaction stirred for 1.5 h. The reaction was quenched with water and then diluted with more water. The aqueous layer was extracted with EtOAc (3×). The combined organics were washed with water (4×), brine, and dried with $MgSO_4$. The residue was purified by flash chromatography eluting with 0-30% EtOAc/hexanes to provide the title compound. (1.55 g, 70% yield). LC/MS m/z=311,313 (M+H)+, 0.99 min (ret. time).

(1-Ethyl-4-methyl-1H-benzo[d][1,2,3]triazol-5-yl) (5-(((4-methoxybenzyl)oxy)methyl)-1-methyl-1H-pyrazol-3-yl)methanol

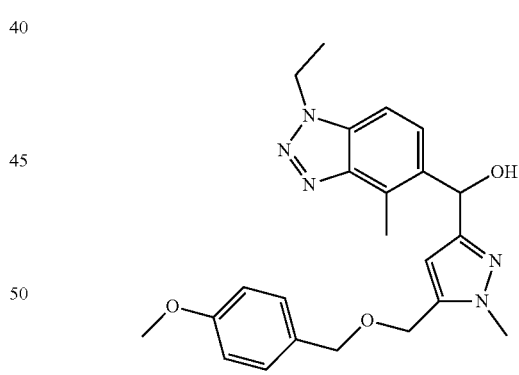

To a solution of 1M ethylmagnesium bromide in THF (1.909 mL, 1.909 mmol) in toluene (11.45 mL) at −40° C. (dry ice/$CH_3CN$ bath), in an oven dried 25 mL flask under argon, was added, dropwise, 1.6M nBuLi in Hexane (2.62 mL, 4.20 mmol) and stirred for 45 min. To this solution was added 3-bromo-5-(((4-methoxybenzyl)oxy)methyl)-1-methyl-1H-pyrazole (1.32 g, 3.82 mmol) in tetrahydrofuran (THF) (10 mL) via syringe and stirred for 2 h. The reaction was monitored by LCMS. Additional 1.6M BuLi in hexane (0.597 mL, 0.954 mmol) was added and the reaction stirred for 1 h. Additional 1.6M BuLi in hexane (0.597 mL, 0.954 mmol) was added and the reaction stirred for 30 min. After which, 1-ethyl-4-methyl-1H-benzo[d][1,2,3]triazole-5-carbaldehyde (0.722 g, 3.82 mmol) in tetrahydrofuran (THF) (10 mL) was added dropwise via an addition funnel and the reaction was allowed to warm to ambient temperature over 18 h. The reaction was quenched with saturated aqueous NH$_4$Cl and diluted with water. The layers were separated and the aqueous layer was extracted with EtOAc (3×). The combined organics were washed with water (3×), brine and dried with MgSO$_4$. The solvent was concentrated and the residue was purified by flash chromatography eluting with 0-5% MeOH/DCM to provide the title compound. (0.543 g, 33% yield). LC/MS m/z=422 (M+H)$^+$, 0.85 min (ret time).

Methyl 3-(1-ethyl-4-methyl-1H-benzo[d][1,2,3]triazol-5-yl)-3-(5-(((4-methoxybenzyl)oxy)methyl)-1-methyl-1H-pyrazol-3-yl)-2,2-dimethylpropanoate

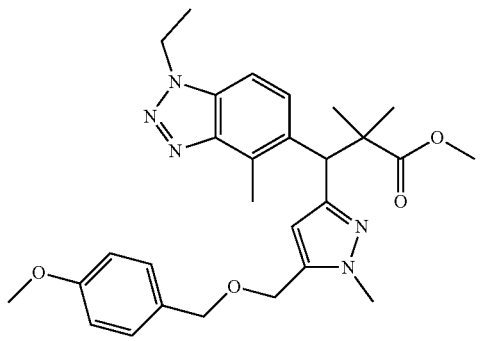

To a solution of (1-ethyl-4-methyl-1H-benzo[d][1,2,3]triazol-5-yl)(5-(((4-methoxybenzyl)oxy)methyl)-1-methyl-1H-pyrazol-3-yl)methanol (0.543 g, 1.288 mmol) in acetonitrile (4.00 mL), under dry argon, was added 2,2,2-trichloroacetonitrile (0.258 mL, 2.58 mmol). DBU (9.71 µl, 0.064 mmol) in acetonitrile (1.000 mL), was then added dropwise, and stirred for 1 h. Additional, 2,2,2-trichloroacetonitrile (0.129 mL, 1.288 mmol) was added followed by DBU (4.27 µl, 0.028 mmol) in acetonitrile (1.00 mL) and stirred for 45 min. ((1-methoxy-2-methylprop-1-en-1-yl)oxy)trimethylsilane (0.654 mL, 3.22 mmol) was then added dropwise, followed by addition of 1,1,1-trifluoro-N-((trifluoromethyl)sulfonyl)methanesulfonamide (0.109 g, 0.386 mmol) in acetonitrile (2.000 mL) and the reaction stirred at ambient temperature for 1 h. The reaction was quenched with saturated aqueous NaHCO$_3$ and the aqueous layer was extracted with EtOAc (4×). The combined organics were washed with brine and dried with MgSO$_4$ and concentrated. The residue was purified by flash chromatography eluting with 0-40% (3:1 EtOAc:EtOH)/Hexane to provide the title compound. (0.380 g, 58% yield). m/z=506 (M+H)$^+$, 1.14 min (ret. Time).

Methyl (S)-3-(1-ethyl-4-methyl-1H-benzo[d][1,2,3]triazol-5-yl)-3-(5-(hydroxymethyl)-1-methyl-1H-pyrazol-3-yl)-2,2-dimethylpropanoate and methyl®-3-(1-ethyl-4-methyl-1H-benzo[d][1,2,3]triazol-5-yl)-3-(5-(hydroxymethyl)-1-methyl-1H-pyrazol-3-yl)-2,2-dimethylpropanoate

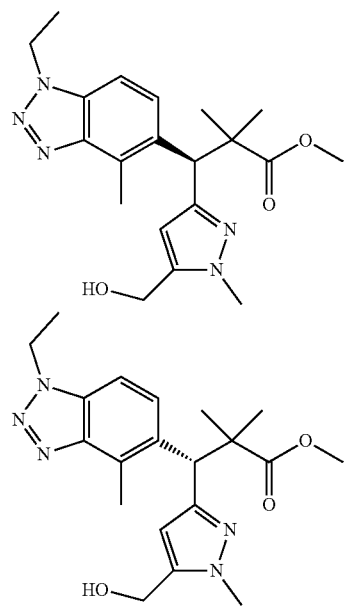

A solution of methyl 3-(1-ethyl-4-methyl-1H-benzo[d][1,2,3]triazol-5-yl)-3-(5-(((4-methoxybenzyl)oxy)methyl)-1-methyl-1H-pyrazol-3-yl)-2,2-dimethylpropanoate (0.380 g, 0.752 mmol) in dichloromethane (DCM) (20 mL) and water (2.000 mL), was cooled to 0° C. and DDQ (0.171 g, 0.752 mmol) was added portion wise over 10 min. and stirred at 0° C. for 3.5 h. The ice bath was removed and the reaction stirred at ambient temperature for 2.5 h. Additional DDQ (0.017 g, 0.075 mmol) was added and the reaction stirred for 45 min. The reaction was diluted with DCM and quenched with saturated aqueous NaHCO$_3$. The layers were separated and the aqueous layer was extracted with DCM (4×). The combined organics were washed with water, brine and dried with MgSO$_4$. The solvent was concentrated and the residue was purified by flash chromatography eluting with 0-50% (3:1 EtOAc:EtOH)/Hexane to provide the title compound as a racemate. (0.189 g, 65% yield). LC/MS m/z=386 (M+H)$^+$, 0.74 min (ret. time). The compound was resolved by chiral SFC (Column: Chiralpak IG 20×250 mm, 5u; Co-solvent: 25% EtOH; Flowrate: 50 g/min; Back pressure: 100Bar) to provide Methyl (S)-3-(1-ethyl-4-methyl-1H-benzo[d][1,2,3]triazol-5-yl)-3-(5-(hydroxymethyl)-1-methyl-1H-pyrazol-3-yl)-2,2-dimethylpropanoate (0.086 g, 29% yield). LCMS m/z=386 (M+H)$^+$, 0.74 min (ret. time), (chiral SFC ret. time: 2.92 min) and Methyl (R)-3-(1-ethyl-4-methyl-1H-benzo[d][1,2,3]triazol-5-yl)-3-(5-(hydroxymethyl)-1-methyl-1H-pyrazol-3-yl)-2,2-dimethylpropanoate (0.086 g, 29% yield). LCMS m/z 386 (M+H)$^+$, 0.74 min (ret. time), (chiral SFC ret. time: 6.97 min).

153

Methyl (R)-3-(1-ethyl-4-methyl-1H-benzo[d][1,2,3]triazol-5-yl)-2,2-dimethyl-3-(1-methyl-5-(((S)-4-methyl-1,1-dioxido-4,5-dihydropyrido[2,3-f][1,2]thiazepin-2(3H)-yl)methyl)-1H-pyrazol-3-yl)propanoate

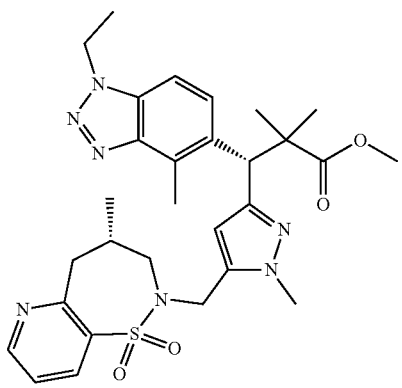 [SMILES: CCn1nnc2c(C)c([C@@H](c3cc(CN4C[C@@H](C)Cc5ncccc5S4(=O)=O)n(C)n3)C(C)(C)C(=O)OC)ccc21]

To a solution of methyl (R)-3-(1-ethyl-4-methyl-1H-benzo[d][1,2,3]triazol-5-yl)-3-(5-(hydroxymethyl)-1-methyl-1H-pyrazol-3-yl)-2,2-dimethylpropanoate (43 mg, 0.112 mmol) in tetrahydrofuran (THF) (4 mL) was added (S)-4-methyl-2,3,4,5-tetrahydropyrido[2,3-f][1,2]thiazepine 1,1-dioxide (47.4 mg, 0.223 mmol) and (E)-diazene-1,2-diylbis(piperidin-1-ylmethanone) (ADDP) (56.3 mg, 0.223 mmol). After all solids were dissolved, the solution was degassed and purged with argon after which tri-n-butylphosphine (0.055 mL, 0.223 mmol) was added and the reaction stirred at ambient temperature for 18 h. Additional tri-n-butylphosphine (0.028 mL, 0.112 mmol) was added and the reaction stirred for 6 h. The residue was purified by reverse phase preparative HPLC under neutral conditions to provide the title compound (0.039 g, 60% yield). LC/MS m/z 580 (M+H)$^+$, 1.04 min (ret. time).

(R)-3-(1-Ethyl-4-methyl-1H-benzo[d][1,2,3]triazol-5-yl)-2,2-dimethyl-3-(1-methyl-5-(((S)-4-methyl-1,1-dioxido-4,5-dihydropyrido[2,3-f][1,2]thiazepin-2(3H)-yl)methyl)-1H-pyrazol-3-yl)propanoic Acid

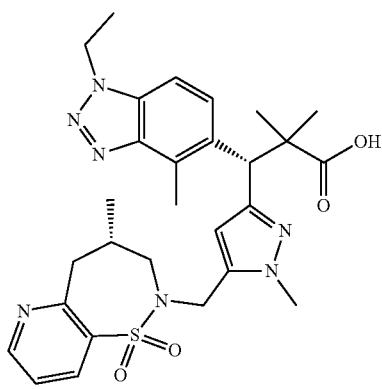 [SMILES: CCn1nnc2c(C)c([C@@H](c3cc(CN4C[C@@H](C)Cc5ncccc5S4(=O)=O)n(C)n3)C(C)(C)C(=O)O)ccc21]

To a solution of methyl (R)-3-(1-ethyl-4-methyl-1H-benzo[d][1,2,3]triazol-5-yl)-2,2-dimethyl-3-(1-methyl-5-(((S)-4-methyl-1,1-dioxido-4,5-dihydropyrido[2,3-f][1,2]

154 thiazepin-2(3H)-yl)methyl)-1H-pyrazol-3-yl)propanoate (39 mg, 0.067 mmol) in tetrahydrofuran (THF) (2 mL), methanol (1 mL) and water (1 mL) in a microwave reaction vessel, was added LiOH (8.06 mg, 0.336 mmol) and the reaction was heated via microwave at 140° C. for 2 h. The solvents were concentrated and the residue was suspended in acetonitrile and acidified with formic acid. The solvent was concentrated and the residue was purified by reverse phase preparative HPLC under neutral conditions to provide the title compound (0.020 g, 53% yield). LC/MS m/z 566 (M+H)$^+$, 0.90 min (ret. time).

Example 24

(S)-3-(4-(((R)-4-Ethyl-1,1-dioxido-3,4-dihydro-2H-pyrido[2,3-b][1,4,5]oxathiazepin-2-yl)methyl)-5-methylthiophen-2-yl)-3-(1-ethyl-4-methyl-1H-benzo[d][1,2,3]triazol-5-yl)propanoic Acid

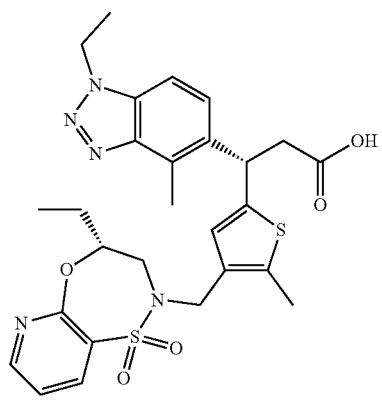 [SMILES: CC[C@@H]1CN(Cc2cc([C@@H](CC(=O)O)c3ccc4c(nnn4CC)c3C)sc2C)S(=O)(=O)c2cccnc2O1]

(S)-Methyl 3-(4-(chloromethyl)-5-methylthiophen-2-yl)-3-(1-ethyl-4-methyl-1H-benzo[d][1,2,3]triazol-5-yl)propanoate

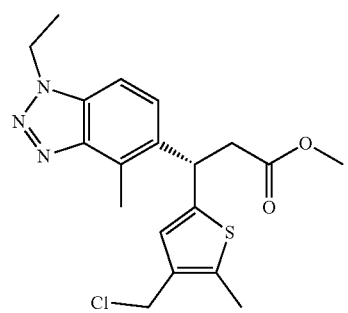 [SMILES: CCn1nnc2c(C)c([C@H](CC(=O)OC)c3cc(CCl)c(C)s3)ccc21]

To a solution of (S)-methyl 3-(1-ethyl-4-methyl-1H-benzo[d][1,2,3]triazol-5-yl)-3-(4-(((4-methoxybenzyl)oxy)methyl)-5-methylthiophen-2-yl)propanoate (0.137 g, 0.278 mmol) in 1,4-dioxane (15 mL) was added 4N HCl in 1,4 dioxane (0.694 mL, 2.78 mmol) and the reaction stirred at ambient temperature for 30 min. No deprotection was observed by LCMS so the solvent was concentrated and the starting material in the residue was purified by flash chromatography eluting with 0-12% EtOAc/Hexane to recover (S)-methyl 3-(1-ethyl-4-methyl-1H-benzo[d][1,2,3]triazol- 5-yl)-3-(4-(((4-methoxybenzyl)oxy)methyl)-5-methylthiophen-2-yl)propanoate. This material was dissolved in 4N HCl in 1,4 dioxane (4.00 mL, 16.00 mmol) and the reaction stirred at ambient temperature for 21 h. The solvent was concentrated and the residue was redissolved in 4N HCl in 1,4 dioxane (4.00 mL, 16.00 mmol) and stirred for 18 h. The solvent was concentrated and the residue was dissolved in dichloromethane (DCM) (5 mL). To this solution was added SOCl$_2$ (10.13 µl, 0.139 mmol) and stirred for 18 h. The solvent was concentrated and the residue was purified by flash chromatography eluting with 0-40% EtOAc/Hexane to provide the title compound. (0.054 g, 44% yield). LC/MS m/z 392 (M+H)$^+$, 1.13 min (ret. time).

(S)-3-(4-(((R)-4-Ethyl-1,1-dioxido-3,4-dihydro-2H-pyrido[2,3-b][1,4,5]oxathiazepin-2-yl)methyl)-5-methylthiophen-2-yl)-3-(1-ethyl-4-methyl-1H-benzo[d][1,2,3]triazol-5-yl)propanoic Acid

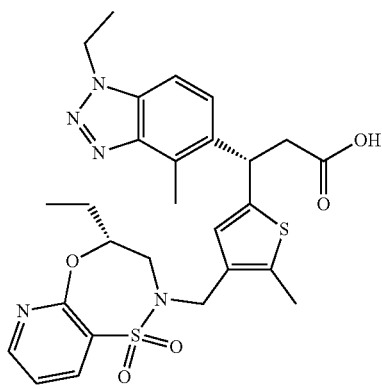 [SMILES: CC[C@@H]1CN(Cc2cc([C@@H](CC(=O)O)c3ccc4c(nnn4CC)c3C)sc2C)S(=O)(=O)c2cccnc2O1]

To a solution of (R)-4-ethyl-3,4-dihydro-2H-pyrido[2,3-b][1,4,5]oxathiazepine 1,1-dioxide (0.039 g, 0.170 mmol) in N,N-dimethylformamide (DMF) (3 mL) under nitrogen and cooled to 0° C., was added 60% NaH (7.85 mg, 0.196 mmol) portion wise. The reaction was warmed to ambient temperature and stirred for 30 min. (S)-methyl 3-(4-(chloromethyl)-5-methylthiophen-2-yl)-3-(1-ethyl-4-methyl-1H-benzo[d][1,2,3]triazol-5-yl)propanoate (0.057 g, 0.131 mmol) in N,N-dimethylformamide (DMF) (3.00 mL) was then added dropwise to the reaction and stirred for 18 h. The reaction was quenched with water and concentrated under vacuum. The residue was dissolved in tetrahydrofuran (THF) (2.00 mL), methanol (2.00 mL) and water (1.00 mL). LiOH (0.016 g, 0.654 mmol) was added and the reaction was stirred at ambient temperature for 19 h. The reaction was acidified with formic acid and the solvents were concentrated. The residue was purified by reverse phase preparative HPLC under neutral conditions to provide the title compound (0.040 g, 53% yield). LC/MS m/z 570 (M+H)$^+$, 1.00 min (ret. time).

Example 25

(S)-3-(4-(((R)-4-Ethyl-1,1-dioxido-3,4-dihydro-2H-pyrido[2,3-b][1,4,5]oxathiazepin-2-yl)methyl)-5-methylthiazol-2-yl)-3-(1-ethyl-4-methyl-1H-benzo[d][1,2,3]triazol-5-yl)-2,2-dimethyl-N-(pyridin-3-yl)propanamide

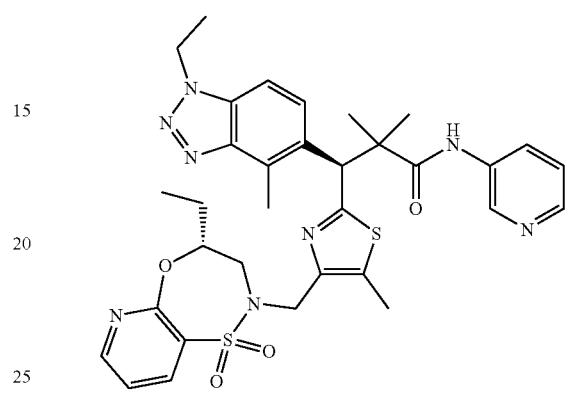

To a solution of (S)-3-(4-(((R)-4-ethyl-1,1-dioxido-3,4-dihydro-2H-pyrido[2,3-b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoic acid (68.0 mg, 0.114 mmol) in isopropanol (2.00 mL) was added phenyl (E)-N-(tert-butyl)-N'-(pyridin-3-yl)carbamimidothioate (27 mg, 0.095 mmol) and ferric acetylacetonate (6.68 mg, 0.019 mmol) and the reaction was heated at 83° C. for 21 h. The solvent was concentrated and the residue was purified by reverse phase preparative HPLC under neutral conditions to provide the title compound (0.031 g, 47% yield). LC/MS m/z 675 (M+H)+, 0.81 min (ret. time).

Example 26

(S)-3-(4-(((R)-4-Ethyl-1,1-dioxido-3,4-dihydro-2H-pyrido[2,3-b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoic Acid

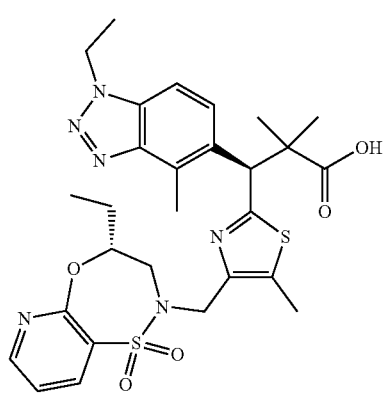 [SMILES: CC[C@@H]1CN(Cc2nc([C@@H](c3ccc4c(nnn4CC)c3C)C(C)(C)C(=O)O)sc2C)S(=O)(=O)c2cccnc2O1]

Benzyl (S)-3-(1-ethyl-4-methyl-1H-benzo[d][1,2,3]
triazol-5-yl)-3-(4-(((4-methoxybenzyl)oxy)methyl)-
5-methylthiazol-2-yl)-2,2-dimethylpropanoate and
benzyl (R)-3-(1-ethyl-4-methyl-1H-benzo[d][1,2,3]
triazol-5-yl)-3-(4-(((4-methoxybenzyl)oxy)methyl)-
5-methylthiazol-2-yl)-2,2-dimethylpropanoate

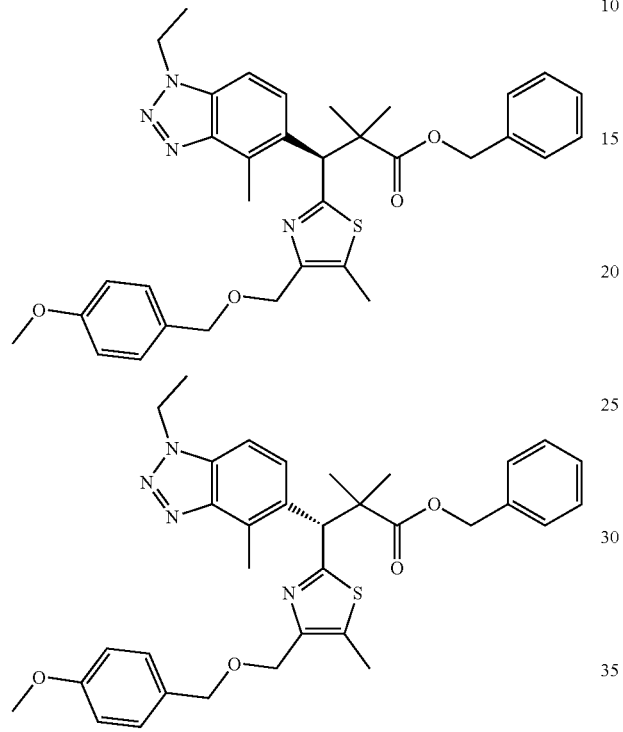

Methyl 3-(1-ethyl-4-methyl-1H-benzo[d][1,2,3]triazol-5-yl)-3-(4-(((4-methoxybenzyl)oxy)methyl)-5-methylthiazol-2-yl)-2,2-dimethylpropanoate (8.31 g, 15.90 mmol) was dissolved into tetrahydrofuran (THF) (75 mL), methanol (75 mL), and water (35 mL) and LiOH (3.81 g, 159 mmol) was added and the reaction was heated to 65° C. for 25 h. The solvents were concentrated, the residue was dissolved in N,N-dimethylformamide (DMF) (60 mL) and benzyl bromide (7.56 mL, 63.6 mmol) was added and the reaction stirred for 1 h. The reaction was diluted with water and EtOAc and the pH was adjusted to neutral with 1N HCl. The layers were separated and aqueous layer was extracted with EtOAc (3×). The combined organics were washed with water (2×), brine and dried with MgSO$_4$. The solvents were concentrated and the residue was purified by flash chromatography eluting with 0-50% EtOAc/Hexane to provide the title compound as a racemate. (9.04 g, 95% yield). LC/MS m/z 599 (M+H)+, 1.46 min (ret. time). The compound was resolved by chiral SFC (Column: Chiralpak IA 20×250 mm, 5u; Co-solvent: 25% EtOH; Flowrate: 50 g/min; Back pressure: 100Bar) to provide Benzyl (S)-3-(1-ethyl-4-methyl-1H-benzo[d][1,2,3]triazol-5-yl)-3-(4-(((4-methoxybenzyl)oxy)methyl)-5-methylthiazol-2-yl)-2,2-dimethylpropanoate (4.09 g, 43% yield). m/z 599 (M+H)+, 1.45 min (ret. time), (chiral SFC ret. time: 3.17 min) and benzyl (R)-3-(1-ethyl-4-methyl-1H-benzo[d][1,2,3]triazol-5-yl)-3-(4-(((4-methoxybenzyl)oxy)methyl)-5-methylthiazol-2-yl)-2,2-dimethylpropanoate (4.45 g, 46% yield). LCMS m/z 599 (M+H)+, 1.45 min (ret. time), (chiral SFC ret. time: 4.26 min).

Benzyl (S)-3-(1-ethyl-4-methyl-1H-benzo[d][1,2,3]
triazol-5-yl)-3-(4-(hydroxymethyl)-5-methylthiazol-
2-yl)-2,2-dimethylpropanoate

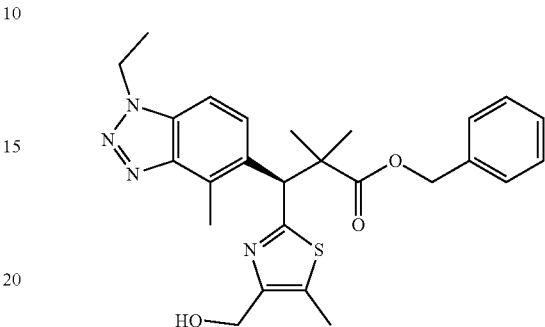

To a solution of benzyl (S)-3-(1-ethyl-4-methyl-1H-benzo[d][1,2,3]triazol-5-yl)-3-(4-(((4-methoxybenzyl)oxy)methyl)-5-methylthiazol-2-yl)-2,2-dimethylpropanoate (4.09 g, 6.83 mmol) in acetonitrile (88 mL) and water (10 mL) was added ceric ammonium nitrate (7.49 g, 13.66 mmol) in acetonitrile (30 mL) and the reaction stirred at ambient temperature for 4 h. Additional ceric ammonium nitrate (0.749 g, 1.366 mmol) was added as a solid and stirred for 1.5 h. Additional ceric ammonium nitrate (0.374 g, 0.683 mmol) was added and the reaction stirred for 30 min. The reaction was diluted with ethyl acetate and washed with water. The water was back extracted with ethyl acetate (3×) and the combined organics were washed with water (2×), brine and dried with MgSO$_4$. The solvent was concentrated and the residue was purified by flash chromatography eluting with 0-50% EtOAc/Hexane to provide the title compound. (2.96 g, 91% yield). LCMS m/z 479 (M+H)+, 1.13 min (ret. time).

Benzyl (S)-3-(4-(((R)-4-ethyl-1,1-dioxido-3,4-di-
hydro-2H-pyrido[2,3-b][1,4,5]oxathiazepin-2-yl)
methyl)-5-methylthiazol-2-yl)-3-(1-ethyl-4-methyl-
1H-benzo[d][1,2,3]triazol-5-yl)-2,2-
dimethylpropanoate

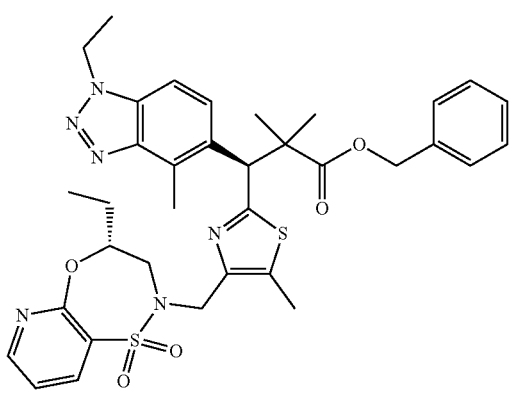 [SMILES: CC[C@@H]1CN(Cc2nc([C@@H](c3ccc4c(nnn4CC)c3C)C(C)(C)C(=O)OCc3ccccc3)sc2C)S(=O)(=O)c2cccnc2O1]

Benzyl (S)-3-(1-ethyl-4-methyl-1H-benzo[d][1,2,3]triazol-5-yl)-3-(4-(hydroxymethyl)-5-methylthiazol-2-yl)-2,2-dimethylpropanoate (100 mg, 0.209 mmol), (R)-4-ethyl-3,4-dihydro-2H-pyrido[2,3-b][1,4,5]oxathiazepine 1,1-dioxide (95 mg, 0.418 mmol) and (E)-diazene-1,2-diylbis(piperidin-1-ylmethanone) (ADDP) (105 mg, 0.418 mmol) were combined and dissolved in tetrahydrofuran (THF) (8 mL). After all solids were dissolved, tri-n-butylphosphine (0.103 mL, 0.418 mmol) was added and the reaction stirred at ambient temperature for 18 h. The solvent was concentrated and the residue was purified by reverse phase preparative HPLC under neutral conditions to provide the title compound (0.106 g, 73% yield). LC/MS m/z 689 (M+H)+, 1.45 min (ret. time).

(S)-3-(4-(((R)-4-Ethyl-1,1-dioxido-3,4-dihydro-2H-pyrido[2,3-b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoic Acid

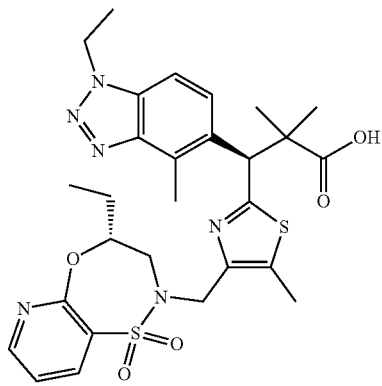 [SMILES: CC[C@@H]1CN(Cc2nc([C@@H](c3ccc4c(nnn4CC)c3C)C(C)(C)C(=O)O)sc2C)S(=O)(=O)c2cccnc2O1]

A solution of benzyl (S)-3-(4-(((R)-4-ethyl-1,1-dioxido-3,4-dihydro-2H-pyrido[2,3-b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoate (0.106 g, 0.154 mmol) in methanol (10 mL) was flushed with nitrogen after which 5% Pd/C (0.016 g, 7.69 µmol) was added to the solution. The flask was evacuated and purged with hydrogen gas and stirred under a hydrogen balloon for 3 h. The reaction was filtered through a filter disk and the solvent was concentrated. The residue was purified by reverse phase preparative HPLC under neutral conditions to provide the title compound (0.078 g, 86% yield). LC/MS m/z 599(M+H)+, 1.07 min (ret. time).

Example 27

(S)-3-(4-(((R)-4-Ethyl-1,1-dioxido-3,4-dihydro-2H-pyrido[4,3-b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoic Acid

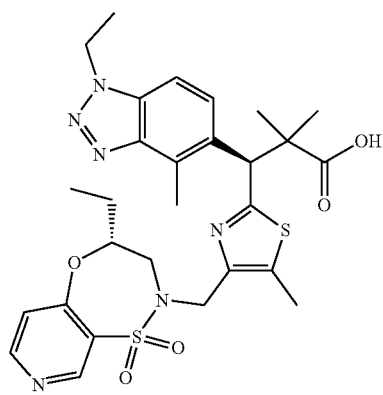 [SMILES: CC[C@@H]1CN(Cc2nc([C@@H](c3ccc4c(nnn4CC)c3C)C(C)(C)C(=O)O)sc2C)S(=O)(=O)c2cnccc2O1]

Benzyl (S)-3-(4-(((R)-4-ethyl-1,1-dioxido-3,4-dihydro-2H-pyrido[4,3-b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoate

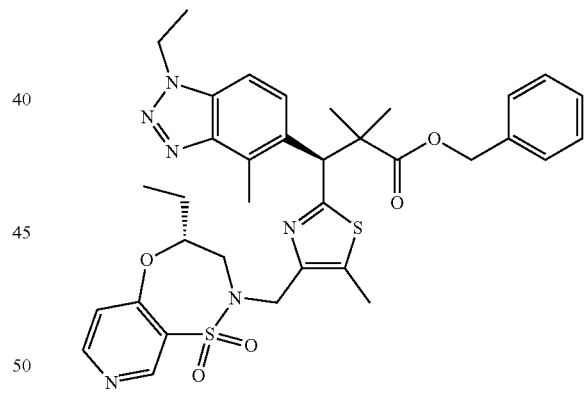

Benzyl (S)-3-(1-ethyl-4-methyl-1H-benzo[d][1,2,3]triazol-5-yl)-3-(4-(hydroxymethyl)-5-methylthiazol-2-yl)-2,2-dimethylpropanoate (100 mg, 0.209 mmol), (R)-4-ethyl-3,4-dihydro-2H-pyrido[4,3-b][1,4,5]oxathiazepine 1,1-dioxide (95 mg, 0.418 mmol) and (E)-diazene-1,2-diylbis(piperidin-1-ylmethanone) (ADDP) (105 mg, 0.418 mmol) were combined and dissolved in tetrahydrofuran (THF) (8 mL). After all solids were dissolved, tri-n-butylphosphine (0.103 mL, 0.418 mmol) was added and the reaction was stirred at ambient temperature for 18 h. The solvent was concentrated and the residue was purified by reverse phase preparative HPLC under neutral conditions to provide the title compound (0.111 g, 77% yield). LC/MS m/z 689 (M+H)+, 1.36 min (ret. time).

(S)-3-(4-(((R)-4-Ethyl-1,1-dioxido-3,4-dihydro-2H-pyrido[4,3-b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoic Acid

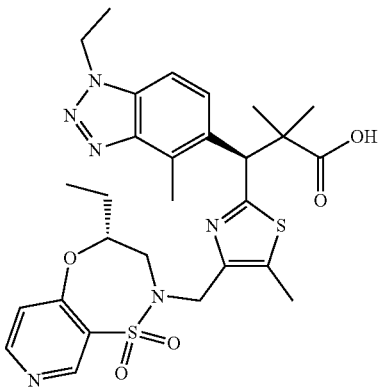 [SMILES: CC[C@@H]1CN(Cc2nc([C@@H](c3ccc4c(nnn4CC)c3C)C(C)(C)C(=O)O)sc2C)S(=O)(=O)c2cnccc2O1]

A solution of benzyl (S)-3-(4-(((R)-4-ethyl-1,1-dioxido-3,4-dihydro-2H-pyrido[4,3-b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoate (0.1112 g, 0.161 mmol) in methanol (10 mL) was flushed with nitrogen, after which 5% Pd/C (0.017 g, 8.07 µmol) was added to the solution. The flask was evacuated and purged with hydrogen gas and stirred under a hydrogen balloon for 23 h. Additional 5% Pd/C (0.069 g, 0.032 mmol) was added and the reaction was stirred under hydrogen for 3.5 h. The reaction was filtered and the solvent was concentrated. The residue was purified by reverse phase preparative HPLC under neutral conditions to provide the title compound (0.064 g, 70% yield). LC/MS m/z 598(M+H)$^+$, 1.05 min (ret. time).

Example 28

(S)-3-(4-(((R)-4-Ethyl-1,1-dioxido-3,4-dihydro-2H-pyrido[4,3-b][1,4,5]oxathiazepin-2-yl)methyl)-5-methylthiazol-2-yl)-3-(1-ethyl-4-methyl-1H-benzo[d][1,2,3]triazol-5-yl)-2,2-dimethyl-N-(pyridin-3-yl)propanamide

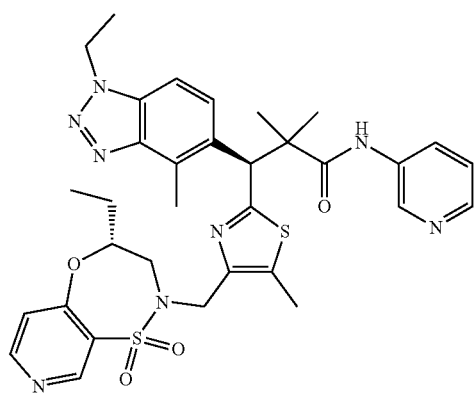 [SMILES: CC[C@@H]1CN(Cc2nc([C@@H](c3ccc4c(nnn4CC)c3C)C(C)(C)C(=O)Nc3cccnc3)sc2C)S(=O)(=O)c2cnccc2O1]

To a solution of (S)-3-(4-(((R)-4-ethyl-1,1-dioxido-3,4-dihydro-2H-pyrido[4,3-b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoic acid (57.1 mg, 0.095 mmol) in isopropanol (2.00 mL) was added phenyl (E)-N-(tert-butyl)-N'-(pyridin-3-yl)carbamimidothioate (22.7 mg, 0.080 mmol) and ferric acetylacetonate (5.62 mg, 0.016 mmol). The vial was heated at 83° C. for 21 h. The solvent was concentrated and the residue was purified by reverse phase preparative HPLC under formic acid conditions to provide the title compound (0.024 g, 46% yield). LC/MS m/z 675 (M+H)+, 0.81 min (ret. time).

(R)-3-fluoro-N-(2-hydroxybutyl)pyridine-2-sulfonamide

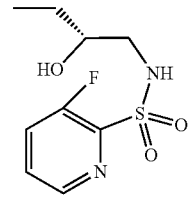 [SMILES: CC[C@@H](O)CNS(=O)(=O)c1ncccc1F]

To the mixture of isopropylmagnesium chloride (17.05 mL, 34.1 mmol) in tetrahydrofuran (15 mL) was added BuLi (21.31 mL, 34.1 mmol) dropwise under nitrogen atmosphere at ambient temperature and stirred for 15 min. The solution was cooled to −10° C. and 2-bromo-3-fluoropyridine (5 g, 28.4 mmol) in tetrahydrofuran (15 mL) was added dropwise over 5 min and stirred for 45 min. The mixture was then added to a solution of sulfuryl chloride (6.93 mL, 85 mmol) in toluene (15.00 mL) at −10° C. and stirred for 20 min. Then temperature was raised to 10° C. and a mixture of 1-amino-2-methylpropan-2-ol (380 mg, 4.26 mmol) and DIEA (0.744 mL, 4.26 mmol) in tetrahydrofuran (1.500 mL) was added and stirred at ambient temperature for 18 hr. The reaction mixture was quenched with saturated NH$_4$Cl solution (15 mL) and extracted with ethylacetate (3×10 mL). The combined organic layer was washed with brine (15 mL) and dried over anhydrous Na$_2$SO$_4$, filtered, concentrated under reduced pressure to give the title compound (2.5 g, 7.61 mmol, 26.8% yield). LCMS m/z 248.89 (M+Na)$^+$, 1.33 min (ret. time).

(R)-4-ethyl-3,4-dihydro-2H-pyrido[3,2-b][1,4,5]oxathiazepine 1,1-dioxide

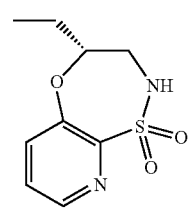

To the mixture of (R)-3-fluoro-N-(2-hydroxybutyl)pyridine-2-sulfonamide (2.5 g, 8.06 mmol) in DMSO (15 mL) was added potassium tert-butoxide (1.810 g, 16.13 mmol) at 0° C. The reaction mixture was stirred at 100° C. for 16 h after which was added 1N HCl to pH 6-7 and the mixture extracted with ethylacetate (3×30 mL). The combined organic layer was washed with brine (30 mL), dried over Na$_2$SO$_4$, filtered and concentrated under reduced pressure, purified with flash silica gel column chromotography using ethyl acetate and hexanes as eluent to give the title compound (750 mg, 3.26 mmol, 40.4% yield). LCMS m/z 229.06 (M+Na)$^+$, 1.50 min (ret. time).

Example 29

(S)-3-(4-(((R)-4-Ethyl-1,1-dioxido-3,4-dihydro-2H-pyrido[3,2-b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoic Acid

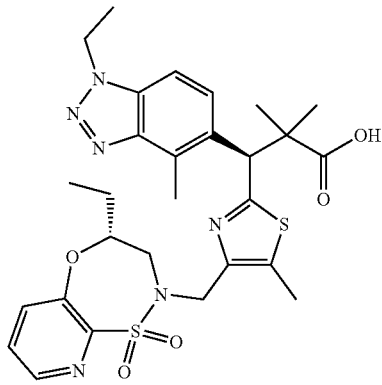 [SMILES: CC[C@@H]1CN(Cc2nc([C@@H](c3ccc4c(nnn4CC)c3C)C(C)(C)C(=O)O)sc2C)S(=O)(=O)c2ncccc2O1]

Benzyl (S)-3-(4-(((R)-4-ethyl-1,1-dioxido-3,4-dihydro-2H-pyrido[3,2-b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoate

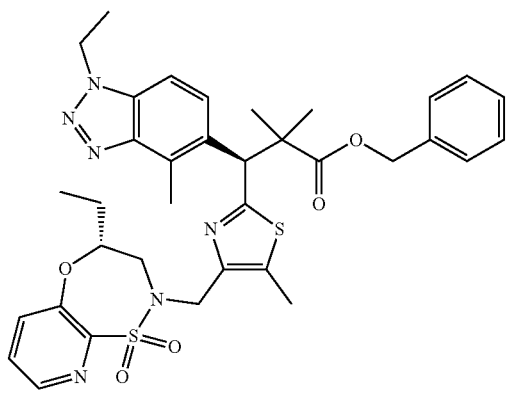 [SMILES: CC[C@@H]1CN(Cc2nc([C@@H](c3ccc4c(nnn4CC)c3C)C(C)(C)C(=O)OCc3ccccc3)sc2C)S(=O)(=O)c2ncccc2O1]

Benzyl (S)-3-(1-ethyl-4-methyl-1H-benzo[d][1,2,3]triazol-5-yl)-3-(4-(hydroxymethyl)-5-methylthiazol-2-yl)-2,2-dimethylpropanoate (100 mg, 0.209 mmol), (R)-4-ethyl-3,4-dihydro-2H-pyrido[3,2-b][1,4,5]oxathiazepine 1,1-dioxide (95 mg, 0.418 mmol) and (E)-diazene-1,2-diylbis(piperidin-1-ylmethanone) (ADDP) (105 mg, 0.418 mmol) were combined and dissolved in tetrahydrofuran (THF) (8 mL). After all solids were dissolved, tri-n-butylphosphine (0.103 mL, 0.418 mmol) was added and the reaction stirred at ambient temperature for 18 h. The solvent was concentrated and the residue was purified by reverse phase preparative HPLC under neutral conditions to provide the title compound (0.110 g, 76% yield). LC/MS m/z 688(M+H)$^+$, 1.43 min (ret. time).

(S)-3-(4-(((R)-4-Ethyl-1,1-dioxido-3,4-dihydro-2H-pyrido[3,2-b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoic Acid

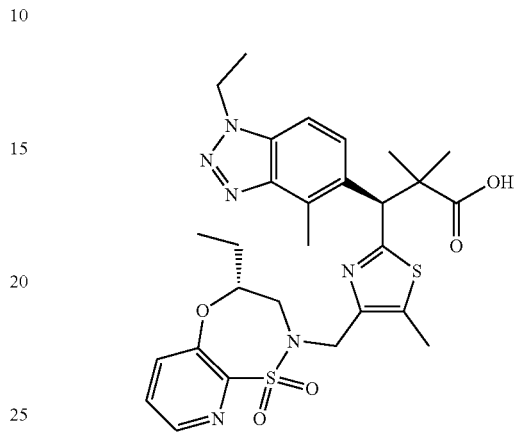

A solution of benzyl (S)-3-(4-(((R)-4-ethyl-1,1-dioxido-3,4-dihydro-2H-pyrido[3,2-b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoate (0.1097 g, 0.159 mmol) in methanol (10 mL) was flushed with nitrogen after which 5% Pd/C (0.017 g, 7.96 µmol) was added to the solution. The flask was evacuated and purged with hydrogen gas and stirred under a hydrogen balloon for 23 h. The reaction was filtered and the solvent was concentrated. The residue was purified by reverse phase preparative HPLC under neutral conditions to provide the title compound (0.069 g, 73% yield). LC/MS m/z 598(M+H)$^+$, 1.06 min (ret. time).

Example 30

(S)-3-(4-(((R)-4-Ethyl-1,1-dioxido-3,4-dihydro-2H-pyrido[3,2-b][1,4,5]oxathiazepin-2-yl)methyl)-5-methylthiazol-2-yl)-3-(1-ethyl-4-methyl-1H-benzo[d][1,2,3]triazol-5-yl)-2,2-dimethyl-N-(pyridin-3-yl)propanamide

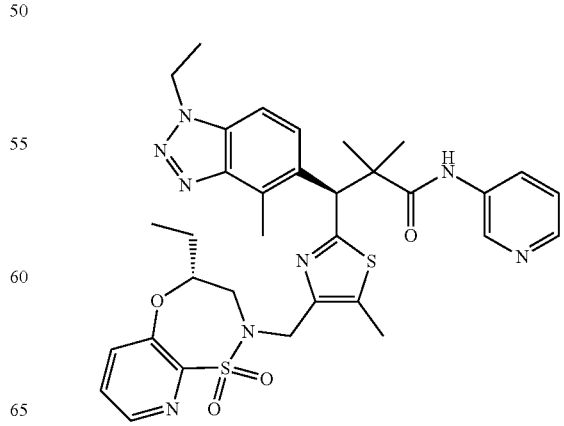

To a solution of (S)-3-(4-(((R)-4-ethyl-1,1-dioxido-3,4-dihydro-2H-pyrido[3,2-b][1,4,5]oxathiazepin-2-yl)methyl)-5-methylthiazol-2-yl)-3-(1-ethyl-4-methyl-1H-benzo[d][1,2,3]triazol-5-yl)-2,2-dimethylpropanoic acid (58.9 mg, 0.098 mmol) in isopropanol (2.00 mL) was added phenyl (E)-N-(tert-butyl)-N'-(pyridin-3-yl)carbamimidothioate (23.4 mg, 0.082 mmol) and ferric acetylacetonate (5.79 mg, 0.016 mmol). The vial was heated at 83° C. for 21 h. The solvent was concentrated and the residue was purified by reverse phase preparative HPLC under formic acid conditions to provide the title compound (0.028 g, 46% yield). LC/MS m/z 675 (M+H)+, 0.81 min (ret. time).

Example 31

(S)-3-(1-Ethyl-4-methyl-1H-benzo[d][1,2,3]triazol-5-yl)-2,2-dimethyl-3-(1-methyl-5-(((S)-4-methyl-1,1-dioxido-4,5-dihydropyrido[2,3-f][1,2]thiazepin-2(3H)-yl)methyl)-1H-pyrazol-3-yl)propanoic Acid

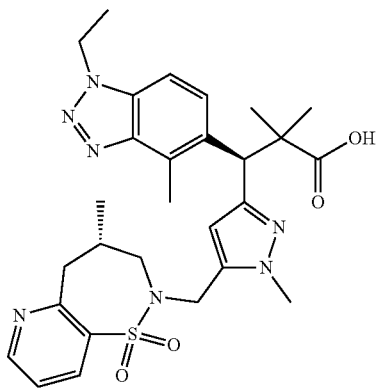 [SMILES: CCn1nnc2c(C)c([C@H](c3cc(CN4C[C@@H](C)Cc5ncccc5S4(=O)=O)n(C)n3)C(C)(C)C(=O)O)ccc21]

Methyl (S)-3-(1-ethyl-4-methyl-1H-benzo[d][1,2,3]triazol-5-yl)-2,2-dimethyl-3-(1-methyl-5-(((S)-4-methyl-1,1-dioxido-4,5-dihydropyrido[2,3-f][1,2]thiazepin-2(3H)-yl)methyl)-1H-pyrazol-3-yl)propanoate

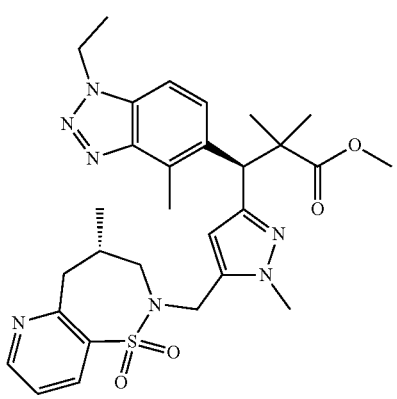 [SMILES: CCn1nnc2c(C)c([C@H](c3cc(CN4C[C@@H](C)Cc5ncccc5S4(=O)=O)n(C)n3)C(C)(C)C(=O)OC)ccc21]

To a solution of methyl (S)-3-(1-ethyl-4-methyl-1H-benzo[d][1,2,3]triazol-5-yl)-3-(5-(hydroxymethyl)-1-methyl-1H-pyrazol-3-yl)-2,2-dimethylpropanoate (43 mg, 0.112 mmol) in tetrahydrofuran (THF) (4 mL) was added (S)-4-methyl-2,3,4,5-tetrahydropyrido[2,3-f][1,2]thiazepine 1,1-dioxide (47.4 mg, 0.223 mmol) and (E)-diazene-1,2-diylbis(piperidin-1-ylmethanone) (ADDP) (56.3 mg, 0.223 mmol). After all solids were dissolved, the solution was degassed and purged with argon after which tri-n-butylphosphine (0.055 mL, 0.223 mmol) was added and the reaction stirred at ambient temperature for 23 h. The solvent was concentrated and the residue was purified by flash chromatography eluting with 0-90% EtOAc/hexanes to provide the title compound. (0.081 g, 83% yield). LC/MS m/z 580 (M+H)+, 1.04 min (ret. time).

(S)-3-(1-Ethyl-4-methyl-1H-benzo[d][1,2,3]triazol-5-yl)-2,2-dimethyl-3-(1-methyl-5-(((S)-4-methyl-1,1-dioxido-4,5-dihydropyrido[2,3-f][1,2]thiazepin-2(3H)-yl)methyl)-1H-pyrazol-3-yl)propanoic Acid

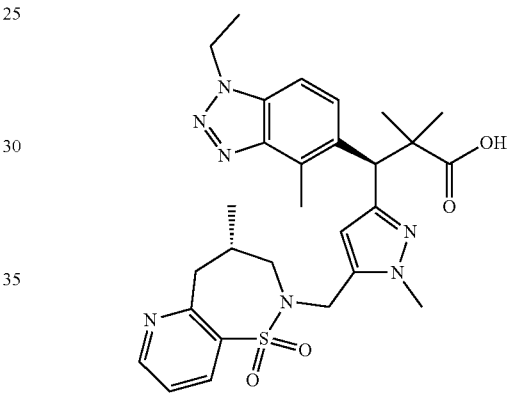

To a solution of methyl (S)-3-(1-ethyl-4-methyl-1H-benzo[d][1,2,3]triazol-5-yl)-2,2-dimethyl-3-(1-methyl-5-(((S)-4-methyl-1,1-dioxido-4,5-dihydropyrido[2,3-f][1,2]thiazepin-2(3H)-yl)methyl)-1H-pyrazol-3-yl)propanoate (81 mg, 0.092 mmol) in tetrahydrofuran (THF) (2 mL), methanol (1 mL) and water (1 mL) in a microwave reaction vessel, was added LiOH (11.04 mg, 0.461 mmol) and the reaction was heated via microwave at 100° C. for 1 h. Additional LiOH (11.04 mg, 0.461 mmol) was added and the reaction was heated via microwave at 140° C. for 3 h. The solvents were concentrated and the residue was suspended in acetonitrile and acidified with formic acid. The solvent was concentrated and the residue was purified by reverse phase preparative HPLC under formic acid conditions to provide the title compound (0.025 g, 48% yield). LC/MS m/z 566 (M+H)+. 0.90 min (ret. time).

Example 32

(S)-3-(4-(((S)-3-(1H-Pyrazol-1-yl)piperidin-1-yl)methyl)-5-methylthiophen-2-yl)-3-(1-ethyl-4-methyl-1H-benzo[d][1,2,3]triazol-5-yl)-2,2-dimethylpropanoic acid

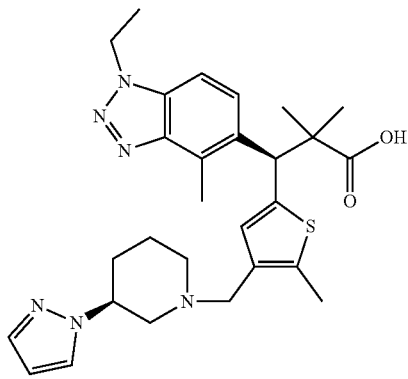 [SMILES: CCn1nnc2c(C)c([C@H](c3cc(CN4CCC[C@H](n5cccn5)C4)c(C)s3)C(C)(C)C(=O)O)ccc21]

Benzyl (S)-3-(4-(((S)-3-(1H-pyrazol-1-yl)piperidin-1-yl)methyl)-5-methylthiophen-2-yl)-3-(1-ethyl-4-methyl-1H-benzo[d][1,2,3]triazol-5-yl)-2,2-dimethylpropanoate

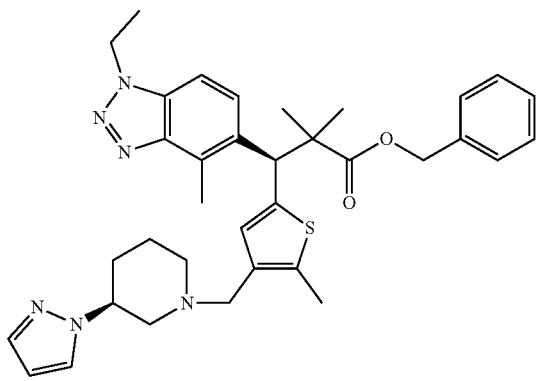 [SMILES: CCn1nnc2c(C)c([C@H](c3cc(CN4CCC[C@H](n5cccn5)C4)c(C)s3)C(C)(C)C(=O)OCc3ccccc3)ccc21]

To a solution of benzyl (S)-3-(1-ethyl-4-methyl-1H-benzo[d][1,2,3]triazol-5-yl)-3-(4-(hydroxymethyl)-5-methylthiophen-2-yl)-2,2-dimethylpropanoate (100 mg, 0.209 mmol) in dichloromethane (DCM) (4 mL) was added thionyl chloride (0.031 mL, 0.419 mmol) and the reaction stirred at ambient temperature for 30 min. The solvent was removed and the residue was dissolved in acetonitrile (4.00 mL) in a 10 mL microwave reaction vessel. To this solution was added (S)-3-(1H-pyrazol-1-yl)piperidine, hydrochloride (39.3 mg, 0.209 mmol) and DIEA (0.183 mL, 1.047 mmol). The reaction was heated via microwave to 120° C. for 30 min. An additional portion of (S)-3-(1H-pyrazol-1-yl)piperidine, hydrochloride (3.93 mg, 0.021 mmol) was added and the reaction was heated via microwave at 120° C. for 20 min. The solvent was concentrated and the residue was purified by flash chromatography eluting with 0-5% MeOH/DCM to provide the title compound. (0.097 g, 76% yield). LC/MS m/z 611 (M+H), 0.88 min (ret. time).

(S)-3-(4-(((S)-3-(1H-Pyrazol-1-yl)piperidin-1-yl)methyl)-5-methylthiophen-2-yl)-3-(1-ethyl-4-methyl-1H-benzo[d][1,2,3]triazol-5-yl)-2,2-dimethylpropanoic Acid

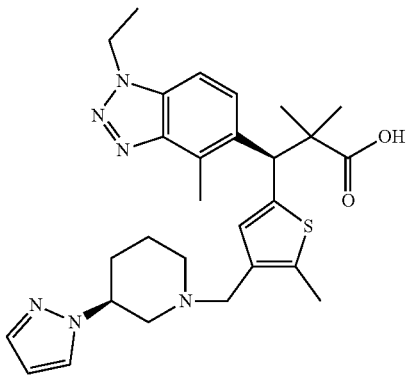 [SMILES: CCn1nnc2c(C)c([C@H](c3cc(CN4CCC[C@H](n5cccn5)C4)c(C)s3)C(C)(C)C(=O)O)ccc21]

A solution of benzyl (S)-3-(4-(((S)-3-(1H-pyrazol-1-yl)piperidin-1-yl)methyl)-5-methylthiophen-2-yl)-3-(1-ethyl-4-methyl-1H-benzo[d][1,2,3]triazol-5-yl)-2,2-dimethylpropanoate (97 mg, 0.159 mmol) in methanol was evacuated and purged with nitrogen. 5% Pd/C (33.8 mg, 0.016 mmol) was then added and the reaction was evacuated and purged with hydrogen gas and then stirred under a balloon of hydrogen gas at ambient temperature for 20.5 h. The reaction was filtered through Celite and concentrated. The residue was purified by reverse phase preparative HPLC under formic acid conditions to provide the title compound (0.047 g, 55% yield). LC/MS m/z 521 (M+H)$^+$. 0.65 min (ret. time).

Example 33

(S)-3-(4-(((S)-4-Ethyl-1,1-dioxido-4,5-dihydropyrido[2,3-f][1,2]thiazepin-2(3H)-yl)methyl)-5-methylthiazol-2-yl)-3-(1-ethyl-4-methyl-1H-benzo[d][1,2,3]triazol-5-yl)-2,2-dimethylpropanoic Acid

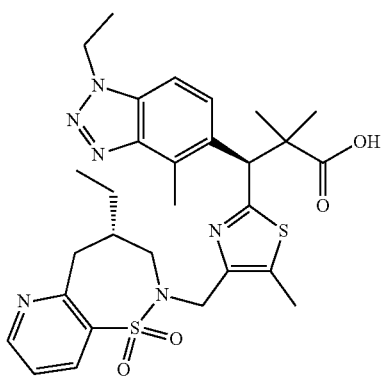 [SMILES: CC[C@H]1Cc2ncccc2S(=O)(=O)N(Cc2nc([C@@H](c3ccc4c(nnn4CC)c3C)C(C)(C)C(=O)O)sc2C)C1]

Benzyl (S)-3-(4-(((S)-4-ethyl-1,1-dioxido-4,5-dihydropyrido[2,3-f][1,2]thiazepin-2(3H)-yl)methyl)-5-methylthiazol-2-yl)-3-(1-ethyl-4-methyl-1H-benzo[d][1,2,3]triazol-5-yl)-2,2-dimethylpropanoate

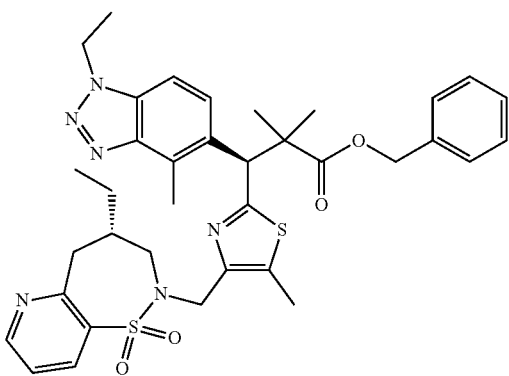 [SMILES: CC[C@H]1Cc2ncccc2S(=O)(=O)N(Cc2nc([C@@H](c3ccc4c(nnn4CC)c3C)C(C)(C)C(=O)OCc3ccccc3)sc2C)C1]

Benzyl (S)-3-(1-ethyl-4-methyl-1H-benzo[d][1,2,3]triazol-5-yl)-3-(4-(hydroxymethyl)-5-methylthiazol-2-yl)-2,2-dimethylpropanoate (100 mg, 0.209 mmol), (S)-4-ethyl-2,3,4,5-tetrahydropyrido[2,3-f][1,2]thiazepine 1,1-dioxide (95 mg, 0.418 mmol) and (E)-diazene-1,2-diylbis(piperidin-1-ylmethanone) (ADDP) (105 mg, 0.418 mmol) were combined and dissolved in tetrahydrofuran (THF) (8 mL). After all solids were dissolved, tri-n-butylphosphine (0.103 mL, 0.418 mmol) was added and the reaction stirred at ambient temperature for 18 h. The solvent was concentrated and the residue was purified by reverse phase preparative HPLC under neutral conditions to provide the title compound (0.121 g, 84% yield). LC/MS m/z 689 (M+H)+, 1.49 min (ret. time).

(S)-3-(4-(((S)-4-Ethyl-1,1-dioxido-4,5-dihydropyrido[2,3-f][1,2]thiazepin-2(3H)-yl)methyl)-5-methylthiazol-2-yl)-3-(1-ethyl-4-methyl-1H-benzo[d][1,2,3]triazol-5-yl)-2,2-dimethylpropanoic Acid

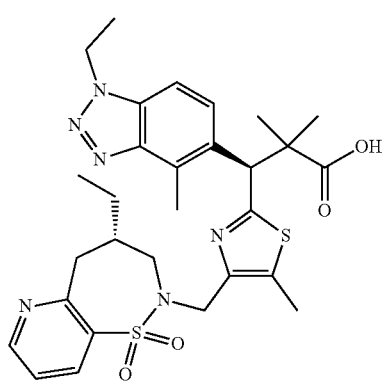 [SMILES: CC[C@H]1Cc2ncccc2S(=O)(=O)N(Cc2nc([C@@H](c3ccc4c(nnn4CC)c3C)C(C)(C)C(=O)O)sc2C)C1]

A solution of benzyl (S)-3-(4-(((S)-4-ethyl-1,1-dioxido-4,5-dihydropyrido[2,3-f][1,2]thiazepin-2(3H)-yl)methyl)-5-methylthiazol-2-yl)-3-(1-ethyl-4-methyl-1H-benzo[d][1,2,3]triazol-5-yl)-2,2-dimethylpropanoate (0.121 g, 0.176 mmol) in methanol (10 mL) was flushed with nitrogen after which 5% Pd/C (0.019 g, 8.81 μmol) was added to the solution. The flask was evacuated and purged with hydrogen gas and stirred under a hydrogen balloon for 2 h.

The reaction was filtered through a filter disk and the solvent was concentrated. The residue was purified by reverse phase preparative HPLC under neutral conditions to provide the title compound (0.092 g, 88% yield). LC/MS m/z 597(M+H)+, 1.13 min (ret. time).

Example 34

(S)-3-(4-(((S)-4-Ethyl-1,1-dioxido-4,5-dihydropyrido[2,3-f][1,2]thiazepin-2(3H)-yl)methyl)-5-methylthiazol-2-yl)-3-(1-ethyl-4-methyl-1H-benzo[d][1,2,3]triazol-5-yl)-2,2-dimethyl-N-(pyridin-3-yl)propanamide

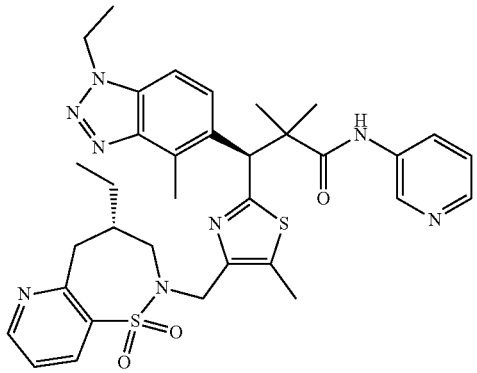 [SMILES: CC[C@H]1Cc2ncccc2S(=O)(=O)N(Cc2nc([C@@H](c3ccc4c(nnn4CC)c3C)C(C)(C)C(=O)Nc3cccnc3)sc2C)C1]

To a solution of (S)-3-(4-(((S)-4-ethyl-1,1-dioxido-4,5-dihydropyrido[2,3-f][1,2]thiazepin-2(3H)-yl)methyl)-5-methylthiazol-2-yl)-3-(1-ethyl-4-methyl-1H-benzo[d][1,2,3]triazol-5-yl)-2,2-dimethylpropanoic acid (80 mg, 0.135 mmol) in isopropanol (2.00 mL) was added phenyl (E)-N-(tert-butyl)-N'-(pyridin-3-yl)carbamimidothioate (32 mg, 0.112 mmol) and ferric acetylacetonate (7.92 mg, 0.022 mmol). The vial was heated at 83° C. for 18 h. The solvent was concentrated and the residue was purified by reverse phase preparative HPLC under formic acid conditions to provide the title compound (0.039 g, 52% yield). LC/MS m/z 673 (M+H)+, 0.88 min (ret. time).

Example 35

(R)-3-(5-Chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-methyl-1H-benzo[d][1,2,3]triazol-5-yl)-2,2-dimethylpropanoic Acid

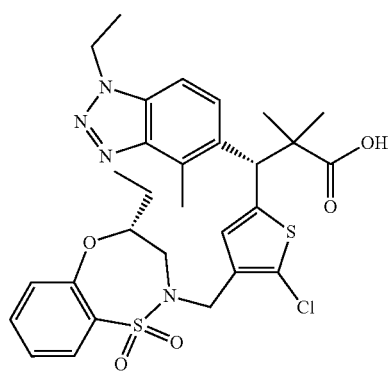 [SMILES: CC[C@@H]1CN(Cc2cc([C@H](c3ccc4c(nnn4CC)c3C)C(C)(C)C(=O)O)sc2Cl)S(=O)(=O)c2ccccc2O1]

(R)-Benzyl 3-(5-chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-methyl-1H-benzo[d][1,2,3]triazol-5-yl)-2,2-dimethylpropanoate

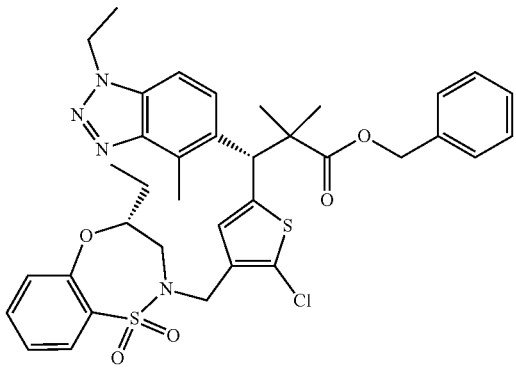

To a solution of (R)-benzyl 3-(5-chloro-4-(hydroxymethyl)thiophen-2-yl)-3-(1-ethyl-4-methyl-1H-benzo[d][1,2,3]triazol-5-yl)-2,2-dimethylpropanoate (61 mg, 0.122 mmol), (R)-4-ethyl-3,4-dihydro-2H-benzo[b][1,4,5]oxathiazepine 1,1-dioxide (55.7 mg, 0.245 mmol) and (E)-diazene-1,2-diylbis(piperidin-1-ylmethanone) (61.8 mg, 0.245 mmol) in tetrahydrofuran (THF) (4 mL) was added tributylphosphine (0.061 mL, 0.245 mmol) and allowed to stir for 1 h. The reaction was concentrated, and was purified by reverse phase preparative HPLC under neutral conditions to provide the title compound (0.090 g, 100% pure). LC/MS m/z 707(M+H)+, 1.54 min (ret. time).

(R)-3-(5-Chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-methyl-1H-benzo[d][1,2,3]triazol-5-yl)-2,2-dimethylpropanoic Acid

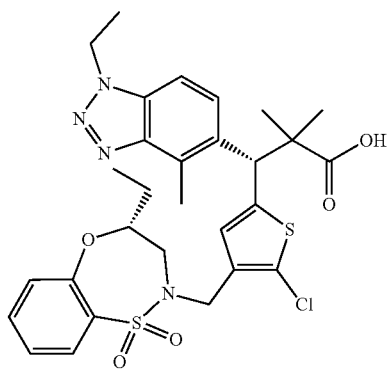 [SMILES: CC[C@@H]1CN(Cc2cc([C@H](c3ccc4c(nnn4CC)c3C)C(C)(C)C(=O)O)sc2Cl)S(=O)(=O)c2ccccc2O1]

(R)-Benzyl 3-(5-chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-methyl-1H-benzo[d][1,2,3]triazol-5-yl)-2,2-dimethylpropanoate (90 mg, 0.127 mmol) was dissolved in tetrahydrofuran (THF) (2 mL), water (1.000 mL) and methanol (2.000 mL) in a microwave reaction vial. Lithium hydroxide (15.24 mg, 0.636 mmol) was added to the reaction mixture and was heated via microwave at 100° C. for 2 h. The reaction was acidified with 10% aqueous formic acid. The reaction was concentrated and purified by reverse phase preparative HPLC under neutral conditions to provide the title compound (0.020 g, 25% yield). LC/MS m/z 617(M+H)+, 1.24 min (ret. time).

Example 36

(R)-3-(5-Chloro-4-(((R)-4-ethyl-1,1-dioxido-3,4-dihydro-2H-pyrido[4,3-b][1,4,5]oxathiazepin-2-yl)methyl)thiophen-2-yl)-3-(1-ethyl-4-methyl-1H-benzo[d][1,2,3]triazol-5-yl)-2,2-dimethylpropanoic Acid

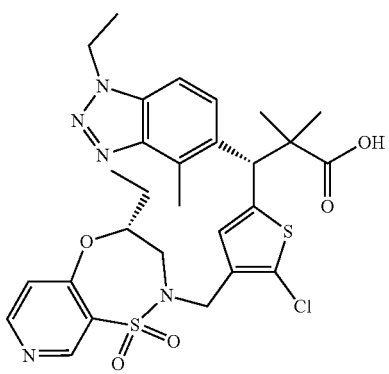 [SMILES: CC[C@@H]1CN(Cc2cc([C@H](c3ccc4c(nnn4CC)c3C)C(C)(C)C(=O)O)sc2Cl)S(=O)(=O)c2cnccc2O1]

(R)-Benzyl 3-(5-chloro-4-(((R)-4-ethyl-1,1-dioxido-3,4-dihydro-2H-pyrido[4,3-b][1,4,5]oxathiazepin-2-yl)methyl)thiophen-2-yl)-3-(1-ethyl-4-methyl-1H-benzo[d][1,2,3]triazol-5-yl)-2,2-dimethylpropanoate

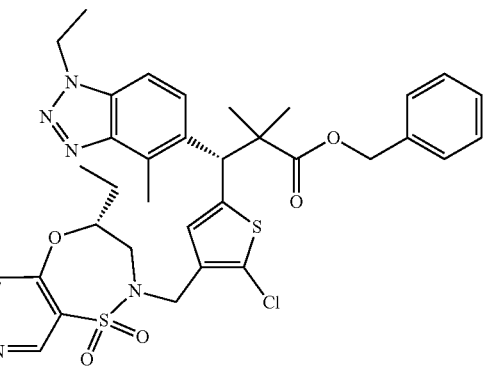

To a solution of (R)-benzyl 3-(5-chloro-4-(hydroxymethyl)thiophen-2-yl)-3-(1-ethyl-4-methyl-1H-benzo[d][1,2,3]triazol-5-yl)-2,2-dimethylpropanoate (65 mg, 0.131 mmol), (R)-4-ethyl-3,4-dihydro-2H-pyrido[4,3-b][1,4,5]oxathiazepine 1,1-dioxide (59.6 mg, 0.261 mmol) and (E)-diazene-1,2-diylbis(piperidin-1-ylmethanone) (65.9 mg, 0.261 mmol) in tetrahydrofuran (THF) (4 mL) was added tributylphosphine (0.065 mL, 0.261 mmol) and the reaction stirred for 1 h. The reaction was concentrated and purified by reverse phase preparative HPLC under neutral conditions to provide the title compound (70 mg, 0.099 mmol, 76% yield). LC/MS m/z 708(M+H)+, 1.38 min (ret. time).

173

(R)-3-(5-Chloro-4-(((R)-4-ethyl-1,1-dioxido-3,4-dihydro-2H-pyrido[4,3-b][1,4,5]oxathiazepin-2-yl)methyl)thiophen-2-yl)-3-(1-ethyl-4-methyl-1H-benzo[d][1,2,3]triazol-5-yl)-2,2-dimethylpropanoic Acid

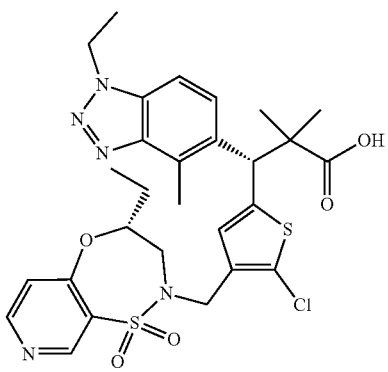

To a solution of (R)-benzyl 3-(5-chloro-4-(((R)-4-ethyl-1,1-dioxido-3,4-dihydro-2H-pyrido[4,3-b][1,4,5]oxathiazepin-2-yl)methyl)thiophen-2-yl)-3-(1-ethyl-4-methyl-1H-benzo[d][1,2,3]triazol-5-yl)-2,2-dimethylpropanoate (70 mg, 0.099 mmol), in chloroform (3 mL), was added methanesulfonic acid (0.039 mL, 0.593 mmol) and the reaction stirred 24 h at ambient temperature. The reaction was concentrated, and was purified by reverse phase preparative HPLC under neutral conditions to provide the title compound (16 mg, 0.026 mmol, 26.2% yield). LC/MS m/z 576(M+H)$^+$, 1.00 min (ret. time).

(S)-4-Methyl-8-(trifluoromethyl)-2,3,4,5-tetrahydrobenzo[f][1,2]thiazepine 1,1-dioxide

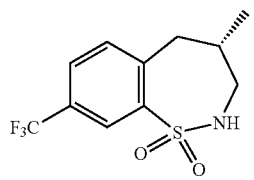 [SMILES: C[C@@H]1CNS(=O)(=O)c2cc(C(F)(F)F)ccc2C1]

(S)-4-Methyl-8-(trifluoromethyl)-2,3,4,5-tetrahydrobenzo[f][1,2]thiazepine 1,1-dioxide of the invention was made using compounds described in WO 2017/060854 on page 137, published Apr. 13, 2017, and incorporated herein by reference.

174

Example 37

(R)-3-(1-Ethyl-4-methyl-1H-benzo[d][1,2,3]triazol-5-yl)-2,2-dimethyl-3-(1-methyl-5-(((S)-4-methyl-1,1-dioxido-8-(trifluoromethyl)-4,5-dihydrobenzo[f][1,2]thiazepin-2(3H)-yl)methyl)-1H-pyrazol-3-yl)propanoic Acid

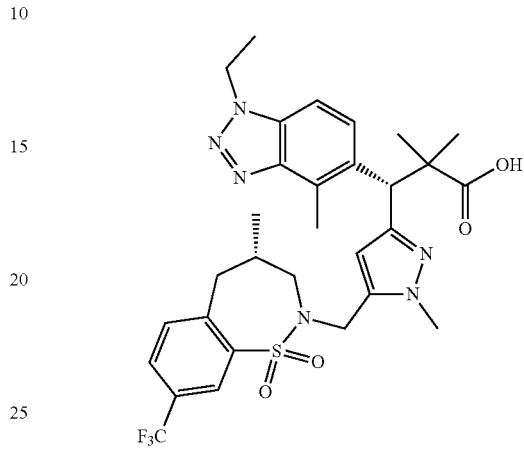

Methyl (R)-3-(1-ethyl-4-methyl-1H-benzo[d][1,2,3]triazol-5-yl)-2,2-dimethyl-3-(1-methyl-5-(((S)-4-methyl-1,1-dioxido-8-(trifluoromethyl)-4,5-dihydrobenzo[f][1,2]thiazepin-2(3H)-yl)methyl)-1H-pyrazol-3-yl)propanoate

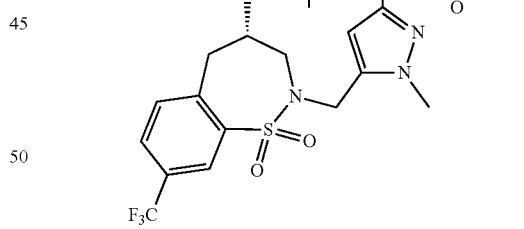

To a solution of methyl (R)-3-(1-ethyl-4-methyl-1H-benzo[d][1,2,3]triazol-5-yl)-3-(5-(hydroxymethyl)-1-methyl-1H-pyrazol-3-yl)-2,2-dimethylpropanoate (43 mg, 0.112 mmol) in tetrahydrofuran (THF) (4 mL) was added (S)-4-methyl-8-(trifluoromethyl)-2,3,4,5-tetrahydrobenzo[f][1,2]thiazepine 1,1-dioxide (62.3 mg, 0.223 mmol) and (E)-diazene-1,2-diylbis(piperidin-1-ylmethanone) (ADDP) (56.3 mg, 0.223 mmol). After all solids were dissolved, the solution was degassed and purged with argon after which tri-n-butylphosphine (0.055 mL, 0.223 mmol) was added and the reaction stirred at ambient temperature for 18 h. Another portion of tri-n-butylphosphine (0.028 mL, 0.112 mmol) was added and the reaction stirred for 24.5 h. The reaction was purified by reverse phase preparative HPLC under neutral conditions to provide the title compound (16 mg, 62% yield). LC/MS m/z 647 (M+H)+, 1.30 min (ret. time).

(R)-3-(1-Ethyl-4-methyl-1H-benzo[d][1,2,3]triazol-5-yl)-2,2-dimethyl-3-(1-methyl-5-(((S)-4-methyl-1,1-dioxido-8-(trifluoromethyl)-4,5-dihydrobenzo[f][1,2]thiazepin-2(3H)-yl)methyl)-1H-pyrazol-3-yl)propanoic Acid

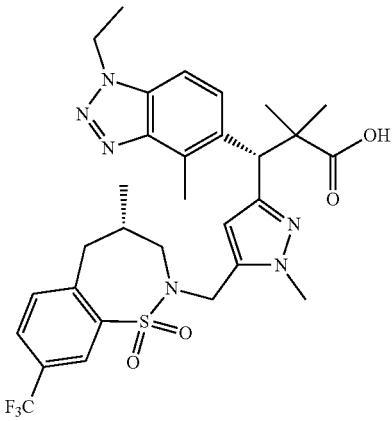 [SMILES: CCn1nnc2c(C)c([C@@H](c3cc(CN4C[C@@H](C)Cc5ccc(C(F)(F)F)cc5S4(=O)=O)n(C)n3)C(C)(C)C(=O)O)ccc21]

To a solution of methyl (R)-3-(1-ethyl-4-methyl-1H-benzo[d][1,2,3]triazol-5-yl)-2,2-dimethyl-3-(1-methyl-5-(((S)-4-methyl-1,1-dioxido-8-(trifluoromethyl)-4,5-dihydrobenzo[f][1,2]thiazepin-2(3H)-yl)methyl)-1H-pyrazol-3-yl)propanoate (45 mg, 0.070 mmol) in tetrahydrofuran (THF) (2 mL), methanol (1 mL) and water (1 mL) in a microwave reaction vessel, was added LiOH (8.33 mg, 0.348 mmol) and the reaction was heated via microwave at 140° C. for 2 h. The reaction was concentrated, and was purified by reverse phase preparative HPLC under formic acid conditions to provide the title compound (0.035 g, 81% yield). LC/MS m/z 633 (M+H)+, 1.18 min (ret. time).

Example 38

(R)-3-(5-Chloro-4-(((R)-4-ethyl-1,1-dioxido-3,4-dihydro-2H-pyrido[2,3-b][1,4,5]oxathiazepin-2-yl)methyl)thiophen-2-yl)-3-(1-ethyl-4-methyl-1H-benzo[d][1,2,3]triazol-5-yl)propanoic Acid

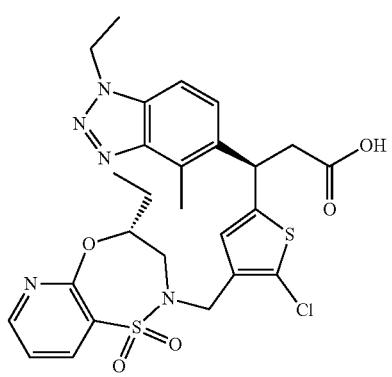 [SMILES: CC[C@@H]1CN(Cc2cc([C@H](CC(=O)O)c3ccc4c(nnn4CC)c3C)sc2Cl)S(=O)(=O)c2cccnc2O1]

(R)-Methyl 3-(5-chloro-4-(((R)-4-ethyl-1,1-dioxido-3,4-dihydro-2H-pyrido[2,3-b][1,4,5]oxathiazepin-2-yl)methyl)thiophen-2-yl)-3-(1-ethyl-4-methyl-1H-benzo[d][1,2,3]triazol-5-yl)propanoate

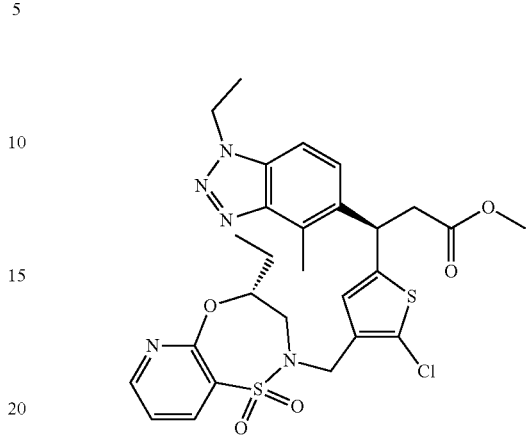

To a solution of (R)-methyl 3-(5-chloro-4-(hydroxymethyl)thiophen-2-yl)-3-(1-ethyl-4-methyl-1H-benzo[d][1,2,3]triazol-5-yl)propanoate (48 mg, 0.122 mmol), (R)-4-ethyl-3,4-dihydro-2H-pyrido[2,3-b][1,4,5]oxathiazepine 1,1-dioxide (55.6 mg, 0.244 mmol) and (E)-diazene-1,2-diylbis(piperidin-1-ylmethanone) (61.5 mg, 0.244 mmol) in tetrahydrofuran (THF) (4 mL) was added tributylphosphine (0.061 mL, 0.244 mmol) and stirred for 1 h. The reaction was concentrated, and was purified by reverse phase preparative HPLC under neutral conditions to provide the title compound (0.063 g, 86% yield). LC/MS m/z 604(M+H)+, 1.17 min (ret. time).

(R)-3-(5-Chloro-4-(((R)-4-ethyl-1,1-dioxido-3,4-dihydro-2H-pyrido[2,3-b][1,4,5]oxathiazepin-2-yl)methyl)thiophen-2-yl)-3-(1-ethyl-4-methyl-1H-benzo[d][1,2,3]triazol-5-yl)propanoic Acid

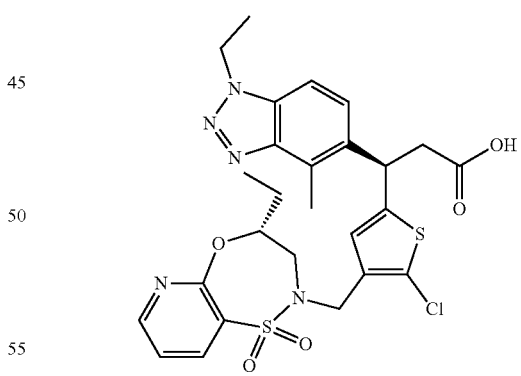

To a solution of (R)-methyl 3-(5-chloro-4-(((R)-4-ethyl-1,1-dioxido-3,4-dihydro-2H-pyrido[2,3-b][1,4,5]oxathiazepin-2-yl)methyl)thiophen-2-yl)-3-(1-ethyl-4-methyl-1H-benzo[d][1,2,3]triazol-5-yl)propanoate (63 mg, 0.104 mmol) was in tetrahydrofuran (THF) (2.000 mL), water (1 mL) and methanol (2.000 mL) was added lithium hydroxide (12.49 mg, 0.521 mmol) and the reaction stirred at ambient temperature for 2 h. The reaction was acidified with 10% aqueous formic acid and concentrated. The reaction was concentrated, and was purified by reverse phase preparative HPLC under formic acid conditions to provide the title compound (0.024 g, 39% yield). LC/MS m/z 590 (M+H)+, 1.08 (ret. time).

Example 39

(S)-3-(1-Ethyl-4-methyl-1H-benzo[d][1,2,3]triazol-5-yl)-2,2-dimethyl-3-(5-methyl-4-(((S)-4-methyl-1,1-dioxido-4,5-dihydrobenzo[f][1,2]thiazepin-2(3H)-yl)methyl)thiophen-2-yl)propanamide

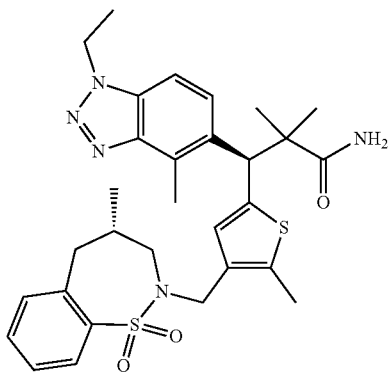 [SMILES: CCn1nnc2c(C)c([C@H](c3cc(CN4C[C@@H](C)Cc5ccccc5S4(=O)=O)c(C)s3)C(C)(C)C(N)=O)ccc21]

A mixture of (S)-3-(1-ethyl-4-methyl-1H-benzo[d][1,2,3]triazol-5-yl)-2,2-dimethyl-3-(5-methyl-4-(((S)-4-methyl-1,1-dioxido-4,5-dihydrobenzo[f][1,2]thiazepin-2(3H)-yl)methyl)thiophen-2-yl)propanoic acid (70 mg, 0.121 mmol) and thionyl chloride (1 mL, 13.70 mmol) was stirred at ambient temperature for 2 h. The reaction was concentrated and the residue was pumped on high vacuum for 5 min. The residue was dissolved in tetrahydrofuran (THF) (5 mL) cooled reaction in an ice bath. Ammonia gas was bubbled into the solution for 1 min and the reaction was stirred for 1 h. The reaction was concentrated, and was purified by reverse phase preparative HPLC under formic acid conditions to provide the title compound (0.038 g, 54% yield). LC/MS m/z 580 (M+H)+, 1.16 min (ret. time).

Example 40

(S)-3-(5-Chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-fluoro-1H-benzo[d][1,2,3]triazol-5-yl)-2,2-dimethylpropanoic Acid

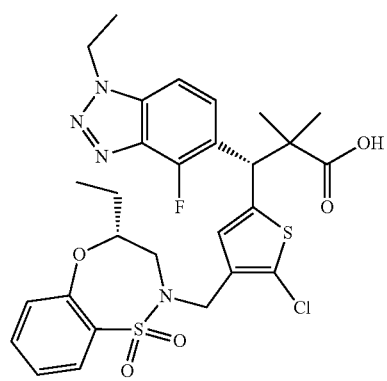 [SMILES: CC[C@@H]1CN(Cc2cc([C@H](c3ccc4c(nnn4CC)c3F)C(C)(C)C(=O)O)sc2Cl)S(=O)(=O)c2ccccc2O1]

N-Ethyl-3-fluoro-2-nitroaniline

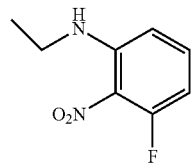

To a solution of 1,3-difluoro-2-nitrobenzene (10 g, 62.9 mmol) in ethanol (300 mL) was added ethanamine (47.2 g, 314 mmol) slowly at 0° C. The reaction mixture was stirred at 0° C. for 0.5 h and then warmed to 25° C. for another 4 h. After removing the solvent, the residue was purified via silica gel chromatography (80 g, PE/EA=5%) to give the title compound (8.0 g, 43.4 mmol, 69.1% yield) as a solid. LC/MS: m/z 185 (M+H)+, 1.70 min (ret. time).

4-Bromo-N-ethyl-3-fluoro-2-nitroaniline

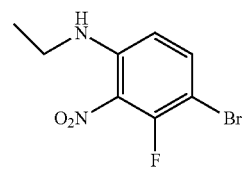

To a solution of N-ethyl-3-fluoro-2-nitroaniline (8.0 g, 43.4 mmol) in DMF (100 mL) at 0° C. was added a solution of N-bromosuccinimide (6.19 g, 34.8 mmol) dropwise. The mixture was stirred at 0° C. for 6 h. The mixture was quenched with water (500 mL) and extracted with ethyl acetate (3×400 mL). The combined organic layer was washed with water (2×100 mL), brine (2×100 mL), dried (Na$_2$SO$_4$) and concentrated. The residue was purified by silica gel chromatography (PE/EA=12%) to give the title compound (8.2 g, 31.2 mmol, 71.8% yield) as yellow oil. LCMS: m/z 263 (M+H)$^+$1.80 min (ret. time) 4-Bromo-N1-ethyl-3-fluorobenzene-1,2-diamine

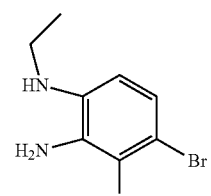

To a solution of 4-bromo-N-ethyl-3-fluoro-2-nitroaniline (8000 mg, 30.4 mmol) in ethanol (100 mL) and 1,2-dichloroethane (DCE) (100 mL) under nitrogen at 0° C. was added Raney nickel (1983 mg, 30.4 mmol, 90% in water) slowly. Hydrazine hydrate (2.237 mL, 45.6 mmol) was added dropwise. The reaction mixture was stirred at 0° C. for 1 h, filtered, and concentrated. The residue was purified by silica gel chromatography (hexane:ethyl acetate=4:1) to give the title compound (6500 mg, 27.9 mmol, 92% yield). LC-MS m/z 233.0 (M+H)$^+$1.90 (ret. time)

5-Bromo-1-ethyl-4-fluoro-1H-benzo[d][1,2,3]triazole

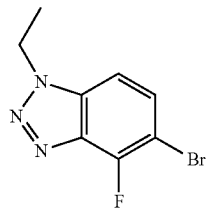

A stirred suspension of 4-bromo-N1-ethyl-3-fluorobenzene-1,2-diamine (6.5 g, 27.9 mmol) and sulfuric acid (5.95 mL, 112 mmol) in water (300 mL) at 0° C. was treated with a solution of sodium nitrite (2.89 g, 41.8 mmol) in water (50 mL). The mixture was stirred at 0° C. for 2 h. The mixture at 0° C. was basified to pH 8 using 2 N NaOH and extracted with DCM (3×200 mL). The combined organics were washed with water (2×80 mL), brine (2×80 mL), dried (Na$_2$SO$_4$) and concentrated. The residue was purified by silica gel chromatography (120 g, PE/EA=60%) to give the title compound (5.2 g, 21.31 mmol, 76% yield) as a colorless oil. LCMS: m/z 243.9 (M+H)$^+$ 1.63 min (ret. time)

5-Chloro-4-(((4-methoxybenzyl)oxy)methyl)thiophene-2-carbaldehyde

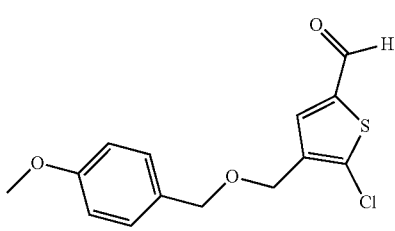 [SMILES: COc1ccc(COCc2cc(C=O)sc2Cl)cc1]

To a solution 5-bromo-2-chloro-3-(((4-methoxybenzyl)oxy)methyl)thiophene (1.4 g, 4.03 mmol) in tetrahydrofuran (THF) (1.00 mL) in an oven dried 50 mL flask under argon and cooled to −70° C., was added, dropwise via syringe, n-butyllithium (1.6M) (2.77 mL, 4.43 mmol) and stirred for 1 h. N,N-dimethylformamide (1.777 mL, 24.16 mmol) was then added dropwise via addition funnel and stirred at −70° C. for 1 h and then at ambient temperature for 45 min. The reaction was subsequently quenched with sat NH$_4$Cl, and purified by flash chromatography eluting with 0-40% EtOAc/Hexanes to provide the title compound. $^1$H NMR (400 MHz, CHLOROFORM-d) δ ppm 9.80 (s, 1H), 7.70 (s, 1H), 7.31 (d, J=7.78 Hz, 2H), 6.93 (d, J=7.78 Hz, 2H), 4.45-4.56 (m, 4H), 3.84 (s, 3H).

(5-Chloro-4-(((4-methoxybenzyl)oxy)methyl)thiophen-2-yl)(1-ethyl-4-fluoro-1H-benzo[d][1,2,3]triazol-5-yl)methanol

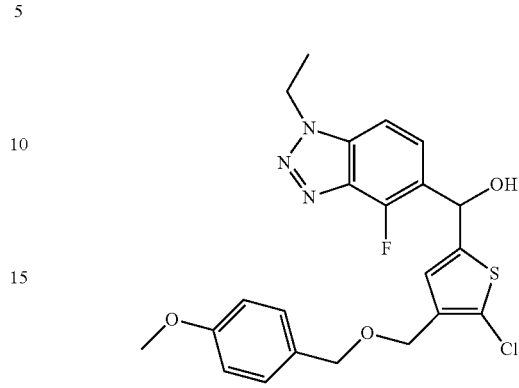

To a solution of 5-bromo-1-ethyl-4-fluoro-1H-benzo[d][1,2,3]triazole (1.122 g, 4.60 mmol), was dissolved in tetrahydrofuran (THF) (10 mL) and cooled to −78° C. was added n-butyllithium (2.55 mL, 4.08 mmol) and allowed to stir for 30 min. A solution of 5-chloro-4-(((4-methoxybenzyl)oxy)methyl)thiophene-2-carbaldehyde (1.1 g, 3.71 mmol) in tetrahydrofuran (THF) (10 mL) was added slowly and the reaction was stirred at −78° C. for 2 h. Afterwards, the reaction was diluted with water (25 mL) and EtOAc (75 mL). The aqueous layer was extracted with EtOAc (50 mL). The combined EtOAc layers were washed with water (50 mL) and saturated aqueous NaCl (50 mL), dried with Na$_2$SO$_4$ and concentrated. The residue was purified by flash chromatography eluting with 0-50% EtOAc/Hexane to provide the title compound. (0.60 g, 30% yield). LC/MS m/z 462 (M+H), 1.24 min (ret. time).

Methyl 3-(5-chloro-4-(((4-methoxybenzyl)oxy)methyl)thiophen-2-yl)-3-(1-ethyl-4-fluoro-1H-benzo[d][1,2,3]triazol-5-yl)-2,2-dimethylpropanoate

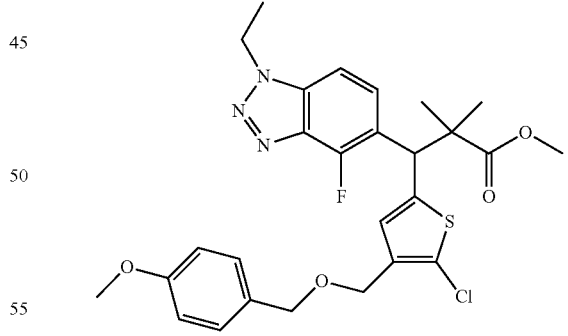

To a solution of (5-chloro-4-(((4-methoxybenzyl)oxy)methyl)thiophen-2-yl)(1-ethyl-4-fluoro-1H-benzo[d][1,2,3]triazol-5-yl)methanol (600 mg, 1.299 mmol), was added 2,2,2-trichloroacetonitrile (0.260 mL, 2.60 mmol) followed by DBU (0.017 mL, 0.065 mmol). Then (((1-methoxy-2-methylprop-1-en-1-yl)oxy)trimethylsilane (0.666 mL, 3.25 mmol) was added and the reaction mixture was stirred at ambient temperature for 1 hr. 1,1,1-trifluoro-N-((trifluoromethyl)sulfonyl) methanesulfonamide (0.027 mL, 0.130 mmol) was dissolved in acetonitrile, and added to the solution via syringe, and the reaction stirred at ambient temperature for 1 h. The reaction was partitioned between saturated aqueous NH₄Cl and EtOAc. The aqueous later was extracted with EtOAc (2×) and the combined organic layers were dried with MgSO₄ and concentrated. The residue was purified by flash chromatography eluting with 0-70% EtOAc/Hexane to provide the title compound. (0.50 g, 70% yield). LC/MS m/z 546 (M+H), 1.41 min (ret. time).

Benzyl (R)-3-(5-chloro-4-(((4-methoxybenzyl)oxy) methyl)thiophen-2-yl)-3-(1-ethyl-4-fluoro-1H-benzo [d][1,2,3]triazol-5-yl)-2,2-dimethylpropanoate and benzyl (S)-3-(5-chloro-4-(((4-methoxybenzyl)oxy) methyl)thiophen-2-yl)-3-(1-ethyl-4-fluoro-1H-benzo [d][1,2,3]triazol-5-yl)-2,2-dimethylpropanoate

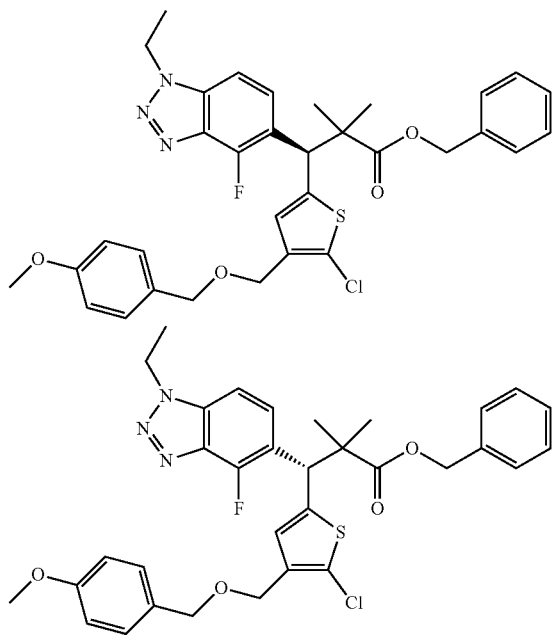

Methyl 3-(5-chloro-4-(((4-methoxybenzyl)oxy)methyl) thiophen-2-yl)-3-(1-ethyl-4-fluoro-1H-benzo[d][1,2,3]triazol-5-yl)-2,2-dimethylpropanoate (0.500 g, 0.897 mmol) was dissolved in tetrahydrofuran (THF) (5 mL), methanol (5 mL), and water (5 mL). LiOH (0.107 g, 4.49 mmol) was added and the reaction was heated via microwave to 100'C for 1.5 h. The solvent was concentrated and the residue was dissolved in N,N-dimethylformamide (DMF) (10 mL). Benzyl bromide (0.427 mL, 3.59 mmol) was added and the reaction was stirred for 2 h. The solvent was concentrated and the residue was diluted with water and EtOAc. Layers were separated and organic layer was washed with water. The aqueous layer was extracted with EtOAc. The combined organics were washed with brine and dried with MgSO₄. The solvent was concentrated and the residue was purified by flash chromatography eluting with 0-50% EtOAc/Hexane to provide the title compound as a racemate. (0.361 g, 64% yield). LC/MS m/z 622 (M+H)⁺, 1.54 min (ret. time). The compound was resolved by chiral SFC (Column: Chiralpak IA 20×250 mm, 5u; Co-solvent: 25% EtOH; Flowrate: 50 g/min; Back pressure: 100Bar, 30° C.) to provide benzyl (R)-3-(5-chloro-4-(((4-methoxybenzyl)oxy)methyl)thiophen-2-yl)-3-(1-ethyl-4-fluoro-1H-benzo[d][1,2,3]triazol-5-yl)-2,2-dimethylpropanoate (0.143 g, 25% yield). LCMS m/z 622 (M+H)⁺, 1.58 min (ret. time), (chiral SFC ret. time: 2.97 min) and benzyl (S)-3-(5-chloro-4-(((4-methoxybenzyl)oxy)methyl)thiophen-2-yl)-3-(1-ethyl-4-fluoro-1H-benzo[d][1,2,3]triazol-5-yl)-2,2-dimethylpropanoate (0.147 g, 26% yield). LCMS m/z 622 (M+H)⁺, 1.57 min (ret. time), (chiral SFC ret. time: 5.19 min).

Benzyl (S)-3-(5-chloro-4-(hydroxymethyl)thiophen-2-yl)-3-(1-ethyl-4-fluoro-1H-benzo[d][1,2,3]triazol-5-yl)-2,2-dimethylpropanoate

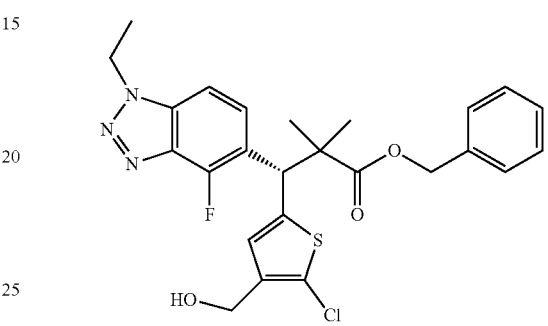

4N HCl in 1,4 dioxane (2.00 mL, 8.00 mmol) was added to benzyl (S)-3-(5-chloro-4-(((4-methoxybenzyl)oxy) methyl)thiophen-2-yl)-3-(1-ethyl-4-fluoro-1H-benzo[d][1, 2,3]triazol-5-yl)-2,2-dimethylpropanoate (0.147 g, 0.236 mmol) and the reaction stirred at ambient temperature for 2 h. The solvent was concentrated and the residue was purified by flash chromatography eluting with 0-50% EtOAc/Hexane to provide the title compound. (0.102 g, 86% yield). LC/MS m/z 502 (M+H)⁺, 1.21 min (ret. time).

Benzyl (S)-3-(5-chloro-4-(((R)-4-ethyl-1,1-dioxido-3,4-dihydro-2H-benzo[b][1,4,5]oxathiazepin-2-yl) methyl)thiophen-2-yl)-3-(1-ethyl-4-fluoro-1H-benzo [d][1,2,3]triazol-5-yl)-2,2-dimethylpropanoate

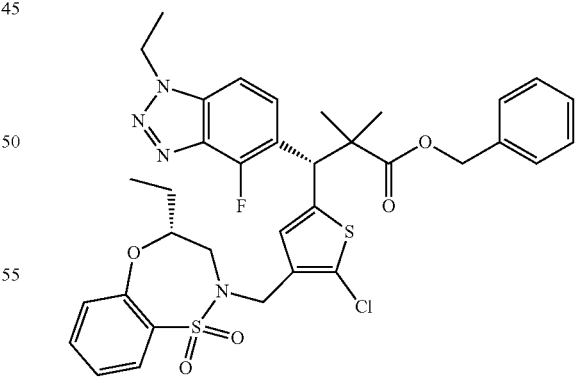

To a solution of benzyl (S)-3-(5-chloro-4-(hydroxymethyl)thiophen-2-yl)-3-(1-ethyl-4-fluoro-1H-benzo[d][1,2, 3]triazol-5-yl)-2,2-dimethylpropanoate (36 mg, 0.072 mmol) in tetrahydrofuran (THF) (2 mL) was added (R)-4-ethyl-3,4-dihydro-2H-benzo[b][1,4,5]oxathiazepine 1,1-dioxide (32.6 mg, 0.143 mmol) and (E)-diazene-1,2-diylbis (piperidin-1-ylmethanone) (ADDP) (36.2 mg, 0.143 mmol).

After all solids were dissolved, tri-n-butylphosphine (0.035 mL, 0.143 mmol) was added and the reaction stirred at ambient temperature for 2 h. Additional portions of (E)-diazene-1,2-diylbis(piperidin-1-ylmethanone) (ADDP) (181 mg, 0.717 mmol) and then tri-n-butylphosphine (0.177 mL, 0.717 mmol) were added and stirred for 3 days The reaction was concentrated, and was purified by reverse phase preparative HPLC under neutral conditions to provide the title compound (0.038 g, 75% yield). LC/MS m/z 711 (M+H)+, 1.55 min (ret. time).

(S)-3-(5-Chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-fluoro-1H-benzo[d][1,2,3]triazol-5-yl)-2,2-dimethylpropanoic Acid

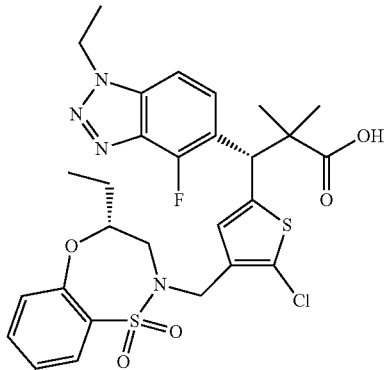 [SMILES: CC[C@@H]1CN(Cc2cc([C@H](c3ccc4c(nnn4CC)c3F)C(C)(C)C(=O)O)sc2Cl)S(=O)(=O)c2ccccc2O1]

To a solution of benzyl (S)-3-(5-chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-fluoro-1H-benzo[d][1,2,3]triazol-5-yl)-2,2-dimethylpropanoate (38.5 mg, 0.054 mmol) in chloroform (3 mL) was added methanesulfonic acid (0.021 mL, 0.325 mmol) and the reaction stirred at ambient temperature for 3.5 h. Additional methanesulfonic acid (0.021 mL, 0.325 mmol) was added and the reaction stirred for 3 days. An additional portion of methanesulfonic acid (0.070 mL, 1.083 mmol) was added and the reaction stirred at 50° C. for 5 h. The reaction was concentrated, and was purified by reverse phase preparative HPLC under formic acid conditions to provide the title compound (0.0027 g, 8% yield). LC/MS m/z 621 (M+H)+, 1.28 min (ret. time).

(S)-4-Ethyl-2,3,4,5-tetrahydrobenzo[f][1,2]thiazepine 1,1-dioxide

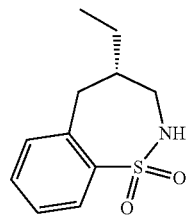

The following compound of the invention was made using compounds described in WO 2017/060854 on page 135, published Apr. 13, 2017, and incorporated herein by reference.

Example 41

(S)-3-(4-(((S)-4-Ethyl-1,1-dioxido-4,5-dihydrobenzo[f][1,2]thiazepin-2(3H)-yl)methyl)-5-methylthiazol-2-yl)-3-(1-ethyl-4-methyl-1H-benzo[d][1,2,3]triazol-5-yl)-2,2-dimethylpropanoic Acid

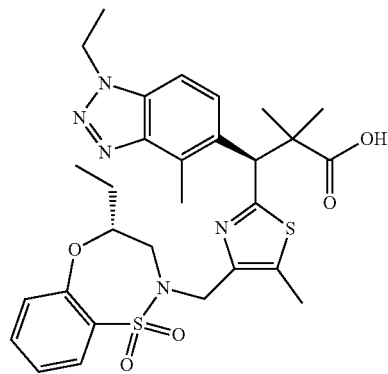 [SMILES: CC[C@@H]1CN(Cc2nc([C@@H](c3ccc4c(nnn4CC)c3C)C(C)(C)C(=O)O)sc2C)S(=O)(=O)c2ccccc2O1]

Benzyl (S)-3-(4-(((S)-4-ethyl-1,1-dioxido-4,5-dihydrobenzo[f][1,2]thiazepin-2(3H)-yl)methyl)-5-methylthiazol-2-yl)-3-(1-ethyl-4-methyl-1H-benzo[d][1,2,3]triazol-5-yl)-2,2-dimethylpropanoate

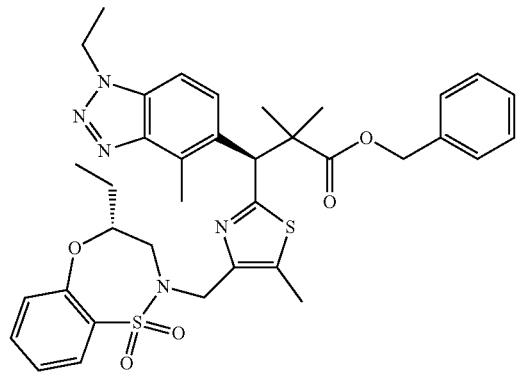 [SMILES: CC[C@@H]1CN(Cc2nc([C@@H](c3ccc4c(nnn4CC)c3C)C(C)(C)C(=O)OCc3ccccc3)sc2C)S(=O)(=O)c2ccccc2O1]

Benzyl (S)-3-(1-ethyl-4-methyl-1H-benzo[d][1,2,3]triazol-5-yl)-3-(4-(hydroxymethyl)-5-methylthiazol-2-yl)-2,2-dimethylpropanoate (100 mg, 0.209 mmol), (S)-4-ethyl-2,3,4,5-tetrahydrobenzo[f][1,2]thiazepine 1,1-dioxide (94 mg, 0.418 mmol) and (E)-diazene-1,2-diylbis(piperidin-1-ylmethanone) (ADDP) (105 mg, 0.418 mmol) were combined and dissolved in tetrahydrofuran (THF) (8 mL). After all solids were dissolved, tri-n-butylphosphine (0.103 mL, 0.418 mmol) was added and the reaction stirred at ambient temperature for 18 h. The reaction was concentrated, and was purified by reverse phase preparative HPLC under formic acid conditions to provide the title compound (0.123 g, 86% yield). LC/MS m/z 686 (M+H)+, 1.65 min (ret. time).

(S)-3-(4-(((S)-4-Ethyl-1,1-dioxido-4,5-dihydrobenzo
[f][1,2]thiazepin-2(3H)-yl)methyl)-5-methylthiazol-
2-yl)-3-(1-ethyl-4-methyl-1H-benzo[d][1,2,3]triazol-
5-yl)-2,2-dimethylpropanoic Acid

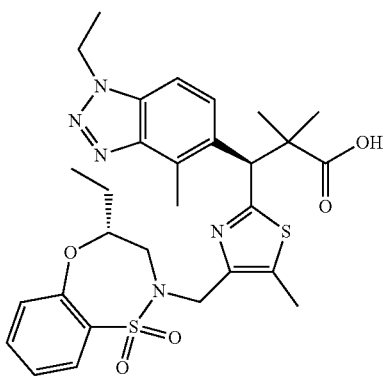 [SMILES: CC[C@@H]1CN(Cc2nc([C@@H](c3ccc4c(nnn4CC)c3C)C(C)(C)C(=O)O)sc2C)S(=O)(=O)c2ccccc2O1]

A solution of benzyl (S)-3-(4-(((S)-4-ethyl-1,1-dioxido-4,5-dihydrobenzo[f][1,2]thiazepin-2(3H)-yl)methyl)-5-methylthiazol-2-yl)-3-(1-ethyl-4-methyl-1H-benzo[d][1,2,3]triazol-5-yl)-2,2-dimethylpropanoate (0.123 g, 0.179 mmol) in methanol (10 mL) was flushed with nitrogen after which 5% Pd/C (0.019 g, 8.97 µmol) was added to the solution. The flask was evacuated and purged with hydrogen gas and stirred under a hydrogen balloon for 20 h. Additional 5% Pd/C (0.007 g, 3.29 µmol) was added and the reaction stirred for 2.5 h. The reaction was filtered and the solvent was concentrated. The residue was purified by reverse phase preparative HPLC under neutral conditions to provide the title compound (0.091 g, 86% yield). LC/MS m/z 596(M+H)$^+$, 1.29 min (ret. time).

Example 42

(S)-3-(4-(((S)-4-Ethyl-1,1-dioxido-4,5-dihydrobenzo
[f][1,2]thiazepin-2(3H)-yl)methyl)-5-methylthiazol-
2-yl)-3-(1-ethyl-4-methyl-1H-benzo[d][1,2,3]triazol-
5-yl)-2,2-dimethyl-N-(pyridin-3-yl)propanamide

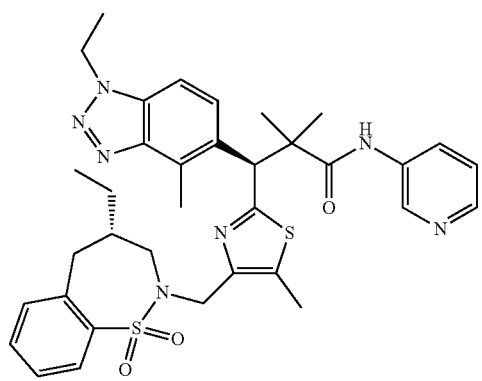 [SMILES: CC[C@H]1Cc2ccccc2S(=O)(=O)N(Cc2nc([C@@H](c3ccc4c(nnn4CC)c3C)C(C)(C)C(=O)Nc3cccnc3)sc2C)C1]

To a solution of (S)-3-(4-(((S)-4-ethyl-1,1-dioxido-4,5-dihydrobenzo[f][1,2]thiazepin-2(3H)-yl)methyl)-5-methylthiazol-2-yl)-3-(1-ethyl-4-methyl-1H-benzo[d][1,2,3]triazol-5-yl)-2,2-dimethylpropanoic acid (78 mg, 0.130 mmol) in isopropanol (2.00 mL) was added phenyl (E)-N-(tert-butyl)-N'-(pyridin-3-yl)carbamimidothioate (31 mg, 0.109 mmol) and ferric acetylacetonate (7.67 mg, 0.022 mmol). The vial was heated at 83° C. for 18 h. The reaction was concentrated, and was purified by reverse phase preparative HPLC under formic acid conditions to provide the title compound (0.038 g, 50% yield). LC/MS m/z 672 (M+H)+, 1.00 min (ret. time).

Example 43

(S)-3-(5-Chloro-4-(((S)-4-methyl-1,1-dioxido-8-
(trifluoromethyl)-4,5-dihydrobenzo[f][1,2]thiazepin-
2(3H)-yl)methyl)thiophen-2-yl)-3-(1-ethyl-4-fluoro-
1H-benzo[d][1,2,3]triazol-5-yl)-2,2-
dimethylpropanoic Acid

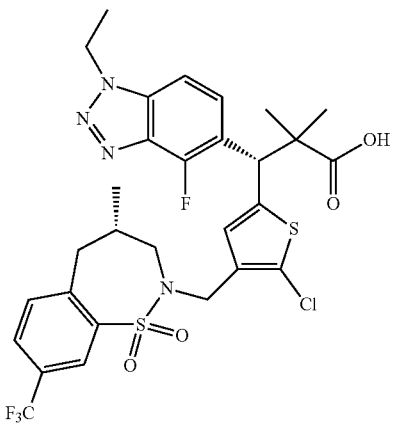 [SMILES: CCn1nnc2c(F)c([C@@H](c3cc(CN4C[C@@H](C)Cc5ccc(C(F)(F)F)cc5S4(=O)=O)c(Cl)s3)C(C)(C)C(=O)O)ccc21]

2-Bromo-N-(2-methylallyl)-4-(trifluoromethyl)ben-
zenesulfonamide

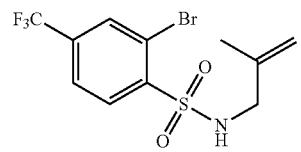 [SMILES: C=C(C)CNS(=O)(=O)c1ccc(C(F)(F)F)cc1Br]

To a solution of 2-bromo-4-(trifluoromethyl)benzene-1-sulfonyl chloride (20 g, 61.8 mmol) in dichloromethane (DCM) (200 mL) at 0° C. was added 2-methylprop-2-en-1-amine (4.84 g, 68.0 mmol) and TEA (17.23 mL, 124 mmol). The reaction mixture was stirred at ambient temperature. The reaction mixture quenched with water (500 mL) and extracted with DCM (2×500 mL). The combined organic layer washed with brine solution (100 mL), dried over anhydrous Na$_2$SO$_4$, filtered and concentrated the solvent under reduced pressure to give the title compound (19 g). LCMS m/z 358 (M+H)$^+$, 2.46 mins (ret. time)

4-Methyl-7-(trifluoromethyl)-2,3,4,5-tetrahydrobenzo[f][1,2]thiazepine 1,1-dioxide

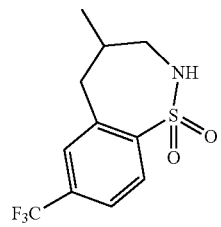

To a solution of 2-bromo-N-(2-methylallyl)-4-(trifluoromethyl)benzenesulfonamide (19 g, 53.0 mmol) in toluene (290 mL) was added AIBN (4.36 g, 26.5 mmol) and the reaction was heated to 70° C. Then Bu$_3$SnH (28.3 mL, 106 mmol) was added into the reaction mixture at this temperature. The reaction was stirred at 110° C. for 16 h. The reaction mixture was cooled to ambient temperature and concentrated under reduced pressure to get crude compound. The crude compound was purified by silica gel column chromatography (Mesh size 100-200) eluted with 30% EtOAc:Hexane to afford the title compound (6 g) as light brownish solid compound. LCMS m/z 278.14 (M−H)$^+$, 2.094 mins (ret. time)

(R)-4-Methyl-7-(trifluoromethyl)-2,3,4,5-tetrahydrobenzo[f][1,2]thiazepine 1,1-dioxide and (S)-4-methyl-7-(trifluoromethyl)-2,3,4,5-tetrahydrobenzo[f][1,2]thiazepine 1,1-dioxide

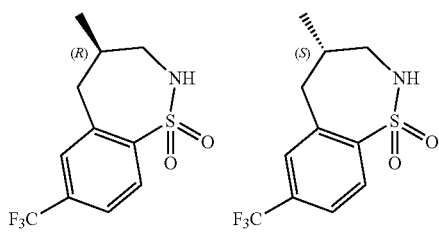

4-Methyl-7-(trifluoromethyl)-2,3,4,5-tetrahydrobenzo[f][1,2]thiazepine 1,1-dioxide (5.4 g, 19.34 mmol) was resolved by Chiral SFC (Column: Chiralpak AS-H (250×30) mm, 5u; co-solvent: 50% IPA; flowrate:100 g/min; Back pressure: 100 Bar) to give (R)-4-methyl-7-(trifluoromethyl)-2,3,4,5-tetrahydrobenzo[f][1,2]thiazepine 1,1-dioxide (2.3 g, 8.17 mmol, 42.3% yield) as white solid 1H NMR (400 MHz, DMSO-d6) δ ppm 7.98 (d, J=7.89 Hz, 1H) 7.75-7.85 (m, 3H) 3.35 (br s, 1H) 3.21 (br s, 3H) 1.85 (br s, 1H) 0.85 (br d, J=5.92 Hz, 3H) LCMS m/z 278.07 (M−H)$^+$, 2.715 mins (ret. time) (chiral SFC ret. time: 11.815 min) and (S)-4-methyl-7-(trifluoromethyl)-2,3,4,5-tetrahydrobenzo[f][1,2]thiazepine 1,1-dioxide (2.06 g, 7.32 mmol, 37.8% yield) as white solid 1H NMR (400 MHz, DMSO-d6) δ ppm 7.98 (d, J=7.89 Hz, 1H) 7.75-7.85 (m, 3H) 3.35 (br s, 1H) 3.21 (br s, 3H) 1.85 (br s, 1H) 0.85 (br d, J=5.92 Hz, 3H) LCMS m/z 278.07 (M−H)$^+$, 2.715 mins (ret. time) (chiral SFC ret. time: 14.631 min)

Benzyl (S)-3-(5-chloro-4-(((S)-4-methyl-1,1-dioxido-8-(trifluoromethyl)-4,5-dihydrobenzo[f][1,2]thiazepin-2(3H)-yl)methyl)thiophen-2-yl)-3-(1-ethyl-4-fluoro-1H-benzo[d][1,2,3]triazol-5-yl)-2,2-dimethylpropanoate

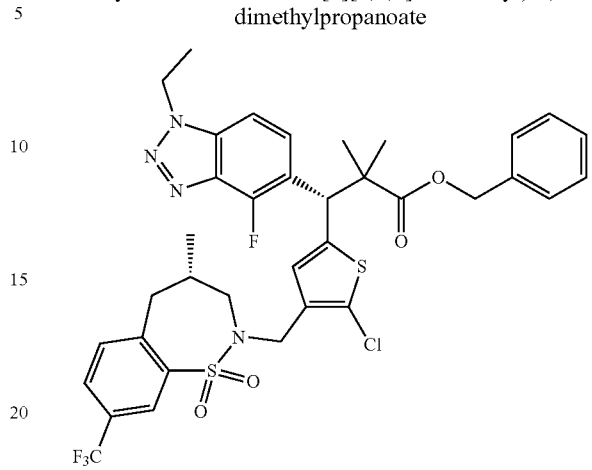

To a solution of benzyl (S)-3-(5-chloro-4-(hydroxymethyl)thiophen-2-yl)-3-(1-ethyl-4-fluoro-1H-benzo[d][1,2,3]triazol-5-yl)-2,2-dimethylpropanoate (50 mg, 0.100 mmol) in tetrahydrofuran (THF) (2 mL) was added (S)-4-methyl-8-(trifluoromethyl)-2,3,4,5-tetrahydrobenzo[f][1,2]thiazepine 1,1-dioxide (55.6 mg, 0.199 mmol) and (E)-diazene-1,2-diylbis(piperidin-1-ylmethanone) (ADDP) (50.3 mg, 0.199 mmol). After all solids were dissolved, tri-n-butylphosphine (0.049 mL, 0.199 mmol) was added and the reaction stirred at ambient temperature for 20 h. Additional portions of (E)-diazene-1,2-diylbis(piperidin-1-ylmethanone) (ADDP) (25.1 mg, 0.100 mmol) and tri-n-butylphosphine (0.025 mL, 0.100 mmol) were added and stirred for 2.5 h. The solvent was concentrated and the residue was purified by reverse phase preparative HPLC under neutral conditions to provide the title compound (0.055 g, 72% yield). LC/MS m/z 763 (M+H)+, 1.64 min (ret. time).

(S)-3-(5-Chloro-4-(((S)-4-methyl-1,1-dioxido-8-(trifluoromethyl)-4,5-dihydrobenzo[f][1,2]thiazepin-2(3H)-yl)methyl)thiophen-2-yl)-3-(1-ethyl-4-fluoro-1H-benzo[d][1,2,3]triazol-5-yl)-2,2-dimethylpropanoic Acid

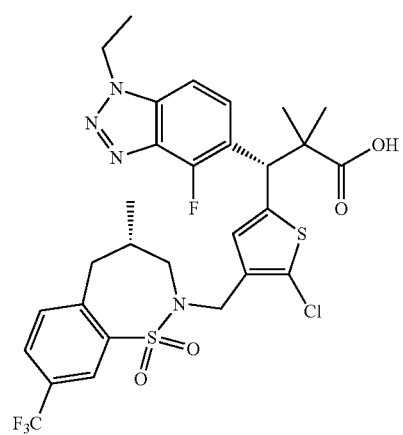 [SMILES: CCn1nnc2c(F)c([C@@H](c3cc(CN4C[C@@H](C)Cc5ccc(C(F)(F)F)cc5S4(=O)=O)c(Cl)s3)C(C)(C)C(=O)O)ccc21]

To a solution of benzyl (S)-3-(5-chloro-4-(((S)-4-methyl-1,1-dioxido-8-(trifluoromethyl)-4,5-dihydrobenzo[f][1,2]thiazepin-2(3H)-yl)methyl)thiophen-2-yl)-3-(1-ethyl-4-fluoro-1H-benzo[d][1,2,3]triazol-5-yl)-2,2-dimethylpropanoate (55 mg, 0.072 mmol) in chloroform (3 mL) was added methanesulfonic acid (0.028 mL, 0.432 mmol) and the reaction stirred at ambient temperature for 3.5 h. Additional methanesulfonic acid (0.028 mL, 0.432 mmol) was added and the reaction stirred for 3 days. An additional portion of methanesulfonic acid (0.094 mL, 1.441 mmol) was added and the reaction stirred for 22 h. The reaction was heated at 50° C. for 5 h. The solvent was concentrated and the residue was purified by reverse phase preparative HPLC under formic acid conditions to provide the title compound (0.0057 g, 11% yield). LC/MS m/z 673 (M+H)+, 1.40 min (ret. time).

Example 44

(S)-3-(1-Ethyl-4-methyl-1H-benzo[d][1,2,3]triazol-5-yl)-2,2-dimethyl-3-(5-methyl-4-(((S)-4-methyl-1,1-dioxido-7-(trifluoromethyl)-4,5-dihydrobenzo[f][1,2]thiazepin-2(3H)-yl)methyl)thiazol-2-yl)propanoic Acid

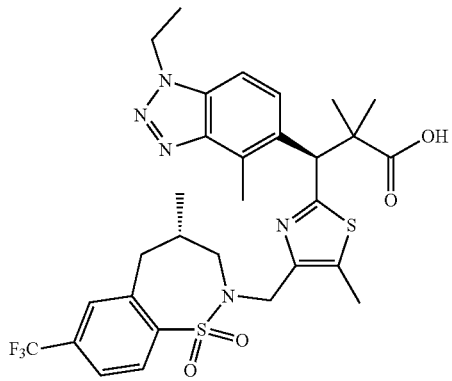 [SMILES: CCn1nnc2c(C)c([C@H](c3nc(CN4C[C@@H](C)Cc5cc(C(F)(F)F)ccc5S4(=O)=O)c(C)s3)C(C)(C)C(=O)O)ccc21]

Benzyl (S)-3-(1-ethyl-4-methyl-1H-benzo[d][1,2,3]triazol-5-yl)-2,2-dimethyl-3-(5-methyl-4-(((S)-4-methyl-1,1-dioxido-7-(trifluoromethyl)-4,5-dihydrobenzo[f][1,2]thiazepin-2(3H)-yl)methyl)thiazol-2-yl)propanoate

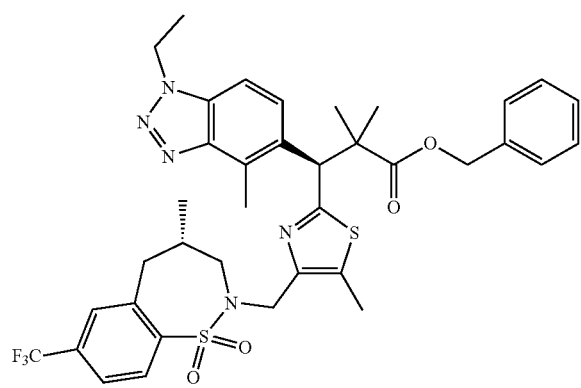 [SMILES: CCn1nnc2c(C)c([C@H](c3nc(CN4C[C@@H](C)Cc5cc(C(F)(F)F)ccc5S4(=O)=O)c(C)s3)C(C)(C)C(=O)OCc3ccccc3)ccc21]

Benzyl (S)-3-(1-ethyl-4-methyl-1H-benzo[d][1,2,3]triazol-5-yl)-3-(4-(hydroxymethyl)-5-methylthiazol-2-yl)-2,2-dimethylpropanoate (102 mg, 0.213 mmol) (S)-4-methyl-7-(trifluoromethyl)-2,3,4,5-tetrahydrobenzo[f][1,2]thiazepine 1,1-dioxide (119 mg, 0.426 mmol) and (E)-diazene-1,2-diylbis(piperidin-1-ylmethanone) (ADDP) (108 mg, 0.426 mmol) were combined and dissolved in dry tetrahydrofuran (THF) (8 mL). After all solids were dissolved, tri-n-butylphosphine (0.105 mL, 0.426 mmol) was added and the reaction stirred at ambient temperature for 18 h. The solvent was concentrated and the residue was purified by reverse phase preparative HPLC under neutral conditions to provide the title compound (0.138 g, 88% yield). LC/MS m/z 740 (M+H)+, 1.68 min (ret. time).

(S)-3-(1-Ethyl-4-methyl-1H-benzo[d][1,2,3]triazol-5-yl)-2,2-dimethyl-3-(5-methyl-4-(((S)-4-methyl-1,1-dioxido-7-(trifluoromethyl)-4,5-dihydrobenzo[f][1,2]thiazepin-2(3H)-yl)methyl)thiazol-2-yl)propanoic Acid

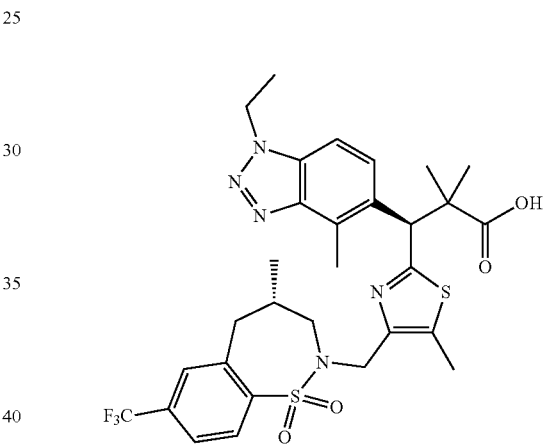

A solution of benzyl (S)-3-(1-ethyl-4-methyl-1H-benzo[d][1,2,3]triazol-5-yl)-2,2-dimethyl-3-(5-methyl-4-(((S)-4-methyl-1,1-dioxido-7-(trifluoromethyl)-4,5-dihydrobenzo[f][1,2]thiazepin-2(3H)-yl)methyl)thiazol-2-yl)propanoate (0.138 g, 0.187 mmol) in methanol (10 mL) was flushed with nitrogen after which 5% Pd/C (0.020 g, 9.33 μmol) was added to the solution. The flask was evacuated and purged with hydrogen gas and stirred under a hydrogen balloon for 20 h. Additional 5% Pd/C (0.006 g, 2.82 μmol) was added and the reaction stirred for 2.5 h. The reaction was filtered with a filter disk and the solvent was concentrated. The residue was purified by reverse phase preparative HPLC under neutral conditions to provide the title compound (0.103 g, 84% yield). LC/MS m/z 650(M+H)+, 1.35 min (ret. time).

Example 45

(S)-3-(1-Ethyl-4-methyl-1H-benzo[d][1,2,3]triazol-5-yl)-2,2-dimethyl-3-(5-methyl-4-(((S)-4-methyl-1,1-dioxido-7-(trifluoromethyl)-4,5-dihydrobenzo[f][1,2]thiazepin-2(3H)-yl)methyl)thiazol-2-yl)-N-(pyridin-3-yl)propanamide

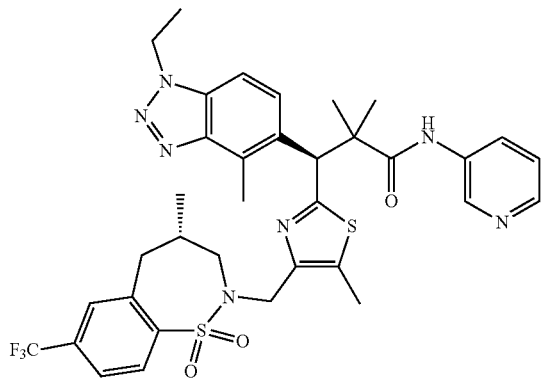 [SMILES: CCn1nnc2c(C)c([C@H](c3nc(CN4C[C@@H](C)Cc5cc(C(F)(F)F)ccc5S4(=O)=O)c(C)s3)C(C)(C)C(=O)Nc3cccnc3)ccc21]

To a solution of (S)-3-(1-ethyl-4-methyl-1H-benzo[d][1,2,3]triazol-5-yl)-2,2-dimethyl-3-(5-methyl-4-(((S)-4-methyl-1,1-dioxido-7-(trifluoromethyl)-4,5-dihydrobenzo[f][1,2]thiazepin-2(3H)-yl)methyl)thiazol-2-yl)propanoic acid (90 mg, 0.139 mmol) in isopropanol (2.00 mL) was added phenyl (E)-N-(tert-butyl)-N'-(pyridin-3-yl)carbamimidothioate (33 mg, 0.116 mmol) and ferric acetylacetonate (2.042 mg, 5.78 μmol). The vial was flushed with oxygen and the reaction was heated at 83° C. for 18 h. Additional ferric acetylacetonate (4.08 mg, 0.012 mmol) was added and heating was continued for 6 h. The solvent was concentrated and the residue was purified by reverse phase preparative HPLC under formic acid conditions to provide the title compound (0.060 g, 72% yield). LC/MS m/z 726 (M+H)+, 1.07 min (ret. time).

Example 46

(R)-3-(4-(((R)-4-Ethyl-1,1-dioxido-3,4-dihydro-2H-pyrido[2,3-b][1,4,5]oxathiazepin-2-yl)methyl)-5-methylthiophen-2-yl)-3-(1-ethyl-4-methyl-1H-benzo[d][1,2,3]triazol-5-yl)propanoic Acid

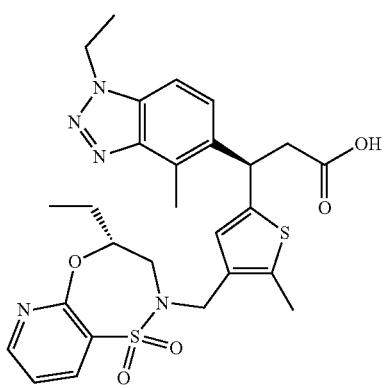 [SMILES: CC[C@@H]1CN(Cc2cc([C@H](CC(=O)O)c3ccc4c(nnn4CC)c3C)sc2C)S(=O)(=O)c2cccnc2O1]

(R)-Methyl 3-(4-(chloromethyl)-5-methylthiophen-2-yl)-3-(1-ethyl-4-methyl-1H-benzo[d][1,2,3]triazol-5-yl)propanoate

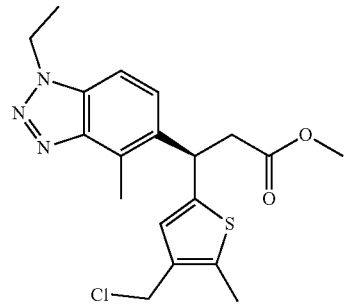 [SMILES: CCn1nnc2c(C)c([C@@H](CC(=O)OC)c3cc(CCl)c(C)s3)ccc21]

To a solution of (R)-methyl 3-(1-ethyl-4-methyl-1H-benzo[d][1,2,3]triazol-5-yl)-3-(4-(((4-methoxybenzyl)oxy)methyl)-5-methylthiophen-2-yl)propanoate (0.138 g, 0.280 mmol) in 1,4-dioxane (15 mL) was added 4N HCl in 1,4 dioxane (4.00 mL, 16.00 mmol) and the reaction stirred at ambient temperature for 23 h. Solvents were concentrated and residue was redissolved in 4N HCl in 1,4 dioxane (4.00 mL, 16.00 mmol) and stirred for 18 h. The reaction was concentrated and the residue was dissolved in dichloromethane (DCM) (5 mL) followed by addition of SOCl₂ (0.020 mL, 0.280 mmol) and stirred for 18 h. The solvent was concentrated and the residue was purified by flash chromatography eluting with 0-40% EtOAc/Hexane to provide the title compound. (0.072 g, 59% yield). LC/MS m/z 392 (M+H)+, 1.13 min (ret. time).

(R)-3-(4-(((R)-4-Ethyl-1,1-dioxido-3,4-dihydro-2H-pyrido[2,3-b][1,4,5]oxathiazepin-2-yl)methyl)-5-methylthiophen-2-yl)-3-(1-ethyl-4-methyl-1H-benzo[d][1,2,3]triazol-5-yl)propanoic Acid

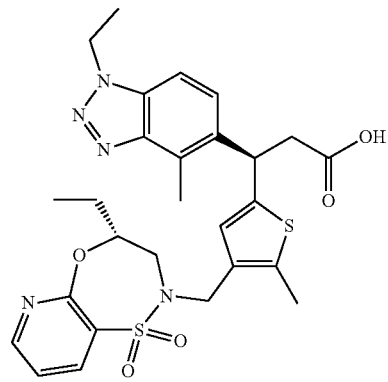 [SMILES: CC[C@@H]1CN(Cc2cc([C@H](CC(=O)O)c3ccc4c(nnn4CC)c3C)sc2C)S(=O)(=O)c2cccnc2O1]

To a solution of (R)-4-ethyl-3,4-dihydro-2H-pyrido[2,3-b][1,4,5]oxathiazepine 1,1-dioxide (0.020 g, 0.088 mmol) in N,N-dimethylformamide (DMF) (3 mL) under nitrogen and cooled to 0° C., was added 60% NaH (4.41 mg, 0.110 mmol) portion wise. The reaction was warmed to ambient temperature and stirred for 30 min. (R)-methyl 3-(4-(chloromethyl)-5-methylthiophen-2-yl)-3-(1-ethyl-4-methyl-1H-benzo[d][1,2,3]triazol-5-yl)propanoate (0.032 g, 0.073 mmol) in N,N-dimethylformamide (DMF) (3.00 mL) was then added dropwise to the reaction and stirred for 18 h. The reaction was quenched with water and concentrated under vacuum. The residue was dissolved in tetrahydrofuran (THF) (3.00 mL), methanol (3.00 mL), and water (3.00 mL) and LiOH (8.80 mg, 0.367 mmol) was added and the reaction stirred at ambient temperature for 19 h. The reaction was acidified with formic acid and was purified by reverse phase preparative HPLC under formic acid conditions to provide the title compound (0.023 g, 54% yield). LC/MS m/z 570 (M+H)+, 1.00 min (ret. time).

Example 47

(R)-3-(4-(((R)-4-Ethyl-1,1-dioxido-3,4-dihydro-2H-pyrido[4,3-b][1,4,5]oxathiazepin-2-yl)methyl)-5-methylthiophen-2-yl)-3-(1-ethyl-4-methyl-1H-benzo[d][1,2,3]triazol-5-yl)propanoic Acid

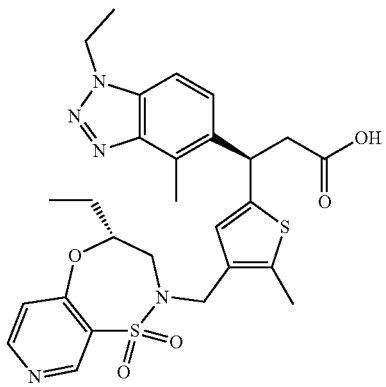 [SMILES: CC[C@@H]1CN(Cc2cc([C@H](CC(=O)O)c3ccc4c(nnn4CC)c3C)sc2C)S(=O)(=O)c2cnccc2O1]

To a solution of (R)-4-ethyl-3,4-dihydro-2H-pyrido[4,3-b][1,4,5]oxathiazepine 1,1-dioxide (0.020 g, 0.088 mmol) in N,N-dimethylformamide (DMF) (3 mL) under nitrogen and cooled to 0° C., was added 60% NaH (4.41 mg, 0.110 mmol) portion wise. The reaction was warmed to ambient temperature and stirred for 30 min. (R)-methyl 3-(4-(chloromethyl)-5-methylthiophen-2-yl)-3-(1-ethyl-4-methyl-1H-benzo[d][1,2,3]triazol-5-yl)propanoate (0.032 g, 0.073 mmol) in N,N-dimethylformamide (DMF) (3.00 mL) was then added dropwise to the reaction and stirred for 18 h. The reaction was quenched with water and concentrated under vacuum. The residue was dissolved in tetrahydrofuran (THF) (3.00 mL), methanol (3.00 mL), and water (3.00 mL) and LiOH (8.80 mg, 0.367 mmol) was added and the reaction stirred at ambient temperature for 19 h. The reaction was acidified with formic acid and was purified by reverse phase preparative HPLC under formic acid conditions to provide the title compound (0.027 g, 62% yield). LC/MS m/z 570 (M+H)+, 0.99 min (ret. time).

Example 48

(S)-3-(4-(((S)-4-Ethyl-1,1-dioxido-8-(trifluoromethyl)-4,5-dihydrobenzo[f][1,2]thiazepin-2(3H)-yl)methyl)-5-methylthiazol-2-yl)-3-(1-ethyl-4-methyl-1H-benzo[d][1,2,3]triazol-5-yl)-2,2-dimethyl-N-(pyridin-3-yl)propanamide

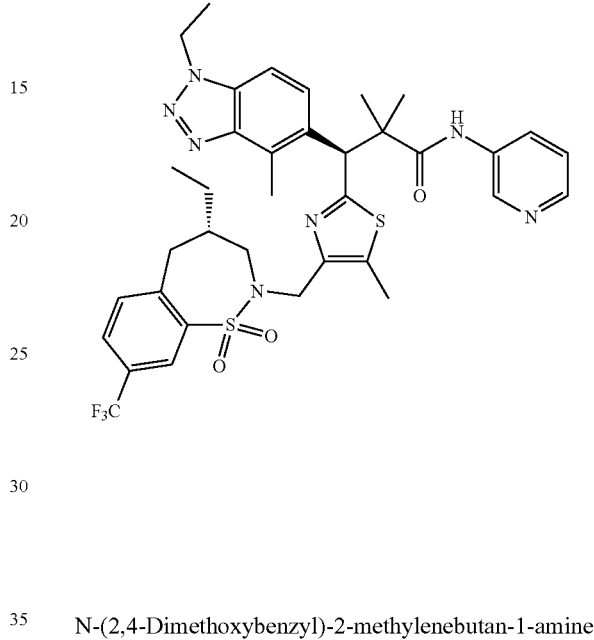

N-(2,4-Dimethoxybenzyl)-2-methylenebutan-1-amine

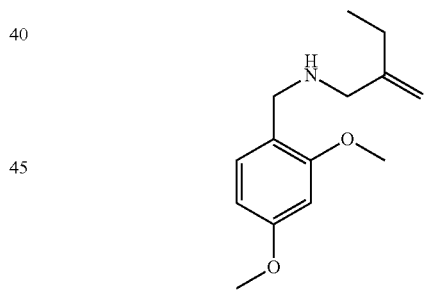

To a solution of 2-methylenebutanal (100 g, 1189 mmol) in toluene (135 mL) was added (2,4-dimethoxyphenyl)methanamine (199 g, 1189 mmol) and stirred at 110° C. for 48 hr.

The reaction mixture was concentrated and dissolved in ethanol (82 mL). NaBH4 (90 g, 2378 mmol) was added at 0° C. and the reaction stirred at ambient temperature for 6 h. The reaction mixture was evaporated under reduced pressure, quenched with water (200 mL) and extracted with DCM (2×200 mL). The organic layer was dried over anhydrous Na2SO4 and filtered. The filtrate was evaporated under reduced pressure and the residue was purified by flash chromatography eluting with 1:9 EtOAc:Hexane. To provide the title compound. (68 g, 16.53% yield). LC/MS m/z 236 (M+H)+, 3.62 min (ret. time).

2-Bromo-N-(2,4-dimethoxybenzyl)-N-(2-methylenebutyl)-5-(trifluoromethyl)benzenesulfonamide

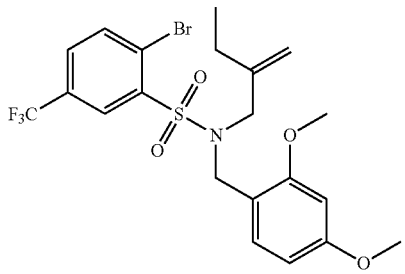 [SMILES: C=C(CC)CN(Cc1ccc(OC)cc1OC)S(=O)(=O)c1cc(C(F)(F)F)ccc1Br]

To a solution of N-(2,4-dimethoxybenzyl)-2-methylenebutan-1-amine (15 g, 43.3 mmol) in dichloromethane (DCM) (300 mL) was added Et$_3$N (12.08 mL, 87 mmol) at 0° C. followed by addition of 2-bromo-5-(trifluoromethyl)benzene-1-sulfonyl chloride (14.02 g, 43.3 mmol) and the reaction allowed to stir at ambient temperature for 16 h. The reaction mixture was evaporated under reduced pressure, quenched with water (300 mL) and extracted with DCM (2×300 mL). The organic layer was dried over anhydrous Na$_2$SO$_4$ and filtered. The filtrate was evaporated under reduced pressure and the residue was purified by flash chromatography eluting with 2%, 4% then 8% petroleum ether/ethyl acetate to provide the title compound. (20 g, 81% yield). GC/MS m/z 521/523 (M+H)$^+$, 10.66 min (ret. time).

2-Bromo-N-(2-methylenebutyl)-5-(trifluoromethyl)benzenesulfonamide

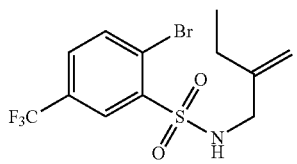 [SMILES: C=C(CC)CNS(=O)(=O)c1cc(C(F)(F)F)ccc1Br]

To a solution of 2-bromo-N-(2,4-dimethoxybenzyl)-N-(2-methylenebutyl)-5-(trifluoromethyl)benzenesulfonamide (39 g, 38.1 mmol) in dichloromethane (DCM) (300 mL) was added TFA (32 mL, 415 mmol) at 0° C. Anisole (10 mL, 92 mmol) was added and the reaction stirred at ambient temperature for 16 h. The reaction mixture was evaporated under reduced pressure, quenched with water (200 mL) and extracted with DCM (2×200 mL). The organic layer was dried over anhydrous Na$_2$SO$_4$ and filtered. The filtrate was evaporated under reduced pressure and the residue was purified by flash chromatography eluting with 2%, 4% then 8% petroleum ether/ethyl acetate to provide the title compound. (17 g, 96% yield). LC/MS m/z 369/371 (M−H)(M), 2.67 min (ret. time).

(S)-4-Ethyl-8-(trifluoromethyl)-2,3,4,5-tetrahydrobenzo[f][1,2]thiazepine 1,1-dioxide and (R)-4-ethyl-8-(trifluoromethyl)-2,3,4,5-tetrahydrobenzo[f][1,2]thiazepine 1,1-dioxide

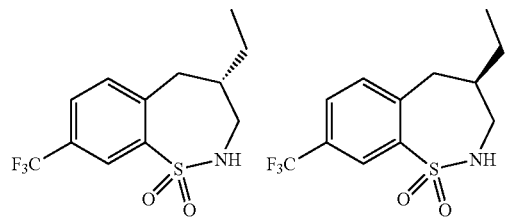 [SMILES: CC[C@@H]1CNS(=O)(=O)c2cc(C(F)(F)F)ccc2C1 ; CC[C@H]1CNS(=O)(=O)c2cc(C(F)(F)F)ccc2C1]

To a solution of 2-bromo-N-(2-methylenebutyl)-5-(trifluoromethyl)benzenesulfonamide (17.5 g, 45.1 mmol) in toluene (200 mL) was added AIBN (3.71 g, 22.57 mmol) and the reaction was heated to 70° C. Tri-n-butyltin hydride (36.4 mL, 135 mmol) was added and the reaction stirred at 110° C. for 16 h. The reaction mixture was cooled to ambient temperature and concentrated under reduced pressure. The residue was purified by flash chromatography eluting with EtOAc: Hexane (15:85) to provide the title compound as a racemate. (11.5 g, 79% yield). LC/MS m/z 292 (M−H), 2.54 min (ret. time). The compound was resolved by chiral SFC (Column: Lux Cellulose-2 30×250 mm, 5u; Co-solvent: 20% (100% IPA); 80% CO2, Flowrate: 90 g/min; Back pressure: 90Bar) to provide (S)-4-ethyl-8-(trifluoromethyl)-2,3,4,5-tetrahydrobenzo[f][1,2]thiazepine 1,1-dioxide (4.2 g, 36% yield). m/z 294 (M+H)$^+$, 3.29 min (ret. time), (chiral SFC ret. time: 4.91 min) and (R)-4-ethyl-8-(trifluoromethyl)-2,3,4,5-tetrahydrobenzo[f][1,2]thiazepine 1,1-dioxide (3.8 g, 32% yield). LCMS m/z 294 (M+H)$^+$, 3.29 min (ret. time), (chiral SFC ret. time: 6.71 min).

Benzyl (S)-3-(4-(((S)-4-ethyl-1,1-dioxido-8-(trifluoromethyl)-4,5-dihydrobenzo[f][1,2]thiazepin-2(3H)-yl)methyl)-5-methylthiazol-2-y)-3-(1-ethyl-4-methyl-1H-benzo[d][1,2,3]triazol-5-yl)-2,2-dimethylpropanoate

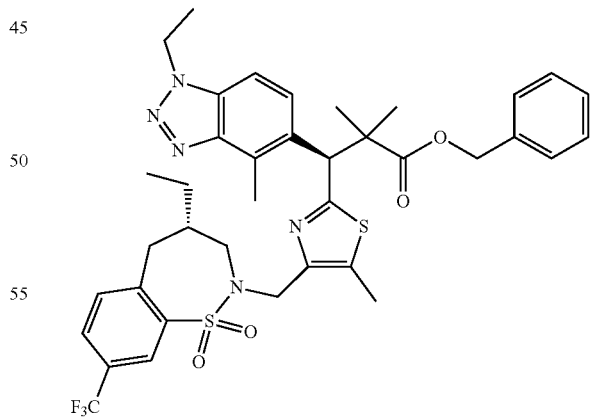

Benzyl (S)-3-(1-ethyl-4-methyl-1H-benzo[d][1,2,3]triazol-5-yl)-3-(4-(hydroxymethyl)-5-methylthiazol-2-yl)-2,2-dimethylpropanoate (102 mg, 0.213 mmol), (S)-4-ethyl-8-(trifluoromethyl)-2,3,4,5-tetrahydrobenzo[f][1,2]thiazepine 1,1-dioxide (125 mg, 0.426 mmol) and (E)-diazene-1,2-diylbis(piperidin-1-ylmethanone) (ADDP) (108 mg, 0.426 mmol) were combined and dissolved in tetrahydrofuran (THF) (8 mL). After all solids were dissolved, tri-n-butylphosphine (0.105 mL, 0.426 mmol) was added and the reaction stirred at ambient temperature for 18 h. The solvent was concentrated and the residue was purified by reverse phase preparative HPLC under neutral conditions to provide the title compound (0.147 g, 91% yield). LC/MS m/z 754 (M+H)+, 1.73 min (ret. time).

(S)-3-(4-(((S)-4-Ethyl-1,1-dioxido-8-(trifluoromethyl)-4,5-dihydrobenzo[f][1,2]thiazepin-2(3H)-yl)methyl)-5-methylthiazol-2-yl)-3-(1-ethyl-4-methyl-1H-benzo[d][1,2,3]triazol-5-yl)-2,2-dimethyl-N-(pyridin-3-yl)propanamide

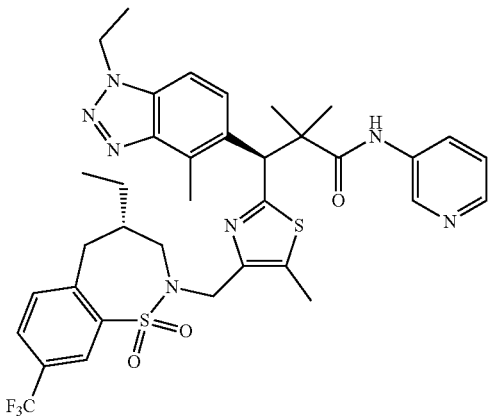 [SMILES: CC[C@H]1Cc2ccc(C(F)(F)F)cc2S(=O)(=O)N(Cc2nc([C@@H](c3ccc4c(nnn4CC)c3C)C(C)(C)C(=O)Nc3cccnc3)sc2C)C1]

To a solution of (S)-3-(4-(((S)-4-ethyl-1,1-dioxido-8-(trifluoromethyl)-4,5-dihydrobenzo[f][1,2]thiazepin-2(3H)-yl)methyl)-5-methylthiazol-2-yl)-3-(1-ethyl-4-methyl-1H-benzo[d][1,2,3]triazol-5-yl)-2,2-dimethylpropanoic acid (81 mg, 0.122 mmol) in isopropanol (2.00 mL) was added phenyl (E)-N-(tert-butyl)-N'-(pyridin-3-yl)carbamimidothioate (30.2 mg, 0.106 mmol) and ferric acetylacetonate (7.47 mg, 0.021 mmol). The vial was heated at 83° C. for 18 h. The solvent was concentrated and the residue was purified by reverse phase preparative HPLC under neutral conditions to provide the title compound (0.037 g, 47% yield). LC/MS m/z 740 (M+H)+, 1.16 min (ret. time).

Example 49

(S)-3-(4-(((S)-4-Ethyl-1,1-dioxido-8-(trifluoromethyl)-4,5-dihydrobenzo[f][1,2]thiazepin-2(3H)-yl)methyl)-5-methylthiazol-2-yl)-3-(1-ethyl-4-methyl-1H-benzo[d][1,2,3]triazol-5-yl)-2,2-dimethylpropanoic Acid

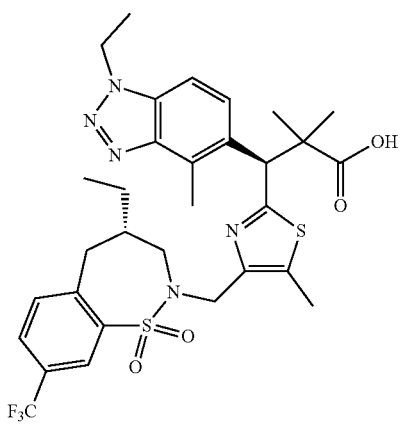 [SMILES: CC[C@H]1Cc2ccc(C(F)(F)F)cc2S(=O)(=O)N(Cc2nc([C@@H](c3ccc4c(nnn4CC)c3C)C(C)(C)C(=O)O)sc2C)C1]

A solution of benzyl (S)-3-(4-(((S)-4-ethyl-1,1-dioxido-8-(trifluoromethyl)-4,5-dihydrobenzo[f][1,2]thiazepin-2(3H)-yl)methyl)-5-methylthiazol-2-yl)-3-(1-ethyl-4-methyl-1H-benzo[d][1,2,3]triazol-5-yl)-2,2-dimethylpropanoate (0.147 g, 0.195 mmol) in methanol (10 mL) was flushed with nitrogen after which 5% Pd/C (0.021 g, 9.75 µmol) was added to the solution. The flask was evacuated and purged with hydrogen gas and stirred under a hydrogen balloon for 20 h. Additional 5% Pd/C (0.005 g, 2.349 µmol) was added and the reaction stirred for 2.5 h. The reaction was filtered with a filter disk and the solvent was concentrated. The residue was purified by reverse phase preparative HPLC under neutral conditions to provide the title compound (0.093 g, 71% yield). LC/MS m/z 664(M+H)+, 1.38 min (ret. time).

Example 50

(S)-3-(1-Ethyl-4-methyl-1H-benzo[d][1,2,3]triazol-5-yl)-2,2-dimethyl-3-(1-methyl-5-(((S)-4-methyl-1,1-dioxido-8-(trifluoromethyl)-4,5-dihydrobenzo[f][1,2]thiazepin-2(3H)-yl)methyl)-1H-pyrazol-3-yl)propanoic Acid

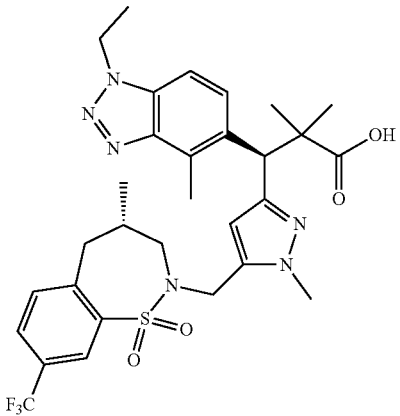 [SMILES: CCn1nnc2c(C)c([C@H](c3cc(CN4C[C@@H](C)Cc5ccc(C(F)(F)F)cc5S4(=O)=O)n(C)n3)C(C)(C)C(=O)O)ccc21]

Methyl (S)-3-(1-ethyl-4-methyl-1H-benzo[d][1,2,3]triazol-5-yl)-2,2-dimethyl-3-(1-methyl-5-(((S)-4-methyl-1,1-dioxido-8-(trifluoromethyl)-4,5-dihydrobenzo[f][1,2]thiazepin-2(3H)-yl)methyl)-1H-pyrazol-3-yl)propanoate

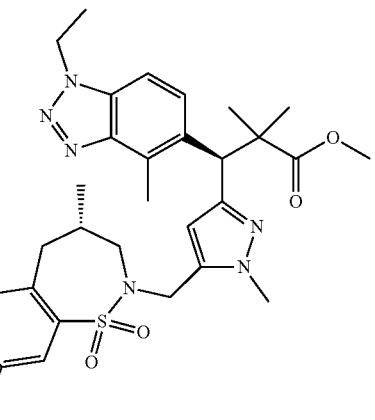

To a solution of methyl (S)-3-(1-ethyl-4-methyl-1H-benzo[d][1,2,3]triazol-5-yl)-3-(5-(hydroxymethyl)-1-methyl-1H-pyrazol-3-yl)-2,2-dimethylpropanoate (43 mg, 0.112 mmol) in tetrahydrofuran (THF) (4 mL) was added (S)-4-methyl-8-(trifluoromethyl)-2,3,4,5-tetrahydrobenzo[f][1,2]thiazepine 1,1-dioxide (62.3 mg, 0.223 mmol) and (E)-diazene-1,2-diylbis(piperidin-1-ylmethanone) (ADDP) (56.3 mg, 0.223 mmol). After all solids were dissolved, the solution was degassed and purged with argon after which tri-n-butylphosphine (0.055 mL, 0.223 mmol) was added and the reaction stirred at ambient temperature for 41 h. The solvent was concentrated and the residue was purified by flash chromatography eluting with 0-90% EtOAc/Hexane to provide the title compound. (0.061 g, 64% yield). LC/MS m/z 647 (M+H)⁺, 1.31 min (ret. time).

(S)-3-(1-Ethyl-4-methyl-1H-benzo[d][1,2,3]triazol-5-yl)-2,2-dimethyl-3-(1-methyl-5-(((S)-4-methyl-1,1-dioxido-8-(trifluoromethyl)-4,5-dihydrobenzo[f][1,2]thiazepin-2(3H)-yl)methyl)-1H-pyrazol-3-yl) propanoic Acid

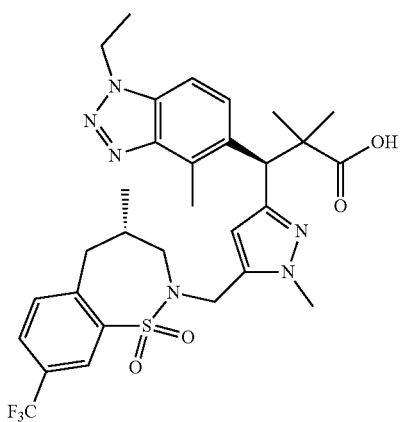 [SMILES: CCn1nnc2c(C)c([C@H](c3cc(CN4C[C@@H](C)Cc5ccc(C(F)(F)F)cc5S4(=O)=O)n(C)n3)C(C)(C)C(=O)O)ccc21]

To a solution of methyl (S)-3-(1-ethyl-4-methyl-1H-benzo[d][1,2,3]triazol-5-yl)-2,2-dimethyl-3-(1-methyl-5-(((S)-4-methyl-1,1-dioxido-8-(trifluoromethyl)-4,5-dihydrobenzo[f][1,2]thiazepin-2(3H)-yl)methyl)-1H-pyrazol-3-yl)propanoate (61 mg, 0.072 mmol) in tetrahydrofuran (THF) (2 mL), methanol (1 mL) and water (1 mL) in a microwave reaction vessel, was added LiOH (8.58 mg, 0.358 mmol) and the reaction was heated via microwave at 100° C. for 1 h. An additional portion of LiOH (8.58 mg, 0.358 mmol) was added and the reaction was heated via microwave at 140° C. for 3 h. The solvents were concentrated and the residue was suspended in acetonitrile and acidified with formic acid.

The solvent was concentrated. The residue was purified by reverse phase preparative HPLC under formic acid conditions to provide the title compound (0.035 g, 77% yield). LC/MS m/z 633 (M+H)⁺1.18 min (ret. time).

Example 51

(S)-3-(4-(((R)-4-Ethyl-1,1-dioxido-3,4-dihydro-2H-benzo[b][1,4,5]oxathiazepin-2-yl)methyl)-5-methyl-thiophen-2-yl)-3-(1-ethyl-4-methyl-1H-benzo[d][1,2,3]triazol-5-yl)-2,2-dimethyl-N-(pyridin-3-yl) propanamide

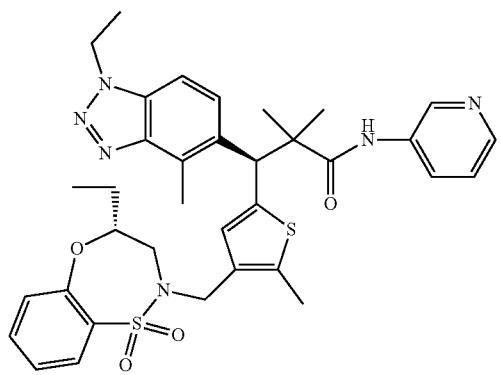 [SMILES: CC[C@@H]1CN(Cc2cc([C@@H](c3ccc4c(nnn4CC)c3C)C(C)(C)C(=O)Nc3cccnc3)sc2C)S(=O)(=O)c2ccccc2O1]

To a solution of (S)-3-(4-(((R)-4-ethyl-1,1-dioxido-3,4-dihydro-2H-benzo[b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoic acid (18.31 mg, 0.031 mmol) in isopropanol (2.00 mL) in a microwave reaction vessel as added phenyl (E)-N-(tert-butyl)-N'-(pyridin-3-yl)carbamimidothioate (12.70 mg, 0.044 mmol) and ferric acetylacetonate (0.542 mg, 1.534 µmol) and the reaction was heated via microwave at 120° C. for 2 h. The solvent was concentrated. The residue was purified by reverse phase preparative HPLC under neutral conditions to provide the title compound (0.011 g, 57% yield). LC/MS m/z 673 (M+H)⁺, 0.95 min (ret. time).

Example 52

(S)-3-(1-Ethyl-4-methyl-1H-benzo[d][1,2,3]triazol-5-yl)-2,2-dimethyl-3-(5-methyl-4-(((S)-4-methyl-1,1-dioxido-4,5-dihydrobenzo[f][1,2]thiazepin-2(3H)-yl)methyl)thiophen-2-yl)-N-(pyridin-3-yl) propanamide

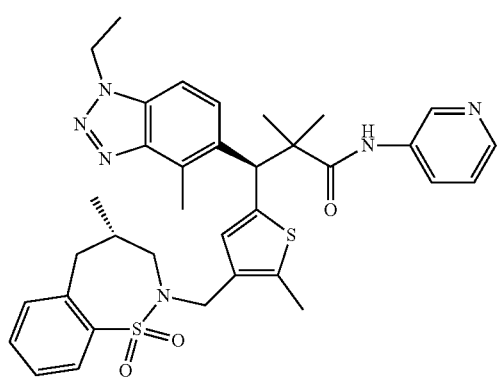 [SMILES: CCn1nnc2c(C)c([C@H](c3cc(CN4C[C@@H](C)Cc5ccccc5S4(=O)=O)c(C)s3)C(C)(C)C(=O)Nc3cccnc3)ccc21]

To a solution of (S)-3-(1-ethyl-4-methyl-1H-benzo[d][1,2,3]triazol-5-yl)-2,2-dimethyl-3-(5-methyl-4-(((S)-4- methyl-1,1-dioxido-4,5-dihydrobenzo[f][1,2]thiazepin-2(3H)-yl)methyl)thiophen-2-yl)propanoic acid (15.5 mg, 0.027 mmol) in isopropanol (2.00 mL) in a microwave reaction vessel as added phenyl (E)-N-(tert-butyl)-N'-(pyridin-3-yl)carbamimidothioate (11.05 mg, 0.039 mmol) and ferric acetylacetonate (0.471 mg, 1.334 µmol) and the reaction was heated via microwave at 120° C. for 2 h. The solvent was concentrated and the residue was purified by reverse phase preparative HPLC under neutral conditions to provide the title compound (0.012 g, 69% yield). LC/MS m/z 657 (M+H)$^+$, 0.97 min (ret. time).

Example 53

(R)-3-(5-Chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-fluoro-1H-benzo[d][1,2,3]triazol-5-yl)-2,2-dimethylpropanoic Acid

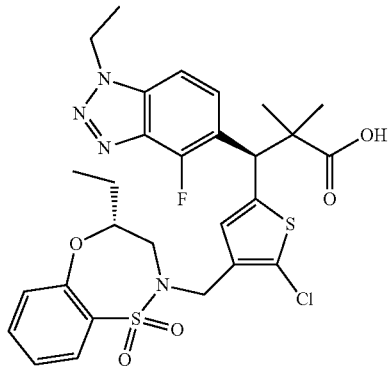 [SMILES: CC[C@@H]1CN(Cc2cc([C@@H](c3ccc4c(nnn4CC)c3F)C(C)(C)C(=O)O)sc2Cl)S(=O)(=O)c2ccccc2O1]

Benzyl (R)-3-(5-chloro-4-(hydroxymethyl)thiophen-2-yl)-3-(1-ethyl-4-fluoro-1H-benzo[d][1,2,3]triazol-5-yl)-2,2-dimethylpropanoate

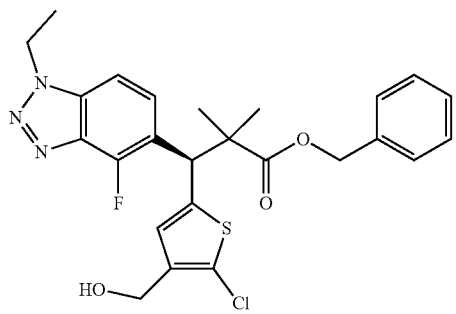 [SMILES: CCn1nnc2c(F)c([C@H](c3cc(CO)c(Cl)s3)C(C)(C)C(=O)OCc3ccccc3)ccc21]

4N HCl in 1,4 dioxane (2.00 mL, 8.00 mmol) was added to benzyl (R)-3-(5-chloro-4-(((4-methoxybenzyl)oxy)methyl)thiophen-2-yl)-3-(1-ethyl-4-fluoro-1H-benzo[d][1,2,3]triazol-5-yl)-2,2-dimethylpropanoate (0.143 g, 0.230 mmol) and the reaction stirred at ambient temperature for 2 h. The solvent was concentrated and the residue was purified by flash chromatography eluting with 0-50% EtOAc/Hexane to provide the title compound. (0.097 g, 82% yield). LC/MS m/z 502 (M+H)$^+$, 1.21 min(ret. time).

Benzyl (R)-3-(5-chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-fluoro-1H-benzo[d][1,2,3]triazol-5-yl)-2,2-dimethylpropanoate

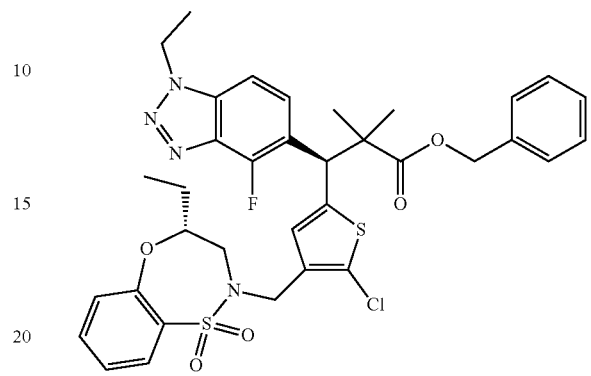

To a solution of benzyl (R)-3-(5-chloro-4-(hydroxymethyl)thiophen-2-yl)-3-(1-ethyl-4-fluoro-1H-benzo[d][1,2,3]triazol-5-yl)-2,2-dimethylpropanoate (50 mg, 0.100 mmol) in tetrahydrofuran (THF) (2 mL) was added (R)-4-ethyl-3,4-dihydro-2H-benzo[b][1,4,5]oxathiazepine 1,1-dioxide (45.3 mg, 0.199 mmol) and (E)-diazene-1,2-diylbis(piperidin-1-ylmethanone) (ADDP) (50.3 mg, 0.199 mmol). After all solids were dissolved, tri-n-butylphosphine (0.049 mL, 0.199 mmol) was added and the reaction stirred at ambient temperature for 20 h. Additional portions of (E)-diazene-1,2-diylbis(piperidin-1-ylmethanone) (ADDP) (0.00 mmol) and tri-n-butylphosphine (0.049 mL, 0.199 mmol) were added and stirred for 2.5 h. The solvent was concentrated and the residue was purified by reverse phase preparative HPLC under neutral conditions to provide the title compound (0.059 g, 83% yield). LC/MS m/z 711 (M+H)$^+$, 1.55 min (ret. time).

(R)-3-(5-Chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-fluoro-1H-benzo[d][1,2,3]triazol-5-yl)-2,2-dimethylpropanoic Acid

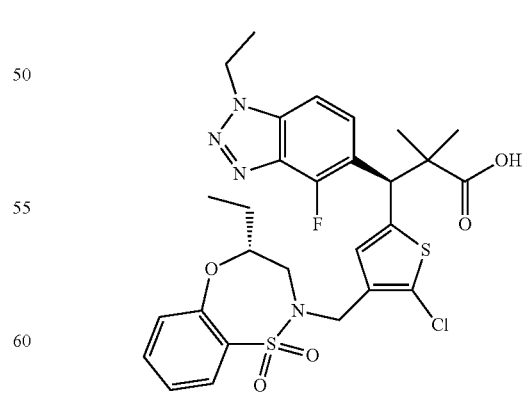

To a solution of benzyl (R)-3-(5-chloro-4-(((R)-4-ethyl-1,1-dioxido-3,4-dihydro-2H-benzo[b][1,4,5]oxathiazepin-2-yl)methyl)thiophen-2-yl)-3-(1-ethyl-4-fluoro-1H-benzo[d][1,2,3]triazol-5-yl)-2,2-dimethylpropanoate (59 mg, 0.083 mmol) in chloroform (3 mL) was added methanesulfonic acid (0.032 mL, 0.498 mmol) and the reaction stirred at ambient temperature for 3.5 h. Additional methanesulfonic acid (0.032 mL, 0.498 mmol) was added and the reaction stirred for 3 days. An additional portion of methanesulfonic acid (0.108 mL, 1.659 mmol) and stirred for 22 h. The solvent was concentrated and the residue was purified by reverse phase preparative HPLC under formic acid conditions to provide the title compound (0.011 g, 21% yield). LC/MS m/z 621 (M+H)+, 1.30 min (ret. time).

Example 54

(S)-3-(5-Chloro-4-(((R)-4-ethyl-1,1-dioxido-3,4-dihydro-2H-pyrido[2,3-b][1,4,5]oxathiazepin-2-yl)methyl)thiophen-2-yl)-3-(1-ethyl-4-methyl-1H-benzo[d][1,2,3]triazol-5-yl)-2,2-dimethylpropanoic Acid

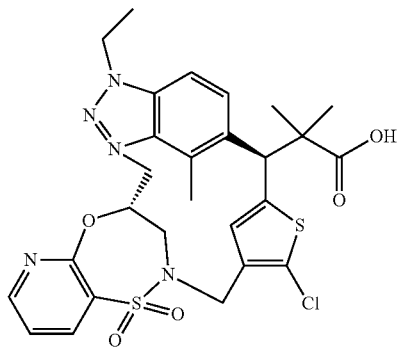

Methyl 3-(5-chloro-4-(((4-methoxybenzyl)oxy)methyl)thiophen-2-yl)-3-(1-ethyl-4-methyl-1H-benzo[d][1,2,3]triazol-5-yl)-2,2-dimethylpropanoate

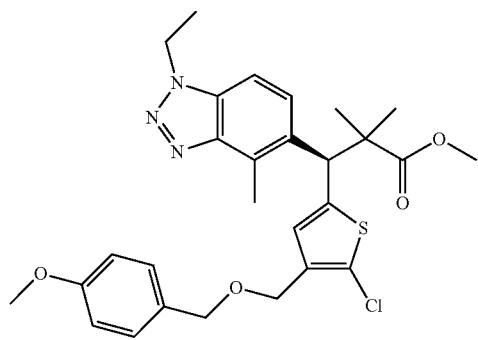

To a solution of (5-chloro-4-(((4-methoxybenzyl)oxy)methyl)thiophen-2-yl)(1-ethyl-4-methyl-1H-benzo[d][1,2,3]triazol-5-yl)methanol (750 mg, 1.638 mmol) in acetonitrile (10 mL) was added 2,2,2-trichloroacetonitrile (0.328 mL, 3.28 mmol), followed by 2,3,4,6,7,8,9,10-octahydropyrimido[1,2-a]azepine (12.47 mg, 0.082 mmol) and the reaction stirred at ambient temperature for 1 h. ((1-methoxy-2-methylprop-1-en-1-yl)oxy)trimethylsilane (0.832 mL, 4.09 mmol) was dissolved in acetonitrile (5.00 mL), and added to the reaction mixture via syringe. This addition was followed by 1,1,1-trifluoro-N-((trifluoromethyl)sulfonyl)methanesulfonamide (0.034 mL, 0.164 mmol) dissolved in acetonitrile and added via syringe. The reaction was stirred at ambient temperature for 1 h. The reaction was partitioned between saturated aqueous NH$_4$Cl and ethyl acetate. The aqueous layer was extracted with ethyl acetate (2×100 mL) and the combined organic phases were dried with MgSO$_4$. The solvent was concentrated and the residue was purified by flash chromatography eluting with 0-70% EtOAc/Hexane to provide the title compound. (0.650 g, 71% yield). LC/MS m/z 542 (M+H)$^+$, 1.38 min(ret. time).

(S)-Benzyl 3-(5-chloro-4-(hydroxymethyl)thiophen-2-yl)-3-(1-ethyl-4-methyl-1H-benzo[d][1,2,3]triazol-5-yl)-2,2-dimethylpropanoate

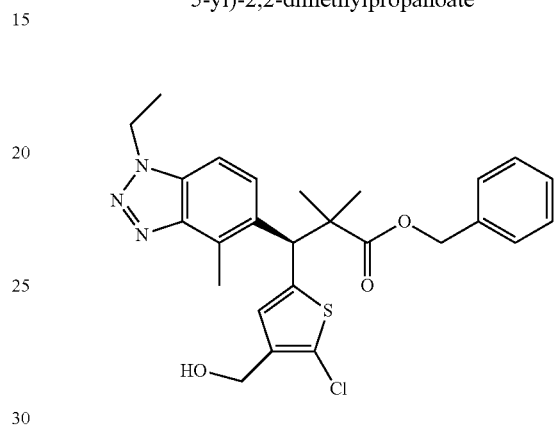

(S)-benzyl 3-(5-chloro-4-(((4-methoxybenzyl)oxy)methyl)thiophen-2-yl)-3-(1-ethyl-4-methyl-1H-benzo[d][1,2,3]triazol-5-yl)-2,2-dimethylpropanoate (260 mg, 0.421 mmol) was dissolved in acetonitrile (5.00 mL) and stirred with ceric ammonium nitrate (346 mg, 0.631 mmol) and water (1 mL) at 0° C. for 2 h. The reaction was diluted with EtOAc (100 mL) and water (50 mL), and the phases were separated. The aqueous layer was extracted with EtOAc (50 mL) and the combined EtOAc layers were washed with water (50 mL), saturated aqueous NaCl and dried with Na$_2$SO$_4$. The solvent was concentrated and the residue was purified by flash chromatography eluting with 0-100% EtOAc/Hexane to provide the title compound. (0.125 g, 59% yield). LC/MS m/z 498 (M+H)$^+$, 1.2 min (ret. time).

(S)-Benzyl 3-(5-chloro-4-(((R)-4-ethyl-1,1-dioxido-3,4-dihydro-2H-pyrido[2,3-b][1,4,5]oxathiazepin-2-yl)methyl)thiophen-2-yl)-3-(1-ethyl-4-methyl-1H-benzo[d][1,2,3]triazol-5-yl)-2,2-dimethylpropanoate

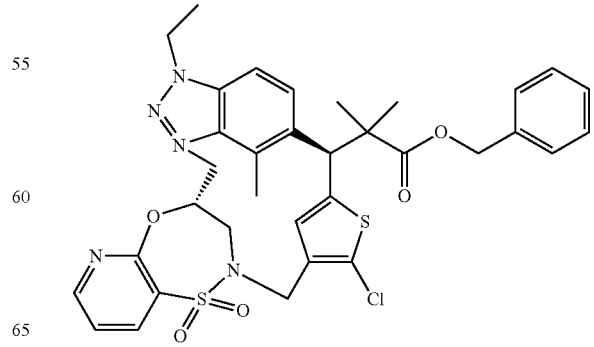

205

To a solution of (S)-benzyl 3-(5-chloro-4-(hydroxymethyl)thiophen-2-yl)-3-(1-ethyl-4-methyl-1H-benzo[d][1,2,3]triazol-5-yl)-2,2-dimethylpropanoate (61 mg, 0.122 mmol), (R)-4-ethyl-3,4-dihydro-2H-pyrido[2,3-b][1,4,5]oxathiazepine 1,1-dioxide (55.9 mg, 0.245 mmol) and (E)-diazene-1,2-diylbis(piperidin-1-ylmethanone) (61.8 mg, 0.245 mmol) in tetrahydrofuran (THF) (4 mL) was added tributylphosphine (0.061 mL, 0.245 mmol) and stirred for 1 h. The solvent was concentrated and the residue was purified by reverse phase preparative HPLC under neutral conditions to provide the title compound (0.075 g, 86% yield). LC/MS m/z 708 (M+H)$^+$, 1.38 min (ret. time).

(S)-3-(5-Chloro-4-(((R)-4-ethyl-1,1-dioxido-3,4-dihydro-2H-pyrido[2,3-b][1,4,5]oxathiazepin-2-yl)methyl)thiophen-2-yl)-3-(1-ethyl-4-methyl-1H-benzo[d][1,2,3]triazol-5-yl)-2,2-dimethylpropanoic Acid

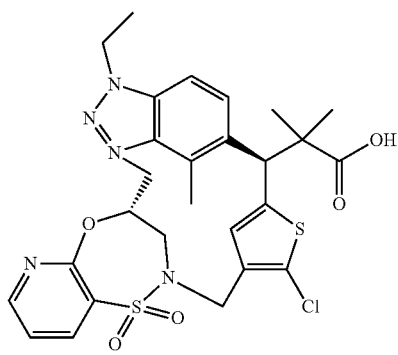

To a solution of (S)-benzyl 3-(5-chloro-4-(((R)-4-ethyl-1,1-dioxido-3,4-dihydro-2H-pyrido[2,3-b][1,4,5]oxathiazepin-2-yl)methyl)thiophen-2-yl)-3-(1-ethyl-4-methyl-1H-benzo[d][1,2,3]triazol-5-yl)-2,2-dimethylpropanoate (75 mg, 0.106 mmol) in chloroform (3 mL), was added methanesulfonic acid (0.041 mL, 0.635 mmol) and allowed to stir for 24 h.

The solvent was concentrated and the residue was purified by reverse phase preparative HPLC under neutral conditions to provide the title compound (0.010 g, 15% yield). LC/MS m/z 618 (M+H)+, 1.09 min (ret. time).

Example 55

(S)-3-(4-(((S)-4-Ethyl-1,1-dioxido-8-(trifluoromethyl)-4,5-dihydrobenzo[f][1,2]thiazepin-2(3H)-yl)methyl)-5-methylthiophen-2-yl)-3-(1-ethyl-4-methyl-1H-benzo[d][1,2,3]triazol-5-yl)-2,2-dimethylpropanoic Acid

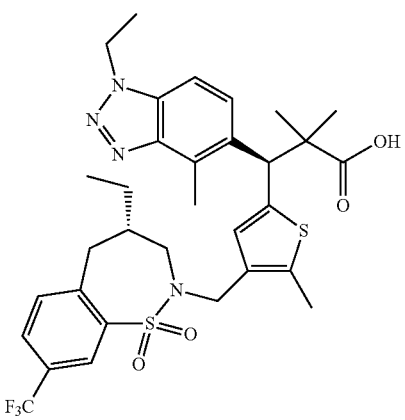 [SMILES: CC[C@H]1Cc2ccc(C(F)(F)F)cc2S(=O)(=O)N(Cc2cc([C@@H](c3ccc4c(nnn4CC)c3C)C(C)(C)C(=O)O)sc2C)C1]

206

Methyl 3-(1-ethyl-4-methyl-1H-benzo[d][1,2,3]triazol-5-yl)-3-(4-(((4-methoxybenzyl)oxy)methyl)-5-methylthiophen-2-yl)-2,2-dimethylpropanoate

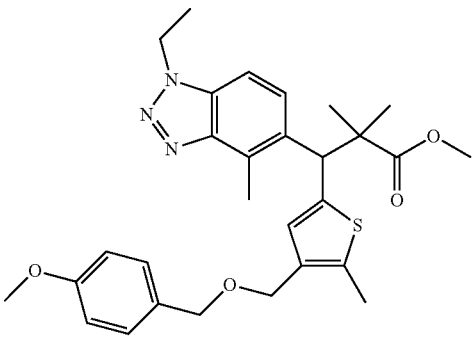

To a solution of (1-ethyl-4-methyl-1H-benzo[d][1,2,3]triazol-5-yl)(4-(((4-methoxybenzyl)oxy)methyl)-5-methylthiophen-2-yl)methanol (8.71 g, 19.91 mmol) and ((1-methoxy-2-methylprop-1-en-1-yl)oxy)trimethylsilane (12.13 mL, 59.7 mmol) in dichloromethane (DCM) (800 mL) in an oven dried flask, at −5° C. under nitrogen atmosphere, was added a solution of 1M titanium tetrachloride in DCM (19.91 mL, 19.91 mmol) diluted in dichloromethane (DCM) (125 mL), over 3 h and was stirred at −5° C. for an additional 30 min. The reaction was quenched with 300 mL of 5% NaHSO$_4$ while cooled. The layers were separated in a separatory funnel and the organic layer was washed with water (2×). The combined aqueous layers were washed with DCM (3×). The combined organics were washed with saturated NaHCO$_3$, brine and dried with MgSO$_4$. The solvent was concentrated and the residue was purified by flash chromatography eluting with 0-50% EtOAc/Hexane to provide the title compound. (6.26 g, 54% yield). LC/MS m/z 522 (M+H)+, 1.33 min (ret. time).

Benzyl (S)-3-(1-ethyl-4-methyl-1H-benzo[d][1,2,3]triazol-5-yl)-3-(4-(((4-methoxybenzyl)oxy)methyl)-5-methylthiophen-2-yl)-2,2-dimethylpropanoate and benzyl (R)-3-(1-ethyl-4-methyl-1H-benzo[d][1,2,3]triazol-5-yl)-3-(4-(((4-methoxybenzyl)oxy)methyl)-5-methylthiophen-2-yl)-2,2-dimethylpropanoate

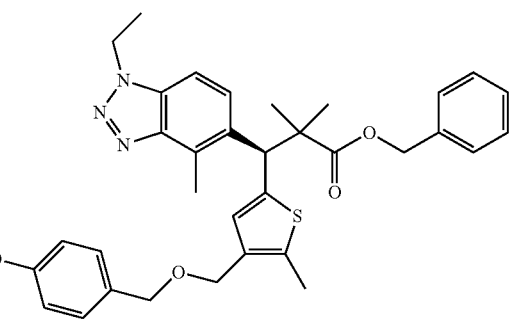

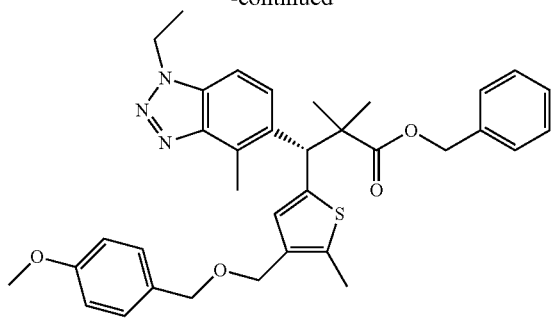

To a solution of methyl 3-(1-ethyl-4-methyl-1H-benzo[d][1,2,3]triazol-5-yl)-3-(4-(((4-methoxybenzyl)oxy)methyl)-5-methylthiophen-2-yl)-2,2-dimethylpropanoate (6.26 g, 12.00 mmol) dissolved in tetrahydrofuran (THF) (65 mL), methanol (65 mL), and water (32 mL) was added LiOH (1.437 g, 60.0 mmol) and the reaction was heated to 65$^C$ for 20 h. Additional LiOH (0.575 g, 24.00 mmol) was added and continued heating for 5.5 h. Another portion of LiOH (0.287 g, 12.00 mmol) was added and the reaction was heated to 75° C. for 2 h, at 65° C. for 24 h and then at ambient temperature for 2 days. The solvents were concentrated and the residue was dissolved in N,N-dimethylformamide (DMF) (60 mL) and benzyl bromide (5.71 mL, 48.0 mmol) was added and the reaction stirred for 1 h. The reaction was diluted with water and EtOAc and acidified with 1N HCl. The layers were separated and the aqueous layer was extracted with EtOAc (2×). The combined organics were washed with water, brine and dried with MgSO$_4$. The solvent was concentrated and the residue was purified by flash chromatography eluting with 0-40% EtOAc/Hexane to provide the title compound as a racemate. (6.17 g, 86% yield). LC/MS m/z 598 (M+H)+, 1.51 min (ret. time). The compound was resolved by chiral SFC (Column: Chiralpak IA 20×250 mm, 5u; Co-solvent: 30% EtOH; Flowrate: 50 g/min; Back pressure: 100Bar, 30° C.) to provide benzyl (S)-3-(1-ethyl-4-methyl-1H-benzo[d][1,2,3]triazol-5-yl)-3-(4-(((4-methoxybenzyl)oxy)methyl)-5-methylthiophen-2-yl)-2,2-dimethylpropanoate (2.74 g, 38% yield). m/z 598 (M+H)$^+$, 1.48 min (ret. time) (chiral SFC ret. time: 1.9 min) and benzyl (R)-3-(1-ethyl-4-methyl-1H-benzo[d][1,2,3]triazol-5-yl)-3-(4-(((4-methoxybenzyl)oxy)methyl)-5-methylthiophen-2-yl)-2,2-dimethylpropanoate (2.81 g, 39% yield). LCMS m/z 598 (M+H)+, 1.48 min (ret. time), (chiral SFC ret. time: 3.38 min).

Benzyl (S)-3-(1-ethyl-4-methyl-1H-benzo[d][1,2,3]triazol-5-yl)-3-(4-(hydroxymethyl)-5-methylthiophen-2-yl)-2,2-dimethylpropanoate

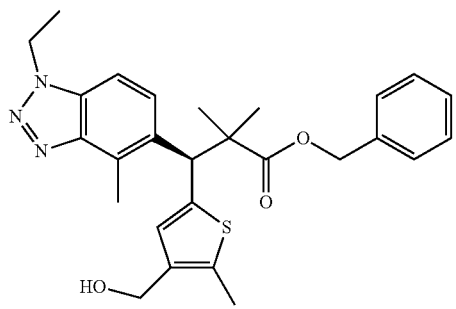 [SMILES: CCn1nnc2c(C)c([C@H](c3cc(CO)c(C)s3)C(C)(C)C(=O)OCc3ccccc3)ccc21]

To a solution of benzyl (S)-3-(1-ethyl-4-methyl-1H-benzo[d][1,2,3]triazol-5-yl)-3-(4-(((4-methoxybenzyl)oxy)methyl)-5-methylthiophen-2-yl)-2,2-dimethylpropanoate (2.64 g, 4.42 mmol) in dichloromethane (DCM) (60 mL) and water (5.5 mL) cooled to 0° C., was added DDQ (1.003 g, 4.42 mmol) portion wise over 10 min. and stirred at 0° C. for 2.5 h. Additional DDQ (0.100 g, 0.442 mmol) was added and the reaction stirred at 0° C. for 3.5 h. The reaction was warmed to ambient temperature and stirred for 1 h. It was then diluted with DCM and quenched with saturated NaHCO$_3$. The layers were separated and the aqueous layer was extracted with DCM (4×). Added brine to break up the emulsions. Washed combined organics with water, brine and dried with MgSO$_4$. The solvent was concentrated and the residue was purified by flash chromatography eluting with 0-40% EtOAc/Hexane to provide the title compound as a racemate. (1.81 g, 86% yield). LC/MS m/z 478 (M+H)+, 1.15 min (ret. time).

Benzyl (S)-3-(4-(((S)-4-ethyl-1,1-dioxido-8-(trifluoromethyl)-4,5-dihydrobenzo[f][1,2]thiazepin-2(3H)-yl)methyl)-5-methylthiophen-2-yl)-3-(1-ethyl-4-methyl-1H-benzo[d][1,2,3]triazol-5-yl)-2,2-dimethylpropanoate

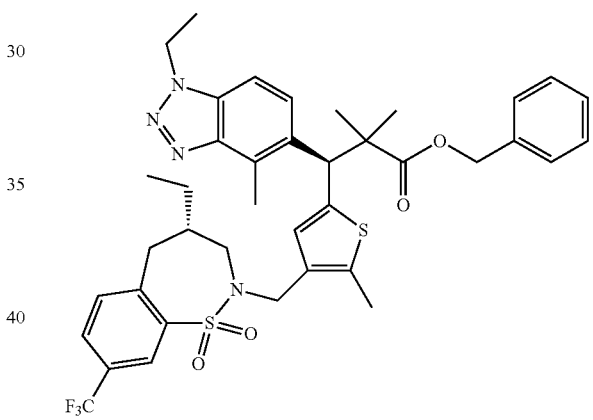

Benzyl (S)-3-(1-ethyl-4-methyl-1H-benzo[d][1,2,3]triazol-5-yl)-3-(4-(hydroxymethyl)-5-methylthiophen-2-yl)-2,2-dimethylpropanoate (104 mg, 0.218 mmol), (S)-4-ethyl-8-(trifluoromethyl)-2,3,4,5-tetrahydrobenzo[f][1,2]thiazepine 1,1-dioxide (63.9 mg, 0.218 mmol) and (E)-diazene-1,2-diylbis(piperidin-1-ylmethanone) (ADDP) (54.9 mg, 0.218 mmol) were combined and dissolved in tetrahydrofuran (THF) (7 mL). After all solids were dissolved, the reaction was flushed with nitrogen and tri-n-butylphosphine (0.054 mL, 0.218 mmol) was added and the reaction stirred at ambient temperature for 1 h. Additional tri-n-butylphosphine (0.054 mL, 0.218 mmol) was added and the reaction stirred for 30 min. Additional portions of (E)-diazene-1,2-diylbis(piperidin-1-ylmethanone) (ADDP) (54.9 mg, 0.218 mmol) followed by tri-n-butylphosphine (0.054 mL, 0.218 mmol) and (S)-4-ethyl-8-(trifluoromethyl)-2,3,4,5-tetrahydrobenzo[f][1,2]thiazepine 1,1-dioxide (63.9 mg, 0.218 mmol) were added and stirred for 1 h. The reaction was purified by flash chromatography eluting with 0-30% EtOAc/Hexane to provide the title compound as a racemate. (0.121 g, 75% yield). LC/MS m/z 753 (M+H)$^+$, min (ret. time).

(S)-3-(4-(((S)-4-Ethyl-1,1-dioxido-8-(trifluoromethyl)-4,5-dihydrobenzo[f][1,2]thiazepin-2(3H)-yl)methyl)-5-methylthiophen-2-yl)-3-(1-ethyl-4-methyl-1H-benzo[d][1,2,3]triazol-5-yl)-2,2-dimethylpropanoic Acid

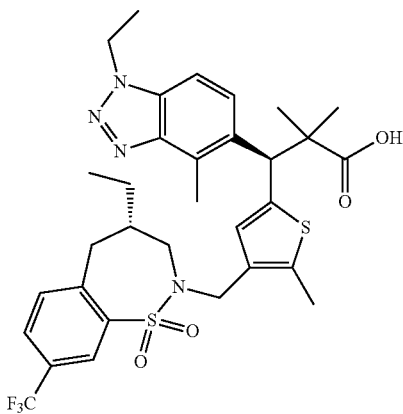 [SMILES: CC[C@H]1Cc2ccc(C(F)(F)F)cc2S(=O)(=O)N(Cc2cc([C@@H](c3ccc4c(nnn4CC)c3C)C(C)(C)C(=O)O)sc2C)C1]

A solution of benzyl (S)-3-(4-(((S)-4-ethyl-1,1-dioxido-8-(trifluoromethyl)-4,5-dihydrobenzo[f][1,2]thiazepin-2(3H)-yl)methyl)-5-methylthiophen-2-yl)-3-(1-ethyl-4-methyl-1H-benzo[d][1,2,3]triazol-5-yl)-2,2-dimethylpropanoate (0.125 g, 0.166 mmol) in methanol (8 mL) was flushed with nitrogen after which 5% Pd/C (0.035 g, 0.017 mmol) was added to the solution. The flask was evacuated and purged with hydrogen gas and stirred under a hydrogen balloon 18 h. The reaction was filtered through Celite and the solvent was concentrated. The residue was purified by reverse phase preparative HPLC under neutral conditions to provide the title compound (0.090 g, 82% yield). LC/MS m/z 663 (M+H)+, 1.38 min (ret. time).

Example 56

(S)-3-(5-Chloro-4-(((R)-4-ethyl-1,1-dioxido-3,4-dihydro-2H-pyrido[4,3-b][1,4,5]oxathiazepin-2-yl)methyl)thiophen-2-yl)-3-(1-ethyl-4-methyl-1H-benzo[d][1,2,3]triazol-5-yl)-2,2-dimethylpropanoic Acid

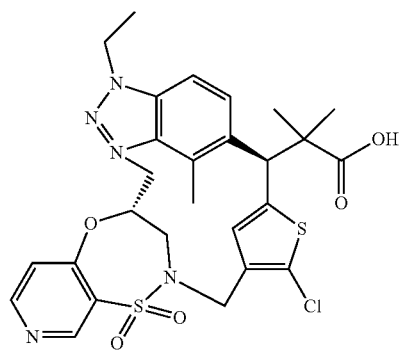

(S)-Benzyl 3-(5-chloro-4-(((R)-4-ethyl-1,1-dioxido-3,4-dihydro-2H-pyrido[4,3-b][1,4,5]oxathiazepin-2-yl)methyl)thiophen-2-yl)-3-(1-ethyl-4-methyl-1H-benzo[d][1,2,3]triazol-5-yl)-2,2-dimethylpropanoate

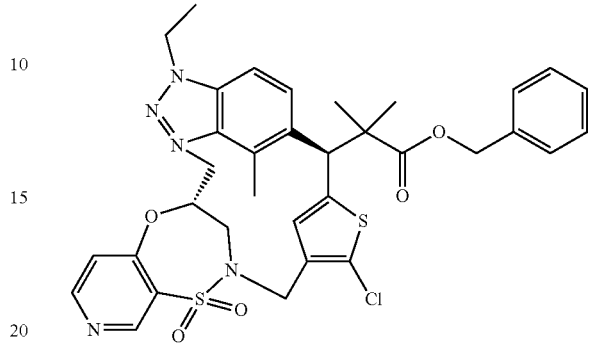

To a solution of (S)-benzyl 3-(5-chloro-4-(hydroxymethyl)thiophen-2-yl)-3-(1-ethyl-4-methyl-1H-benzo[d][1,2,3]triazol-5-yl)-2,2-dimethylpropanoate (64 mg, 0.129 mmol), (R)-4-ethyl-3,4-dihydro-2H-pyrido[4,3-b][1,4,5]oxathiazepine 1,1-dioxide (58.7 mg, 0.257 mmol) and (E)-diazene-1,2-diylbis(piperidin-1-ylmethanone) (64.8 mg, 0.257 mmol) in tetrahydrofuran (THF) (4 mL) was added tributylphosphine (0.064 mL, 0.257 mmol) and stirred for 1 h. The solvent was concentrated and the residue was purified by reverse phase preparative HPLC under neutral conditions to provide the title compound (0.070 g, 77% yield). LC/MS m/z 708(M+H)+, 1.38 (ret. time).

(S)-3-(5-Chloro-4-(((R)-4-ethyl-1,1-dioxido-3,4-dihydro-2H-pyrido[4,3-b][1,4,5]oxathiazepin-2-yl)methyl)thiophen-2-yl)-3-(1-ethyl-4-methyl-1H-benzo[d][1,2,3]triazol-5-yl)-2,2-dimethylpropanoic Acid

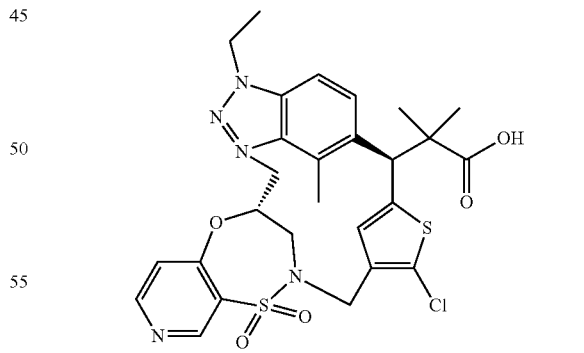

To a solution of (S)-benzyl 3-(5-chloro-4-(((R)-4-ethyl-1,1-dioxido-3,4-dihydro-2H-pyrido[4,3-b][1,4,5]oxathiazepin-2-yl)methyl)thiophen-2-yl)-3-(1-ethyl-4-methyl-1H-benzo[d][1,2,3]triazol-5-yl)-2,2-dimethylpropanoate (70 mg, 0.099 mmol) in chloroform (3 mL), was added methanesulfonic acid (0.039 mL 0.593 mmol) and stirred for 24 hours at ambient temperature. The solvent was concentrated and the residue was purified by reverse phase preparative HPLC under formic acid conditions to provide the title compound (0.006 g, 9.8% yield). LC/MS m/z 618(M+H)+ 1.09 (ret. time).

Example 57

(R)-3-(5-Chloro-4-(((S)-4-methyl-1,1-dioxido-8-(trifluoromethyl)-4,5-dihydrobenzo[f][1,2]thiazepin-2(3H)-yl)methyl)thiophen-2-yl)-3-(1-ethyl-4-fluoro-1H-benzo[d][1,2,3]triazol-5-yl)-2,2-dimethylpropanoic Acid

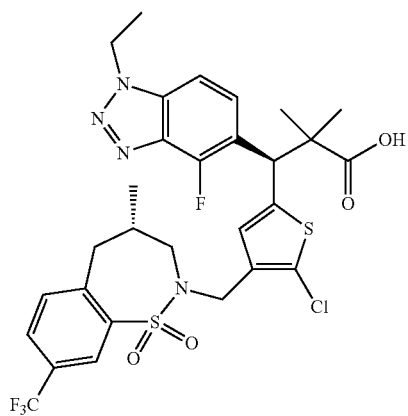 [SMILES: CCn1nnc2c(F)c([C@H](c3cc(CN4C[C@@H](C)Cc5ccc(C(F)(F)F)cc5S4(=O)=O)c(Cl)s3)C(C)(C)C(=O)O)ccc21]

Benzyl (R)-3-(5-chloro-4-(((S)-4-methyl-1,1-dioxido-8-(trifluoromethyl)-4,5-dihydrobenzo[f][1,2]thiazepin-2(3H)-yl)methyl)thiophen-2-yl)-3-(1-ethyl-4-fluoro-1H-benzo[d][1,2,3]triazol-5-yl)-2,2-dimethylpropanoate

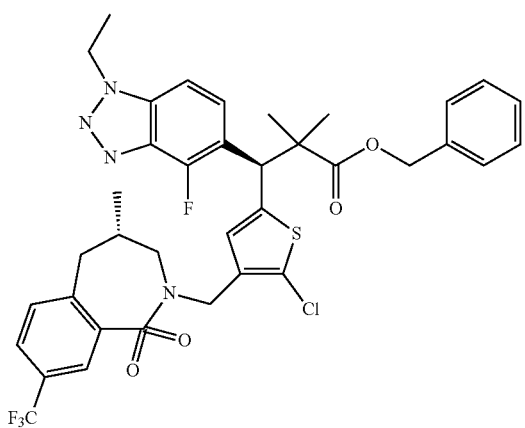

To a solution of benzyl (R)-3-(5-chloro-4-(hydroxymethyl)thiophen-2-yl)-3-(1-ethyl-4-fluoro-1H-benzo[d][1,2,3]triazol-5-yl)-2,2-dimethylpropanoate (31 mg, 0.062 mmol) in tetrahydrofuran (THF) (2 mL) was added (S)-4-methyl-8-(trifluoromethyl)-2,3,4,5-tetrahydrobenzo[f][1,2]thiazepine 1,1-dioxide (34.5 mg, 0.124 mmol) and (E)-diazene-1,2-diylbis(piperidin-1-ylmethanone) (ADDP) (31.2 mg, 0.124 mmol). After all solids were dissolved, tri-n-butylphosphine (0.030 mL, 0.124 mmol) was added and the reaction stirred at ambient temperature for 2 h. An additional portion of (E)-diazene-1,2-diylbis(piperidin-1-ylmethanone) (ADDP) (31.2 mg, 0.124 mmol) was added followed by the addition of tri-n-butylphosphine (0.030 mL, 0.124 mmol). The reaction was stirred for 4 h. Afterwards, an additional portion of (E)-diazene-1,2-diylbis(piperidin-1-ylmethanone) (ADDP) (31.2 mg, 0.124 mmol) was added followed by the addition of tri-n-butylphosphine (0.152 mL, 0.618 mmol) and stirred for 1 h. A white solid that formed was filtered through a filter cartridge and (E)-diazene-1,2-diylbis(piperidin-1-ylmethanone) (ADDP) (312 mg, 1.236 mmol) was added followed by tri-n-butylphosphine (0.152 mL, 0.618 mmol) and stirred for 18 h. The solvent was concentrated and the residue was purified by reverse phase preparative HPLC under formic acid conditions to provide the title compound (0.027 g, 57% yield). LC/MS m/z 762 (M+H)+, 1.60 min (ret. time).

(R)-3-(5-Chloro-4-(((S)-4-methyl-1,1-dioxido-8-(trifluoromethyl)-4,5-dihydrobenzo[f][1,2]thiazepin-2(3H)-yl)methyl)thiophen-2-yl)-3-(1-ethyl-4-fluoro-1H-benzo[d][1,2,3]triazol-5-yl)-2,2-dimethylpropanoic Acid

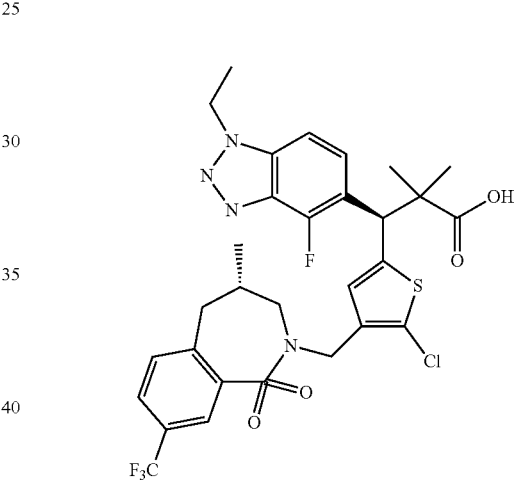

To a solution of benzyl (R)-3-(5-chloro-4-(((S)-4-methyl-1,1-dioxido-8-(trifluoromethyl)-4,5-dihydrobenzo[f][1,2]thiazepin-2(3H)-yl)methyl)thiophen-2-yl)-3-(1-ethyl-4-fluoro-1H-benzo[d][1,2,3]triazol-5-yl)-2,2-dimethylpropanoate (27 mg, 0.035 mmol) in chloroform (3 mL) was added methanesulfonic acid (0.014 mL, 0.212 mmol) and the reaction stirred at ambient temperature for 3.5 h. Additional methanesulfonic acid (0.014 mL, 0.212 mmol) was added and the reaction stirred for 3 days. Afterwards, an additional portion of methanesulfonic acid (0.046 mL, 0.707 mmol) was added and the reaction stirred for 22.5 h. The reaction was heated to 50° C. for 5 h. The solvent was concentrated and the residue was purified by reverse phase preparative HPLC under formic acid conditions to provide the title compound (0.0048 g, 19% yield). LC/MS m/z 673 (M+H)+, 1.40 min (ret. time).

Example 58

(R)-3-(4-(((R)-4-Ethyl-1,1-dioxido-3,4-dihydro-2H-pyrido[2,3-b][1,4,5]oxathiazepin-2-yl)methyl)-5-methylthiophen-2-yl)-5-(1-ethyl-1H-1,2,3-triazol-4-yl)-2,2-dimethylpentanoic Acid

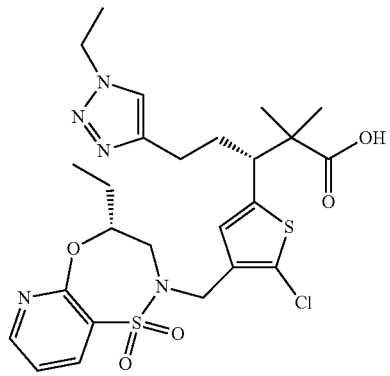 [SMILES: CC[C@@H]1CN(Cc2cc([C@H](CCc3cn(CC)nn3)C(C)(C)C(=O)O)sc2Cl)S(=O)(=O)c2cccnc2O1]

5-(Trimethylsilyl)pent-4-yn-1-ol

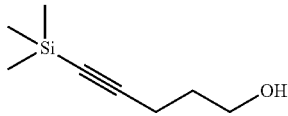

To a solution of n-butyllithium (319 mL, 797 mmol) at −60° C., was added a solution of pent-4-yn-1-ol (33.5 g, 398 mmol) in diethyl ether (500 mL) and stirred for 1 h. Trimethylchlorosilane (204 mL, 1593 mmol) was then added to the reaction mixture and left to stir for additional 15 min, after which the reaction mixture was warmed to 0° C. and quenched with water (50 mL). The aqueous layer was washed with 1N HCl (3×). The combined organic phases were washed with water (2×50 mL), brine (50 mL) and dried over $Na_2SO_4$, concentrated under reduced pressure to give 5-(trimethylsilyl)pent-4-yn-1-ol (30 g, 173 mmol, 43.4% yield). $^1H$ NMR (400 MHz, $CDCl_3$) δ 3.75 (d, J=6.0 Hz, 2H), 2.35 (t, J=6.9 Hz, 2H), 1.77 (dd, J=9.6, 3.4 Hz, 2H), 0.18-0.12 (m, 9H).

5-(Trimethylsilyl)pent-4-ynal

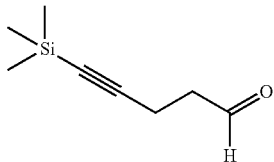

To a solution of 5-(trimethylsilyl)pent-4-yn-1-ol (5 g, 32.0 mmol) in dichloromethane (DCM) (100 mL) was added PCC (8.27 g, 38.4 mmol) and 8.27 g of silica gel. The reaction mixture was stirred at 20° C. for 16 h. The crude product was added to a silica gel column and was eluted with ether to give 5-(trimethylsilyl)pent-4-ynal (3.3 g, 19.25 mmol, 60.2% yield). 1H NMR (500 MHz, CDCl3) δ 9.79 (s, 1H), 2.68 (t, J=7.3 Hz, 2H), 2.33 (t, J=7.1 Hz, 2H), 0.14 (s, 9H).

1-(4-(((4-Methoxybenzyl)oxy)methyl)-5-methylthiophen-2-yl)-5-(trimethylsilyl)pent-4-yn-1-ol

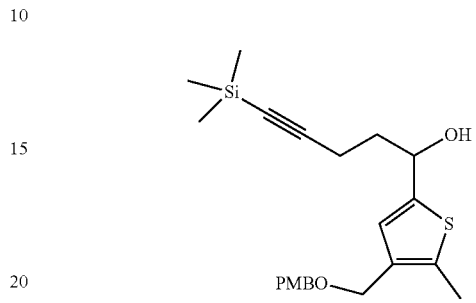

To a stirred solution of 5-bromo-3-(((4-methoxybenzyl)oxy)methyl)-2-methylthiophene (10 g, 30.6 mmol) in THF (80 mL) was added butyllithium (13.45 mL, 33.6 mmol, 2.5 M solution in Hexanes) dropwise at −78° C. under nitrogen. The mixture was stirred at −78° C. for 30 mins. 5-(trimethylsilyl)pent-4-ynal (8.25 g, 53.5 mmol) in 20 mL of THF was added slowly under nitrogen and stirred for 2 h at −78° C. The reaction was quenched by saturated $NH_4Cl$ (50 mL) and extracted with EtOAc (3×100 mL). The organic layer was washed with brine (100 mL) and dried over $Na_2SO_4$. After removing solvent, the residue was purified by flash chromatography eluting with 3:1 hexane:ethyl acetate to give the 1-(4-(((4-methoxybenzyl)oxy)methyl)-5-methylthiophen-2-yl)-5-(trimethylsilyl)pent-4-yn-1-ol (6.9 g, 9.94 mmol, 32.5% yield). LC/MS m/z 425 (M+Na)$^+$, 1.97 min (ret. time).

1-(4-(((4-Methoxybenzyl)oxy)methyl)-5-methylthiophen-2-yl)pent-4-yn-1-ol

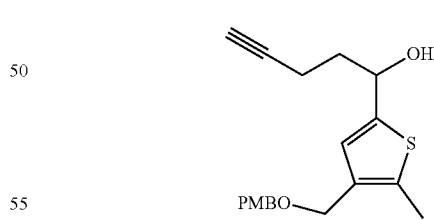

To a solution of 1-(4-(((4-methoxybenzyl)oxy)methyl)-5-methylthiophen-2-yl)-5-(trimethylsilyl)pent-4-yn-1-ol (6.9 g, 17.14 mmol) in methanol (30 mL), was added $K_2CO_3$ (9.47 g, 68.6 mmol). The reaction mixture was stirred at 20° C. for 2 h. Afterwards, water (50 mL) was added, and was extracted with ethyl acetate (3×50 mL). The organic layer was washed with brine (100 mL) and dried over $Na_2SO_4$. After filtrated and concentrated to give the title compound (5.1 g, 11.79 mmol, 68.8% yield). LC/MS m/z 313 (M-17)+, 1.75 min (ret. time).

Methyl 3-(4-(((4-methoxybenzyl)oxy)methyl)-5-methylthiophen-2-yl)-2,2-dimethylhept-6-ynoate

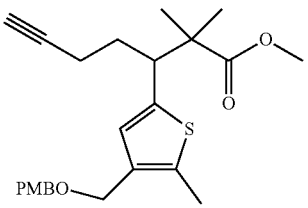

To a solution of 1-(4-(((4-methoxybenzyl)oxy)methyl)-5-methylthiophen-2-yl)pent-4-yn-1-ol (3.1 g, 9.38 mmol) in dry acetonitrile (60 mL) was slowly added DBU (1.414 mL, 9.38 mmol) and 2,2,2-trichloroacetonitrile (1.761 g, 12.20 mmol) under $N_2$ protection at 20° C. The mixture was stirred at 20° C. for 30 min. ((1-methoxy-2-methylprop-1-en-1-yl)oxy)trimethylsilane (4.09 g, 23.45 mmol) was added into reaction, subsequently 1,1,1-trifluoro-N-((trifluoromethyl)sulfonyl) methanesulfonamide (0.158 g, 0.563 mmol) was added into the reaction under $N_2$ protection. The mixture was stirred at 20° C. for 16 h. The reaction was quenched with $H_2O$ (50 mL). The mixture was extracted with ethyl acetate (3×150 mL) and the organic layer was washed with brine (200 mL) and dried over $Na_2SO_4$. The solvent was removed and the residue was purified by flash chromatography eluting with 4:1 petroleum ether:EtOAc to give the title compound. (1.5 g, 3.51 mmol, 37.4% yield). LC/MS m/z 437 (M-23)+, 1.98 min (ret. time).

Methyl 5-(1-ethyl-1H-1,2,3-triazol-4-yl)-3-(4-(((4-methoxybenzyl)oxy)methyl)-5-methylthiophen-2-yl)-2,2-dimethylpentanoate

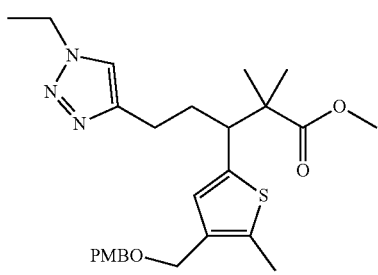

To a solution of methyl 3-(4-(((4-methoxybenzyl)oxy)methyl)-5-methylthiophen-2-yl)-2,2-dimethylhept-6-ynoate (2.5 g, 6.03 mmol) in tetrahydrofuran (THF) (50 mL) and water (30 mL) was slowly added sodium azide (1.176 g, 18.09 mmol), iodoethane (2.82 g, 18.09 mmol), copper(I) iodide (0.230 g, 1.206 mmol) and sodium bicarbonate (1.520 g, 18.09 mmol) under nitrogen. The reaction mixture was stirred at 70° C. for 16 h. The reaction was quenched with $H_2O$ (30 mL). The mixture was extracted with ethyl acetate (3×50 mL) and the organic layer was washed with brine (80 mL) and dried over $Na_2SO_4$. The solvent was removed and the residue was purified by flash chromatography eluting with 2:1 petroleum ether:EtOAc to give the title compound. (1.8 g, 3.52 mmol, 58.4% yield). LC/MS m/z 486 (M+H)+, 1.84 min (ret. time).

Benzyl 5-(1-ethyl-1H-1,2,3-triazol-4-yl)-3-(4-(((4-methoxybenzyl)oxy)methyl)-5-methylthiophen-2-yl)-2,2-dimethylpentanoate

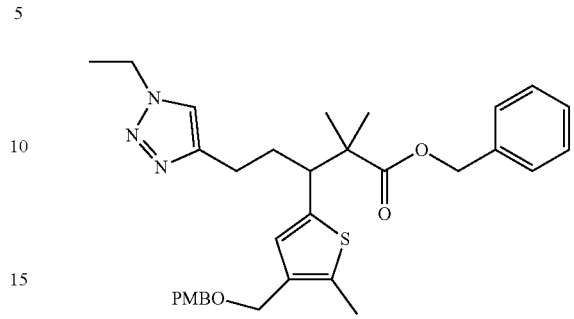

To a solution of methyl 5-(1-ethyl-1H-1,2,3-triazol-4-yl)-3-(4-(((4-methoxybenzyl)oxy)methyl)-5-methylthiophen-2-yl)-2,2-dimethylpentanoate (1.8 g, 3.71 mmol) in tetrahydrofuran (THF) (10 mL)/methanol (10.00 mL) was added LiOH (0.444 g, 18.53 mmol) in water (10.00 mL) The reaction mixture was stirred at 100° C. for 16 h. The solvent was removed. The residue was dissolved in N,N-dimethylformamide (DMF) (20 mL) and (bromomethyl)benzene (2.54 g, 14.83 mmol) was added. The reaction mixture was stirred at 70° C. for 16 h. Then $H_2O$ (20 mL) was added, the mixture was extracted with ethyl acetate (3×80 mL). The combined organic layers were dried over $Na_2SO_4$ and evaporated. The residue was purified by flash chromatography eluting with 3:1 petroleum ether:EtOAc to give the title compound as a racemate. (1 g, 1.780 mmol, 48.0% yield). LC/MS m/z 562 (M+H)+, 1.95 min (ret. time).

Benzyl (S)-5-(1-ethyl-1H-1,2,3-triazol-4-yl)-3-(4-(((4-methoxybenzyl)oxy)methyl)-5-methylthiophen-2-yl)-2,2-dimethylpentanoate and benzyl (R)-5-(1-ethyl-1H-1,2,3-triazol-4-yl)-3-(4-(((4-methoxybenzyl)oxy)methyl)-5-methylthiophen-2-yl)-2,2-dimethylpentanoate

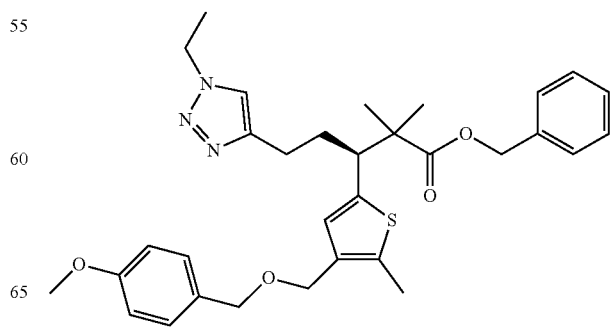

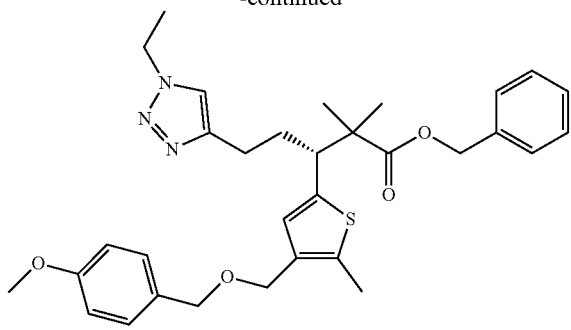

Racemic benzyl 5-(1-ethyl-1H-1,2,3-triazol-4-yl)-3-(4-(((4-methoxybenzyl)oxy)methyl)-5-methylthiophen-2-yl)-2,2-dimethylpentanoate was resolved by chiral SFC (Column: Chiralpak AY 20×250 mm, 5u; Co-solvent: 30% IPA; Flowrate: 50 g/min; Back pressure: 100Bar, 30° C.) to provide Benzyl (S)-5-(1-ethyl-1H-1,2,3-triazol-4-yl)-3-(4-(((4-methoxybenzyl)oxy)methyl)-5-methylthiophen-2-yl)-2,2-dimethylpentanoate (0.400 g, 100% pure). m/z 562 (M+H)+, 1.42 min(ret. time) (chiral SFC ret. time: 2.8 min) and benzyl (R)-5-(1-ethyl-1H-1,2,3-triazol-4-yl)-3-(4-(((4-methoxybenzyl)oxy)methyl)-5-methylthiophen-2-yl)-2,2-dimethylpentanoate (0.428 g, 100% pure). LCMS m/z 562 (M+H)$^+$, 1.41 min(ret. time), (chiral SFC ret. time: 3.85 min).

Benzyl (R)-5-(1-ethyl-1H-1,2,3-triazol-4-yl)-3-(4-(hydroxymethyl)-5-methylthiophen-2-yl)-2,2-dimethylpentanoate

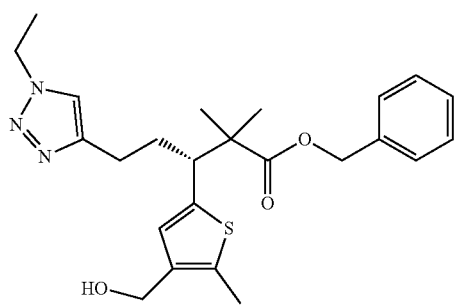 [SMILES: CCn1cc(CC[C@@H](c2cc(CO)c(C)s2)C(C)(C)C(=O)OCc2ccccc2)nn1]

To a solution of benzyl (R)-5-(1-ethyl-1H-1,2,3-triazol-4-yl)-3-(4-(((4-methoxybenzyl)oxy)methyl)-5-methylthiophen-2-yl)-2,2-dimethylpentanoate (0.428 g, 0.762 mmol) in dichloromethane (DCM) (87 mL) was added DDQ (0.173 g, 0.762 mmol) at ambient temperature. Water (8.66 mL) was then added to reaction and the reaction stirred at ambient temperature for 23 h. Additional DDQ (0.043 g, 0.190 mmol) was added and the reaction stirred at ambient temperature for 2 h. The reaction was quenched with saturated NaHCO$_3$. The layers were separated and aqueous layer was extracted with DCM (3×). The combined organics were washed with water, brine, dried with MgSO$_4$. The solvent was concentrated and the residue was purified by flash chromatography eluting with 0-80% EtOAc/Hexane to provide the title compound. (0.190 g, 56% yield). LC/MS m/z 442 (M+H)$^+$, 1.03 min (ret. time).

Benzyl (R)-3-(4-(((R)-4-ethyl-1,1-dioxido-3,4-dihydro-2H-pyrido[2,3-b][1,4,5]oxathiazepin-2-yl)methyl)-5-methylthiophen-2-yl)-5-(1-ethyl-1H-1,2,3-triazol-4-yl)-2,2-dimethylpentanoate

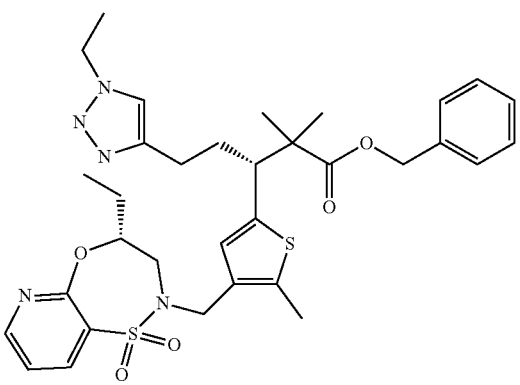 [SMILES: CC[C@@H]1CN(Cc2cc([C@H](CCC3=CN(CC)NN3)C(C)(C)C(=O)OCc3ccccc3)sc2C)S(=O)(=O)c2cccnc2O1]

To a solution of benzyl (R)-5-(1-ethyl-1H-1,2,3-triazol-4-yl)-3-(4-(hydroxymethyl)-5-methylthiophen-2-yl)-2,2-dimethylpentanoate (0.064 g, 0.145 mmol) in tetrahydrofuran (THF) (3.00 mL) was added (R)-4-ethyl-3,4-dihydro-2H-pyrido[2,3-b][1,4,5]oxathiazepine 1,1-dioxide (0.066 g, 0.290 mmol) and (E)-diazene-1,2-diylbis(piperidin-1-yl-methanone) (ADDP) (0.073 g, 0.290 mmol). The reaction was evacuated and purged with nitrogen and tri-n-butylphosphine (0.072 mL, 0.290 mmol) was added and the reaction stirred at ambient temperature for 18 h. The solvent was concentrated and the residue was purified by reverse phase preparative HPLC under neutral conditions to provide the title compound (0.055 g, 59% yield). LC/MS m/z 652 (M+H)$^+$, 1.28 min (ret. time).

(R)-3-(4-(((R)-4-Ethyl-1,1-dioxido-3,4-dihydro-2H-pyrido[2,3-b][1,4,5]oxathiazepin-2-yl)methyl)-5-methylthiophen-2-yl)-5-(1-ethyl-1H-1,2,3-triazol-4-yl)-2,2-dimethylpentanoic Acid

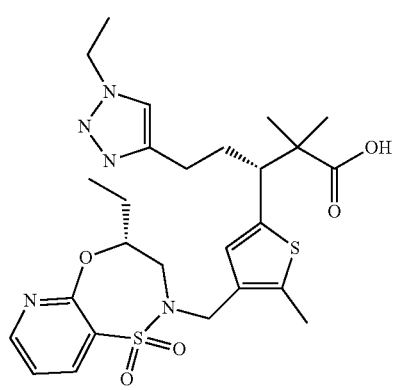 [SMILES: CC[C@@H]1CN(Cc2cc([C@H](CCC3=CN(CC)NN3)C(C)(C)C(=O)O)sc2C)S(=O)(=O)c2cccnc2O1]

A solution of benzyl (R)-3-(4-(((R)-4-ethyl-1,1-dioxido-3,4-dihydro-2H-pyrido[2,3-b][1,4,5]oxathiazepin-2-yl)methyl)-5-methylthiophen-2-yl)-5-(1-ethyl-1H-1,2,3-triazol-4-yl)-2,2-dimethylpentanoate (58.8 mg, 0.090 mmol) in methanol (5 mL), was purged with nitrogen and 5% Pd/C (19.20 mg, 9.02 µmol) was added. The reaction was evacuated and purged with hydrogen and stirred under a hydrogen balloon for 2 h. The reaction was filtered through a filter cartridge. The solvent was concentrated and the residue was purified by reverse phase preparative HPLC under formic acid conditions to provide the title compound (0.034 g, 68% yield). LC/MS m/z 562 (M+H)+, 0.96 min (ret. time).

Example 59

(S)-3-(4-(((R)-4-Ethyl-1,1-dioxido-3,4-dihydro-2H-pyrido[2,3-b][1,4,5]oxathiazepin-2-yl)methyl)-5-methylthiophen-2-yl)-5-(1-ethyl-1H-1,2,3-triazol-4-yl)-2,2-dimethylpentanoic Acid

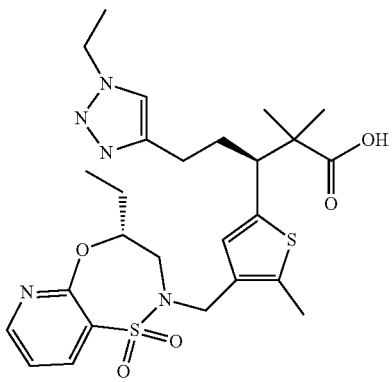 [SMILES: CC[C@@H]1CN(Cc2cc([C@@H](CCC3=CN(CC)NN3)C(C)(C)C(=O)O)sc2C)S(=O)(=O)c2cccnc2O1]

Benzyl (S)-5-(1-ethyl-1H-1,2,3-triazol-4-yl)-3-(4-(hydroxymethyl)-5-methylthiophen-2-yl)-2,2-dimethylpentanoate

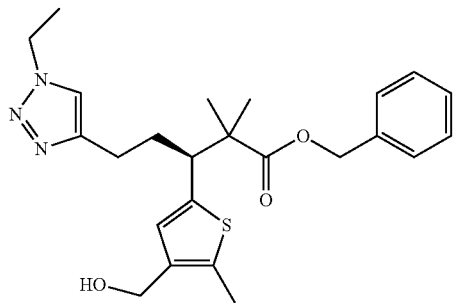 [SMILES: CCn1cc(CC[C@H](c2cc(CO)c(C)s2)C(C)(C)C(=O)OCc2ccccc2)nn1]

To a solution of benzyl (S)-5-(1-ethyl-1H-1,2,3-triazol-4-yl)-3-(4-(((4-methoxybenzyl)oxy)methyl)-5-methylthiophen-2-yl)-2,2-dimethylpentanoate (0.400 g, 0.712 mmol) in dichloromethane (DCM) (81 mL) was added DDQ (0.162 g, 0.712 mmol) at ambient temperature. Water (8.09 mL) was then added to reaction and the reaction stirred at ambient temperature for 18 h. The reaction was quenched with saturated NaHCO₃. The layers were separated and aqueous layer was extracted with DCM (4×). The combined organics were washed with water (2×), brine, and dried with MgSO₄. The solvent was concentrated and the residue was purified by flash chromatography eluting with 0-40% 3:1 EtOAc:EtOH/Hexane to provide the title compound. (0.280 g, 66% yield). LC/MS m/z 442 (M+H)+, 1.03 min (ret. time).

Benzyl (S)-3-(4-(((R)-4-ethyl-1,1-dioxido-3,4-dihydro-2H-pyrido[2,3-b][1,4,5]oxathiazepin-2-yl)methyl)-5-methylthiophen-2-yl)-5-(1-ethyl-1H-1,2,3-triazol-4-yl)-2,2-dimethylpentanoate

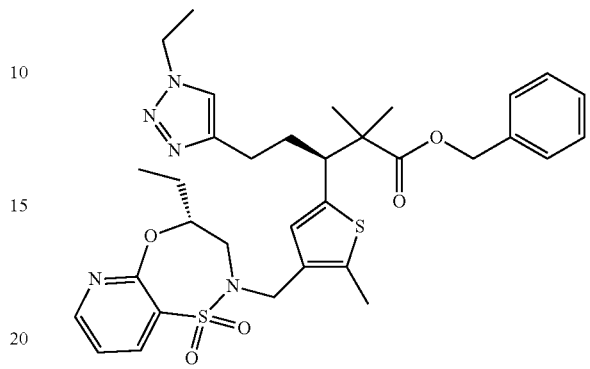

To a solution of benzyl (S)-5-(1-ethyl-1H-1,2,3-triazol-4-yl)-3-(4-(hydroxymethyl)-5-methylthiophen-2-yl)-2,2-dimethylpentanoate (0.070 g, 0.159 mmol) in tetrahydrofuran (THF) (3.00 mL) was added (R)-4-ethyl-3,4-dihydro-2H-pyrido[2,3-b][1,4,5]oxathiazepine 1,1-dioxide (0.072 g, 0.317 mmol) and (E)-diazene-1,2-diylbis(piperidin-1-yl-methanone) (ADDP) (0.080 g, 0.317 mmol). The reaction was evacuated and purged with nitrogen and tri-n-butylphosphine (0.078 mL, 0.317 mmol) was added and the reaction stirred at ambient temperature for 18 h. The solvent was concentrated and the residue was purified by reverse phase preparative HPLC under neutral conditions to provide the title compound (0.083 g, 81% yield). LC/MS m/z 652 (M+H)+, 1.25 min (ret. time).

(S)-3-(4-(((R)-4-Ethyl-1,1-dioxido-3,4-dihydro-2H-pyrido[2,3-b][1,4,5]oxathiazepin-2-yl)methyl)-5-methylthiophen-2-yl)-5-(1-ethyl-1H-1,2,3-triazol-4-yl)-2,2-dimethylpentanoic Acid

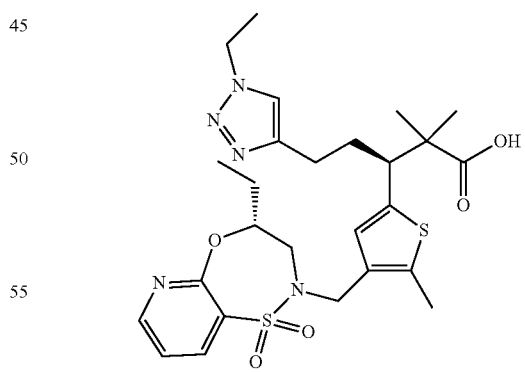

A solution of benzyl (S)-3-(4-(((R)-4-ethyl-1,1-dioxido-3,4-dihydro-2H-pyrido[2,3-b][1,4,5]oxathiazepin-2-yl)methyl)-5-methylthiophen-2-yl)-5-(1-ethyl-1H-1,2,3-triazol-4-yl)-2,2-dimethylpentanoate (48.2 mg, 0.074 mmol) in methanol (5 mL), was purged with nitrogen and 5% Pd/C (15.74 mg, 7.39 μmol) was added. The reaction was evacuated and purged with hydrogen and stirred under a hydrogen balloon for 2 h. The reaction was filtered through a cartridge filter and the solvent was concentrated. The residue was purified by reverse phase preparative HPLC under formic acid conditions to provide the title compound (0.035 g, 86% yield). LC/MS m/z 562 (M+H)⁺, 0.98 min (ret. time).

Example 60

(S)-3-(4-(((R)-2-Ethyl-2,3-dihydropyrido[2,3-f][1,4]oxazepin-4(5H)-yl)methyl)-5-methylthiophen-2-yl)-3-(1-ethyl-4-methyl-1H-benzo[d][1,2,3]triazol-5-yl)-2,2-dimethylpropanoic Acid

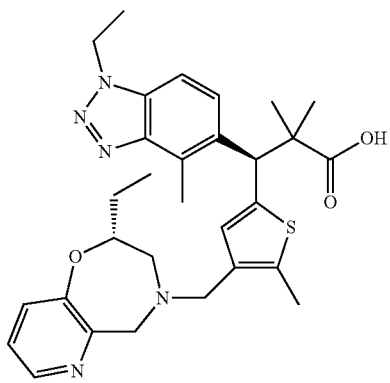 [SMILES: CC[C@@H]1CN(Cc2cc([C@@H](c3ccc4c(nnn4CC)c3C)C(C)(C)C(=O)O)sc2C)Cc2ncccc2O1]

(R)-1-Azidobutan-2-ol

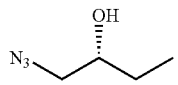

To a round bottom flask equipped with a reflux condenser was added (R)-2-ethyloxirane (26.0 g, 361 mmol), sodium azide (28.1 g, 433 mmol) and ammonium chloride (23.15 g, 433 mmol) followed by a solution of ethanol (200 mL) and water (200 mL). The reaction mixture was heated at 100° C. for 24 hr. The reaction mixture was cooled, the ethanol removed under reduced pressure and the residual aqueous layer extracted with diethyl ether (3×250 mL). The organic extracts were combined, washed with brine, dried over sodium sulfate, filtered and the solvent evaporated under reduced pressure to afford an oil. The oil was purified by silica gel chromatography (0-10% MeOH/DCM) to afford (R)-1-azidobutan-2-ol (19.8 g, 172 mmol, 47.7% yield). ¹H NMR (CHCl₃-d) δ: 3.64-3.76 (m, 1H), 3.35-3.46 (m, 1H), 3.20-3.34 (m, 1H), 2.19 (s, 1H), 1.47-1.60 (m, 2H), 0.90-1.06 (m, 3H)

(R)-1-Aminobutan-2-ol

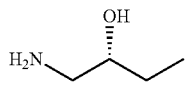

To a solution of (R)-1-azidobutan-2-ol (19.80 g, 172 mmol) in ethanol (250 mL) was added 10% palladium on carbon (1.830 g, 17.20 mmol) and the suspension was placed under a hydrogen atmosphere for 72 hr. Additional 10% palladium on carbon (1.830 g, 17.20 mmol) was added at 24 and 48 hr time points. The reaction mixture was filtered through Celite and then evaporated under reduced pressure to afford a light yellow oil (R)-1-aminobutan-2-ol (13.5 g, 151 mmol, 88% yield). ¹H NMR (CHCl₃-d) δ: 3.43 (m, 1H), 2.77 (m, 1H), 2.64 (br. s., 3H), 2.52 (m, 1H), 1.36-1.48 (m, 2H), 0.87-0.96 (m, 3H).

(R)-1-(((3-Fluoropyridin-2-yl)methyl)amino)butan-2-ol

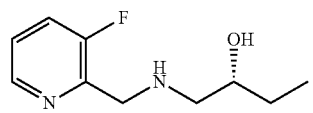

To a solution of (R)-1-aminobutan-2-ol (3.70 g, 41.5 mmol) in methanol (150 mL) was added 3-fluoropicolinaldehyde (4.67 g, 37.4 mmol) followed by magnesium sulfate (4.50 g, 37.4 mmol) and the reaction mixture was stirred at 0° C. for 1 hr. The reaction mixture was filtered through Celite and washed with methanol (300 mL). Sodium borohydride (1.413 g, 37.4 mmol) was added in two portions to the filtrate and the reaction mixture was stirred at ambient temperature for 30 min. The reaction mixture was quenched with 10% sodium bicarbonate solution and the methanol evaporated under reduced pressure. The remaining aqueous phase was extracted with ethyl acetate (3×125 mL) and the combined organic extracts were washed with brine, dried over sodium sulfate, filtered and the solvent evaporated under reduced pressure. The crude residue was purified by silica gel chromatography (0-100%/3:1 ethyl acetate:ethanol/hexanes) to afford a yellow oil (R)-1-(((3-fluoropyridin-2-yl)methyl)amino)butan-2-ol (5.3 g, 24.06 mmol, 58.0% yield). ¹H NMR (CHCl₃-d) δ: 8.36-8.45 (m, 1H), 7.37-7.45 (m, 1H), 7.22-7.32 (m, 1H), 4.10-4.16 (m, 2H), 3.68-3.77 (m, 1H), 2.89 (m, 1H), 2.64 (m, 1H), 1.43-1.55 (m, 2H), 0.90-1.02 (m, 3H). LC-MS: m/z 199.2 (M+H)⁺

(R)-Tert-butyl 2-ethyl-2,3-dihydropyrido[2,3-f][1,4]oxazepine-4(5H)-carboxylate

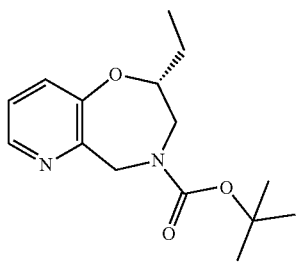 [SMILES: CC[C@@H]1CN(C(=O)OC(C)(C)C)Cc2ncccc2O1]

To a solution of (R)-1-(((3-fluoropyridin-2-yl)methyl)amino)butan-2-ol (5.20 g, 26.2 mmol) in dimethyl sulfoxide (100 mL) was added potassium tert-butoxide (3.68 g, 32.8 mmol) and the reaction mixture was stirred at 90° C. for 45 min. The reaction mixture was cooled to ambient temperature to afford a deep red-colored solution. Boc-anhydride (6.09 mL, 26.2 mmol) was added and the reaction mixture was allowed to stir for 18 hr. The reaction mixture was diluted with ethyl acetate (500 mL) and the organic phase washed with water (4×200 mL), brine, dried over sodium sulfate, filtered and the solvent evaporated under reduced pressure. The crude residue was purified by silica gel chromatography (0-50% ethyl acetate/hexanes) to afford an orange oil (R)-tert-butyl 2-ethyl-2,3-dihydropyrido[2,3-t][1,4]oxazepine-4(5H)-carboxylate (4.84 g, 17.39 mmol, 66.3% yield). $^1$H NMR (DMSO-$d_6$) δ: 8.17 (m, 1H), 7.36 (m, 1H), 7.24 (m, 1H), 4.49-4.76 (m, 2H), 3.93 (br. s., 1H), 3.47-3.74 (m, 2H), 1.52-1.66 (m, 2H), 1.36 (br. s., 4H), 1.25 (s, 5H), 0.96-1.07 (m, 3H). LC-MS: m/z 279.2 (M+H)$^+$.

(R)-2-Ethyl-2,3,4,5-tetrahydropyrido[2,3-f][1,4]oxazepine, Hydrochloride

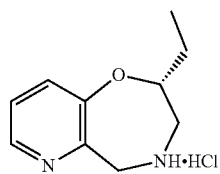

To a solution of (R)-tert-butyl 2-ethyl-2,3-dihydropyrido[2,3-f][1,4]oxazepine-4(5H)-carboxylate (4.84 g, 17.39 mmol) in 1,4-dioxane (20 mL), at ambient temperature, was added 4N HCl in dioxane (100 mL, 400 mmol) and the reaction mixture was stirred at ambient temperature for 2 h. The solvent was evaporated under reduced pressure and azeotroped with diethyl ether (3×) to afford a cream solid (R)-2-ethyl-2,3,4,5-tetrahydropyrido[2,3-f][1,4]oxazepine, hydrochloride (3.55 g, 16.54 mmol, 95% yield). $^1$H NMR (DMSO-$d_6$) δ: 9.95-10.36 (m, 2H), 8.38 (m, 1H), 7.66 (m, 1H), 7.51 (m, 1H), 4.39-4.57 (m, 2H), 4.04-4.18 (m, 1H), 3.47-3.60 (m, 1H), 3.24-3.40 (m, 1H), 1.69 (m, 2H), 1.05 (m, 3H). LC-MS: m/z 179.2 (M+H)$^+$ R)-2-Chloro-N-(2-hydroxybutyl)pyridine-3-sulfonamide

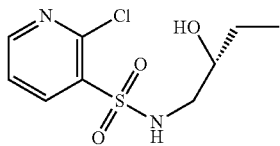 [SMILES: CC[C@@H](O)CNS(=O)(=O)c1cccnc1Cl]

To a solution of 2-chloropyridine-3-sulfonyl chloride (15 g, 70.7 mmol) in tetrahydrofuran (THF) (100 mL) was added (R)-1-aminobutan-2-ol (6.31 g, 70.7 mmol), potassium carbonate (9.78 g, 70.7 mmol) and water (30 mL). The reaction mixture was stirred for 2 h at ambient temperature. The reaction mixture was quenched with water (20 mL) and extracted with EtOAc (3×20 mL). The combined organic layer was dried over anhydrous Na$_2$SO$_4$, filtered and concentrated to give the title compound (14 g, 43.6 mmol, 61.7% yield). LC-MS m/z 262.95 (M−H)$^+$, 2.627 min (ret. time).

(R)-4-Ethyl-3,4-dihydro-2H-pyrido[2,3-b][1,4,5]oxathiazepine 1,1-dioxide

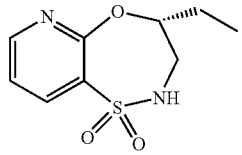

To a solution of (R)-2-chloro-N-(2-hydroxybutyl)pyridine-3-sulfonamide (13 g, 49.1 mmol) in tetrahydrofuran (THF) (130 mL) at 5° C. was added potassium tert-butoxide (16.53 g, 147 mmol), and the reaction was heated to 75° C. for 3 h. The reaction mixture was cooled to ambient temperature and then quenched with ice water (200 mL) and neutralized with 1N HCl (10 mL) solution. It was extracted with ethyl acetate (4×100 mL). The combined organic layer was washed with ice cold water (30 mL), washed with brine solution (30 mL), dried over anhydrous Na$_2$SO$_4$, filtered and concentrated. The crude residue was purified via flash chromatography eluting with EtOAc: hexane (4:6). Desired fractions were concentrated to give the title compound (4.9 g, 20.77 mmol, 42.3% yield) as an off-white solid. LCMS m/z=229.08 (M+H)$^+$, 2.555 min (ret. time).

Benzyl (S)-3-(4-(((R)-2-ethyl-2,3-dihydropyrido[2,3-f][1,4]oxazepin-4(5H)-yl)methyl)-5-methylthiophen-2-yl)-3-(1-ethyl-4-methyl-1H-benzo[d][1,2,3]triazol-5-yl)-2,2-dimethylpropanoate

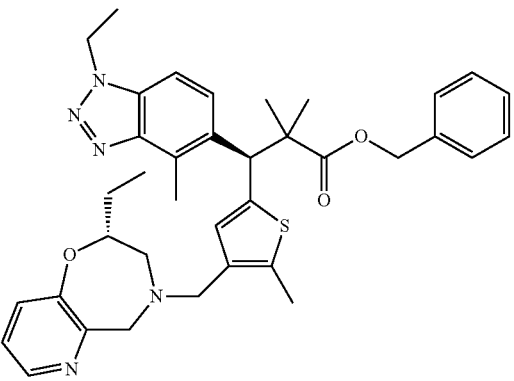 [SMILES: CC[C@@H]1CN(Cc2cc([C@@H](c3ccc4c(nnn4CC)c3C)C(C)(C)C(=O)OCc3ccccc3)sc2C)Cc2ncccc2O1]

To a solution of benzyl (S)-3-(1-ethyl-4-methyl-1H-benzo[d][1,2,3]triazol-5-yl)-3-(4-(hydroxymethyl)-5-methylthiophen-2-yl)-2,2-dimethylpropanoate (100 mg, 0.209 mmol) in dichloromethane (DCM) (4 mL) was added thionyl chloride (0.031 mL, 0.419 mmol) and the reaction stirred at ambient temperature for 30 min. The solvent was removed and the residue was dissolved in acetonitrile (4.00 mL) in a 10 mL microwave reaction vessel. To this solution was added (R)-2-ethyl-2,3,4,5-tetrahydropyrido[2,3-f][1,4]oxazepine, hydrochloride (49.4 mg, 0.230 mmol) and DIEA (0.183 mL, 1.047 mmol). The reaction was heated via microwave to 120° C. for 30 min. The reaction was purified by flash chromatography eluting with 0-5% MeOH/DCM to provide the title compound. (0.109 g, 82% yield). LC/MS m/z 638 (M+H), 0.96 min (ret. time).

225

(S)-3-(4-(((R)-2-Ethyl-2,3-dihydropyrido[2,3-f][1,4]oxazepin-4(5H)-yl)methyl)-5-methylthiophen-2-yl)-3-(1-ethyl-4-methyl-1H-benzo[d][1,2,3]triazol-5-yl)-2,2-dimethylpropanoic Acid

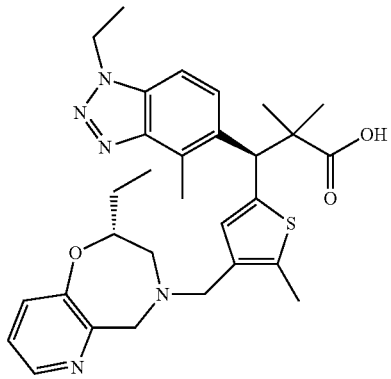 [SMILES: CC[C@@H]1CN(Cc2cc([C@@H](c3ccc4c(nnn4CC)c3C)C(C)(C)C(=O)O)sc2C)Cc2ncccc2O1]

A solution of benzyl (S)-3-(4-(((R)-2-ethyl-2,3-dihydropyrido[2,3-f][1,4]oxazepin-4(5H)-yl)methyl)-5-methylthiophen-2-yl)-3-(1-ethyl-4-methyl-1H-benzo[d][1,2,3]triazol-5-yl)-2,2-dimethylpropanoate (109 mg, 0.171 mmol) in methanol (5 mL) was evacuated and purged with nitrogen. 5% Pd/C (36.4 mg, 0.017 mmol) was then added and the reaction was evacuated and purged with hydrogen gas and stirred under a balloon of hydrogen gas at ambient temperature for 2 h. The reaction was filtered through Celite and the solvent was concentrated. The residue was purified by reverse phase preparative HPLC under formic acid conditions to provide the title compound (0.065 g, 68% yield). LC/MS m/z 548 (M+H)+. 0.73 min (ret. time).

Example 61

(R)-5-(1-Ethyl-1H-1,2,3-triazol-4-yl)-2,2-dimethyl-3-(5-methyl-4-(((S)-4-methyl-1,1-dioxido-4,5-dihydropyrido[2,3-f][1,2]thiazepin-2(3H)-yl)methyl)thiophen-2-yl)pentanoic Acid

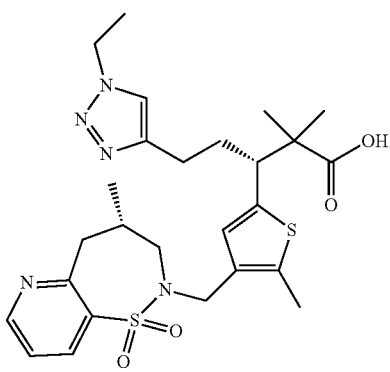 [SMILES: CCn1cc(CC[C@@H](c2cc(CN3C[C@@H](C)Cc4ncccc4S3(=O)=O)c(C)s2)C(C)(C)C(=O)O)nn1]

226

Benzyl (R)-5-(1-ethyl-1H-1,2,3-triazol-4-yl)-2,2-dimethyl-3-(5-methyl-4-(((S)-4-methyl-1,1-dioxido-4,5-dihydropyrido[2,3-f][1,2]thiazepin-2(3H)-yl)methyl)thiophen-2-yl)pentanoate

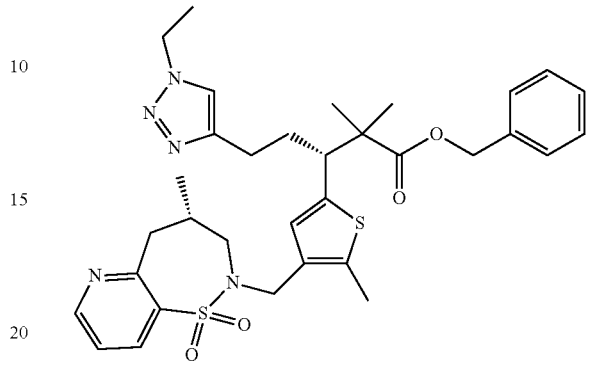

To a solution of benzyl (R)-5-(1-ethyl-1H-1,2,3-triazol-4-yl)-3-(4-(hydroxymethyl)-5-methylthiophen-2-yl)-2,2-dimethylpentanoate (0.0644 g, 0.146 mmol) in tetrahydrofuran (THF) (3.00 mL) was added (S)-4-methyl-2,3,4,5-tetrahydropyrido[2,3-f][1,2]thiazepine 1,1-dioxide (0.065 g, 0.308 mmol) and (E)-diazene-1,2-diylbis(piperidin-1-yl-methanone) (ADDP) (0.074 g, 0.292 mmol). The reaction was evacuated and purged with nitrogen and tri-n-butylphosphine (0.072 mL, 0.292 mmol) was added and the reaction stirred at ambient temperature for 18 h. The solvent was concentrated and the residue was purified by reverse phase preparative HPLC under neutral conditions to provide the title compound (0.059 g, 64% yield). LC/MS m/z 636 (M+H)+, 1.29 min (ret. time).

(R)-5-(1-Ethyl-1H-1,2,3-triazol-4-yl)-2,2-dimethyl-3-(5-methyl-4-(((S)-4-methyl-1,1-dioxido-4,5-dihydropyrido[2,3-f][1,2]thiazepin-2(3H)-yl)methyl)thiophen-2-yl)pentanoic Acid A solution of benzyl (R)-5-(1-ethyl-1H-1,2,3-triazol-4-yl)-2,2-dimethyl-3-(5-methyl-4-(((S)-4-methyl-1,1-dioxido-4,5-dihydropyrido[2,3-f][1,2]thiazepin-2(3H)-yl)methyl)thiophen-2-yl)pentanoate (59.5 mg, 0.094 mmol) in methanol (5 mL), was purged with nitrogen and 5% Pd/C (19.92 mg, 9.36 µmol) was added. The reaction was evacuated and purged with hydrogen and stirred under a hydrogen balloon for 2 h. The reaction was filtered through a cartridge filter and the solvent was concentrated. The residue was purified by reverse phase preparative HPLC under formic acid conditions to provide the title compound (0.031 g, 62% yield). LC/MS m/z 546 (M+H)+, 0.97 min (ret. time).

Example 62

(S)-5-(1-Ethyl-1H-1,2,3-triazol-4-yl)-2,2-dimethyl-3-(5-methyl-4-(((S)-4-methyl-1,1-dioxido-4,5-dihydropyrido[2,3-f][1,2]thiazepin-2(3H)-yl)methyl)thiophen-2-yl)pentanoic Acid

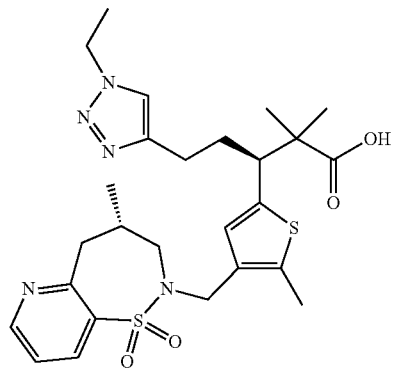 [SMILES: CCn1cc(CC[C@H](c2cc(CN3C[C@@H](C)Cc4ncccc4S3(=O)=O)c(C)s2)C(C)(C)C(=O)O)nn1]

Benzyl (S)-5-(1-ethyl-1H-1,2,3-triazol-4-yl)-2,2-dimethyl-3-(5-methyl-4-(((S)-4-methyl-1,1-dioxido-4,5-dihydropyrido[2,3-f][1,2]thiazepin-2(3H)-yl)methyl)thiophen-2-yl)pentanoate

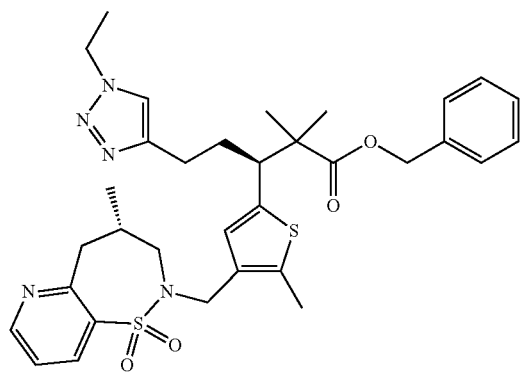 [SMILES: CCn1cc(CC[C@H](c2cc(CN3C[C@@H](C)Cc4ncccc4S3(=O)=O)c(C)s2)C(C)(C)C(=O)OCc2ccccc2)nn1]

To a solution of benzyl (S)-5-(1-ethyl-1H-1,2,3-triazol-4-yl)-3-(4-(hydroxymethyl)-5-methylthiophen-2-yl)-2,2-dimethylpentanoate (0.0715 g, 0.162 mmol) in tetrahydrofuran (THF) (3.00 mL) was added (S)-4-methyl-2,3,4,5-tetrahydropyrido[2,3-f][1,2]thiazepine 1,1-dioxide (0.073 g, 0.342 mmol) and (E)-diazene-1,2-diylbis(piperidin-1-ylmethanone) (ADDP) (0.082 g, 0.324 mmol). The reaction was evacuated and purged with nitrogen and tri-n-butylphosphine (0.080 mL, 0.324 mmol) was added and the reaction stirred at ambient temperature for 18 h. The solvent was concentrated and the residue was purified by reverse phase preparative HPLC under neutral conditions to provide the title compound (0.087 g, 85% yield). LC/MS m/z 636 (M+H)+, 1.27 min (ret. time).

(S)-5-(1-Ethyl-1H-1,2,3-triazol-4-yl)-2,2-dimethyl-3-(5-methyl-4-(((S)-4-methyl-1,1-dioxido-4,5-dihydropyrido[2,3-f][1,2]thiazepin-2(3H)-yl)methyl)thiophen-2-yl)pentanoic Acid

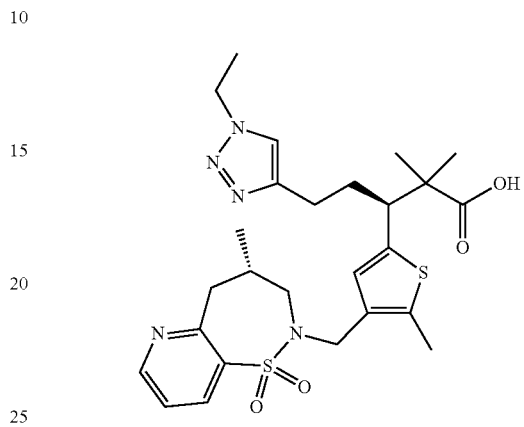

To a solution of benzyl (S)-5-(1-ethyl-1H-1,2,3-triazol-4-yl)-2,2-dimethyl-3-(5-methyl-4-(((S)-4-methyl-1,1-dioxido-4,5-dihydropyrido[2,3-f][1,2]thiazepin-2(3H)-yl)methyl)thiophen-2-yl)pentanoate (49.2 mg, 0.077 mmol) in tetrahydrofuran (THF) (2 mL), methanol (2 mL), water (1 mL) was added LiOH (9.26 mg, 0.387 mmol) and the reaction was heated via microwave at 100° C. for 4 h. Additional LiOH (9.26 mg, 0.387 mmol) was added and the reaction was heated at 100° C. for 2 h. The solvents were concentrated. The residue was acidified with formic acid and was purified by reverse phase preparative HPLC under formic acid conditions to provide the title compound (0.034 g, 81% yield). LC/MS m/z 546 (M+H)+, 0.99 min (ret. time).

Example 63

(S)-3-(4-(((R)-4-Ethyl-1,1-dioxido-3,4-dihydro-2H-benzo[b][1,4,5]oxathiazepin-2-yl)methyl)-5-methylthiophen-2-yl)-5-(1-ethyl-1H-1,2,3-triazol-4-yl)-2,2-dimethylpentanoic Acid

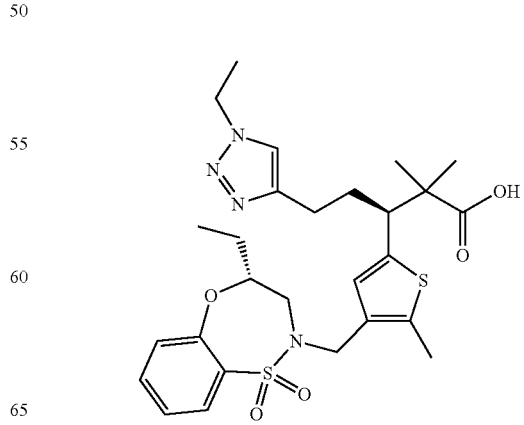

Benzyl (S)-3-(4-(((R)-4-ethyl-1,1-dioxido-3,4-dihydro-2H-benzo[b][1,4,5]oxathiazepin-2-yl)methyl)-5-methylthiophen-2-yl)-5-(1-ethyl-1H-1,2,3-triazol-4-yl)-2,2-dimethylpentanoate

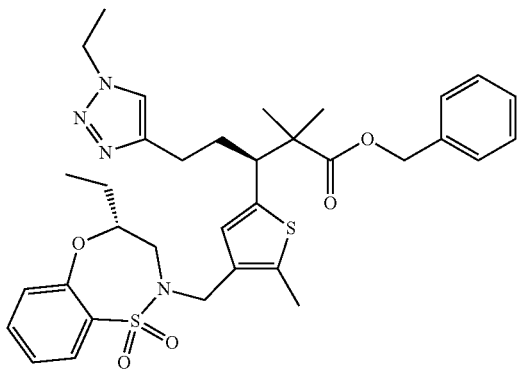 [SMILES: CC[C@@H]1CN(Cc2cc([C@@H](CCc3cn(CC)nn3)C(C)(C)C(=O)OCc3ccccc3)sc2C)S(=O)(=O)c2ccccc2O1]

To a solution of benzyl (S)-5-(1-ethyl-1H-1,2,3-triazol-4-yl)-3-(4-(hydroxymethyl)-5-methylthiophen-2-yl)-2,2-dimethylpentanoate (0.064 g, 0.145 mmol) in tetrahydrofuran (THF) (3.00 mL) was added (R)-4-ethyl-3,4-dihydro-2H-benzo[b][1,4,5]oxathiazepine 1,1-dioxide (0.066 g, 0.290 mmol) and (E)-diazene-1,2-diylbis(piperidin-1-ylmethanone) (ADDP) (0.073 g, 0.290 mmol). The reaction was evacuated and purged with nitrogen and tri-n-butylphosphine (0.072 mL, 0.290 mmol) was added and the reaction stirred at ambient temperature for 18 h. The solvent was concentrated and the residue was purified by reverse phase preparative HPLC under neutral conditions to provide the title compound (0.065 g, 68% yield). LC/MS m/z 651 (M+H)$^+$, 1.37 min (ret. time).

(S)-3-(4-(((R)-4-Ethyl-1,1-dioxido-3,4-dihydro-2H-benzo[b][1,4,5]oxathiazepin-2-yl)methyl)-5-methylthiophen-2-yl)-5-(1-ethyl-1H-1,2,3-triazol-4-yl)-2,2-dimethylpentanoic Acid

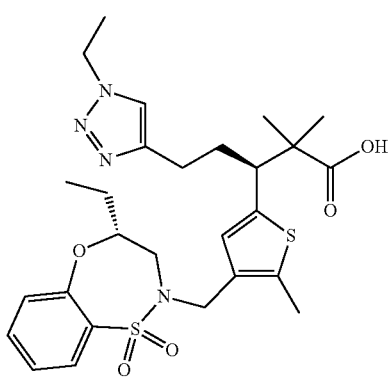 [SMILES: CC[C@@H]1CN(Cc2cc([C@@H](CCc3cn(CC)nn3)C(C)(C)C(=O)O)sc2C)S(=O)(=O)c2ccccc2O1]

To a solution of benzyl (S)-3-(4-(((R)-4-ethyl-1,1-dioxido-3,4-dihydro-2H-benzo[b][1,4,5]oxathiazepin-2-yl)methyl)-5-methylthiophen-2-yl)-5-(1-ethyl-1H-1,2,3-triazol-4-yl)-2,2-dimethylpentanoate (19 mg, 0.029 mmol) in tetrahydrofuran (THF) (1 mL), methanol (1.000 mL), water (0.50 mL) was added LiOH (3.50 mg, 0.146 mmol) and the reaction was heated via microwave at 100° C. for 4 h. Additional LiOH (3.50 mg, 0.146 mmol) was added and the reaction was heated for 2 h at 100° C. The solvents were concentrated. The residue was acidified with formic acid and was purified by reverse phase preparative HPLC under formic acid conditions to provide the title compound (0.012 g, 73% yield). LC/MS m/z 561 (M+H)$^+$, 1.22 min (ret. time).

Example 64

(R)-3-(4-(((R)-4-Ethyl-1,1-dioxido-3,4-dihydro-2H-benzo[b][1,4,5]oxathiazepin-2-yl)methyl)-5-methylthiophen-2-yl)-5-(1-ethyl-1H-1,2,3-triazol-4-yl)-2,2-dimethylpentanoic Acid

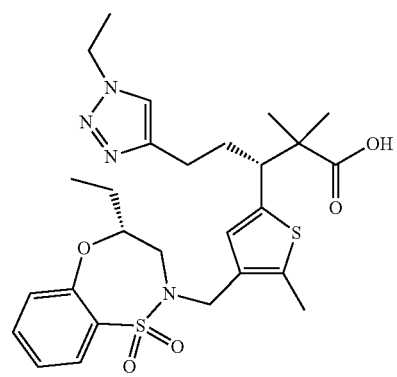 [SMILES: CC[C@@H]1CN(Cc2cc([C@H](CCc3cn(CC)nn3)C(C)(C)C(=O)O)sc2C)S(=O)(=O)c2ccccc2O1]

Benzyl (R)-3-(4-(((R)-4-ethyl-1,1-dioxido-3,4-dihydro-2H-benzo[b][1,4,5]oxathiazepin-2-yl)methyl)-5-methylthiophen-2-yl)-5-(1-ethyl-1H-1,2,3-triazol-4-yl)-2,2-dimethylpentanoate

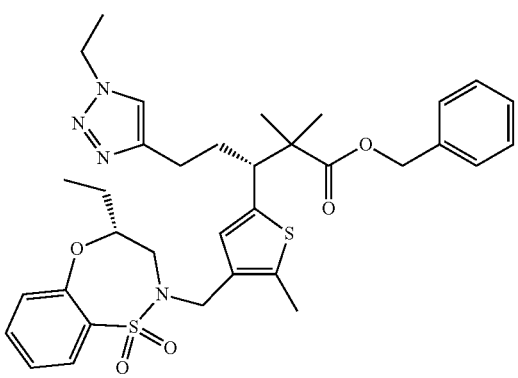 [SMILES: CC[C@@H]1CN(Cc2cc([C@H](CCc3cn(CC)nn3)C(C)(C)C(=O)OCc3ccccc3)sc2C)S(=O)(=O)c2ccccc2O1]

To a solution of benzyl (R)-5-(1-ethyl-1H-1,2,3-triazol-4-yl)-3-(4-(hydroxymethyl)-5-methylthiophen-2-yl)-2,2-dimethylpentanoate (0.064 g, 0.145 mmol) in tetrahydrofuran (THF) (3.00 mL) was added (R)-4-ethyl-3,4-dihydro-2H-benzo[b][1,4,5]oxathiazepine 1,1-dioxide (0.066 g, 0.290 mmol) and (E)-diazene-1,2-diylbis(piperidin-1-ylmethanone) (ADDP) (0.073 g, 0.290 mmol). The reaction was evacuated and purged with nitrogen and tri-n-butylphosphine (0.072 mL, 0.290 mmol) was added and the reaction stirred at ambient temperature for 18 h. The solvent was concentrated and the residue was purified by reverse phase preparative HPLC under neutral conditions to provide the title compound (0.052 g, 55% yield). LC/MS m/z 651 (M+H)+, 1.40 min (ret. time).

(R)-3-(4-(((R)-4-Ethyl-1,1-dioxido-3,4-dihydro-2H-benzo[b][1,4,5]oxathiazepin-2-yl)methyl)-5-methyl-thiophen-2-yl)-5-(1-ethyl-1H-1,2,3-triazol-4-yl)-2,2-dimethylpentanoic Acid

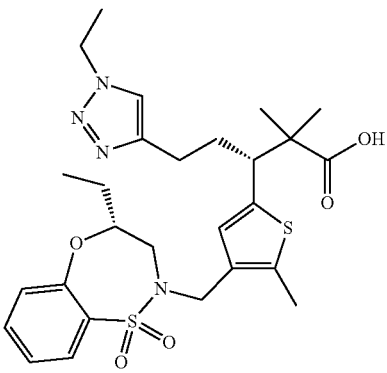

A solution of benzyl (R)-3-(4-(((R)-4-ethyl-1,1-dioxido-3,4-dihydro-2H-benzo[b][1,4,5]oxathiazepin-2-yl)methyl)-5-methylthiophen-2-yl)-5-(1-ethyl-1H-1,2,3-triazol-4-yl)-2,2-dimethylpentanoate (52.7 mg, 0.081 mmol) in methanol (5 mL), was purged with nitrogen and 5% Pd/C (17.23 mg, 8.10 μmol) was added. The reaction was evacuated and purged with hydrogen and stirred under a hydrogen balloon for 5.5 h. The reaction was filtered through a cartridge filter and the solvent was concentrated. The residue was purified by reverse phase preparative HPLC under formic acid conditions to provide the title compound (0.031 g, 70% yield). LC/MS m/z 561 (M+H)+, 1.10 min (ret. time).

Example 65

(S)-3-(4-(((R)-4-Ethyl-1,1-dioxido-3,4-dihydro-2H-benzo[b][1,4,5]oxathiazepin-2-yl)methyl)-5-methyl-thiophen-2-yl)-3-(1-ethyl-4-methyl-1H-benzo[d][1,2,3]triazol-5-yl)-2,2-dimethyl-N-(1H-tetrazol-5-yl)propanamide, 0.10Formic Acid Salt

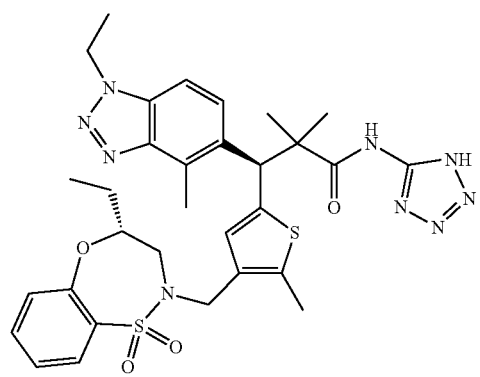 [SMILES: CC[C@@H]1CN(Cc2cc([C@@H](c3ccc4c(nnn4CC)c3C)C(C)(C)C(=O)Nc3nnn[nH]3)sc2C)S(=O)(=O)c2ccccc2O1]

To a dry 10 mL microwave reaction vial was added under nitrogen (S)-3-(4-(((R)-4-ethyl-1,1-dioxido-3,4-dihydro-2H-benzo[b][1,4,5]oxathiazepin-2-yl)methyl)-5-methylthi-ophen-2-yl)-3-(1-ethyl-4-methyl-1H-benzo[d][1,2,3]triazol-5-yl)-2,2-dimethylpropanoic acid (0.050 g, 0.084 mmol) and 1-(fluoro(pyrrolidin-1-yl)methylene)pyrrolidin-1-ium hexafluorophosphate(V) (BTFFH) (0.040 g, 0.126 mmol) and dichloromethane (DCM) (2 mL). DIEA (0.066 mL, 0.377 mmol) was then added and stirred for 1.5 h. 1H-tetrazol-5-amine (7.84 mg, 0.092 mmol) was then added and the vial was heated via microwave at 100° C. for 1.5 h. The solvent was concentrated and the residue was purified by reverse phase preparative HPLC under formic acid conditions to provide the title compound (0.020 g, 34% yield). LC/MS m/z 634 (M+H)+, 1.24 min (ret. time).

What is claimed is:

1. A compound which is (S)-3-(4-(((R)-4-Ethyl-1,1-dioxido-3,4-dihydro-2H-pyrido[4,3-b][1,4,5]oxathiazepin-2-yl)methyl)-5-methylthiophen-2-yl)-3-(1-ethyl-4-methyl-1H-benzo[d][1,2,3]triazol-5-yl)-2,2-dimethylpropanoic acid

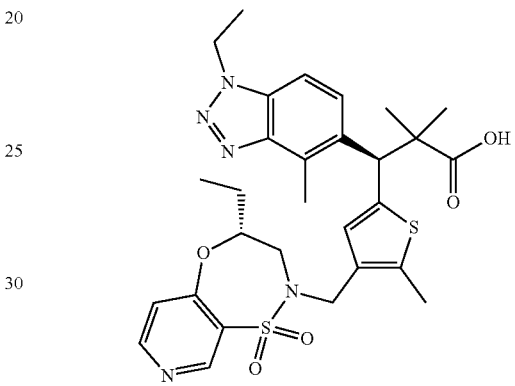

or a pharmaceutically acceptable salt thereof.

2. A pharmaceutical composition comprising the compound of claim 1, or a pharmaceutically acceptable salt thereof, and a pharmaceutically acceptable excipient.

3. A method of treating COPD which comprises administering to a human in need thereof, a therapeutically effective amount of a compound, or a pharmaceutically acceptable salt thereof, according to claim 1.

4. The method according to claim 3 wherein the compound, or a pharmaceutically acceptable salt thereof, is administered orally.

5. The method according to claim 3 wherein the compound, or a pharmaceutically acceptable salt thereof, is administered intravenously.

6. The method according to claim 3 wherein the compound, or a pharmaceutically acceptable salt thereof, is administered by inhalation.

7. A method of treating heart failure which comprises administering to a human in need thereof, a therapeutically effective amount of a compound, or a pharmaceutically acceptable salt thereof, according to claim 1.

8. The method according to claim 7 wherein the compound, or a pharmaceutically acceptable salt thereof, is administered orally.

9. The method according to claim 7 wherein the compound, or a pharmaceutically acceptable salt thereof, is administered intravenously.

10. The method according to claim 7 wherein the compound, or a pharmaceutically acceptable salt thereof, is administered by inhalation.

* * * * *